United States Patent
Torisu et al.

(10) Patent No.: US 6,743,793 B2
(45) Date of Patent: Jun. 1, 2004

(54) INDOLE DERIVATIVES, PROCESS FOR PREPARATION OF THE SAME AND USE THEREOF

(75) Inventors: Kazuhiko Torisu, Mishima-gun (JP); Kaoru Kobayashi, Mishima-gun (JP); Fumio Nambu, Mishima-gun (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 10/220,806
(22) PCT Filed: Mar. 8, 2001
(86) PCT No.: PCT/JP01/01817
§ 371 (c)(1), (2), (4) Date: Dec. 13, 2002
(87) PCT Pub. No.: WO01/66520
PCT Pub. Date: Sep. 13, 2001

(65) Prior Publication Data
US 2003/0176400 A1 Sep. 18, 2003

(30) Foreign Application Priority Data
Mar. 9, 2000 (JP) .......................... 2000-064696
Jul. 31, 2000 (JP) .......................... 2000-231857

(51) Int. Cl.$^7$ ................ C07D 209/00; A61K 31/495
(52) U.S. Cl. .............. 514/249; 514/250; 514/301; 514/397; 514/300; 514/339; 514/414; 514/415; 546/114; 546/256; 546/122; 546/113; 544/353; 544/350; 548/454; 548/305.1; 548/491; 548/465
(58) Field of Search ............... 546/114, 113, 546/122, 256; 548/454, 305.1, 491, 465; 544/353, 350; 514/250, 301, 414, 300, 249, 397, 415, 339

(56) References Cited

U.S. PATENT DOCUMENTS 5,811,439 A * 9/1998 Ogawa et al. ............... 514/369

FOREIGN PATENT DOCUMENTS

| BE | 649166 | * 12/1964 |
| EP | 0 284 202 | 9/1988 |
| EP | 0 458 642 | 5/1991 |
| EP | 0 780 389 | 6/1997 |
| WO | WO 97/00853 | 1/1997 |
| WO | WO 98/15502 | 4/1998 |
| WO | WO 98/25915 | 6/1998 |
| WO | WO 98/25919 | 6/1998 |

OTHER PUBLICATIONS

Cannon, Joseph et al., J. Heterocyclic Chem, 19, (Sep.–Oct. 1982) pp. 1195–1199.

* cited by examiner

Primary Examiner—Joseph K. McKane
Assistant Examiner—Andrea D Small
(74) Attorney, Agent, or Firm—Sughrue Mion, PLLC

(57) ABSTRACT

Indole derivatives represented by formula (I):

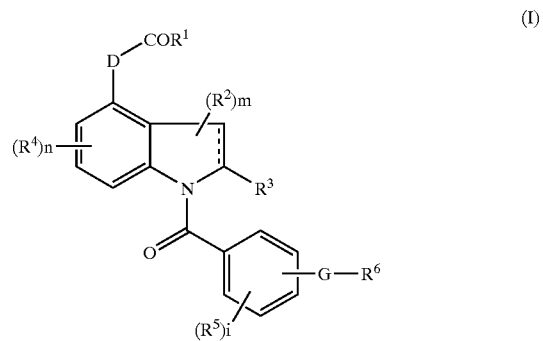

(wherein all symbols are described in the description), a process for the preparation of the same and a DP receptor antagonist comprising it as an active ingredient. Since the compounds of formula (I) binds to and are antagonistic to a DP receptor, they are useful in for the prevention and/or treatment of diseases, for example, allergic diseases (allergic rhinitis, allergic conjunctivitis, atopic dermatitis, bronchial asthma, food allergy, etc., systemic mastocytosis; disorders due to systemic mastocyte activation, anaphylactic shock, bronchoconstriction, urticaria, eczema, etc.), diseases accompanied with itching (atopic dermatitis, urticaria, etc.), secondary diseases caused by behaviors (scratching behaviors, beating, etc.) (cataract, retinal detachment, inflammation, infection, sleep disorder, etc.), inflammation, chronic obstructive pulmonary disease, ischemic reperfusion disorder, cerebrovascular disorder, pleuritis complicated by rheumatoid arthritis, ulcerative colitis, and the like.

4 Claims, No Drawings

US 6,743,793 B2

INDOLE DERIVATIVES, PROCESS FOR PREPARATION OF THE SAME AND USE THEREOF

This application is a 371 of PCT/JP01/01817 Mar. 8, 2001.

TECHNICAL FIELD

The present invention relates to indole derivatives.

More specifically, the present invention relates to indole derivatives represented by formula (I):

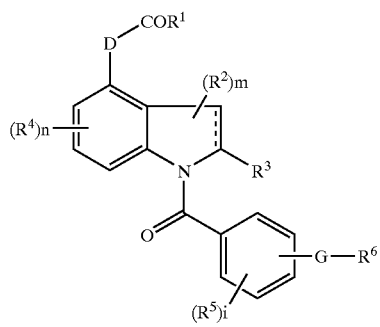

(wherein all symbols have the same meanings as described below), a process for the preparation of the same and use thereof.

BACKGROUND ART

Prostaglandin D (hereinafter referred to as "PGD") are known as a metabolite in the arachidonic acid cascade, and are known to have effects of bronchoconstriction, vasodilatation or vasoconstriction and platelet aggregation inhibition. PGD is considered to be produced from mast cells, and the increase of PGD concentration has been recognized among systemic mastocytosis patients (*New Eng. J. Med.*, 303, 1400–1404 (1980)). Also, PGD is considered to relate to neuro activities, especially, sleep and hormone secretion. Furthermore, there are reports suggesting participations in platelet aggregation, glycogen metabolism, ocular tension adjustment and the like.

PGD shows its effects by binding to a DP receptor which is a receptor thereof. A DP receptor antagonist binds to and is antagonistic to its receptor so that it can inhibit the function of PGD. Accordingly, it is considered to be useful for the prevention and/or treatment of diseases, for example, allergic diseases such as allergic rhinitis, allergic conjunctivitis, atopic dermatitis, bronchial asthma, food allergy, etc.; systemic mastocytosis; disorders due to systemic mastocyte activation; anaphylactic shock; bronchoconstriction; urticaria; eczema; allergic bronchopulmonary aspergillosis; inflammatory paranasal sinus; nasal polyp; hypersensitive angitis; eosinophilia; contact dermatitis; diseases accompanied with itching, such as atopic dermatitis, urticaria, allergic conjunctivitis, allergic rhinitis, contact dermatitis, etc.; secondary diseases caused by behaviors (scratching behaviors, beating, etc.), such as cataract, retinal detachment, inflammation, infection, sleep disorder, etc.; inflammation; chronic obstructive pulmonary disease; ischemic reperfusion disorder; cerebrovascular disorder; pleuritis complicated by rheumatoid arthritis; ulcerative colitis; and the like. Moreover, it is considered to relate to sleeping and platelet aggregation and to be useful for these diseases.

Some DP receptor antagonists are known until now, and BW-A868C represented by formula (A) is considered to be the most selective:

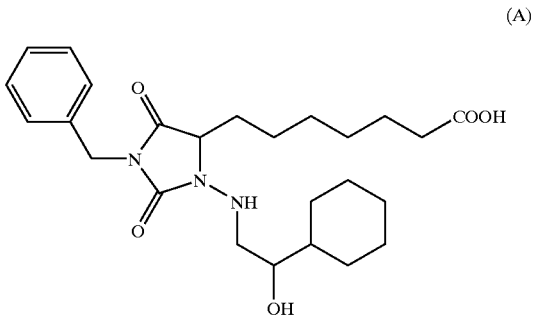

Also, recently, DP receptor antagonists which are thromboxane derivatives have been published in WO 98/25915, WO 98/25919, WO 97/00853, WO 98/15502 and the like.

On the other hand, as a compound similar to the compound of the present invention, an indole compound represented by formula (B) is known as a synthetic intermediate (*J. Heterocyclic Chem.*, 19, 1195 (1982)).

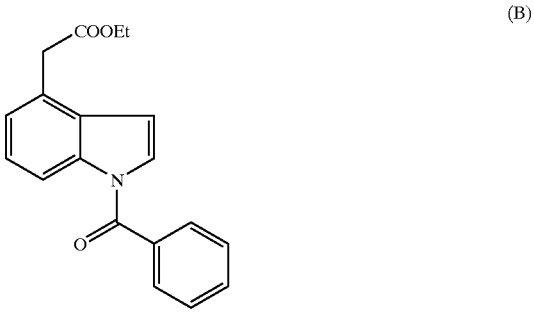

DISCLOSURE OF THE INVENTION

The present inventors intensively studied to find a compound which specifically binds to DP receptor and show an antagonistic activity and found that the object could be attained by indole derivatives represented by formula (I), and thus the present invention has been completed.

That is, the present invention relates to an indole derivative represented by formula (I):

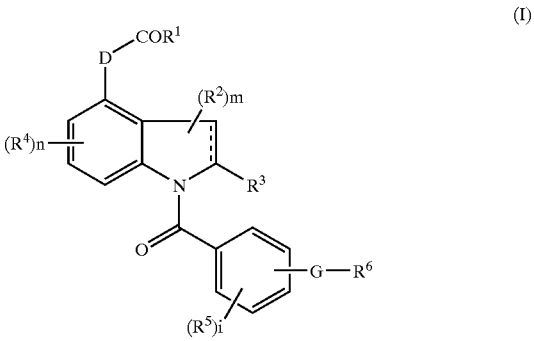

wherein $R^1$ represents hydroxy, C1–6 alkoxy, or $NR^8R^9$, in which $R^8$ and $R^9$ each independently represents a hydrogen atom, C1–6 alkyl, or $SO_2R^{13}$, in which $R^{13}$ represents C1–6 alkyl, a C3–15 saturated or unsaturated carbocyclic ring or a 4- to 15-membered heterocyclic ring containing 1 to 5 nitrogen atom(s), sulfur atom(s) and/or oxygen atom(s);

$R^2$ represents a hydrogen atom, C1–6 alkyl, C1–6 alkoxy, C2–6 alkoxyalkyl, a halogen atom, amino, trihalomethyl, cyano, hydroxy, benzyl, or 4-methoxybenzyl;

$R^3$ represents a hydrogen atom, C1–6 alkyl, C1–6 alkoxy, a halogen atom, trihalomethyl, cyano, or hydroxy;

$R^4$ and $R^5$ each independently represents a hydrogen atom, C1–6 alkyl, C1–6 alkoxy, C2–6 alkoxyalkyl, a halogen atom, nitro, amino, trihalomethyl, cyano, or hydroxy;

D represents a single bond, C1–6 alkylene, C2–6 alkenylene, or C1–6 oxyalkylene;

in $-G-R^6$,

1) G represents a single bond, C1–6 alkylene which may be substituted with 1 to 2 oxygen atom(s) and/or sulfur atom(s), C2–6 alkenylene which may be substituted with 1 to 2 oxygen atom(s) and/or sulfur atom(s), in which the alkylene and the alkenylene may be substituted with hydroxy or C1–4 alkoxy, —C(O)NH—, —NHC(O)—, —SO$_2$NH—, —NHSO$_2$—, or diazo;

$R^6$ represents a C3–15 saturated or unsaturated carbocyclic ring, or a 4- to 15-membered heterocyclic ring containing 1 to 5 nitrogen atom(s), sulfur atom(s) and/or oxygen atom(s), in which the ring may be substituted with 1 to 5 substituent(s) selected from C1–6 alkyl, C1–10 alkoxy, C2–6 alkoxyalkyl, a halogen atom, hydroxy, trihalomethyl, nitro, amino, phenyl, phenoxy, oxo, C2–6 acyl, C1–6 alkanesulfonyl and cyano, 2) G and $R^6$ are taken together to represent
   (i) C1–15 alkyl which may be substituted with 1 to 5 oxygen atom(s) and/or sulfur atom(s);
   (ii) C2–15 alkenyl which may be substituted with 1 to 5 oxygen atom(s) and/or sulfur atom(s); or
   (iii) C2–15 alkynyl which may be substituted with 1 to 5 oxygen atom(s) and/or sulfur atom(s),
   in which the alkyl, the alkenyl and the alkynyl may be substituted with 1 to 12 substituent(s) selected from C1–6 alkoxy, a halogen atom, hydroxy, cyano, oxo and $NR^{11}R^{12}$, in which $R^{11}$ and $R^{12}$ each independently represents a hydrogen atom, C1–6 alkyl, C2–6 alkenyl, phenyl, benzoyl, naphthyl, phenyl substituted with C1–6 alkyl, or C1–6 alkyl substituted with phenyl or cyano;
   n represents 1 to 3;
   m represents 1 to 3;
   i represents 1 to 4; and
   ----- represents a single bond or a double bond, or a non-toxic salt thereof;

(2) a process for the preparation thereof;

(3) a pharmaceutical agent comprising it as an active ingredient; and (4) 2-methylindole-4-acetic acid which is a novel synthetic intermediate.

In formula (I), the C1–6 alkyl represented by $R^2$, $R^3$, $R^4$, $R^5$, $R^6$, $R^8$, $R^9$, $R^{11}$, $R^{12}$ or $R^{13}$ includes, methyl, ethyl, propyl, butyl, pentyl, hexyl, and isomers thereof.

In formula (I), the C1–6 alkoxy represented by $R^1$, $R^2$, $R^3$, $R^4$ or $R^5$ includes methoxy, ethoxy, propyloxy, butyloxy, pentyloxy, hexyloxy, and isomers thereof.

In formula (I), the C1–10 alkoxy represented by $R^6$ includes methoxy, ethoxy, propyloxy, butyloxy, pentyloxy, hexyloxy, heptyloxy, octyloxy, nonyloxy, decyloxy, and isomers thereof.

In formula (I), the C1–15 alkyl represented by G and $R^6$ taken together includes methyl, ethyl, propyl, butyl, pentyl, hexyl, heptyl, octyl, nonyl, decyl, undecyl, dodecyl, tridecyl, tetradecyl, pentadecyl, and isomers thereof.

In formula (I), the C1–15 alkyl which may be substituted with 1 to 5 oxygen atom(s) and/or sulfur atom(s) represented by G and $R^6$ taken together represents the above alkyl in which any 1 to 5 carbon atom(s) are substituted with an oxygen atom(s) and/or a sulfur atom(s).

In formula (I), the C2–15 alkenyl represented by G and $R^6$ which are taken together includes vinyl, propenyl, butenyl, pentenyl, hexenyl, heptenyl, octenyl, nonenyl, decenyl, undecenyl, dodecenyl, tridecenyl, tetradecenyl, pehtadecenyl, and isomers thereof.

In formula (I), the C2–15 alkenyl which may be substituted with 1 to 5 oxygen atom(s) and/or sulfur atom(s) represented by G and $R^6$ which are taken together represents the above alkenyl in which any 1 to 5 carbon atom(s) are substituted with an oxygen atom(s) and/or a sulfur atom(s).

In formula (I), the C2–15 alkynyl represented by G and $R^6$ which are taken together includes ethynyl, propynyl, butynyl, pentynyl, hexynyl, heptynyl, octynyl, nonynyl, decynyl, undecynyl, dodecynyl, tridecynyl, tetradecynyl, pentadecynyl, and isomers thereof.

In formula (I), the C2–15 alkynyl which may be substituted with 1 to 5 oxygen atom(s) and/or sulfur atom(s) represented by G and $R^6$ which are taken together represents the above alkynyl in which any 1 to 5 carbon atom(s) are substituted with an oxygen atom(s) and/or a sulfur atom(s).

In formula (I), the C2–6 alkoxyalkyl represented by $R^2$, $R^4$, $R^5$ or $R^6$ includes methoxymethyl, methoxyethyl, methoxypropyl, methoxybutyl, methoxypentyl, ethoxymethyl, ethoxyethyl, ethoxypropyl, ethoxybutyl, propyloxymethyl, propyloxyethyl, propyloxypropyl, butyloxymethyl, butyloxyethyl, pentyloxymethyl, and isomers thereof.

In formula (I), the C1–6 alkylene represented by D or G includes methylene, ethylene, trimethylene, tetramethylene, pentamethylene, hexamethylene, and isomers thereof.

In formula (I), the C2–6 alkenylene represented by D includes vinylene, propenylene, butenylene, pentenylene, hexenylene, and isomers thereof.

In formula (I), the C1–6 oxyalkylene represented by D includes oxymethylene, oxyethylene, oxybutylene, oxypehtylene, oxyhexylene, and isomers thereof.

In formula (I), the C1–6 alkylene which may by substituted with 1 to 2 oxygen atom(s) and/or sulfur atom(s) represented by G includes the above C1–6 alkylene in which any carbon atom(s) is/are substituted with an oxygen atom (s) and/or a sulfur atom(s).

In formula (I), the C2–6 alkenylene which may by substituted with 1 to 2 oxygen atom(s) and/or sulfur atom(s) represented by G includes the above C2–6 alkenylene in which any saturated carbon atom(s) is/are substituted with an oxygen atom(s) and/or a sulfur atom(s).

In formula (I), the C2–6 alkenyl represented by $R^{11}$ or $R^{12}$ includes vinyl, propenyl, butenyl, pentenyl, hexenyl, and isomers thereof.

In formula (I), the halogen atom represented by $R^2$, $R^3$, $R^4$, $R^5$ or $R^6$ includes fluorine, chlorine, bromine, and iodine.

In formula (I), the trihalomethyl represented by $R^2$, $R^3$, $R^4$, $R^5$ or $R^6$ includes trifluoromethyl, trichloromethyl, tribromomethyl, and triiodomethyl.

In formula (I), the C1–10 alkoxy represented by $R^{10}$ includes methoxy, ethoxy, propyloxy, butyloxy, pentyloxy, hexyloxy, heptyloxy, octyloxy, nonyloxy, decyloxy, and isomers thereof.

In formula (I), the C2–6 acyl represented by $R^6$ includes acetyl, propionyl, butyly, valeryl, hexanoyl, and isomers thereof.

In formula (I), the C1–6 alkanesulfonyl represented by $R^6$ includes methanesulfonyl, ethanesulfonyl, propanesulfonyl, butanesulfonyl, pentanesulfonyl, hexanesulfonyl, and isomers thereof.

In formula (I), the C3–15 carbocyclic ring represented by $R^6$ or $R^{13}$ includes monocyclic, bicyclic or tricyclic unsaturated or saturated carbocyclic ring having carbon numbers of 3 to 15.

Examples of the monocyclic, bicyclic or tricyclic unsaturated or saturated carbocyclic ring having carbon numbers of 3 to 15 include cyclopropane, cyclobutane, cyclopentane, cyclohexane, cycloheptane, cyclooctane, cyclopentene, cyclohexene, cyclopentadiene, cyclohexadiene, benzene, pentalene, indene, naphthalene, azulene, perhydropentalene, perhydroindene, dihydronaphthalene, tetrahydronaphthalene, perhydronaphthalene, perhydroazulene, heptalene, biphenylene, fluorene, phenanthrene, anthracene, dihydroanthracene, tetrahydroanthracene, perhydroanthracene, fluorene, dihydrofluorene, tetrahydrofluorene, perhydrofluorene, norbornane, norpinane, norbornane, norbornene, norpinane, norpinene rings and the like.

In formula (I), the 4- to 15-membered heterocyclic ring containing 1 to 5 nitrogen atom(s), sulfur atom(s) and/or oxygen atom(s) represented by $R^6$ or $R^{13}$ is unsaturated or saturated, and examples includes the following formulas:

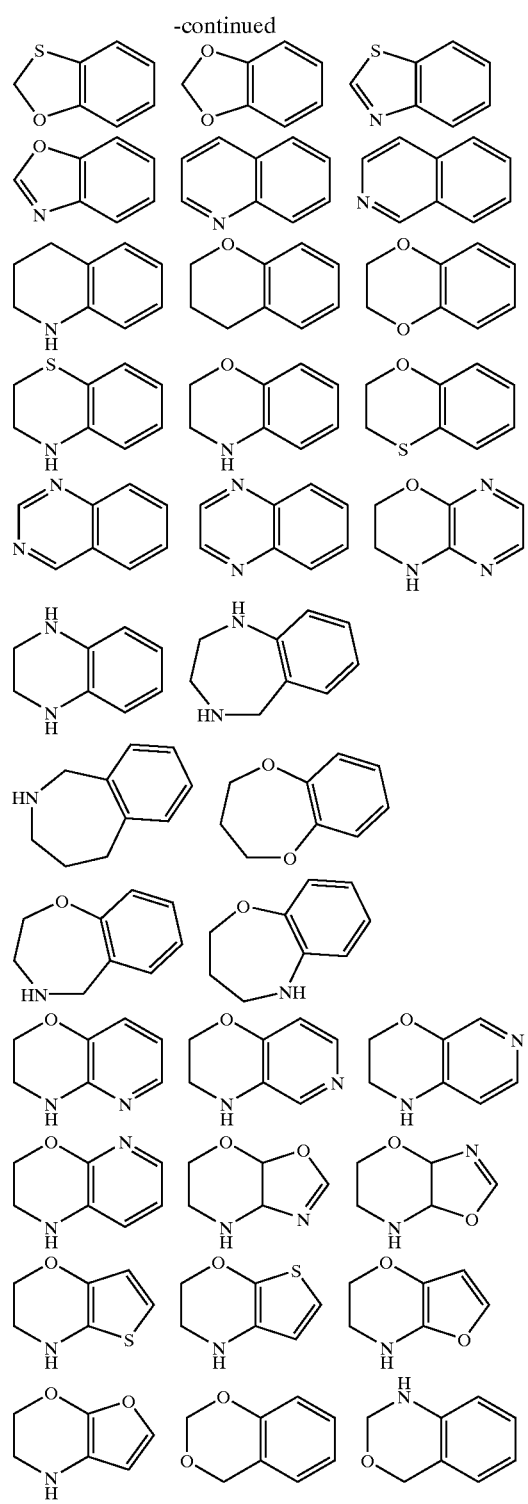

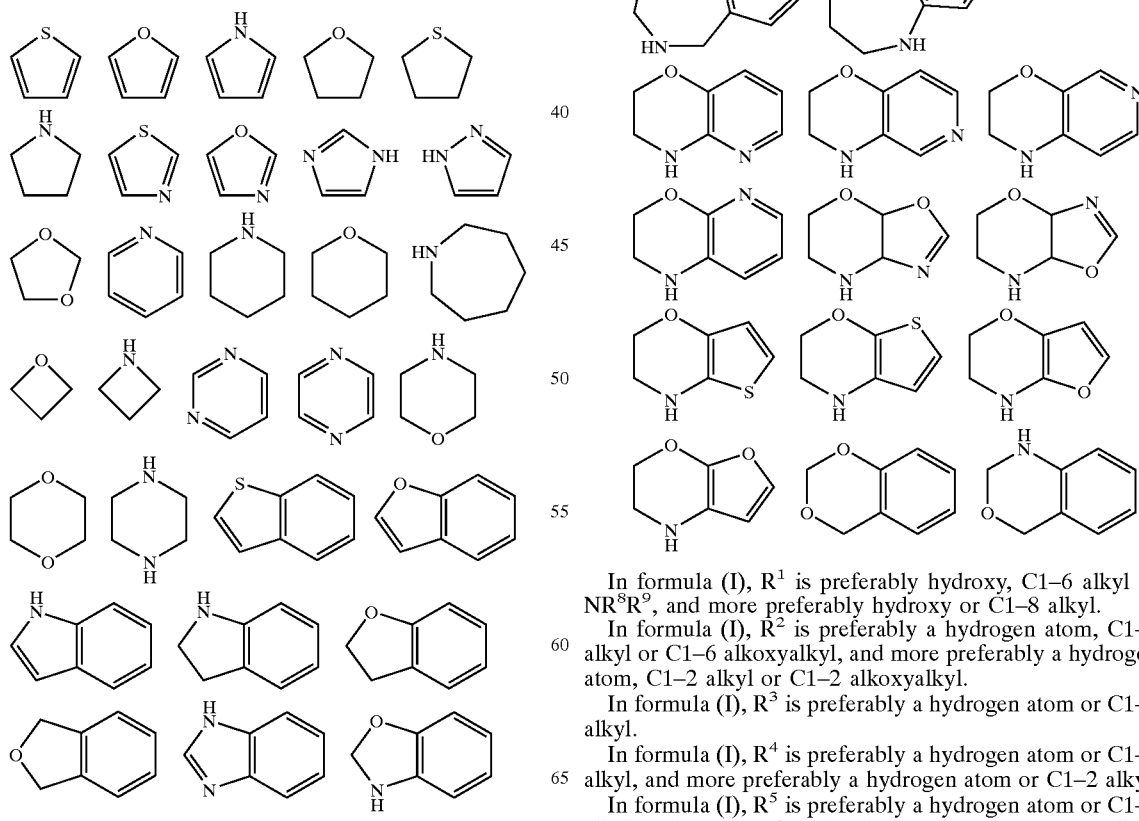

In formula (I), $R^1$ is preferably hydroxy, C1–6 alkyl or $NR^8R^9$, and more preferably hydroxy or C1–8 alkyl.

In formula (I), $R^2$ is preferably a hydrogen atom, C1–6 alkyl or C1–6 alkoxyalkyl, and more preferably a hydrogen atom, C1–2 alkyl or C1–2 alkoxyalkyl.

In formula (I), $R^3$ is preferably a hydrogen atom or C1–6 alkyl.

In formula (I), $R^4$ is preferably a hydrogen atom or C1–6 alkyl, and more preferably a hydrogen atom or C1–2 alkyl.

In formula (I), $R^5$ is preferably a hydrogen atom or C1–6 alkyl, and more preferably a hydrogen atom or C1–2 alkyl.

In formula (I), D is preferably a single bond or C1–6 alkylene, and more preferably a single bond or C1–2 alkylene.

In formula (I), G is preferably C1–6 alkylene which may be substituted with 1 or 2 oxygen atom(s), and more preferably C1–2 alkylene which may be substituted with one oxygen atom.

In formula (I), $R^6$ is preferably a C5–10 carbocyclic ring or a monocyclic or bicyclic 5- to 10-membered heterocyclic ring containing 1 to 3 nitrogen, oxygen and/or sulfur atom(s), which each may be substituted, and more preferably a bicyclic 9- or 10-membered heterocyclic ring containing 1 to 3 nitrogen, oxygen and/or sulfur atoms(s) which may be substituted.

Also, G and $R^6$ are preferably taken together to represent C1–10 alkyl which may be substituted with 1 to 4 oxygen and/or sulfur atom(s), C2–10 alkenyl which may be substituted with 1 to 4 oxygen and/or sulfur atom(s), or C2–10 alkynyl which may be substituted with 1 to 4 oxygen and/or sulfur atom(s).

Unless otherwise indicated, all isomers are included in the present invention. For example, the alkyl, alkenyl and alkynyl groups and alkylene group include straight-chain groups and branched-chain groups. In addition, isomers in double bond, ring, fused ring (E-, Z-, cis-, trans-isomer), isomers generated from asymmetric carbon atom(s) (R-, S-, α-, β-isomer, enantiomer, diastereomer), optically active isomers having optical rotation (D-, L-, d-, l-isomer), polar compounds separated by chromatography (high polar compound, low polar compound), equilibrium compounds, mixtures thereof at arbitrary ratios and racemic mixtures are included in the present invention.

Among the compounds of the present invention represented by formula (I), preferred compounds are compounds shown in Examples, compounds represented by formula (I-A1):

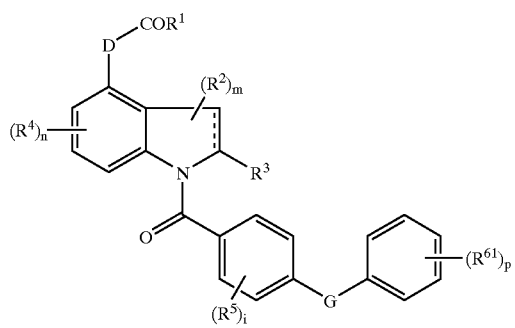
(I-A1)

(wherein when $R^6$ represents a ring, $R^{61}$ represents a substituent of the ring; p is 0 or an integer of 1 to 3; and other symbols have the same meanings as described above), formula (I-A2):

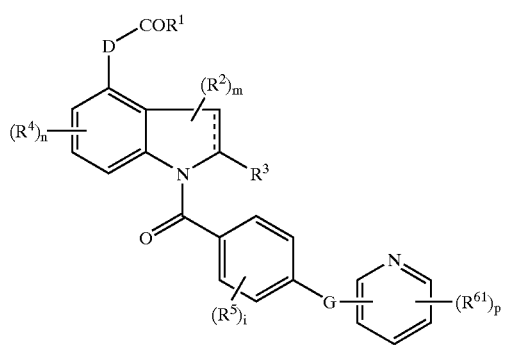
(I-A2)

(wherein all symbols have the same meanings as described above), formula (I-A3):

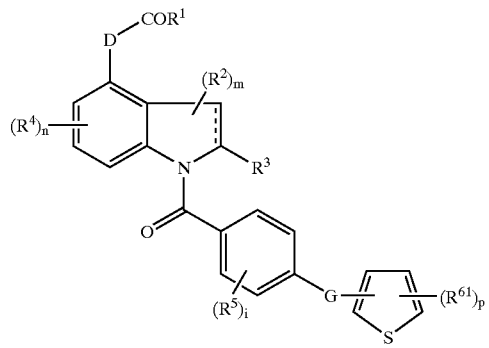
(I-A3)

(wherein all symbols have the same meanings as described above), formula (I-A4):

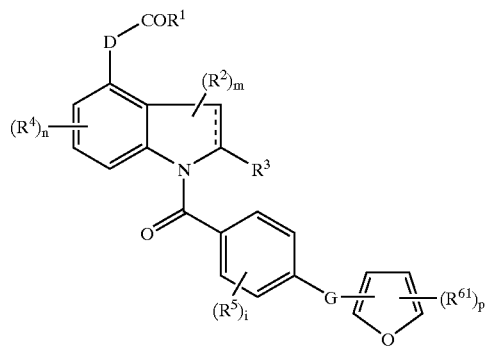
(I-A4)

(wherein all symbols have the same meanings as described above), formula (I-A5):

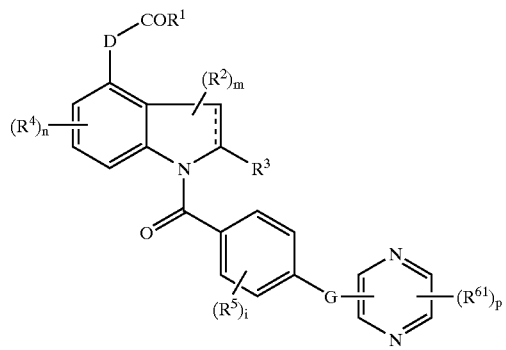
(I-A5)

(wherein all symbols have the same meanings as described above), formula (I-A6):

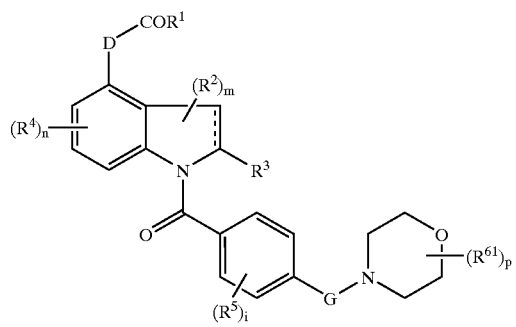
(I-A6)

(wherein all symbols have the same meanings as described above), formula (I-A7):

(I-A7)

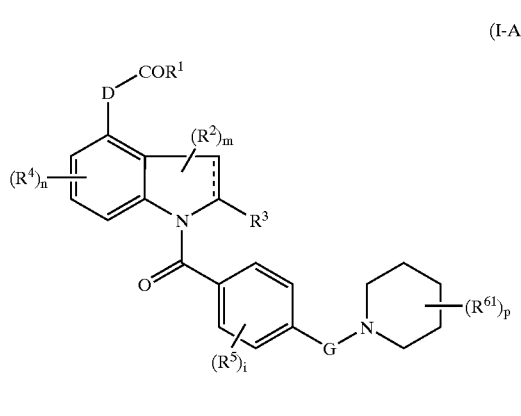

(wherein all symbols have the same meanings as described above), formula (I-A8):

(I-A8)

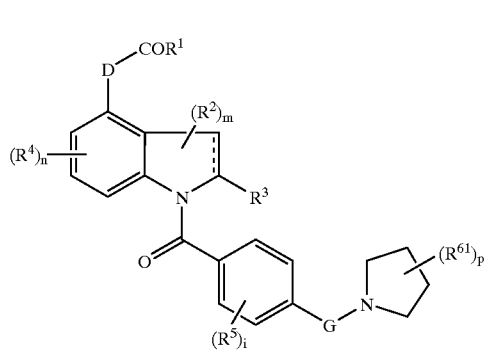

(wherein all symbols have the same meanings as described above), formula (I-A9):

(I-A9)

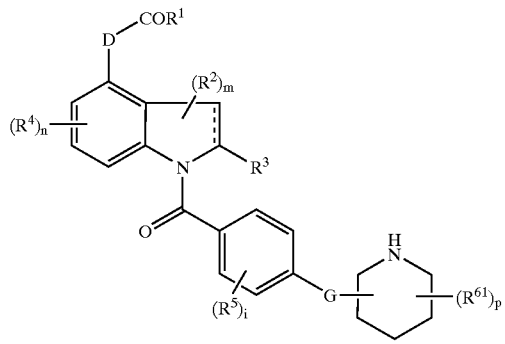

(wherein all symbols have the same meanings as described above), formula (I-A10):

(I-A10)

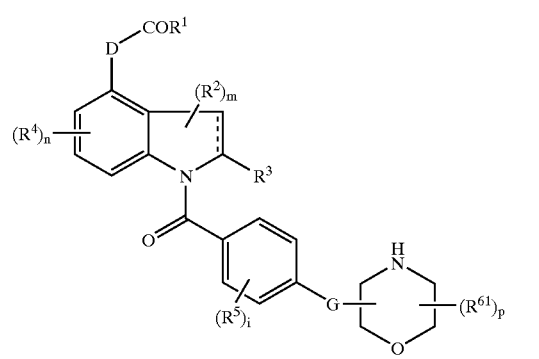

(wherein all symbols have the same meanings as described above), formula (I-B1)1

(I-B1)

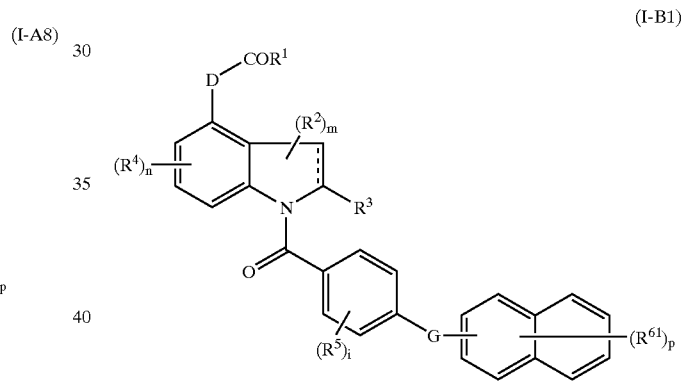

(wherein all symbols have the same meanings as described above), formula (I-B2):

(I-B2)

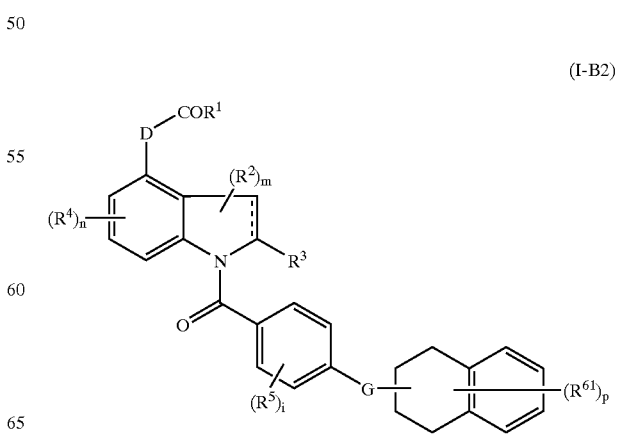

(wherein all symbols have the same meanings as described above), formula (I-B3):

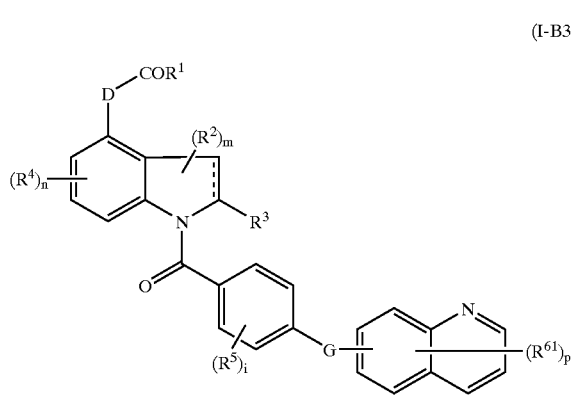

(I-B3)

(wherein all symbols have the same meanings as described above), formula (I-B4):

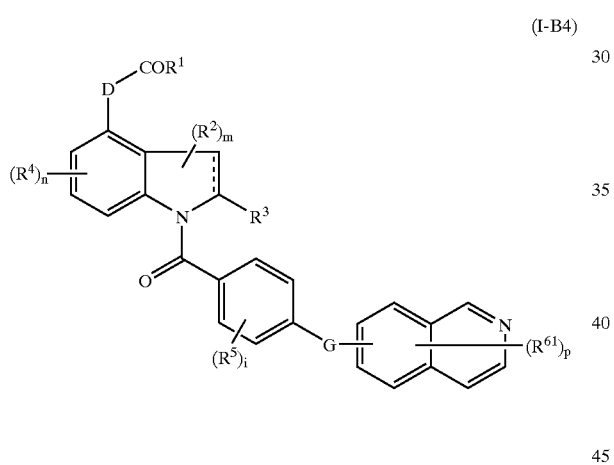

(I-B4)

(wherein all symbols have the same meanings as described above), formula (I-B5):

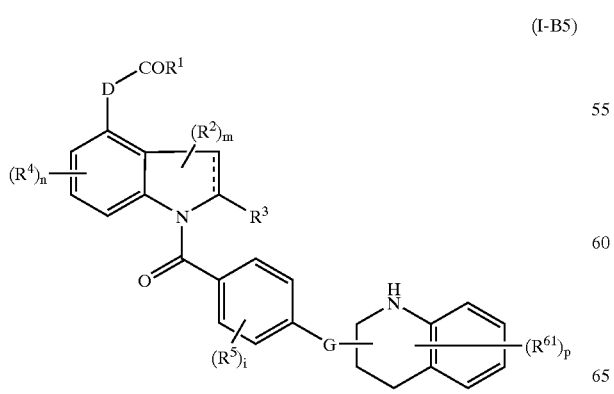

(I-B5)

(wherein all symbols have the same meanings as described above), formula (I-B6):

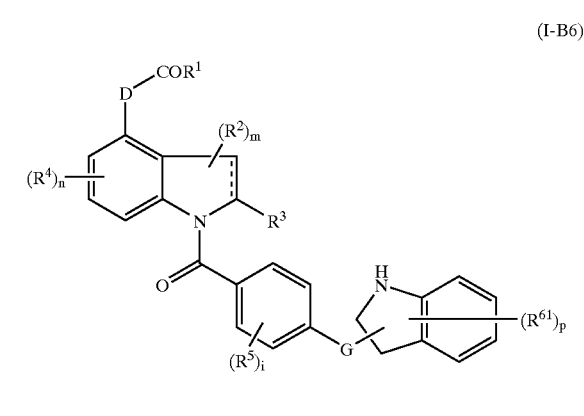

(I-B6)

(wherein all symbols have the same meanings as described above), formula (I-B7):

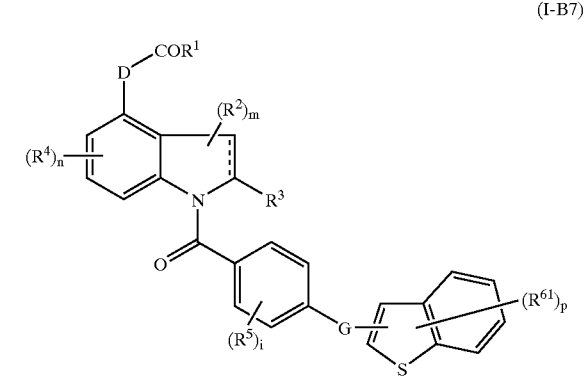

(I-B7)

(wherein all symbols have the same meanings as described above), formula (I-B8):

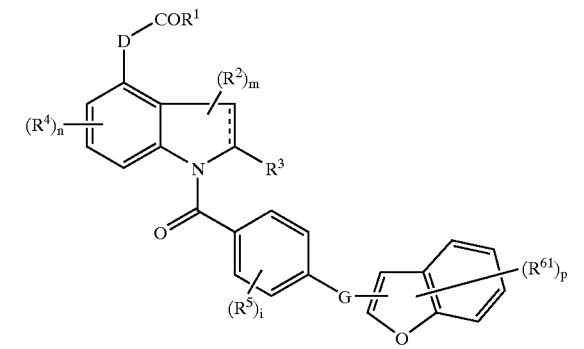

(I-B8)

(wherein all symbols have the same meanings as described above), formula (I-C1):

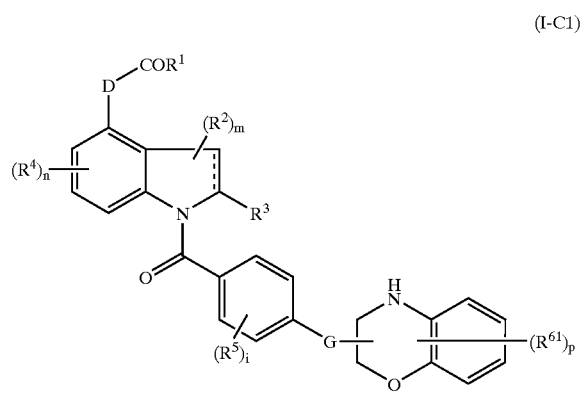

(I-C1)

(wherein all symbols have the same meanings as described above), formula (I-C2):

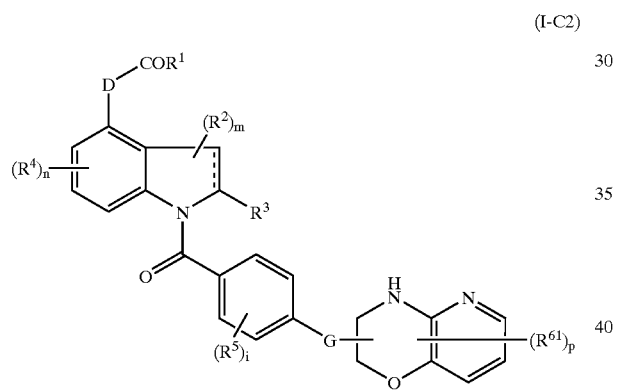

(I-C2)

(wherein all symbols have the same meanings as described above), formula (I-C3):

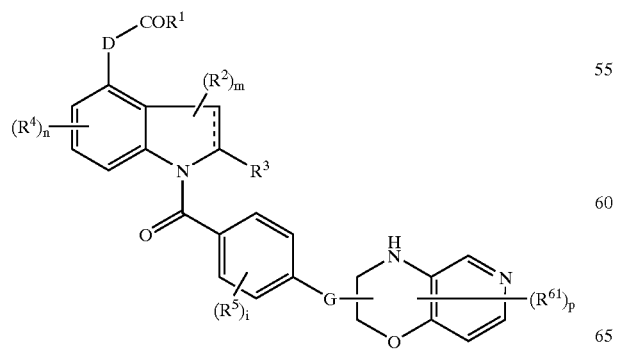

(I-C3)

(wherein all symbols have the same meanings as described above), formula (I-C4):

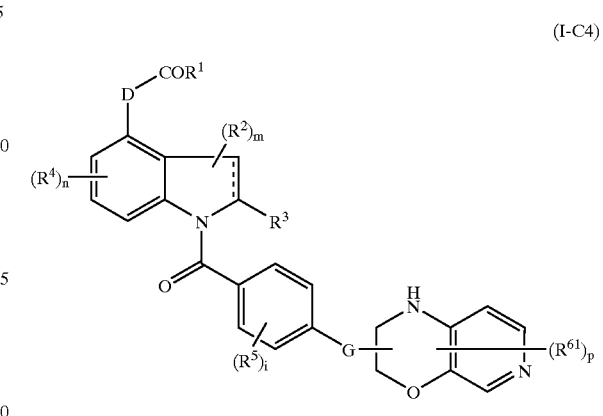

(I-C4)

(wherein all symbols have the same meanings as described above), formula (I-C5):

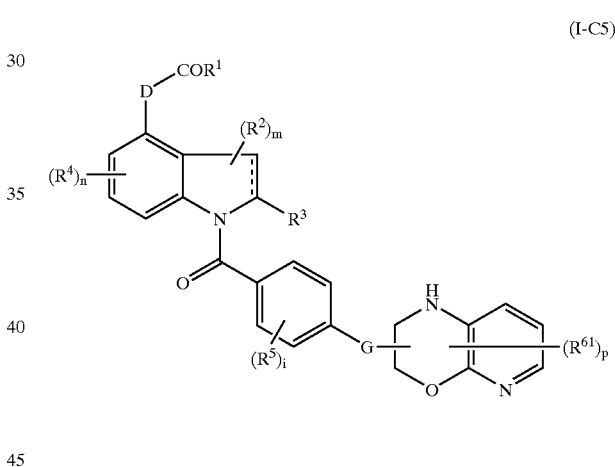

(I-C5)

(wherein all symbols have the same meanings as described above), formula (I-C6):

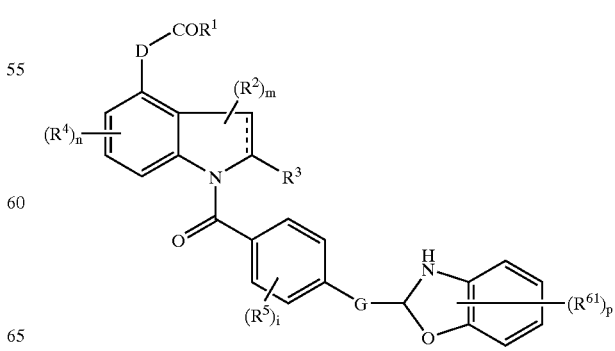

(I-C6)

(wherein all symbols have the same meanings as described above), formula (I-C7):

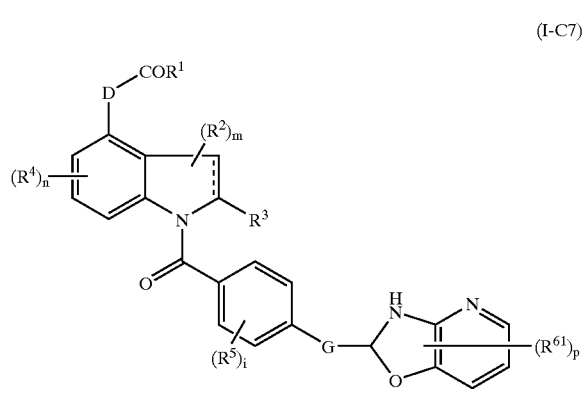

(I-C7)

(wherein all symbols have the same meanings as described above), formula

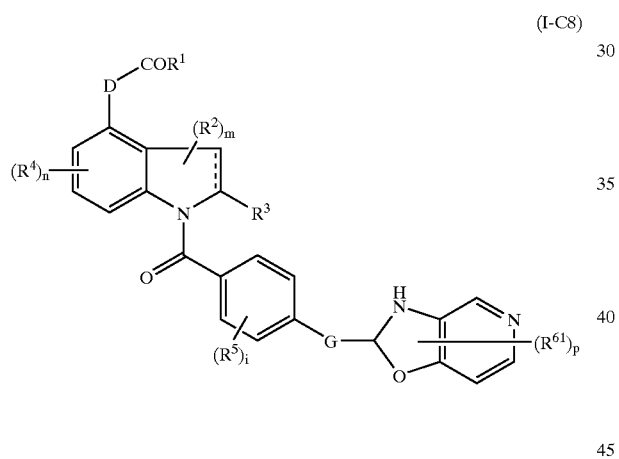

(I-C8)

(wherein all symbols have the same meanings as described above), formula (I-C9):

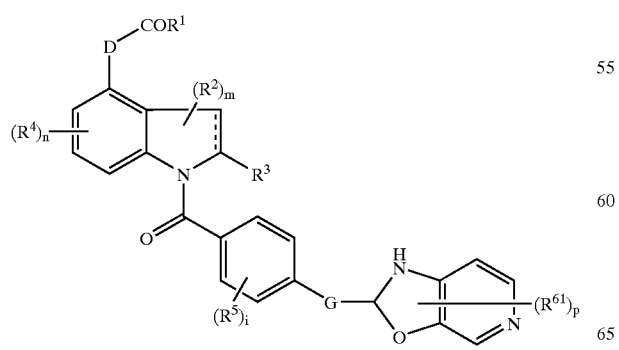

(I-C9)

(wherein all symbols have the same meanings as described above), formula (I-C10):

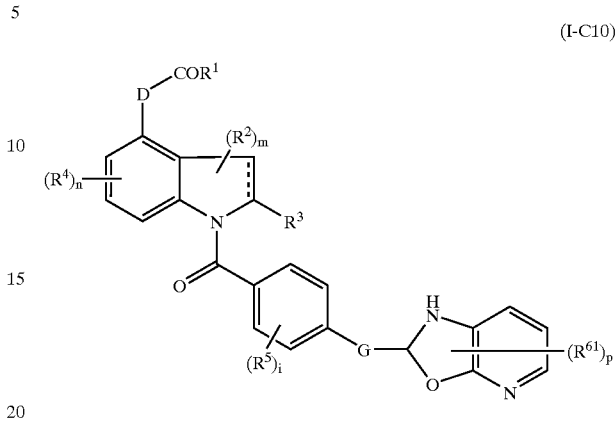

(I-C10)

(wherein all symbols have the same meanings as described above), formula (I-C11):

(I-C11)

(wherein all symbols have the same meanings as described above), formula (I-C12)

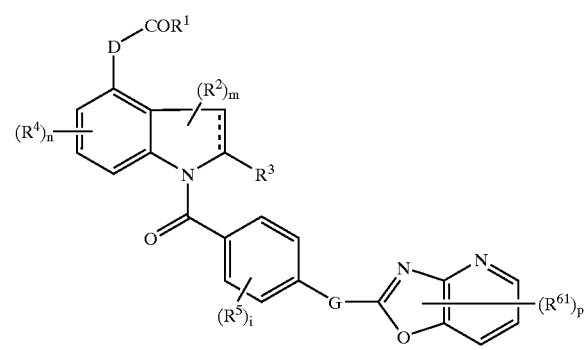

(I-C12)

(wherein all symbols have the same meanings as described above), formula (I-C13)

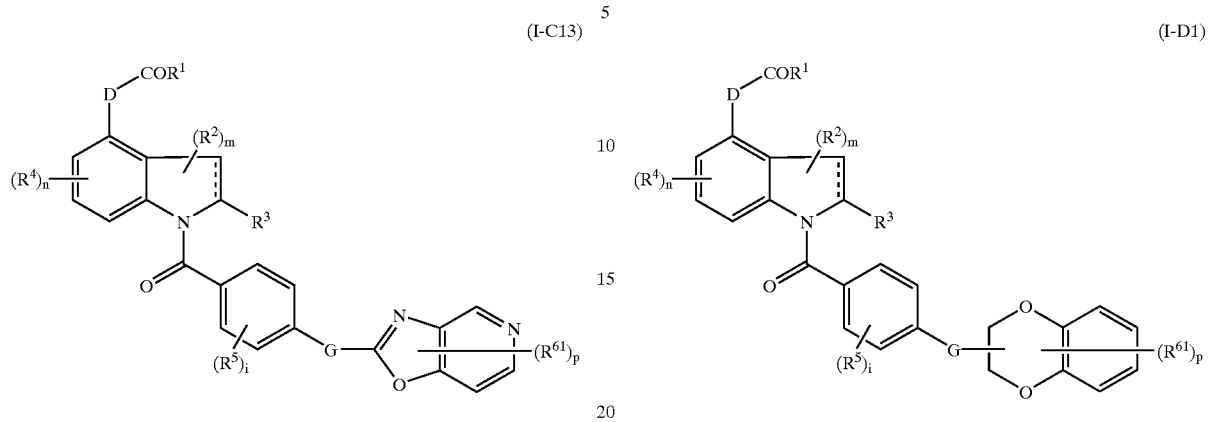

(wherein all symbols have the same meanings as described above), formula (I-C14)

(wherein all symbols have the same meanings as described above), formula (I-C15):

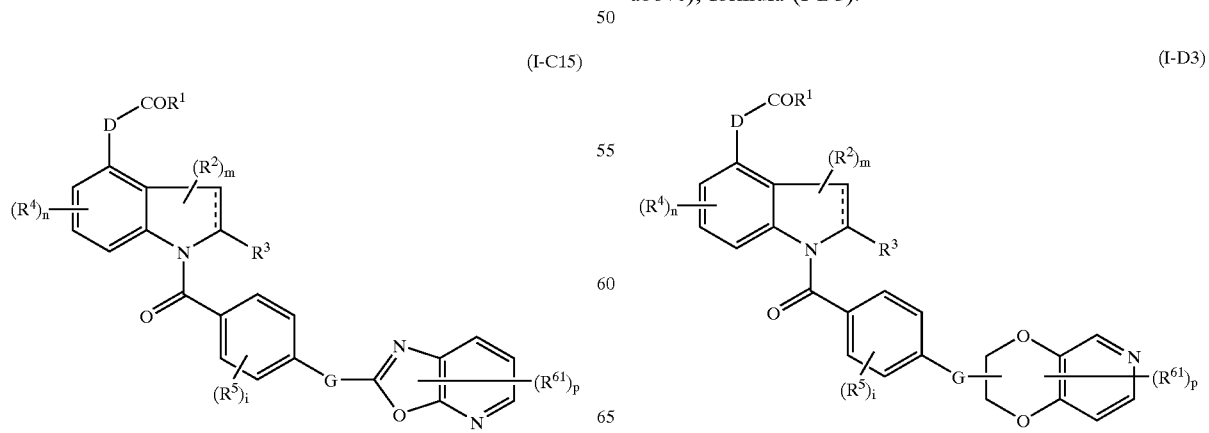

(wherein all symbols have the same meanings as described above), formula (I-D1):

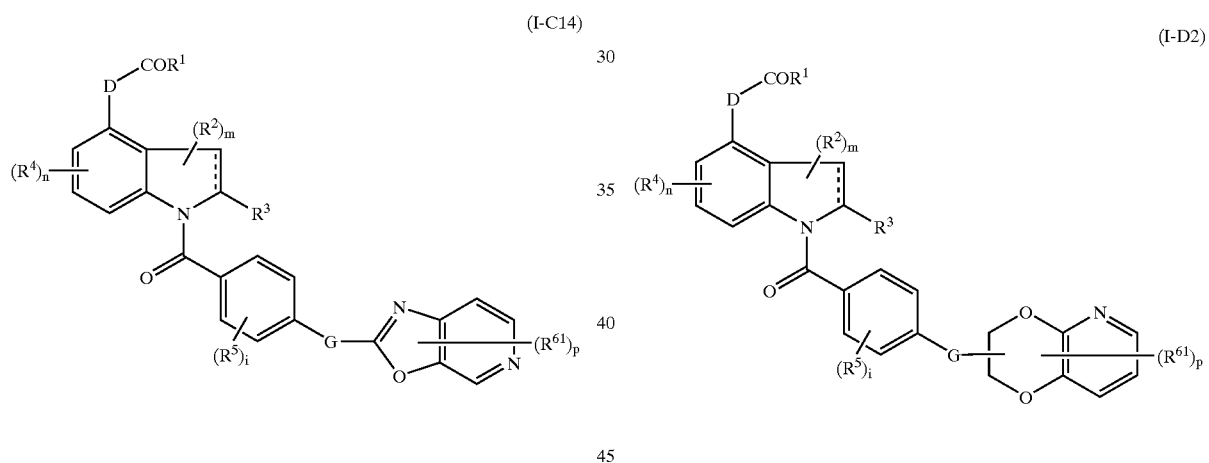

(wherein all symbols have the same meanings as described above), formula (I-D2):

(wherein all symbols have the same meanings as described above), formula (I-D3):

(wherein all symbols have the same meanings as described above), formula (I-D4):

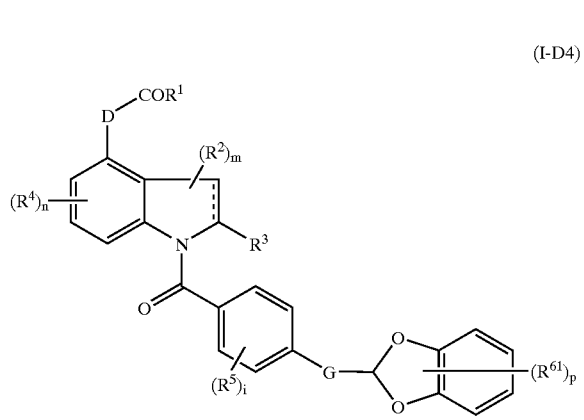

(I-D4)

(wherein all symbols have the same meanings as described above), formula (I-D5):

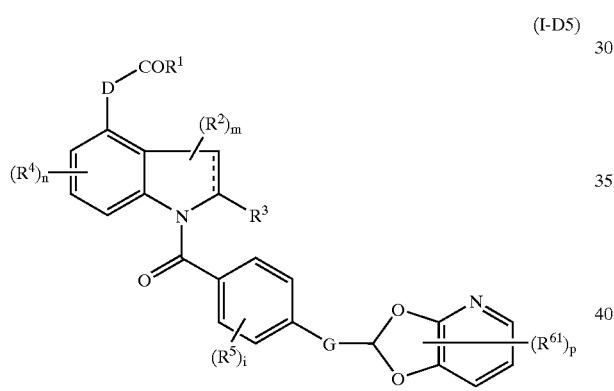

(I-D5)

(wherein all symbols have the same meanings as described above), formula (I-D6):

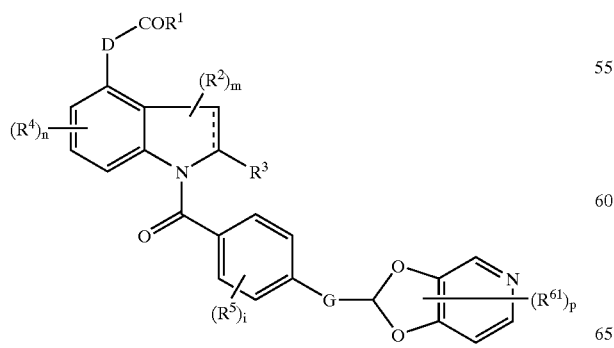

(I-D6)

(wherein all symbols have the same meanings as described above), formula (I-D7):

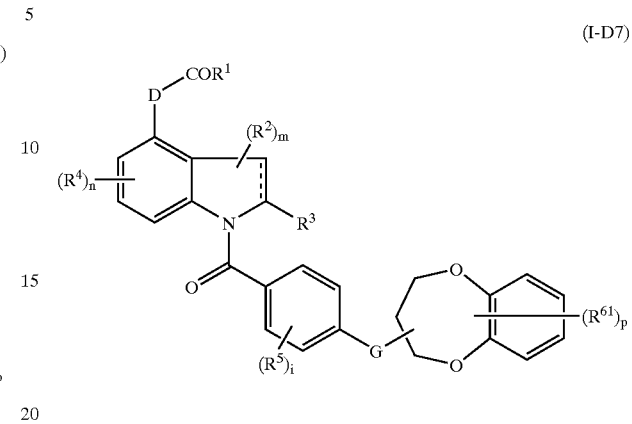

(I-D7)

(wherein all symbols have the same meanings as described above), formula (I-D8):

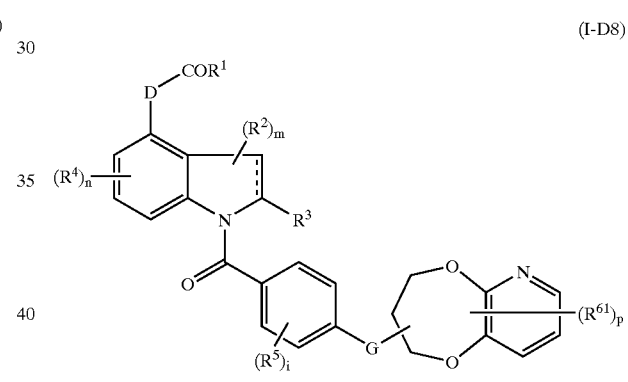

(I-D8)

(wherein all symbols have the same meanings as described above), formula (I-D9):

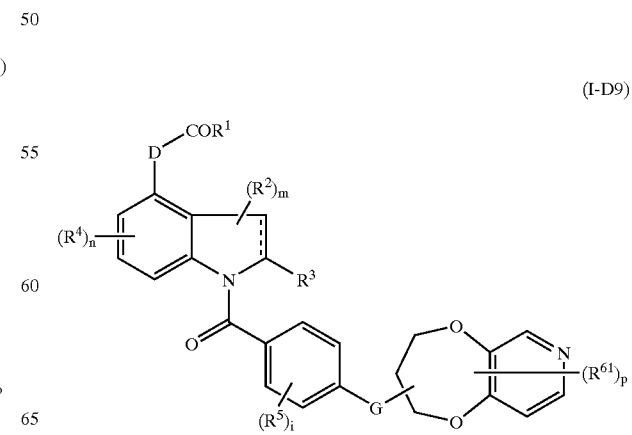

(I-D9)

(wherein all symbols have the same meanings as described above), formula (I-E1):

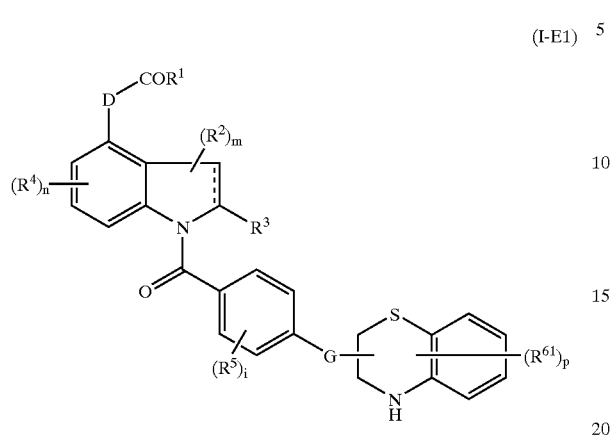

(I-E1)

(wherein all symbols have the same meanings as described above), formula (I-E2):

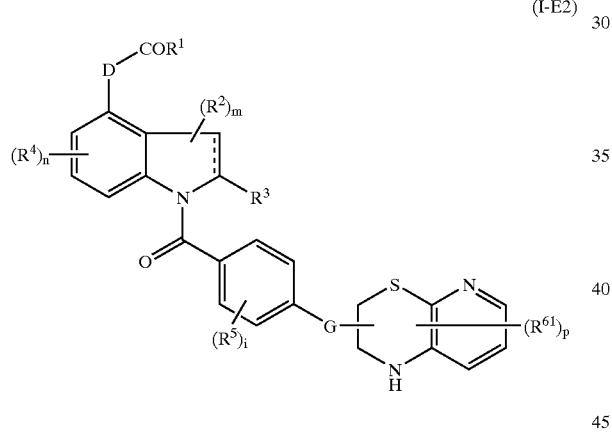

(I-E2)

(wherein all symbols have the same meanings as described above), formula (I-E3):

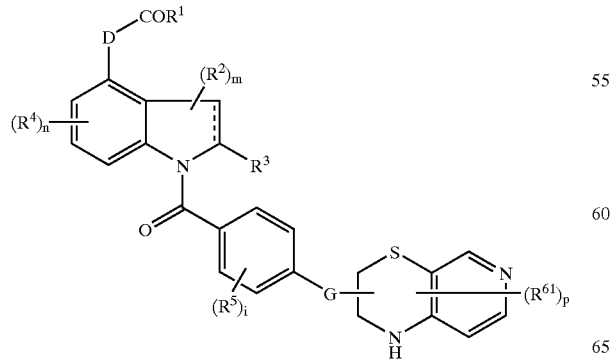

(I-E3)

(wherein all symbols have the same meanings as described above), formula (I-E4):

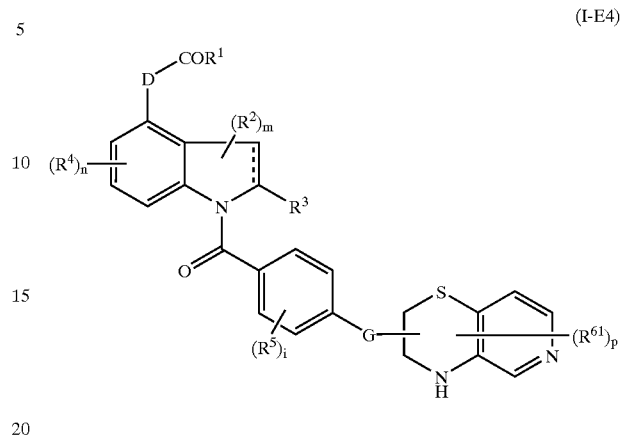

(I-E4)

(wherein all symbols have the same meanings as described above), formula (I-E5):

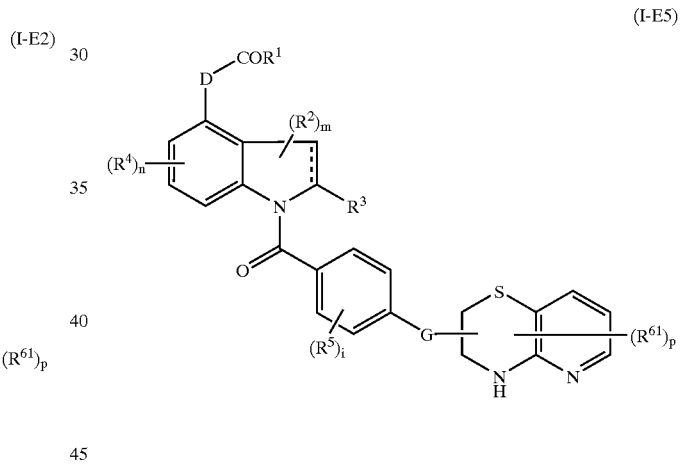

(I-E5)

(wherein all symbols have the same meanings as described above), formula (I-E6):

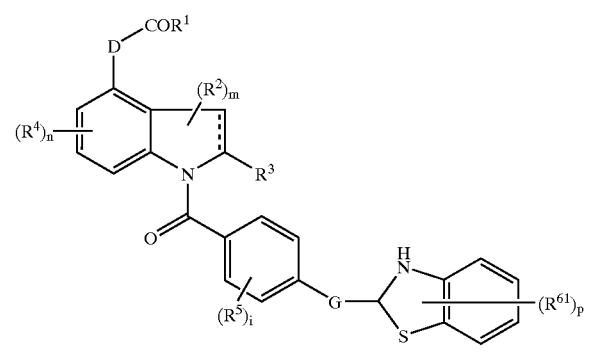

(I-E6)

(wherein all symbols have the same meanings as described above), formula (I-E7):

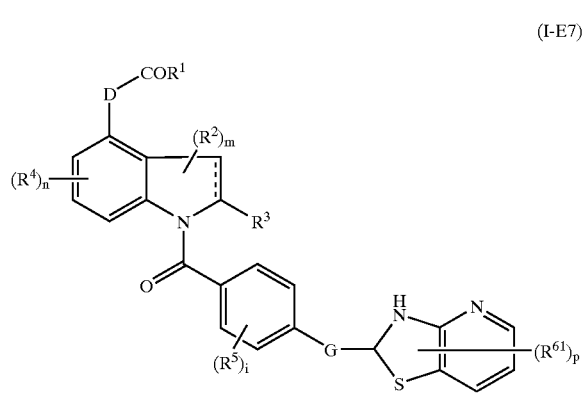

(I-E7)

(wherein all symbols have the same meanings as described above), formula (I-E8):

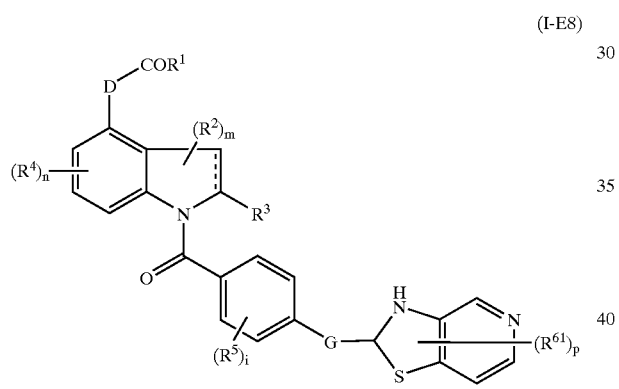

(I-E8)

(wherein all symbols have the same meanings as described above), formula (I-E9):

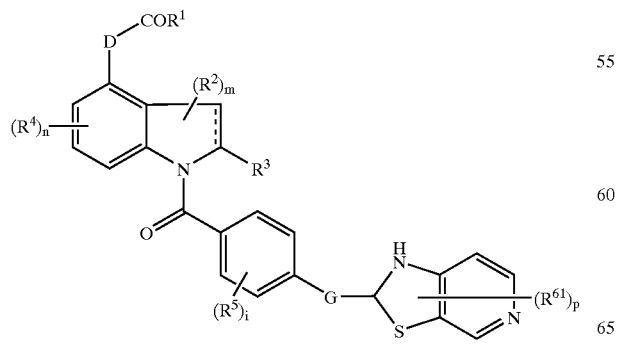

(I-E9)

(wherein all symbols have the same meanings as described above), formula (I-E10):

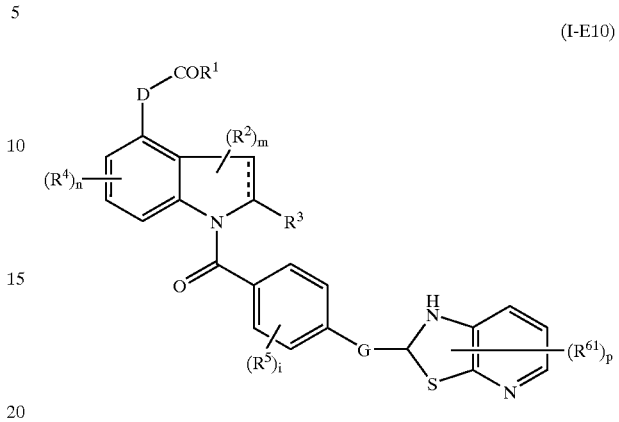

(I-E10)

(wherein all symbols have the same meanings as described above), formula (I-E12):

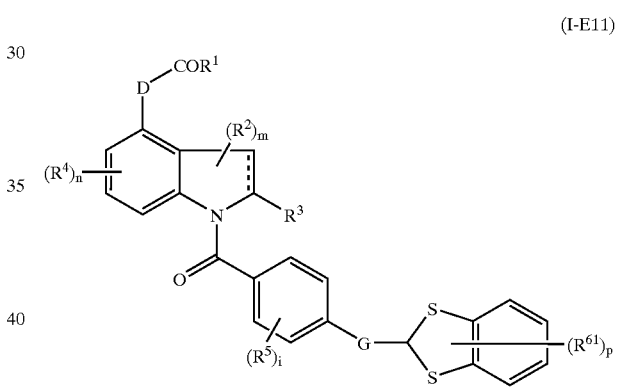

(I-E11)

(wherein all symbols have the same meanings as described above), formula (I-E12):

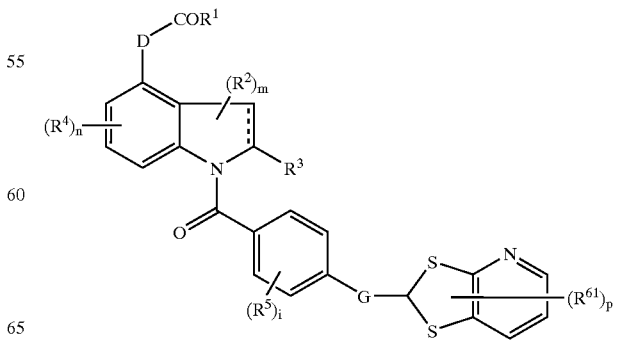

(I-E12)

(wherein all symbols have the same meanings as described above), formula (I-E13):

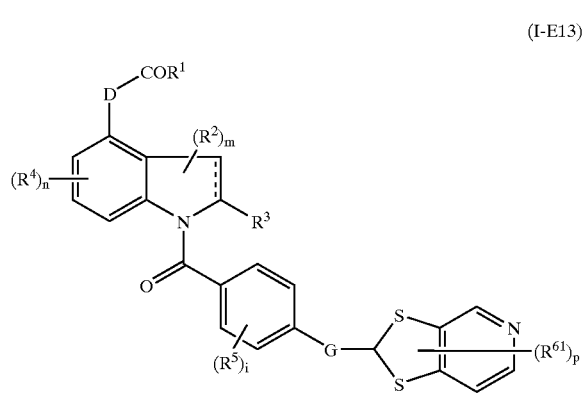

(I-E13)

(wherein all symbols have the same meanings as described above), formula (I-E14):

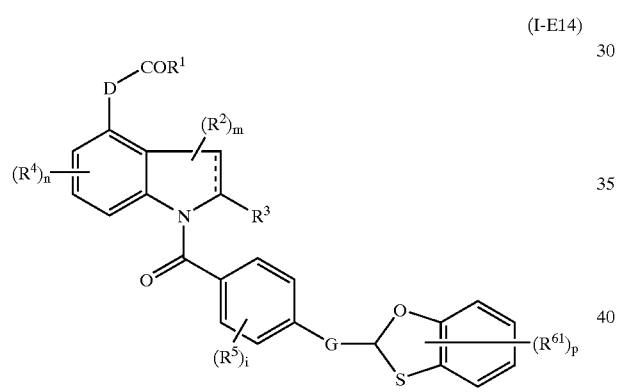

(I-E14)

(wherein all symbols have the same meanings as described above), formula (I-E15):

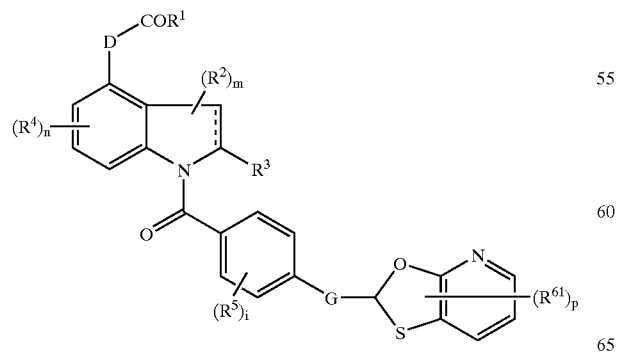

(I-E15)

(wherein all symbols have the same meanings as described above), formula (I-E16):

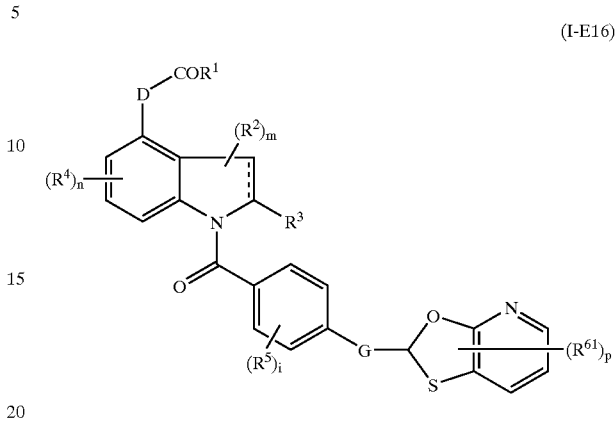

(I-E16)

(wherein all symbols have the same meanings as described above), formula (I-E17):

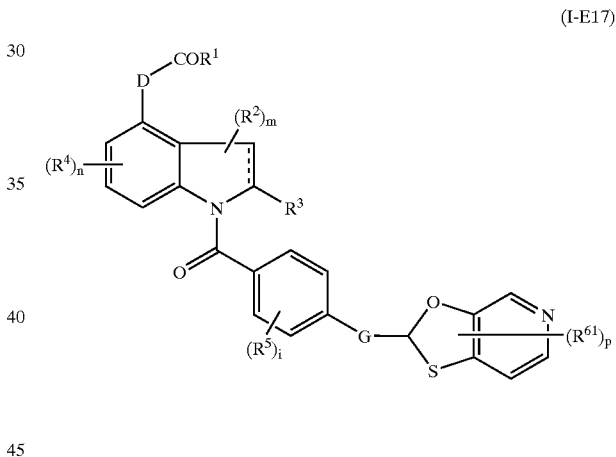

(I-E17)

(wherein all symbols have the same meanings as described above), formula (I-E18):

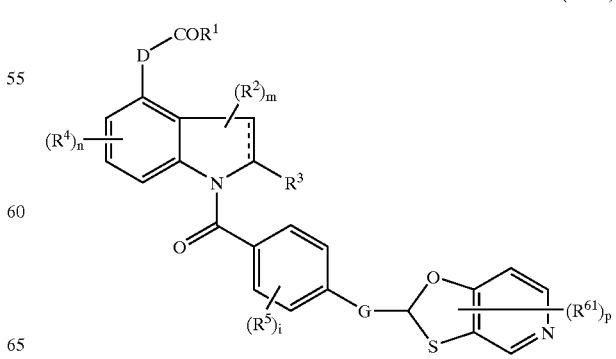

(I-E18)

(wherein all symbols have the same meanings as described above), formula (I-E19):

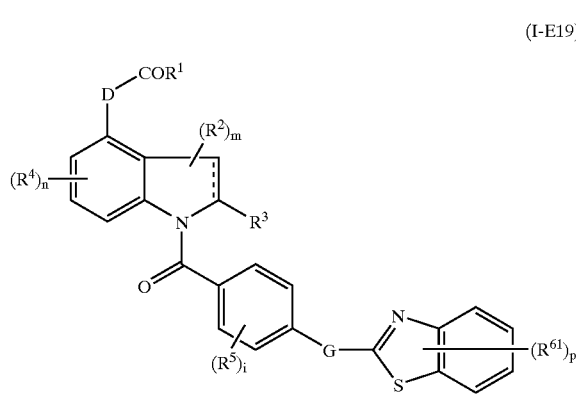

(wherein all symbols have the same meanings as described above), formula (I-E20):

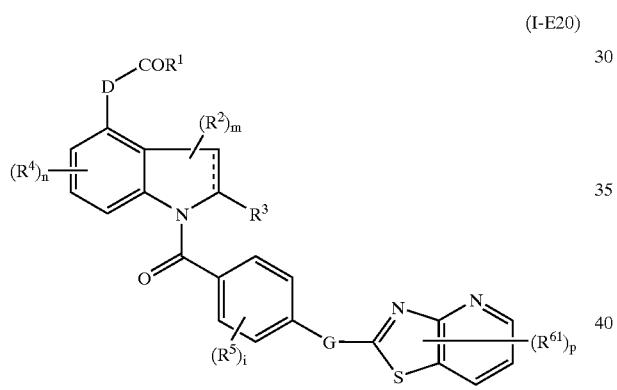

(wherein all symbols have the same meanings as described above), formula (I-E21)

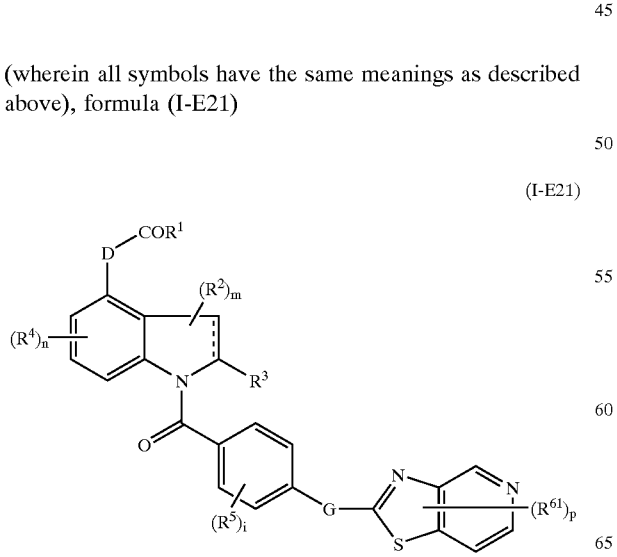

(wherein all symbols have the same meanings as described above), formula (I-E22)

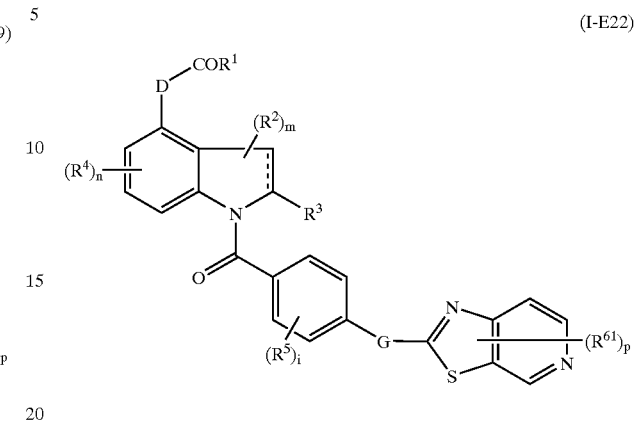

(wherein all symbols have the same meanings as described above), formula (I-E23):

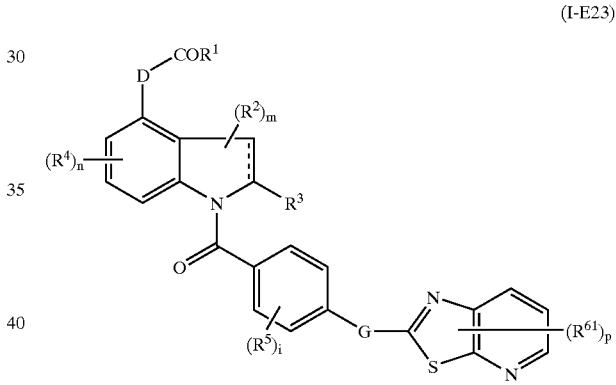

(wherein all symbols have the same meanings as described above), formula (I-F1):

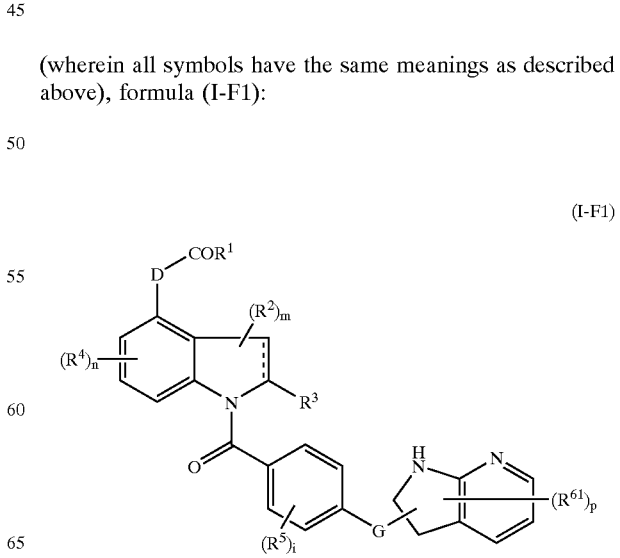

(wherein all symbols have the same meanings as described above), formula (I-F2):

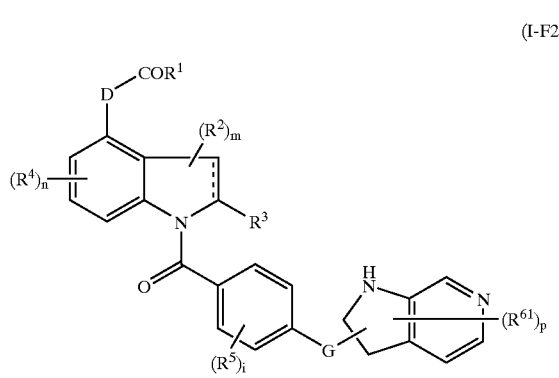
(I-F2)

(wherein all symbols have the same meanings as described above), formula (I-F3):

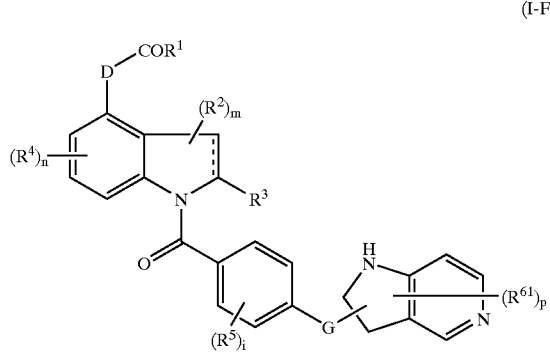
(I-F3)

(wherein all symbols have the same meanings as described above), formula (I-F4):

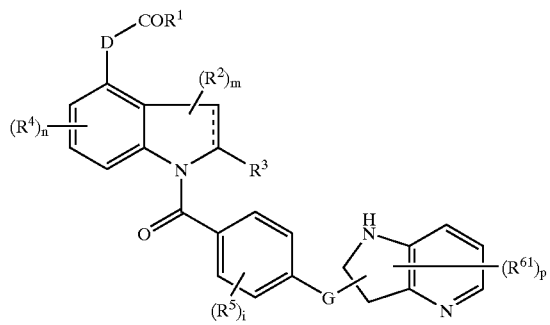
(I-F4)

(wherein all symbols have the same meanings as described above), formula (I-F5):

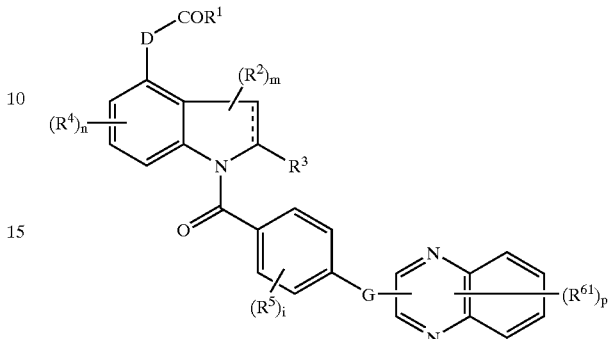
(I-F5)

(wherein all symbols have the same meanings as described above), formula (I-F6):

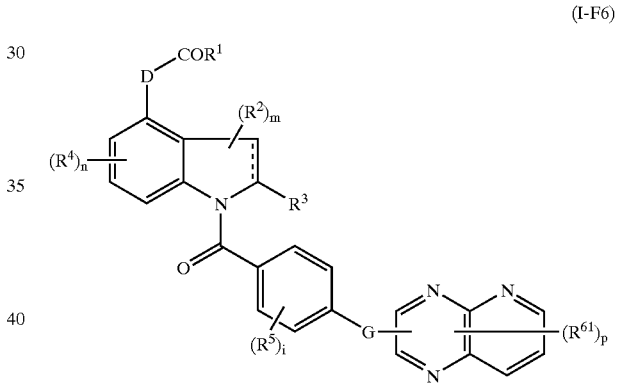
(I-F6)

(wherein all symbols have the same meanings as described above), formula (I-F7):

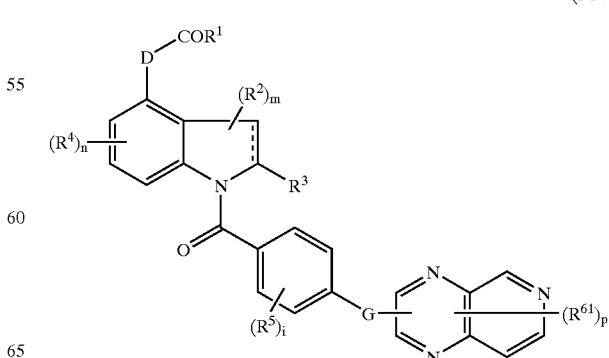
(I-F7)

(wherein all symbols have the same meanings as described above), formula (I-F8):

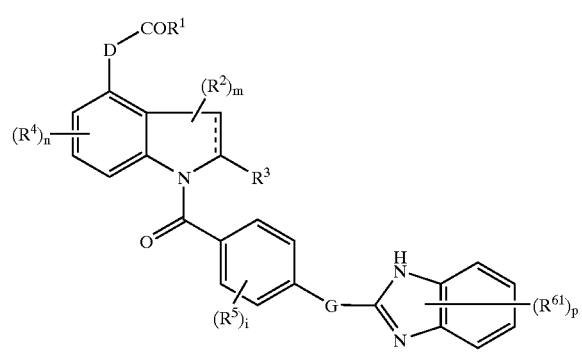

(I-F8)

(wherein all symbols have the same meanings as described above), formula (I-F9):

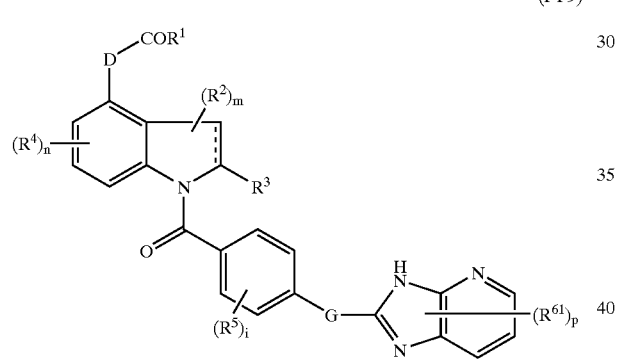

(I-F9)

(wherein all symbols have the same meanings as described above), formula (I-F10):

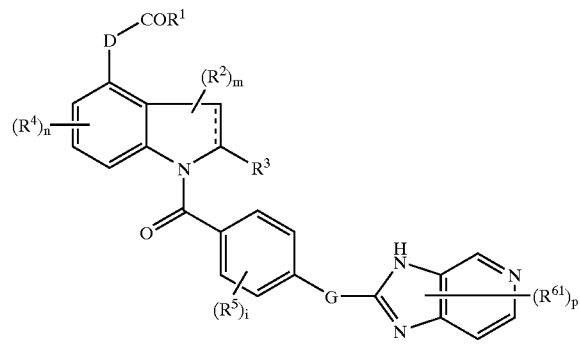

(I-F10)

(wherein all symbols have the same meanings as described above), formula (I-F11):

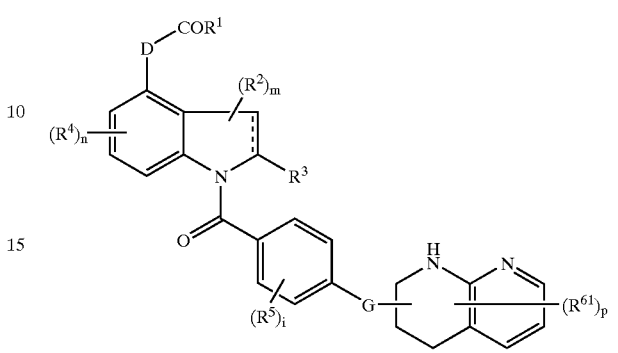

(I-F11)

(wherein all symbols have the same meanings as described above), formula (I-F12):

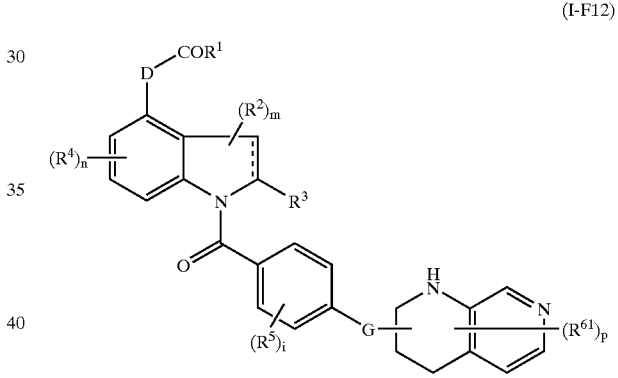

(I-F12)

(wherein all symbols have the same meanings as described above), formula (I-F13):

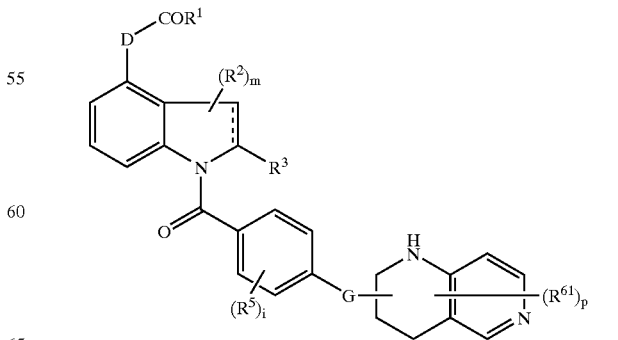

(I-F13)

(wherein all symbols have the same meanings as described above), formula (I-F14):
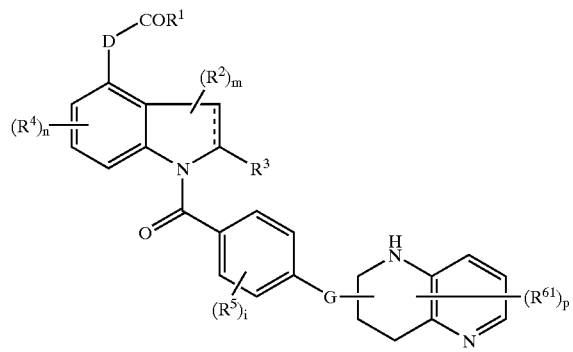
(I-F14)
(wherein all symbols have the same meanings as described above), compounds shown in Tables 1 to 5, and non-toxic salts of the compounds.
TABLE 1
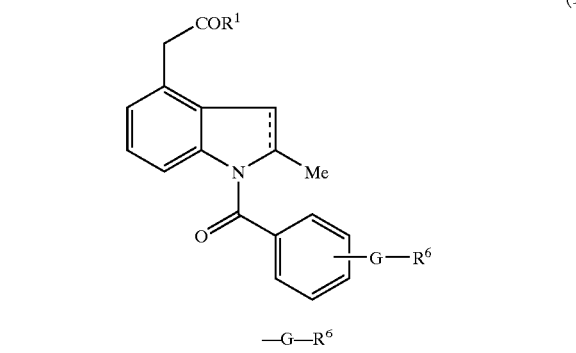
(1)
—G—R$^6$
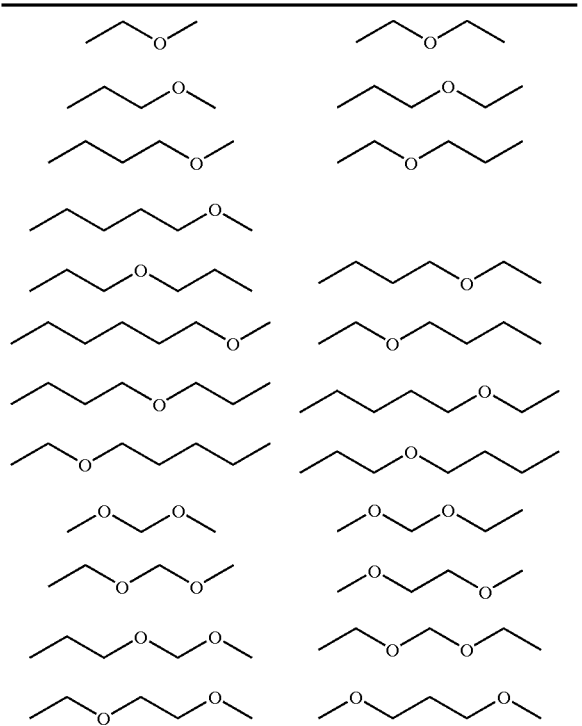
TABLE 1-continued
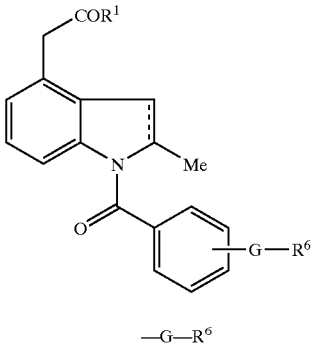
(1)
—G—R$^6$
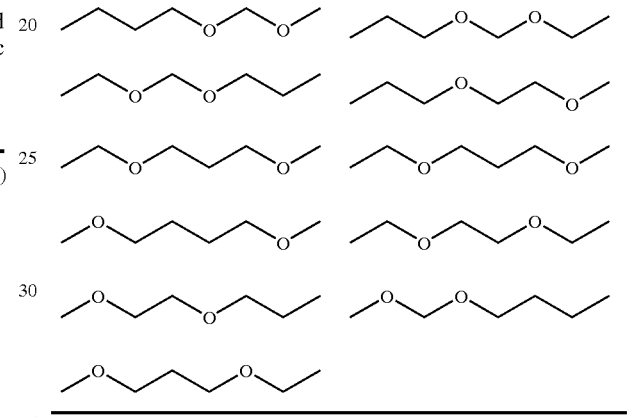
TABLE 2
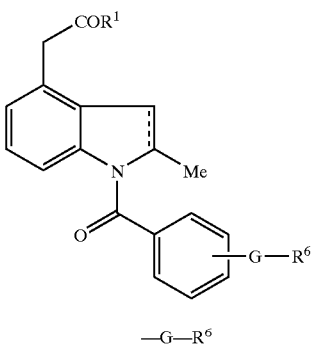
(2)
—G—R$^6$
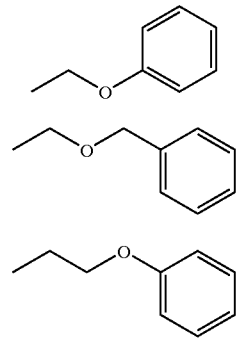

TABLE 2-continued
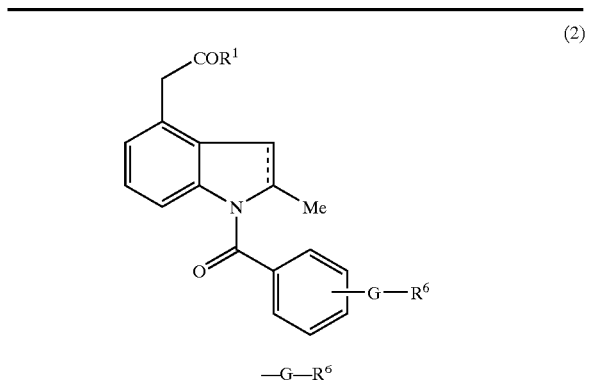
(2)
| —G—R⁶ |
|---|
| 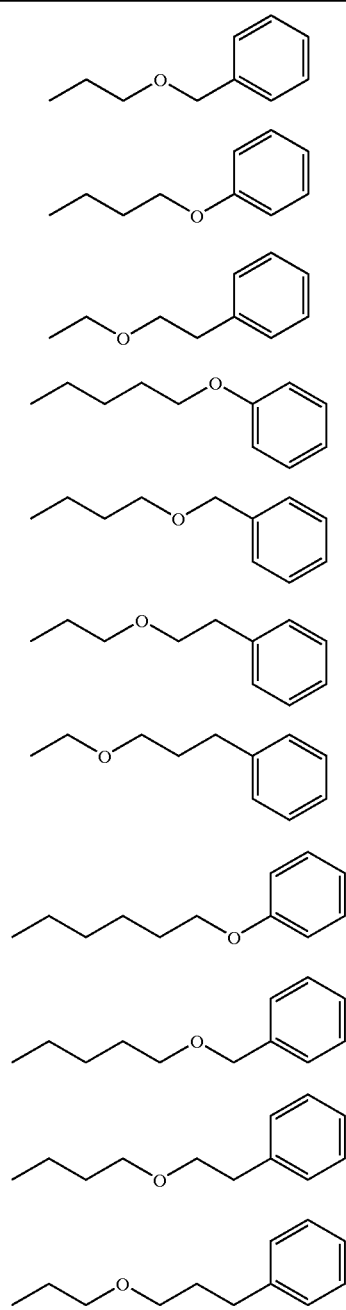 |
TABLE 2-continued
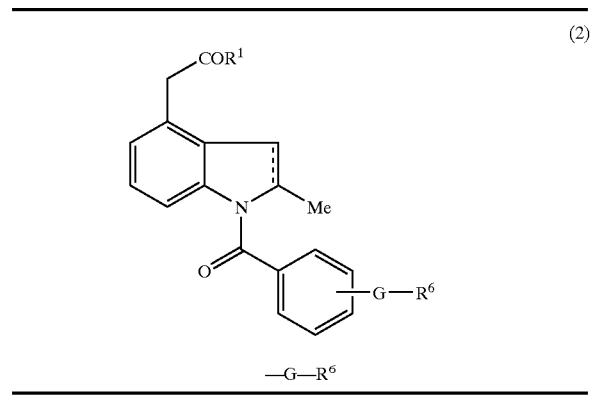
(2)
| —G—R⁶ |
|---|
| 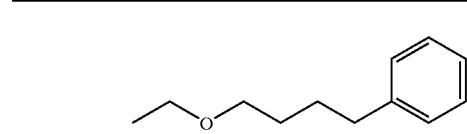 |
TABLE 3
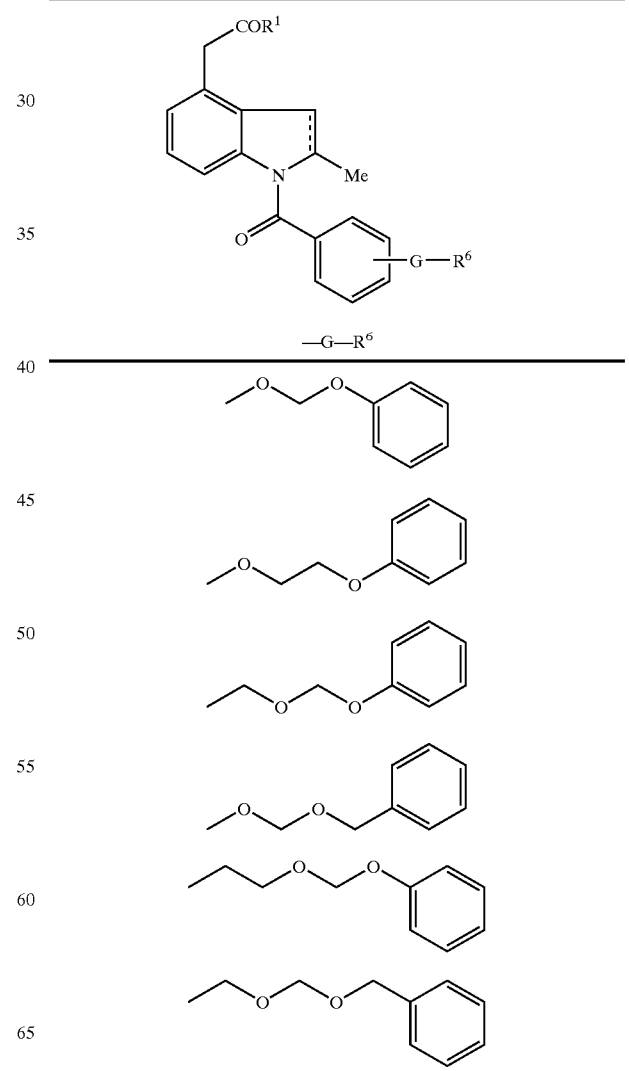

TABLE 3-continued
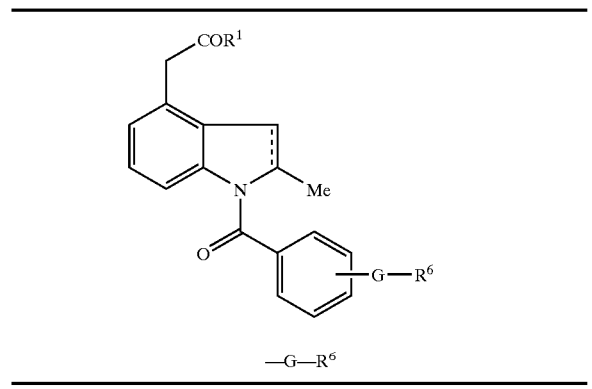
—G—R⁶
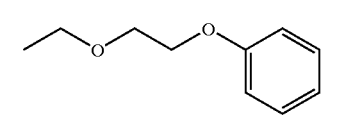
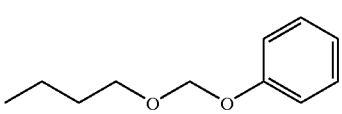
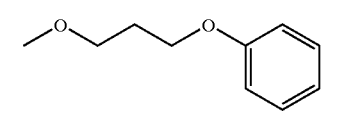
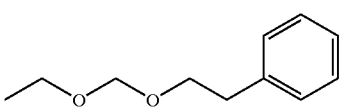
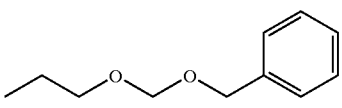
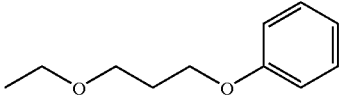
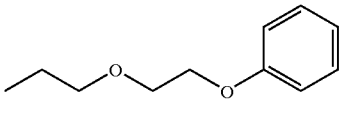
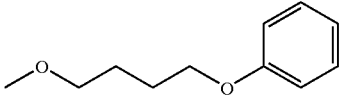
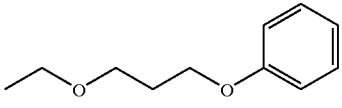
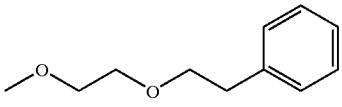
TABLE 3-continued
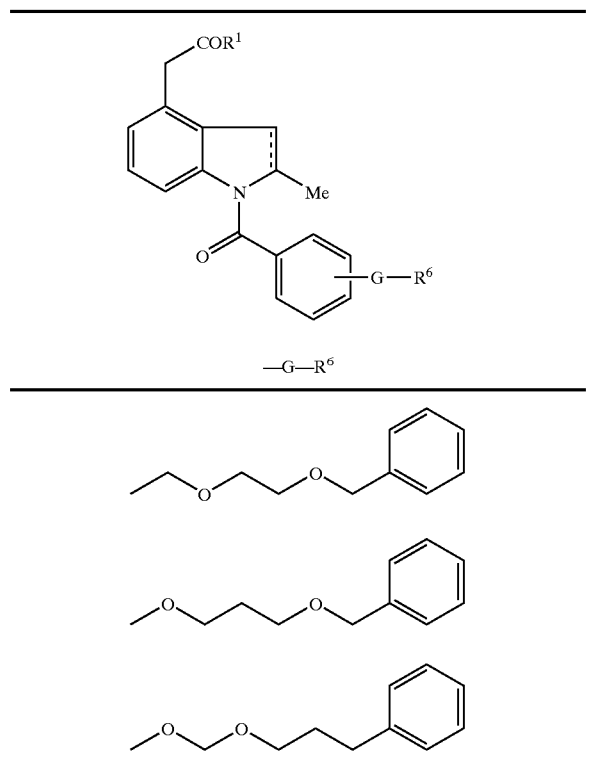
—G—R⁶
TABLE 4
(4)
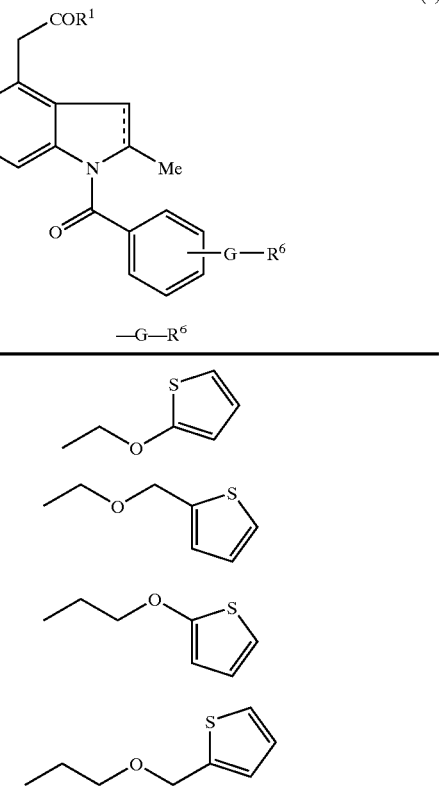
—G—R⁶

TABLE 4-continued
(4)
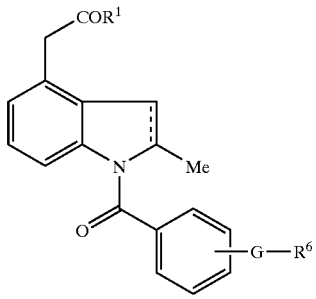
—G—R⁶
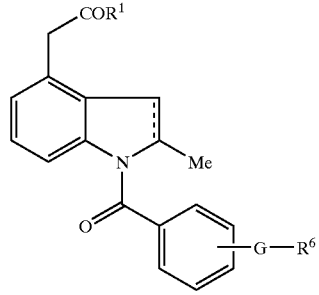
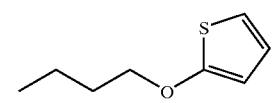
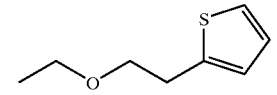
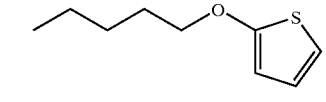
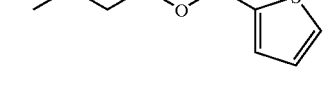
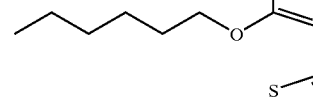
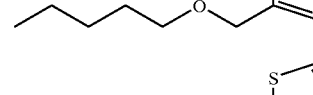
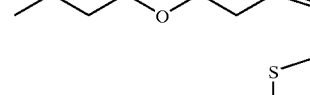
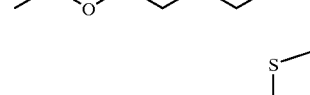
TABLE 5
(5)
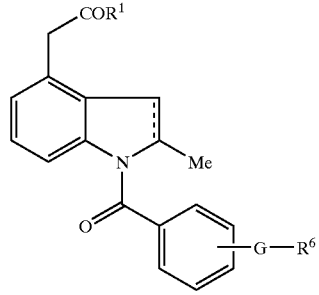
—G—R⁶
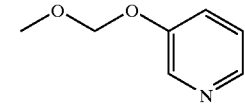
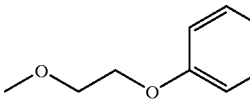
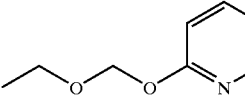
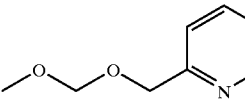
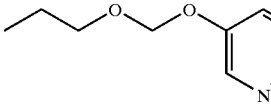
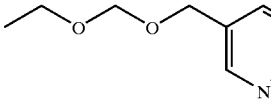
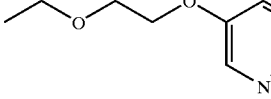
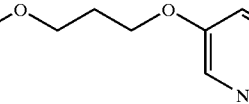
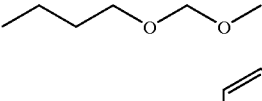
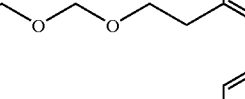

TABLE 5-continued

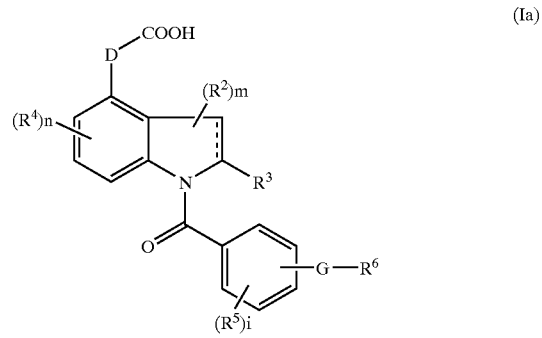

| —G—R⁶ |
|---|
| 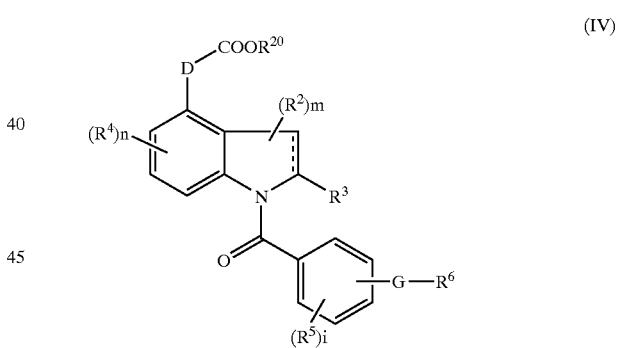 |

Salt:

The compound of the present invention represented by formula (I) can be converted into a corresponding salt by known methods. The salt is preferably a non-toxic and water-soluble salt. Appropriate salts include salts of alkali metals (potassium, sodium, etc.), salts of alkaline earth metals, ammonium salts (tetramethylammonium, tetrabutylammonium salts, etc.), and pharmaceutically acceptable organic amines (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.).

The compound of the present invention represented by formula (I) and a salt thereof can also be converted into a hydrate by known methods.

Processes for the Preparation of the Compound of the Present Invention:

The compound of the present invention represented by formula (I) can be prepared by the following processes and the processes shown in Examples.

(a) Among the compounds represented by formula (I), a compound wherein $R^1$ is hydroxy, i.e., a compound represented by formula (Ia):

(Ia)

(wherein all symbols have the same meanings as described above) can be prepared by subjecting to a deprotection reaction a compound represented by formula (IV):

(IV)

(wherein $R^{20}$ is an allyl or benzyl group; and other symbols have the same meanings as described above).

The deprotection reaction of ally ester or benzyl ester is known, for example, it is carried out in an organic solvent (e.g., methanol, ethanol, tetrahydrofuran, dioxane, ethyl acetate, etc.) at −10 to 90° C. by 1) using tetrakis(triphenylphosphine)palladium and morpholine, or
2) using palladium carbon, palladium, platinum, sponge nickel (trade name: Raney Nickel), etc. under hydrogen atmosphere.

(b) Among the compounds represented by formula (I), a compound wherein $R^1$ is C1–6 alkoxy (wherein all symbols have the same meanings as described above), i.e., a compound represented by formula (Ib):

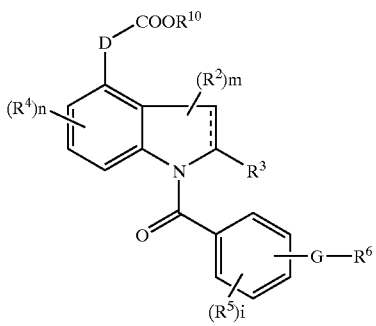

(wherein $R^{10}$ represents C1–6 alkyl; and other all symbols have the same meanings as described above) can be prepared by subjecting to an esterification reaction a compound represented by formula (Ia) with a compound represented by formula:

$$R^{10}—OH \tag{III}$$

(wherein all symbols have the same meanings as described above), followed by optionally a deprotection reaction.

The esterification reaction is known, for example, it is carried out in an inert organic solvent (tetrahydrofuran, methylene chloride, benzene, acetone, acetonitrile, a mixture thereof, etc.) in the presence or absence of a tertiary amine (dimethylaminopyridine, pyridine, triethylamine, etc.) using a condensing agent (1,3-dicyclohexylcarbodiimide (DCC), 1-ethyl-3-[3-(dimethylamino)propyl]carbodiimide (EDC), etc.) or acid halide (oxalyl chloride, thionyl chloride, phosphorus oxychloride, etc.) at 0 to 50° C.

(c) Among the compounds represented by formula (I), a compound wherein $R^1$ is —$NR^8R^9$ (wherein all symbols have the same meanings as described above), i.e., a compound represented by formula (Ic):

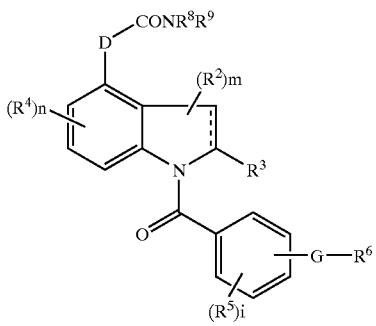

(wherein all symbols have the same meanings as described above) can be prepared by subjecting to an amidation reaction a compound represented by formula (Ia) with a compound represented by formula:

$$HNR^{10}R^{11} \tag{II}$$

(wherein all symbols have the same meanings as described above), followed by optionally a deprotection reaction.

The amidation reaction is known, for example, it is carried out in an inert organic solvent (tetrahydrofuran, methylene chloride, benzene, acetone, acetonitrile, a mixture thereof, etc.) in the presence or absence of a tertiary amine (dimethylaminopyridine, pyridine, triethylamine, etc.) using a condensing agent (1,3-dicyclohexylcarbodiimide (DCC), 1-ethyl-3-[3-(dimethylamino)propyl]carbodiimide (EDC), etc.) or acid halide (oxalyl chloride, thionyl chloride, phosphorus oxychloride, etc.) at of 0 to 50° C.

The compound represented by formula (IV) can prepared by subjecting to a compound represented by formula (V):

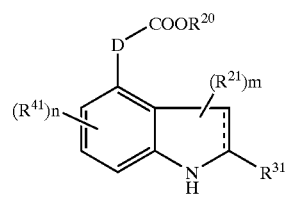

(wherein $R^{21}$, $R^{31}$ and $R^{41}$ have the same meanings as $R^2$, $R^3$ and $R^4$, respectively, and when they represent an amino group or a hydroxy group, they are protected with a protecting group; and other symbols have the same meanings as described above) with a compound represented by formula (VI):

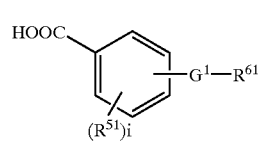

(wherein $R^{51}$ has the same meaning as $R^5$, and when it represents an amino group or a hydroxy group, it is protected with a protecting group; and $G^1$ and $R^{61}$ have the same meanings as G and $R^6$, respectively, and when they contains an amino group or a hydroxy group, it is protected with a protecting group), followed by optionally a deprotection reaction. The amidation reaction can be carried out by the above method.

The compounds represented by formula (II), (III), (V) and (VI) are known per se or can be prepared by known methods.

Among the compounds represented by formula (Ia), a compound wherein D is alkylene can be prepared by reducing a compound represented by formula (Ia), or can be prepared by increasing the carbon of the alkylene part.

In each reaction in the present specification, reaction products can be purified by conventional purification techniques, e.g., by distillation under atmospheric or reduced pressure, high performance liquid chromatography, thin layer chromatography or column chromatography using silica gel or magnesium silicate, washing, recrystallization or the like. Purification can be carried out after each reaction or after some reactions.

Pharmacological Activities:

The compound of the present invention represented by formula (I) potently binds to a DP receptor and show an antagonistic activity. For example, in a laboratory test, such effects were confirmed by the following receptor binding test using prostanoid receptor-expressing cells.

(i) Receptor Binding Test Using Prostanoid DP Receptor-Expressing Cells

CHO cells expressing a mouse DP receptor was prepared according to the method of Hirata et al. (*Proc. Natl. Acad. Sci.*, 91, 11192–11196 (1994)) and used as a membrane standard.

A reaction solution (200 μL) containing the prepared membrane standard (30–166 μg) and $^3H$-PGD$_2$ was incubated at room temperature for 20 minutes. The reaction was stopped with an ice-cold buffer (1 mL) and the binding $^3$H-PGD$_2$ was trapped in on a glass filter by immediate aspiration-filtration under a reduced pressure, and its binding radioactivity was measured using a liquid scintillation counter.

A Kd value and a Bmax value were obtained from Scatchard plots (*Ann. N.Y. Acad. Sci.*, 51, 660 (1949)). Non-specific binding was obtained as the binding radioactivity in the presence of unlabeled PGD$_2$ at an excess amount (10 μmol/L). $^3$H-PGD$_2$ binding inhibition by the compound of the present invention was measured by adding $^3$H-PGD$_2$ (2.5 mmol/L) and the compound of the present invention as various concentrations. Also, the following buffers were used for the reactions.

Incubation buffer:
  HEPES-NaOH (25 mmol/L, pH 7.4)
  EDTA (1 mmol/L)
  MgCl$_2$ (5 mmol/L)
  MnCl$_2$ (10 mmol/L)
Buffer for washing:
  Tris-HCl (10 mmol/L, pH 7.5)
  NaCl (0.1 mol/L)
  Bovine serum albumin (0.01%)

The dissociation constant (Ki) (μmol/L) of each compound was obtained by the following equation.
  Ki=IC$_{50}$/(1+([L]*/Kd))
  [L*]: Concentration of radioligand
The results are shown in Table 6.

TABLE 6

| Example No. | DP Ki (μM) |
| --- | --- |
| 1(3) | 0.0018 |
| 1(4) | 0.0043 |

As shown in the above results, it is apparent that the compound of the present invention potently binds to a DP receptor.

(ii) DP Antagonistic Activity Assay Using Prostanoid DP Receptor-Expressing Cells CHO cells expressing a mouse DP receptor were prepared according to the method of Nishigaki et al. (*FEBS lett.*, 364, 339–341 (1995)), inoculated onto a 24-well microplate at 10$^5$ cells/well, followed by culturing for 2 days, and used for the assay. Each well was washed with 500 μL of MEM (minimum essential medium), and 450 μL of assay medium (MEM containing 1 mmol/L IBMX and 0.1 or 1% BSA), followed by incubation at 37° C. for 10 minutes. Then, an assay medium (50 μL) containing PGD$_2$ alone or PGD$_2$ with a test compound was added thereto to start the reaction, and after the reaction at 37° C. for 10 minutes, 500 μL of ice-cold trichloroacetatic acid (TCA) (10% w/v) was added thereto to stop the reaction. The reaction solution was frozen once (−80° C.) and thawed, and cells were peeled using a scraper, followed by centrifugation at 13,000 rpm for 3 minutes. The cAMP concentration was measured with a cAMP assay kit using the resulting supernatant. That is, [$^{125}$I]-cAMP assay kit buffer was added to 125 μL of the supernatant to give a total amount of 500 μL, and the resulting mixture was mixed with 1 mL of a chloroform solution of 0.5 mol/L tri-n-octylamine. Trichloro acetic acid (TCA) was extracted to the chloroform layer and removed, the cAMP amount in a sample was determined using the aqueous layer as the sample according to the method described in the [$^{125}$I]cAMP assay kit.

Also, with regard to the antagonistic activity (IC$_{50}$) of the test compound, the IC$_{50}$ value was calculated as an inhibition rate based on the reaction at 100 nM which was a concentration showing submaximal cAMP production by PGD$_2$ alone.

TABLE 7

| Example No. | DP antagonistic activity IC$_{50}$ (μM) |
| --- | --- |
| 1(3) | 0.12 |

As shown in the above results, it is apparent that the compound of the present invention has an antagonistic activity against a DP receptor.

Toxicity:

The toxicity of the compound represented by formula (I) of the present invention is very low so that it is confirmed that the compound is sufficiently safe for using as a pharmaceutical.

INDUSTRIAL APPLICABILITY

Application to Pharmaceuticals:

Since the compound of the present invention represented by formula (I) bind to and is antagonistic to a DP receptor, it is considered that the compound is useful for the prevention and/or treatment of diseases, for example, allergic diseases such as allergic rhinitis, allergic conjunctivitis, atopic dermatitis, bronchial asthma, food allergy, etc.; systemic mastocytosis; disorders due to systemic mastocyte activation; anaphylactic shock; bronchoconstriction; urticaria; eczema; allergic bronchopulmonary aspergillosis; inflammatory paranasal sinus; nasal polyp; hypersensitive angitis; eosinophilia; contact dermatitis; diseases accompanied with itching, such as atopic dermatitis, urticaria, allergic conjunctivitis, allergic rhinitis, contact dermatitis, etc.; secondary diseases caused by behaviors (scratching behaviors, beating, etc.), such as cataract, retinal detachment, inflammation, infection, sleep disorder, etc.; inflammation; chronic obstructive pulmonary disease; ischemic reperfusion disorder; cerebrovascular disorder; pleuritis complicated by rheumatoid arthritis; ulcerative colitis; and the like. Moreover, the compound is considered to relate to sleeping and platelet aggregation and to be useful for these diseases.

Among the compounds of the present invention represented by formula (I), one having a weak binding activity to a compound other than a DP receptor would be used as a pharmaceutical having less side effects because it does not show other activity.

When the compound represented by formula (I) of the present invention, a non-toxic salt or a cyclodextrin inclusion compound thereof is normally administered systemically or topically and orally or parenterally.

The dosages are determined depending on age, body weight, symptom, therapeutic effect, administration route, duration of the treatment and the like. Generally, 1 μg to 100 mg per adult is orally administered once to several times per day, or 0.1 μg to 10 mg per adult is parenterally administered (preferably by intravenous administration) once to several times per day, or continuously administered from vein for 1 to 24 hours per day.

Since the dose changes depending on various conditions as described above, there are cases in which doses lower than or greater than the above ranges may be used.

The compounds of the present invention may be administered in the form of solid compositions, liquid compositions or other compositions for oral administration, and injections, liniments, suppositories and the like for parenteral administration.

Solid compositions for oral administration include compressed tablets, pills, capsules, dispersible powders, granules and the like.

Capsules include hard capsules and soft capsules.

In such solid compositions, one or more active compound (s) is/are mixed with at least one inert diluent such as lactose, mannitol, glucose, hydroxypropyl cellulose, microcrystalline cellulose, starch, polyvinyl pyrrolidone or magnesium metasilicate aluminate.

The compositions may also contain additional substances other than inert diluents, e.g., lubricating agents such as magnesium stearate, disintegrating agents such as cellulose calcium glycolate, and assisting agents for dissolving such as glutamic acid, asparatic acid according to usual methods. The tablets or pills may, if desired, be coated with film of gastric- or enteric-coating agents such as sugar, gelatin, hydroxypropyl cellulose or hydroxypropyl cellulose phthalate, or be coated with two or more films. Furthermore, capsules of absorbable materials such as gelatin are included Liquid compositions for oral administration include pharmaceutically acceptable emulsions, solutions, syrups and elixirs. In such compositions, one or more active compound (s) is/are dissolved, suspended or emulsified in an inert diluent commonly used (e.g., purified water, ethanol). Furthermore, such liquid compositions may also contain wetting agents or suspending agents, emulsifying agents, sweetening agents, flavoring agents, perfuming agents, and preserving agents.

Other compositions for oral administration include sprays containing one or more active compound(s) which are prepared by known methods. Spray compositions may contain stabilizing agents such as sodium hydrogen sulfate, stabilizing agents to give isotonicity, isotonic solutions such as sodium chloride, sodium citrate or citric acid, other than inert diluents. The process for preparing the sprays are described in U.S. Pat. Nos. 2,868,691 and 3,095,355.

Injections for parenteral administration include sterile aqueous or non-aqueous solutions, suspensions and emulsions. Aqueous solutions or suspensions include, for example, distilled water for injection and a physiological salt solution. Non-aqueous solutions or suspensions include propylene glycol, polyethylene glycol, plant oil such as olive oil, alcohol such as ethanol, POLYSORBATE80 (registered trade mark), and the like.

Such compositions may contain additional diluents such as preserving agents, wetting agents, emulsifying agents, dispersing agents, stabilizing agents, assisting agents such as assistant agents for dissolving (e.g., glutamic acid, aspartic acid). They may be sterilized by filtration through a bacteria-retaining filter, or incorporation or irradiation of a sterilizing agent. They may also be manufactured in the form of sterile solid compositions which can be dissolved in sterile water or other sterile diluent for injection immediately before use.

Other compositions for parenteral administration include liquids for external use, endemic liniments, ointments, suppositories for intrarectal administration and pessaries for intravaginal administration containing one or more active compound(s) which can be prepared by known methods.

BEST MODE FOR CARRYING OUT THE INVENTION

The following Reference Examples and examples illustrate the present invention, but do not limit the present invention.

In the following chemical formula, Tf represents a trifluoromethanesulfoxy group, Boc represents a t-butoxycarbonyl group, TMS represents a trimethylsilyl group, and Bn represents a benzyl group.

The solvents in the parentheses show the developing or eluting solvents and the ratios of the solvents used are by volume in chromatographic separations or TLC.

The solvents in the parentheses in NMR show the solvents for measurement.

REFERENCE EXAMPLE 1

2-Methyl-4-trifluoromethanesulfoxyindole

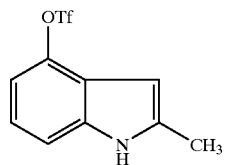

A solution of 2-methyl-4-hydroxyindole (10 g) in methylene chloride (100 ml) was stirred at 0° C. To the solution was added lutidine (10.28 ml) and trifluoromethanesulfonic anhydride (13.72 ml), and the solution was maintained at the same temperature for 1 hours. To the mixture was added water and then extracted with ethyl acetate. The aqueous layer was extracted with ethyl acetate. The combined organic layer was washed with water and a saturated aqueous solution of sodium chloride, successively, dried over anhydrous magnesium sulfate, and concentrated under reduced pressure to give the title compound having the following physical data. The compound was used to next reaction without further purification.

TLC: Rf 0.57 (hexane:ethyl acetate=7:3).

REFERENCE EXAMPLE 2

1-t-Butoxycarbonyl-2-methyl-4-trifluoromethanesulfoxyindole

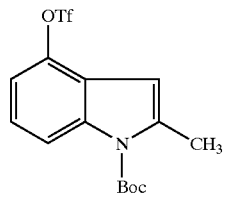

To a solution of 2-methyl-4-trifluoromethanesulfoxyindole (1 g; prepared in Reference Example 1) and di-t-butyl dicarbonate (1 ml) in acetonitrile (12 ml) was added dimethylaminopyridine (catalytic amounts), and the mixture was stirred at room temperature overnight. To the reaction solution was added water and ethyl acetate, and then the mixture was separated. The organic layer was washed with water and a saturated aqueous solution of sodium chloride, successively, dried over anhydrous magnesium sulfate, and concentrated under reduced pressure to give the title compound (1.38 g) having the following physical data.

TLC: Rf 0.50 (hexane:ethyl acetate=1:1).

REFERENCE EXAMPLE 3

1-t-Butoxycarbonyl-2-methyl-4-(2-trimethylsilylethynyl) indole

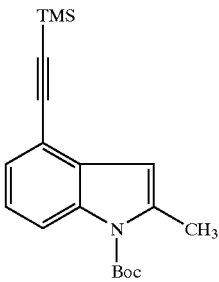

To a solution of 1-t-butoxycarbonyl-2-methyl-4-trifluoromethanesulfoxyindole (17.9 g; prepared in Reference Example 2), dichlorobis(triphenylphosphine)palladium (1.6 g), copper iodide (0.88 g) and tetrabutylammonium iodide (3.4 g) in N,N-dimethylformamide (180 ml) was added trimethylsilylacetylene (11 ml), and the mixture was stirred at 65° C. for 2 hours. To the mixture was added 0.5N hydrochloric acid—ethyl acetate, and then insoluble material was removed by filtration through Celite (trademark). The organic layer was washed with water (twice) and a saturated aqueous solution of sodium chloride, successively, dried and concentrated under reduced pressure. The residue was purified by column chromatography on silica gel (hexane:ethyl acetate=10:1) to give the title compound (15.0 g) having the following physical data.

NMR (CDCl$_3$): δ 8.09–8.05 (d, J=8.5 Hz, 1H), 7.32–7.29 (m, 1H), 7.17–7.08 (m, 1H), 6.49 (s, 1H), 2.61 (s, 3H), 0.29 (s, 9H).

REFERENCE EXAMPLE 4

1-t-Butoxycarbonyl-2-methylindole-4-acetic Acid

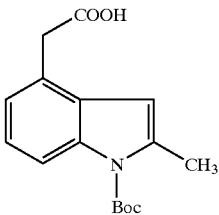

A solution of cyclohexane (16.1 ml) in tetrahydrofuran (160 ml) was cooled at −10° C., and then to the mixture was added dropwise borane-tetrahydrofuran complex (1M, 80 ml), and the mixture was stirred at 0° C. for 1 hour. To the solution was added dropwise a solution of 1-t-butoxycarbonyl-2-methyl-4-(2-trimethylsilylethynyl)indole (13.1 g; prepared in Reference Example 3) in tetrahydrofuran (60 ml), the mixture was stirred for 1 hour at room temperature. To a reaction solution was added dropwise 3N aqueous solution of sodium hydroxide (40 ml) and 30% hydrogen peroxide (in water, 45 ml), successively, and the mixture was stirred for 12 hours. The reaction mixture was extracted with water—diethyl ether. The aqueous layer was adjusted to acidic condition with hydrochloric acid and then extracted with ethyl acetate. The extraction was washed with water and a saturated aqueous solution of sodium chloride, successively, dried and concentrated under reduced pressure to give the title compound (10.4 g; crude).

REFERENCE EXAMPLE 5

2-Methylindole-4-acetic Acid

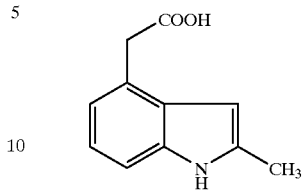

To a mixture of 1-t-butoxycarbonyl-2-methylindole-4-acetic acid (96.3 g) in methanol (200 ml)—water (100 ml) was added dropwise 5N aqueous solution of sodium hydroxide (200 ml) at room temperature, and the mixture was stirred at 50° C. for 3 hours and then stirred at room temperature for 12 hours. The reaction mixture was extracted with hexane—ether. The aqueous layer was adjusted to acidic condition with hydrochloric acid and then extracted with ethyl acetate. The extraction was washed with water and a saturated aqueous solution of sodium chloride, successively, dried and concentrated under reduced pressure to give the title compound (53.9 g; crude).

In addition, this intermediate compound is novel compound that does not have a publication in literature.

REFERENCE EXAMPLE 6

2-Methylindole-4-acetic Acid Allyl Ester

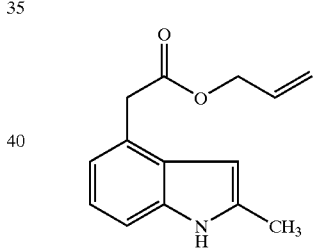

To a solution of 2-methylindole-4-acetic acid (53 g) in N,N-dimethylformamide (500 ml) was added dropwise allyl bromide (31 ml), and added anhydrous potassium carbonate (59 g). The mixture was stirred at 50° C. for 1 hour. After cooling to room temperature, the reaction mixture was poured into a mixture of 2N hydrochloric acid—ethyl acetate and then extracted with ethyl acetate. The extraction was washed with water and a saturated aqueous solution of sodium chloride, successively, dried and concentrated under reduced pressure. The residue was purified by column chromatography on silica gel (hexane—ethyl acetate) to give the title compound (43.5 g) having the following physical data.

TLC: Rf 0.50 (hexane:ethyl acetate=1:2);

NMR (CDCl$_3$): δ 7.92 (brs, 1H), 7.19 (d, J=7.0 Hz, 1H), 7.06 (t, J=1H), 6.96 (dd, J=7.0, 1.2 Hz, 1H), 6.27 (m, 1H), 5.90 (ddt, J=17.2, 10.4, 5.4 Hz, 1H), 5.25 (d, J=17.2 Hz, 1H), 5.18 (d, J=10.4 Hz, 1H), 4.59 (m, 2H), 3.88 (s, 2H), 2.43 (s, 3H).

REFERENCE EXAMPLE 7

4-(2-Propyloxyethoxy)benzoic Acid

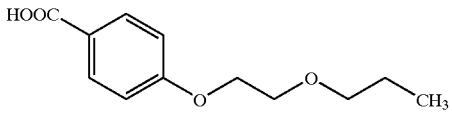

To a solution of 4-hydroxybenzoic acid (3.04 g) and anhydrous potassium carbonate (5.52 g) in N,N-dimethylformamide (20 ml) was added 2-propyloxyethyl chloride (2.94 g), and the mixture was stirred at room temperature overnight, and then stirred at 80° C. for 8 hours. To a reaction solution was added water, and then the mixture was extracted with ethyl acetate. The organic layer was washed with water and a saturated aqueous solution of sodium chloride, successively, dried and concentrated under reduced pressure to give the title compound (5.21 g; crude).

TLC: Rf 0.47 (hexane:ethyl acetate=2:1).

REFERENCE EXAMPLE 8

1-(4-(2-Propyloxyethoxy)benzoyl)-2-methylindole-4-acetic Acid Allyl Ester

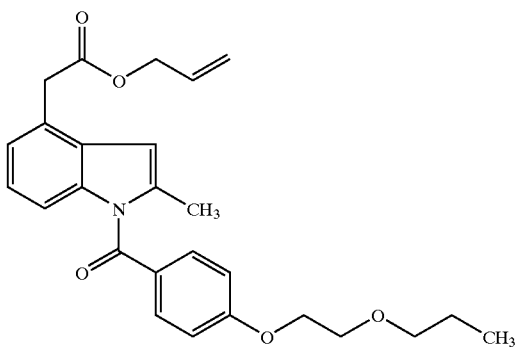

To a solution of 4-(2-propyloxyethoxy)benzoic acid (448 mg; prepared in Reference Example 7) in toluene (5 ml) was added N,N-dimethylformamide (catalytic amounts) and oxalyl chloride (350 µl), and the mixture was stirred for 30 minutes at room temperature, then concentrated. A solution of the residue in methylene chloride (2 ml) was added to a solution of 2-methylindole-4-acetic acid allyl ester (230 mg; prepared in Reference Example 6), sodium hydroxide (200 mg) and tetrabutylammonium chloride (15 mg) in methylene chloride (8 ml), and the mixture was stirred for 30 minutes at room temperature. To a reaction solution was added 1N hydrochloric acid—ethyl acetate. The organic layer was washed with water and a saturated aqueous solution of sodium chloride, successively, dried and concentrated under reduced pressure. The residue was purified by column chromatography on silica gel (n-hexane—ethyl acetate) to give the title compound (276 mg) having the following physical data.

TLC: Rf 0.39 (hexane:ethyl acetate=2:1).

EXAMPLE 1

1-(4-(2-Propyloxyethoxy)benzoyl)-2-methylindole-4-acetic Acid

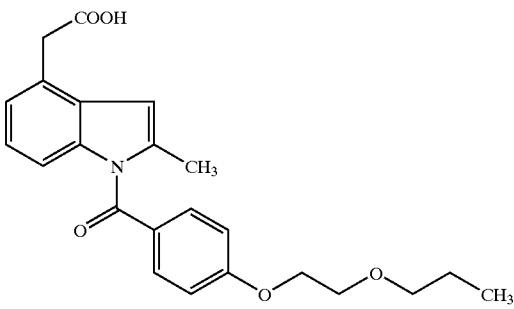

To a solution of 1-(4-(2-propyloxyethoxy)benzoyl)-2-methylindole-4-acetic acid allyl ester (276 mg; prepared in Reference Example 8) and morpholine (275 µl) in tetrahydrofuran (3 ml) was added tetrakis(triphenylphosphine) palladium (35 mg) and the mixture was stirred for 2 hours at room temperature. To the reaction solution was added 1 N hydrochloric acid—ethyl acetate. The organic layer was washed with water and a saturated aqueous solution of sodium chloride, successively, dried and concentrated under reduced pressure. The residue was dissolved in hexane—ethyl acetate (½) and then the insoluble material was filtered off. To the filtrate was added cyclohexylamine (70 mg) and the mixture was stirred for 30 minutes at room temperature. The reaction solution was filtered. To the obtained crystal was added 1N hydrochloric acid—ethyl acetate. The organic layer was washed with water and a saturated aqueous solution of sodium chloride, successively, dried and concentrated to give the compound of the present invention (204 mg) having the following physical data.

TLC: Rf 0.20 (ethyl acetate);

NMR (CDCl$_3$): δ 7.71–7.69 (m, 2H), 7.04–6.92 (m, 5H), 6.48 (s, 1H), 4.23–4.19 (m, 2H), 3.86 (s, 2H), 3.86–3.81 (m, 2H), 3.51 (t, J=7.0 Hz, 2H), 2.44 (s, 3H), 1.65 (tq, J=7.0, 7.5 Hz, 2H), 0.94 (t, J=7.5 Hz, 3H).

EXAMPLES 1 (1) TO 1 (75)

Each compound having the following physical data was obtained by the same procedures as a series of reactions of Reference Examples 1, 2, 3, 4, 5, 6, 7, 8 and Example 1. In Example 1(8), 1(51), 1(67), 1(68) and 1(69), hydroxy or amino group was protected by protective group, and the protective group was removed before the reaction corresponding Example 1.

EXAMPLE 1(1)

1-(4-Butoxybenzoyl)-2-methylindole-4-acetic Acid

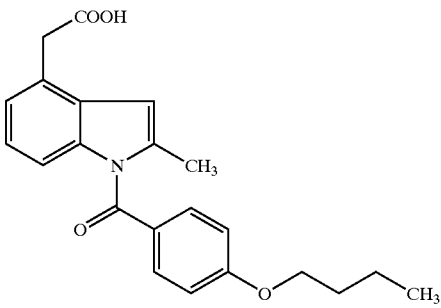

TLC: Rf 0.46 (chloroform:methanol=9:1);

NMR (CDCl$_3$): δ 7.70 (d, J=9.0 Hz, 2H), 7.08–6.90 (m, 5H), 6.49 (s, 1H), 4.05 (t, J=6.6 Hz, 2H), 3.87 (s, 2H), 2.45

(s, 3H), 1.88–1.74 (m, 2H), 1.80–1.40 (br, 1H), 1.60–1.45 (m, 2H), 1.00 (t, J=7.5 Hz, 3H).

EXAMPLE 1(2)

1-(4-Propyloxybenzoyl)-2-methylindole-4-acetic Acid

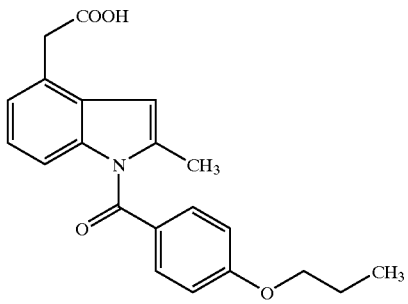

TLC: Rf 0.52 (chloroform:methanol=10:1);

NMR (CDCl$_3$): δ 7.74–7.69 (m, 2H), 7.12–6.90 (m, 5H), 6.49 (s, 1H), 4.01 (t, J=6.6 Hz, 2H), 3.87 (s, 2H), 2.45 (s, 3H), 1.86 (dt, J=7.5, 6.6 Hz, 2H), 1.07 (t, J=7.5 Hz, 3H).

EXAMPLE 1(3)

1-(4-(2-Phenoxy)benzoyl)-2-methylindole-4-acetic Acid

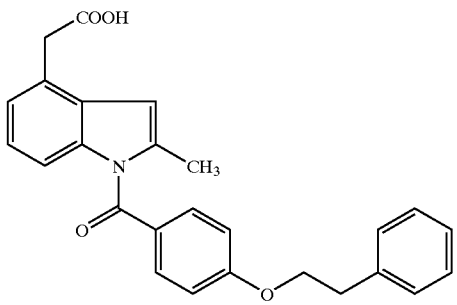

TLC: Rf 0.60 (chloroform:methanol=10:1);

NMR (CDCl$_3$): δ 7.72–7.66 (m, 2H), 7.38–7.23 (m, 5H), 7.07–6.92 (m, 5H), 6.49 (s, 1H), 4.26 (t, J=6.9 Hz, 2H), 3.86 (s, 2H), 3.14 (t, J=6.9 Hz, 2H), 2.44 (s, 3H).

EXAMPLE 1(4)

1-(4-Pentyloxybenzoyl)-2-methylindole-4-acetic Acid

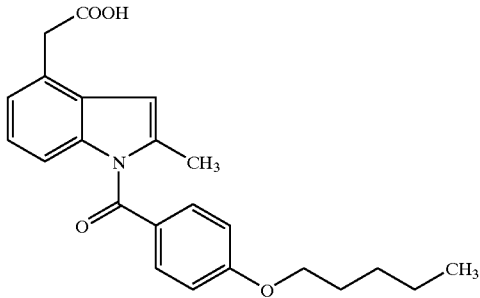

TLC: Rf 0.64 (chloroform:methanol=10:1);

NMR (CDCl$_3$): δ 7.73–7.66 (m, 2H), 7.07–6.92 (m, 5H), 6.49 (s, 1H), 4.04 (t, J=6.6 Hz, 2H), 3.87 (s, 2H), 2.44 (s, 3H), 1.86–1.23 (m, 6H), 0.95 (t, J=6.9 Hz, 3H).

EXAMPLE 1(5)

1-(4-1-Pentyloxybenzoyl)-2-methylindole-4-acetic Acid

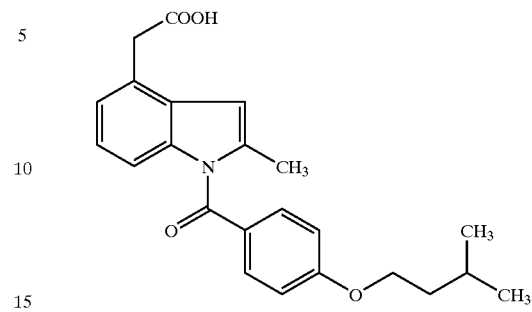

TLC: Rf 0.34 (chloroform:methanol=10:1);

NMR (CDCl$_3$): δ 7.73–7.67 (m, 2H), 7.06–6.91 (m, 5H), 6.48 (s, 1H), 4.07 (t, J=6.6 Hz, 2H), 3.86 (s, 2H), 2.45 (s, 3H), 1.84 (m, 1H), 1.72 (m, 2H), 0.98 (d, J=6.4 Hz, 6H).

EXAMPLE 1(6)

1-(4-(2-Ethoxyethoxy)benzoyl)-2-methylindole-4-acetic Acid

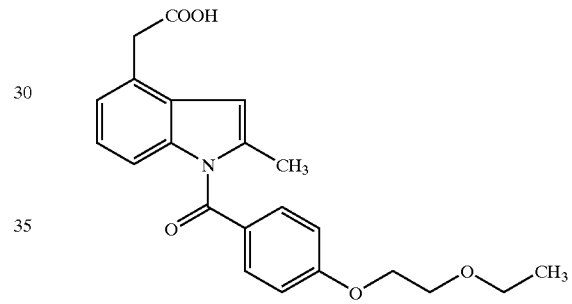

TLC: Rf 0.50 (chloroform:methanol=10:1);

NMR (CDCl$_3$): δ 7.70 (d, J=8.7 Hz, 2H), 7.08–6.92 (m, 5H), 6.49 (s, 1H), 4.21 (t, J=4.8 Hz, 2H), 3.87–3.81 (m, 4H), 3.62 (q, J=7.5 Hz, 2H), 2.45 (s, 3H), 1.26 (t, J=7.5 Hz, 3H).

EXAMPLE 1(7)

1-(4-Benzyloxybenzoyl)-2-methylindole-4-acetic Acid

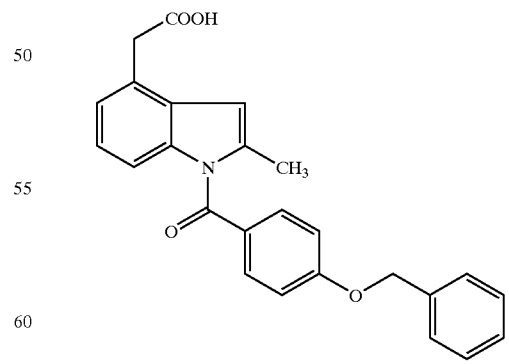

TLC: Rf 0.55 (chloroform:methanol=10:1);

NMR (CDCl$_3$): δ 7.65–7.33 (d, J=8.8 Hz, 2H), 7.45–7.36 (m, 5H), 7.05–6.90 (m, 5H), 6.48 (s, 1H), 5.14 (s, 2H), 3.85 (s, 2H), 2.43 (d, J=1.0 Hz, 3H).

EXAMPLE 1(8)
1-(4-(2-(4-Hydroxyphenyl)ethoxy))benzoyl)-2-methylindole-4-acetic Acid

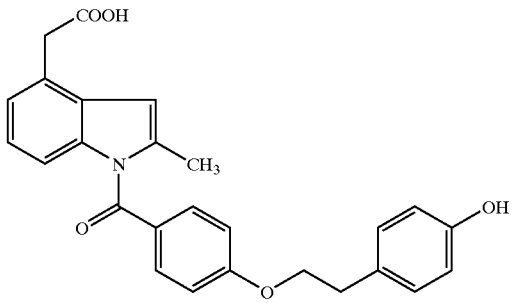

TLC: Rf 0.30 (chloroform:methanol=10:1);

NMR (CDCl$_3$): δ 7.68 (d, J=8.6 Hz, 2H), 7.14 (d, J=8.2 Hz, 2H), 7.08–6.89 (m, 5H), 6.78 (d, J=8.0 Hz, 2H), 6.48 (s, 1H), 4.20 (t, J=7.0 Hz, 2H), 3.85 (s, 2H), 3.05 (t, J=7.0 Hz, 2H), 2.43 (s, 3H).

EXAMPLE 1(9)
1-(4-Butoxybenzoyl)indole-4-acetic Acid

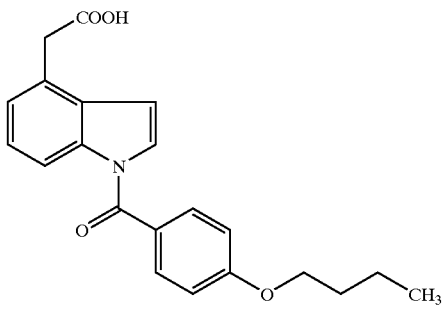

TLC: Rf 0.25 (hexane:ethyl acetate=1:1);

NMR (CDCl$_3$): δ 8.26 (d, J=8.2 Hz, 1H), 7.72–7.68 (m, 2H), 7.38–7.16 (m, 3H), 7.00–6.96 (m, 2H), 6.65 (d, J=3.6 Hz, 1H), 4.05 (t, J=6.4 Hz, 2H), 3.87 (s, 2H), 1.82 (m, 2H), 1.52 (m, 2H), 1.00 (t, J=7.2 Hz, 3H).

EXAMPLE 1(10)
1-(4-(3-Phenylpropyl)benzoyl)-2-methylindole-4-acetic Acid

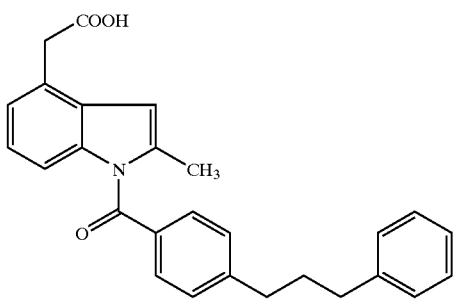

TLC: Rf 0.61 (chloroform:methanol=10:1);

NMR (CDCl$_3$): δ 7.64 (d, J=8.0 Hz, 2H), 7.38–7.16 (m, 7H), 7.08–6.93 (m, 3H), 6.49 (s, 1H), 3.85 (s, 2H), 2.82–2.60 (m, 4H), 2.42 (s, 3H), 2.05 (m, 2H).

EXAMPLE 1(11)
1-(4-(2-(4-Methoxyphenyl)ethoxy)benzoyl)-2-methylindole-4-acetic Acid

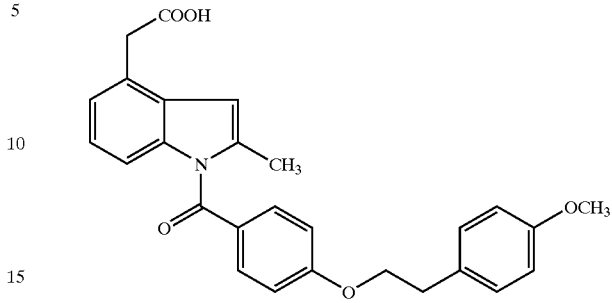

TLC: Rf 0.50 (chloroform:methanol=10:1);

NMR (CDCl$_3$): δ 7.72–7.65 (m, 2H), 7.23–7.17 (m, 2H), 7.06–6.84 (m, 7H), 6.47 (s, 1H), 4.21 (t, J=7.0 Hz, 2H), 3.85 (s, 2H), 3.80 (s, 3H), 3.08 (t, J=7.0 Hz, 2H), 2.43 (s, 3H).

EXAMPLE 1(12)
1-(4-(2-(2-Pyridyl)ethoxy)benzoyl)-2-methylindole-4-acetic Acid

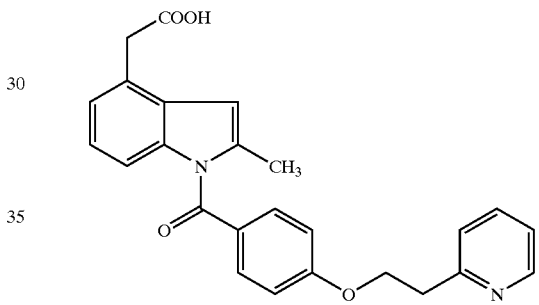

TLC: Rf 0.40 (chloroform:methanol=9:1);

NMR (CDCl$_3$) δ 8.59 (d, J=5.2 Hz, 1H), 7.68–6.88 (m, 10H), 6.52 (s, 1H), 4.39 (t, J=6.6 Hz, 2H), 3.86 (s, 2H), 3.31 (t, J=6.6 Hz, 2H), 2.43 (s, 3H).

EXAMPLE 1(13)
1-(4-(2-Cyclopropylethoxy)benzoyl)-2-methylindole-4-acetic Acid

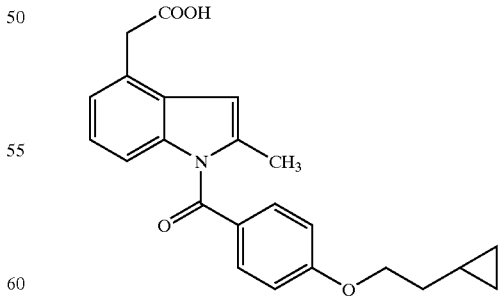

TLC: Rf 0.37 (ethyl acetate);

NMR (CDCl$_3$): δ 7.73–7.69 (m, 2H), 7.08–6.94 (m, 5H), 6.49 (s, 1H), 4.12 (t, J=6.5 Hz, 2H), 3.87 (s, 2H), 2.45 (s, 3H), 1.72 (q, J=6.5 Hz, 2H), 0.96–0.80 (m, 1H), 0.56–0.47 (m, 2H), 0.18–0.13 (m, 2H).

EXAMPLE 1(14)
1-(4-(2-i-Propoxyethoxy)benzoyl)-2-methylindole-4-acetic Acid

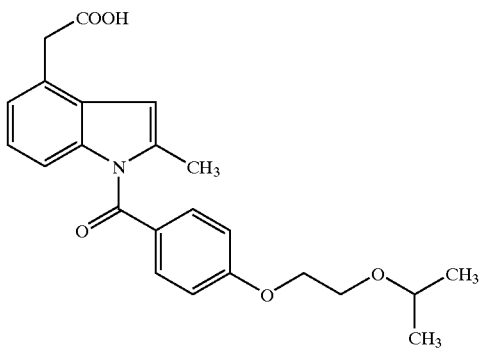

TLC: Rf 0.35 (ethyl acetate);
NMR (CDCl$_3$): δ 7.72–7.67 (m, 2H), 7.04–6.90 (m, 5H), 6.48 (s, 1H), 4.22–4.17 (m, 2H), 3.86 (s, 2H), 3.84–3.80 (m, 2H), 3.78–3.62 (m, 1H), 2.44 (s, 3H), 1.21 (d, J=6.0 Hz, 6H).

EXAMPLE 1(15)
1-(4-(4-Methoxybenzyloxy)benzoyl)-2-methylindole-4-acetic Acid

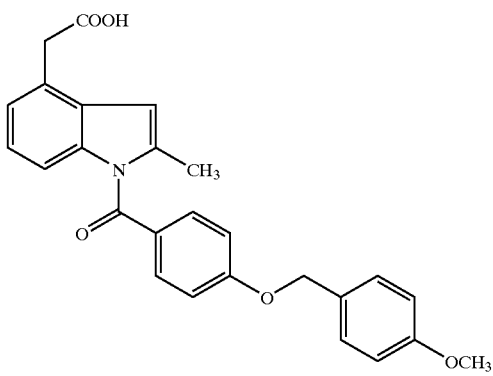

TLC: Rf 0.33 (ethyl acetate);
NMR (CDCl$_3$): δ 7.74–7.69 (m, 2H), 7.40–7.35 (m, 2H), 7.08–6.92 (m, 7H), 6.49 (s, 1H), 5.07 (s, 2H), 3.87 (s, 2H), 3.83 (s, 3H), 2.45 (s, 3H).

EXAMPLE 1(16)
1-(4-(2-Ethylthioethoxy)benzoyl)-2-methylindole-4-acetic Acid

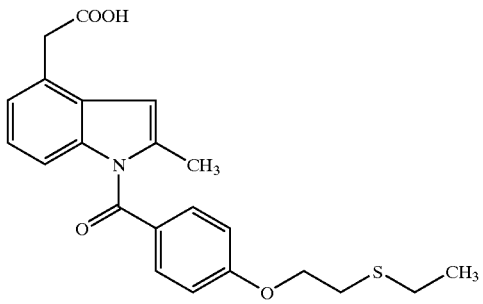

TLC: Rf 0.50 (chloroform:methanol=10:1);
NMR (CDCl$_3$): δ 7.71 (d, J=9.0 Hz, 2H), 7.05–6.93 (m, 5H), 6.48 (s, 1H), 4.22 (t, J=6.8 Hz, 2H), 3.86 (s, 2H), 2.95 (t, J=6.8 Hz, 2H), 2.67 (q, J=7.4 Hz, 2H), 2.44 (s, 3H), 1.31 (t, J=7.4 Hz, 3H).

EXAMPLE 1(17)
1-(4-(3,3-Dimethylbutoxy)benzoyl)-2-methylindole-4-acetic Acid

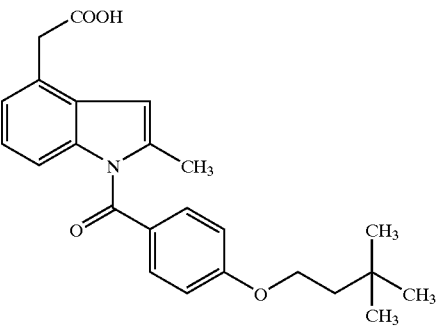

TLC: Rf 0.45 (chloroform:methanol=10:1);
NMR (CDCl$_3$): δ 7.68 (d, J=8.8 Hz, 2H), 7.08–6.86 (m, 5H), 6.47 (s, 1H), 4.09 (t, J=7.2 Hz, 2H), 3.83 (s, 2H), 2.43 (s, 3H), 1.76 (t, J=7.2 Hz, 2H), 1.00 (s, 9H).

EXAMPLE 1(18)
1-(4-Benzyloxymethylbenzoyl)-2-methylindole-4-acetic Acid

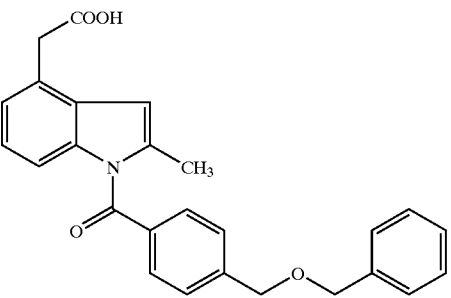

TLC: Rf 0.50 (chloroform:methanol=10:1);
NMR (CDCl$_3$): δ 7.72 (d, J=8.4 Hz, 2H), 7.48 (d, J=8.4 Hz, 2H), 7.39–7.31 (m, 4H), 7.06–6.96 (m, 4H), 6.50 (s, 1H), 4.66 (s, 2H), 4.63 (s, 2H), 3.86 (s, 2H), 2.42 (s, 3H).

EXAMPLE 1(19)
1-(4-(3-Ethoxypropoxy)benzoyl)-2-methylindole-4-acetic Acid

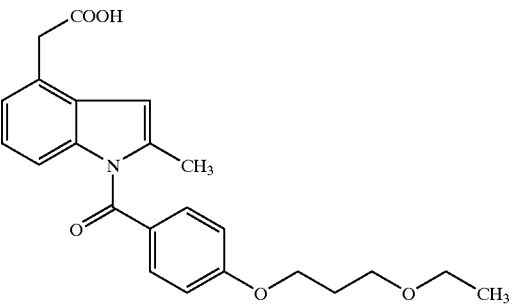

TLC: Rf 0.22 (ethyl acetate:hexane=3:1);
NMR (CDCl$_3$): δ 7.70 (d, J=9.0 Hz, 2H), 7.10–6.86 (m, 5H), 6.49 (s, 1H), 4.16 (t, J=6.4 Hz, 2H), 3.86 (s, 2H), 3.62 (t, J=6.4 Hz, 2H), 3.51 (q, J=6.8 Hz, 2H), 2.45 (s, 3H), 2.09 (m, 2H), 1.21 (t, J=6.8 Hz, 3H).

EXAMPLE 1(20)
1-(4-(4-Methylpentyloxy)benzoyl)-2-methylindole-4-acetic Acid

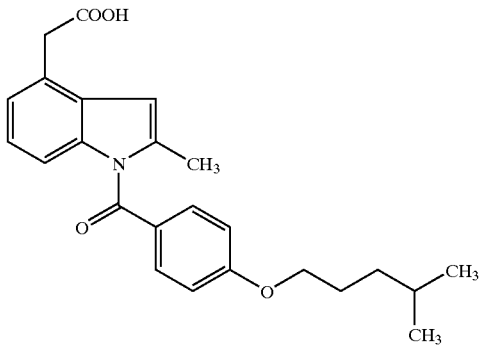

TLC: Rf 0.43 (ethyl acetate:hexane=3:1);
NMR (CDCl$_3$): δ 7.70 (d, J=8.6 Hz, 2H), 7.07–6.88 (m, 5H), 6.48 (s, 1H), 4.03 (t, J=6.8 Hz, 2H), 3.86 (s, 2H), 2.45 (s, 3H), 1.92–1.73 (m, 2H), 1.73–1.52 (m, 1H), 1.43–1.11 (m, 2H), 0.94 (d, J=6.8 Hz, 6H).

EXAMPLE 1(21)
1-(4-(2-(3-Fluorophenyl)ethoxy)benzoyl)-2-methylindole-4-acetic Acid

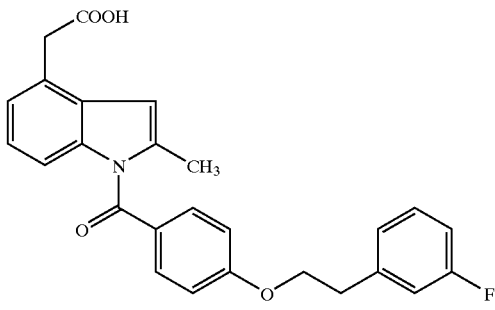

TLC: Rf 0.45 (chloroform:methanol=10:1);
NMR (CDCl$_3$): δ 7.69 (d, J=8.8 Hz, 2H), 7.35–7.20 (m, 2H), 7.09–6.85 (m, 7H), 6.47 (s, 1H), 4.25 (t, J=6.6 Hz, 2H), 3.84 (s, 2H), 3.12 (t, J=6.6 Hz, 2H), 2.42 (s, 3H).

EXAMPLE 1(22)
1-(4-(2-(3-Methoxyphenyl)ethoxy)benzoyl)-2-methylindole-4-acetic Acid

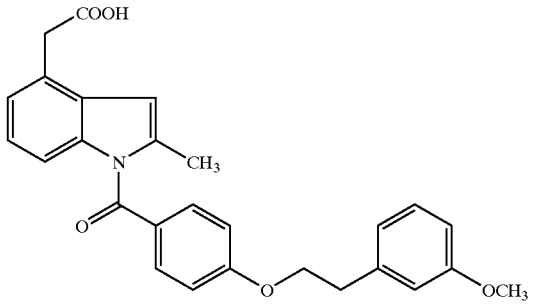

TLC: Rf 0.35 (ethyl acetate);
NMR (CDCl$_3$): δ 7.72–7.68 (m, 2H), 7.44–7.36 (m, 1H), 7.28–7.22 (m, 2H), 7.06–6.88 (m, 6H), 6.48 (s, 1H), 4.24 (t, J=7.0 Hz, 2H), 3.86 (s, 5H), 3.15 (t, J=7.0 Hz, 2H), 2.44 (s, 3H).

EXAMPLE 1(23)
1-(4-(2-(2-Thienyl)ethoxy)benzoyl)-2-methylindole-4-acetic Acid

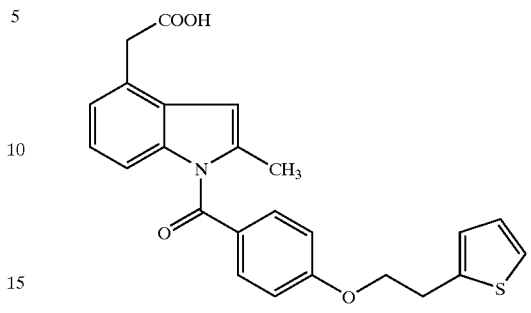

TLC: Rf 0.50 (chloroform:methanol=10:1);
NMR (CDCl$_3$): δ 7.69 (d, J=8.6 Hz, 2H), 7.18 (m, 1H), 7.02–6.90 (m, 7H), 6.47 (s, 1H), 4.26 (t, J=6.8 Hz, 2H), 3.84 (s, 2H), 3.35 (t, J=6.8 Hz, 2H), 2.43 (s, 3H).

EXAMPLE 1(24)
1-(4-(2-(2-Methylphenyl)ethoxy)benzoyl)-2-methylindole-4-acetic Acid

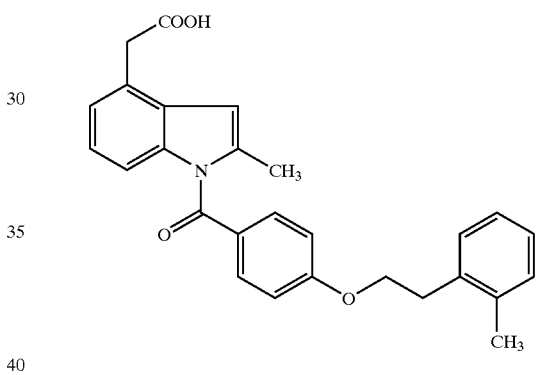

TLC: Rf 0.50 (chloroform:methanol=9:1);
NMR (CDCl$_3$): δ 7.69 (d, J=9.0 Hz, 2H), 7.23–6.91 (m, 9H), 6.48 (s, 1H), 4.23 (t, J=7.2 Hz, 2H), 3.86 (s, 2H), 3.16 (t, J=7.2 Hz, 2H), 2.44 (s, 3H), 2.39 (s, 3H).

EXAMPLE 1(25)
1-(4-(2-(3-Methylphenyl)ethoxy)benzoyl)-2-methylindole-4-acetic Acid

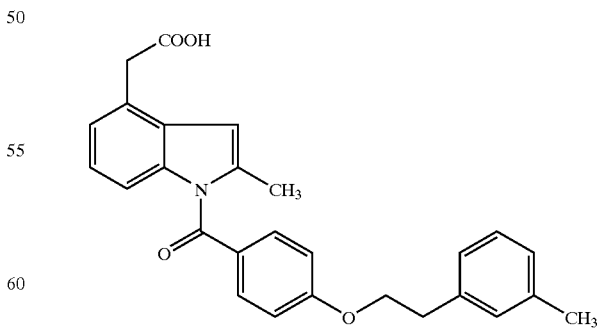

TLC: Rf 0.50 (chloroform:methanol=9:1);
NMR (CDCl$_3$): δ 7.69 (d, J=8.8 Hz, 2H), 7.19–6.92 (m, 9H), 6.48 (s, 1H), 4.24 (t, J=7.2 Hz, 2H), 3.86 (s, 2H), 3.10 (t, J=7.2 Hz, 2H), 2.44 (s, 3H), 2.36 (s, 3H).

EXAMPLE 1(26)
1-(4-(2-(4-Methylphenyl)ethoxy)benzoyl)-2-methylindole-4-acetic Acid

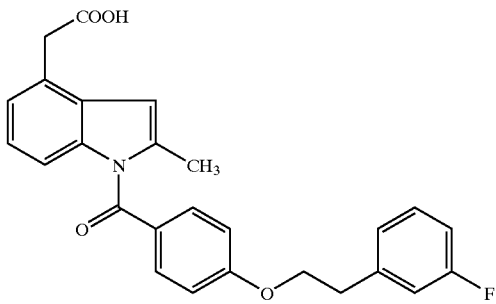

TLC: Rf 0.50 (chloroform:methanol=9:1);
NMR (CDCl$_3$): δ 7.69 (d, J=8.8 Hz, 2H), 7.18–6.92 (m, 9H), 6.49 (s, 1H), 4.23 (t, J=6.6 Hz, 2H), 3.87 (s, 2H), 3.10 (t, J=6.6 Hz, 2H), 2.44 (s, 3H), 2.34 (s, 3H).

EXAMPLE 1(27)
1-(4-(2-Cyclohexylethoxy)benzoyl)-2-methylindole-4-acetic Acid

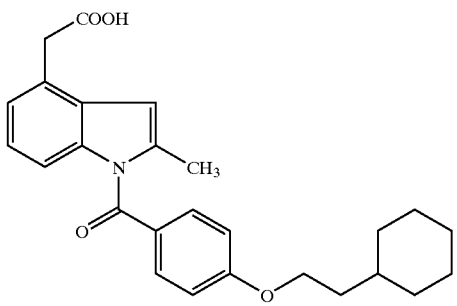

TLC: Rf 0.50 (chloroform:methanol=9:1);
NMR (CDCl$_3$): δ 7.70 (d, J=8.8 Hz, 2H), 7.06–6.91 (m, 5H), 6.48 (s, 1H), 4.08 (t, J=6.8 Hz, 2H), 3.86 (s, 2H), 2.44 (s, 3H), 1.81–0.95 (m, 13H).

EXAMPLE 1(28)
1-(4-(2-(4-Dimethylaminophenyl)ethoxy)benzoyl)-2-methylindole-4-acetic Acid

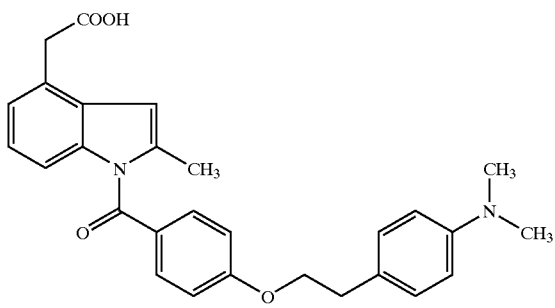

TLC: Rf 0.50 (chloroform methanol=9:1);
NMR (CDCl$_3$): δ 7.69 (d, J=8.6 Hz, 2H), 7.17 (d, J=8.6 Hz, 2H), 7.06–6.92 (m, 5H), 6.73 (d, J=8.6 Hz, 2H), 6.48 (s, 1H), 4.20 (t, J=7.4 Hz, 2H), 3.86 (s, 2H), 3.04 (t, J=7.4 Hz, 2H), 2.93 (s, 6H), 2.44 (s, 3H).

EXAMPLE 1(29)
1-(4-(2-(3-Thienyl)ethoxy)benzoyl)-2-methylindole-4-acetic Acid

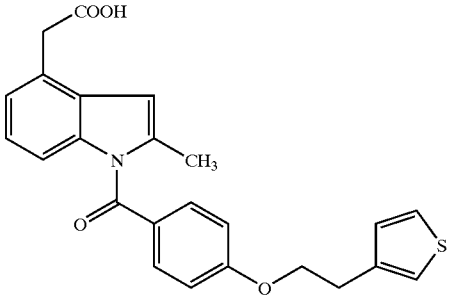

TLC: Rf 0.50 (chloroform:methanol=10:1);
NMR (CDCl$_3$): δ 7.69 (d, J=9.0 Hz, 2H), 7.30 (dd, J=4.0, 3.0 Hz, 1H), 7.11 (m, 1H), 7.06–7.01 (m, 2H), 6.96–6.92 (m, 4H), 6.48 (s, 1H), 4.25 (t, J=6.6 Hz, 2H), 3.85 (s, 2H), 3.17 (t, J=6.6 Hz, 2H), 2.43 (s, 3H).

EXAMPLE 1(30)
1-(4-(2-(4-Chlorophenyl)ethoxy)benzoyl)-2-methylindole-4-acetic Acid

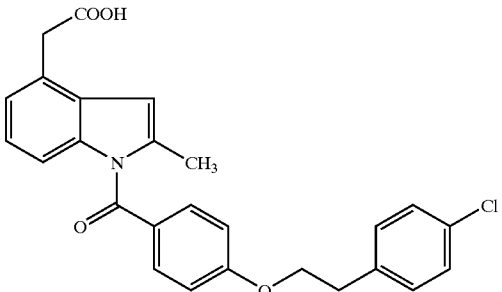

TLC: Rf 0.45 (chloroform:methanol=10:1);
NMR (CDCl$_3$): δ 7.69 (d, J=8.4 Hz, 2H), 7.33–7.20 (m, 5H), 7.04–6.82 (m, 4H), 6.49 (s, 1H), 4.23 (t, J=6.6 Hz, 2H), 3.86 (s, 2H), 3.11 (t, J=6.6 Hz, 2H), 2.44 (s, 3H).

EXAMPLE 1(31)
1-(4-(2-(2-Fluorophenyl)ethoxy)benzoyl)-2-methylindole-4-acetic Acid

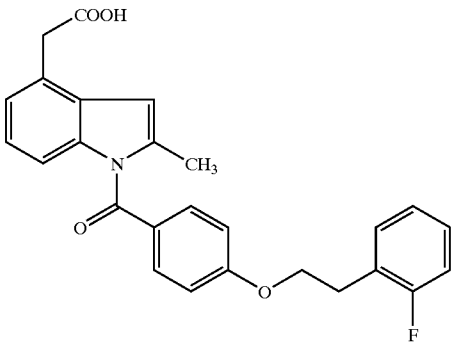

TLC: Rf 0.45 (chloroform:methanol=10:1);
NMR (CDCl$_3$): δ 7.68 (d, J=8.8 Hz, 2H), 7.40–7.08 (m, 4H), 7.05–6.90 (m, 5H), 6.47 (s, 1H), 4.26 (t, J=6.8 Hz, 2H), 3.84 (s, 2H), 3.18 (t, J=6.8 Hz, 2H), 2.43 (s, 3H).

EXAMPLE 1(32)
1-(4-(2-(4-Fluorophenyl)ethoxy)benzoyl)-2-methylindole-4-acetic Acid

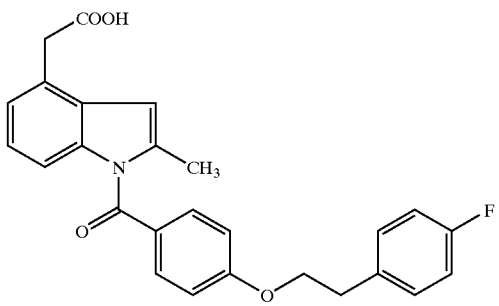

TLC: Rf 0.45 (chloroform:methanol=10:1);
NMR (CDCl$_3$): δ 7.70 (d, J=9.0 Hz, 2H), 7.30–7.21 (m, 2H), 7.06–6.90 (m, 7H), 6.48 (s, 1H), 4.23 (t, J=6.6 Hz, 2H), 3.85 (s, 2H), 3.11 (t, J=6.6 Hz, 2H), 2.43 (s, 3H).

EXAMPLE 1(33)
1-(4-(2-(2-Naphthyl)ethoxy)benzoyl)-2-methylindole-4-acetic Acid

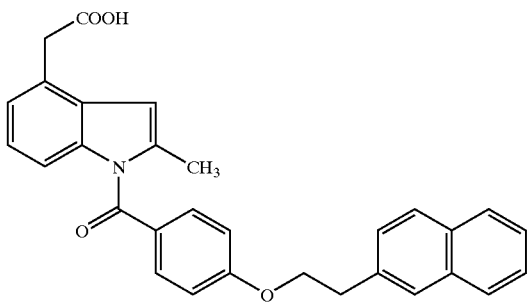

TLC: Rf 0.47 (chloroform:methanol=9:1);
NMR (CDCl$_3$): δ 7.86–6.90 (m, 14H), 6.49 (s, 1H), 4.35 (t, J=7.2 Hz, 2H), 3.86 (s, 2H), 3.31 (t, J=7.2 Hz, 2H), 2.43 (s, 3H).

EXAMPLE 1(34)
1-(4-(2-(4-Cyanophenyl)ethoxy)benzoyl)-2-methylindole-4-acetic Acid

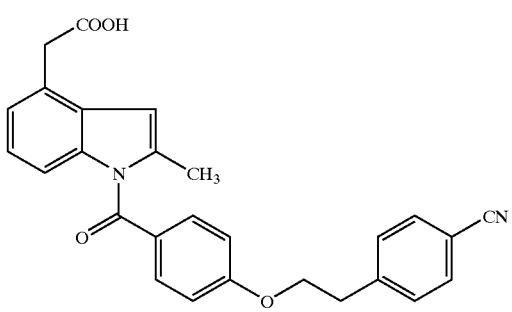

TLC: Rf 0.40 (chloroform:methanol=9:1);
NMR (CDCl$_3$): δ 7.70 (d, J=8.8 Hz, 2H), 7.63 (d, J=8.2 Hz, 2H), 7.42 (d, J=8.2 Hz, 2H), 7.03–6.90 (m, 5H), 6.48 (s, 1H), 4.28 (t, J=6.4 Hz, 2H), 3.85 (s, 2H), 3.20 (t, J=6.4 Hz, 2H), 2.43 (s, 3H).

EXAMPLE 1(35)
1-(4-(2-t-Butoxyethoxy)benzoyl)-2-methylindole-4-acetic Acid

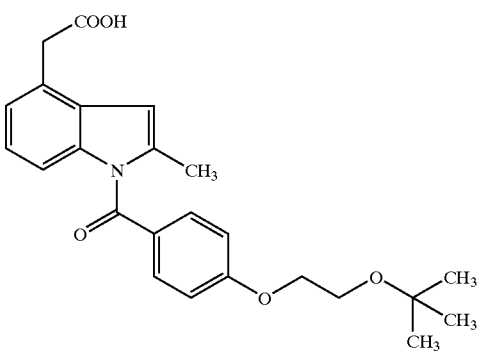

TLC: Rf 0.50 (chloroform:methanol=9:1);
NMR (CDCl$_3$): δ 7.69 (d, J=8.8 Hz, 2H), 7.04–6.94 (m, 5H), 6.48 (s, 1H), 4.17 (t, J=5.2 Hz, 2H), 3.86 (s, 2H), 3.76 (t, J=5.2 Hz, 2H), 2.44 (s, 3H), 1.25 (s, 9H).

EXAMPLE 1(36)
1-(4-(2-(2-Methoxyphenyl)ethoxy)benzoyl)-2-methylindole-4-acetic Acid

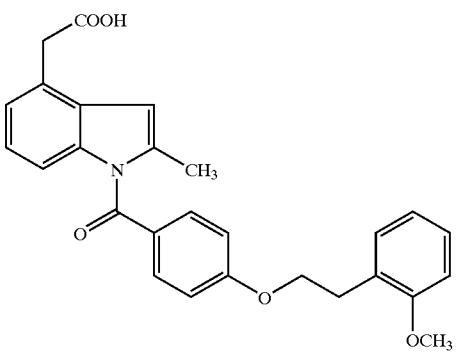

TLC: Rf 0.45 (chloroform:methanol=10:1);
NMR (CDCl$_3$): δ 7.69 (d, J=8.8 Hz, 2H), 7.22 (d, J=7.2 Hz, 2H), 7.04–6.93 (m, 7H), 6.47 (s, 1H), 4.24 (t, J=7.4 Hz, 2H), 3.85 (s, 2H), 3.85 (s, 3H), 3.14 (t, J=7.4 Hz, 2H), 2.43 (s, 3H).

EXAMPLE 1(37)
1-(3-Propoxybenzoyl)-2-methylindole-4-acetic Acid

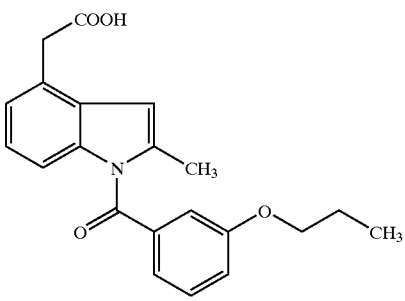

TLC: Rf 0.47 (chloroform:methanol=10:1);
NMR (CDCl$_3$): δ 7.40–6.99 (m, 7H), 6.48 (s, 1H), 3.94 (t, J=6.6 Hz, 2H), 3.85 (s, 2H), 2.41 (s, 3H), 1.81 (m, 2H), 1.03 (t, J=7.4 Hz, 3H).

EXAMPLE 1(38)
1-(4-(2-(3-Pyridyl)ethoxy)benzoyl)-2-methylindole-4-acetic Acid

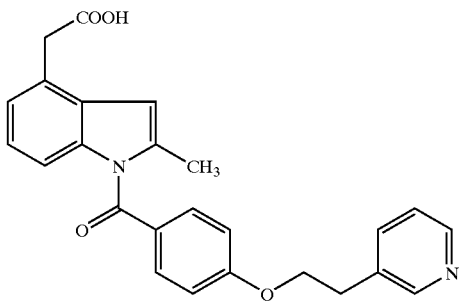

TLC: Rf 0.30 (chloroform:methanol=9:1);
NMR (CDCl$_3$): δ 8.61 (s, 1H), 8.54 (dd, J=3.0 Hz, 1H), 7.71–7.67 (m, 3H), 7.34–7.31 (m, 1H), 7.05–6.89 (m, 5H), 6.52 (s, 1H), 4.25 (t, J=6.4 Hz, 2H), 3.87 (s, 2H), 3.14 (t, J=6.4 Hz, 2H), 2.42 (s, 3H).

EXAMPLE 1(39)
1-(4-(2-(4-Pyridyl)ethoxy)benzoyl)-2-methylindole-4-acetic Acid

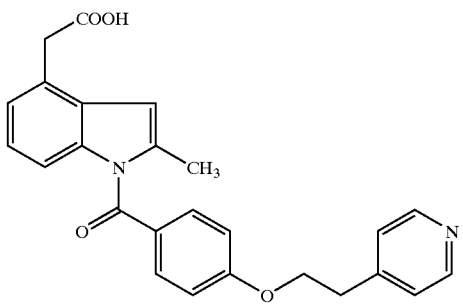

TLC: Rf 0.30 (chloroform:methanol=9:1);
NMR (CDCl$_3$): δ 8.57 (d, J=6.2 Hz, 2H), 7.70 (d, J=8.8 Hz, 2H), 7.29 (m, 2H), 7.04–6.89 (m, 5H), 6.52 (s, 1H), 4.28 (t, J=6.4 Hz, 2H), 3.86 (s, 2H), 3.15 (t, J=6.4 Hz, 2H), 2.42 (s, 3H).

EXAMPLE 1(40)
1-(4-(2-(1-Naphthyl)ethoxy)benzoyl)-2-methylindole-4-acetic Acid

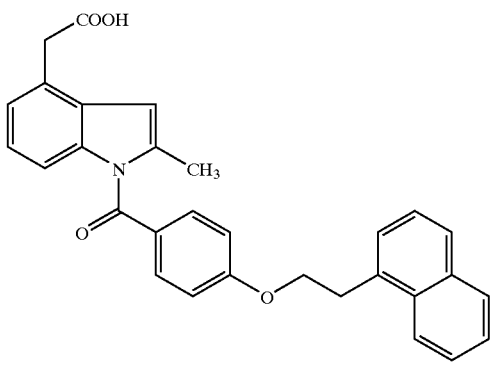

TLC: Rf 0.47 (chloroform:methanol=9:1);
NMR (CDCl$_3$): δ 8.13–8.08 (m, 1H), 7.92–7.87 (m, 1H), 7.83–7.75 (m, 1H), 7.69 (d, J=8.7 Hz, 2H), 7.61–7.47 (m, 2H), 7.48–7.41 (m, 2H), 7.07–6.90 (m, 5H), 6.48 (s, 1H), 4.39 (t, J=7.5 Hz, 2H), 3.87 (s, 2H), 3.63 (t, J=7.5 Hz, 2H), 2.43 (s, 3H).

EXAMPLE 1(41)
1-(4-(3-Ethoxypropoxy)-3-methoxybenzoyl)-2-methylindole-4-acetic Acid

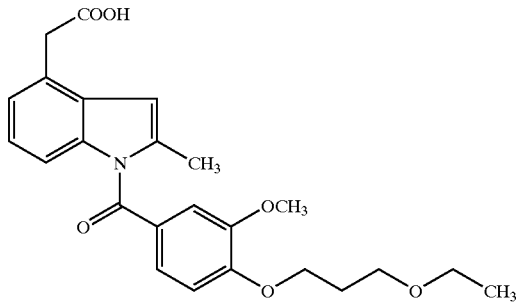

TLC: Rf 0.55 (chloroform:methanol=10:1);
NMR (CDCl$_3$): δ 7.34 (d, J=1.8 Hz, 1H), 7.27 (dd, J=8.4, 1.8 Hz, 1H), 7.10–6.93 (m, 3H), 6.89 (d, J=8.4 Hz, 1H), 6.48 (s, 1H), 4.19 (t, J=6.4 Hz, 2H), 3.85 (s, 3H), 3.83 (s, 2H), 3.62 (t, J=5.8 Hz, 2H), 3.50 (q, J=6.8 Hz, 2H), 2.44 (s, 3H), 2.13 (m, 2H), 1.19 (t, J=6.8 Hz, 3H).

EXAMPLE 1(42)
1-(4-Hexyloxybenzoyl)-2-methylindole-4-acetic Acid

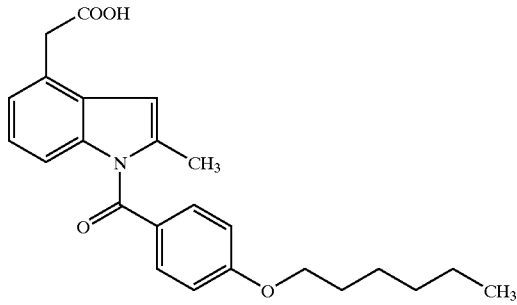

TLC: Rf 0.44 (ethyl acetate);
NMR (CDCl$_3$): δ 7.72–7.69 (m, 2H), 7.06–6.93 (m, 5H), 6.49 (s, 1H), 4.04 (t, J=6.5 Hz, 2H), 3.87 (s, 2H), 2.45 (s, 3H), 1.9–1.8 (m, 2H), 3.87 (s, 2H), 2.45 (s, 3H), 1.9–1.8 (m, 2H), 1.6–1.4 (m, 2H), 1.4–1.3 (m, 4H), 1.0–0.9 (m, 3H).

EXAMPLE 1(43)
1-(4-Butoxybenzoyl)-3-(4-methoxybenzyl)-2-methylindole-4-acetic Acid

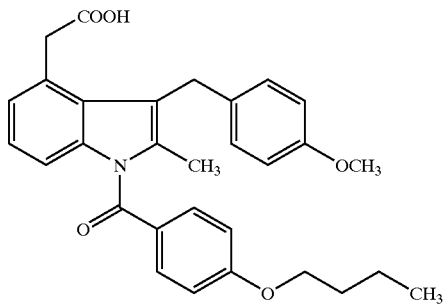

TLC: Rf 0.43 (ethyl acetate);
NMR (CDCl$_3$): δ 7.75–7.72 (m, 2H), 7.11–6.92 (m, 7H), 6.82–6.79 (m, 2H), 4.15 (s, 2H), 4.05 (t, J=6.5 Hz, 2H), 3.76 (s, 3H), 3.72 (s, 2H), 2.35 (s, 3H), 1.9–1.7 (m, 2H), 1.6–1.4 (m, 2H), 1.00 (t, J=7.0 Hz, 3H).

EXAMPLE 1(44)

1-(4-(2-(2-Methoxyethoxy)ethoxy)benzoyl)-2-methylindole-4-acetic Acid

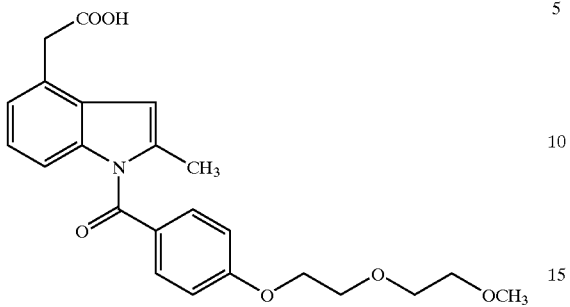

TLC: Rf 0.20 (ethyl acetate);

NMR (CDCl₃): δ 7.71–7.68 (m, 2H), 7.06–6.91 (m, 5H), 6.48 (s, 1H), 4.24–4.21 (m, 2H), 3.92–3.89 (m, 2H), 3.85 (s, 2H), 3.76–3.73 (m, 2H), 3.61–3.58 (m, 2H), 3.40 (s, 3H), 2.44 (s, 3H).

EXAMPLE 1(45)

1-(4-(3-Methoxypropyloxy)benzoyl)-2-methylindole-4-acetic Acid

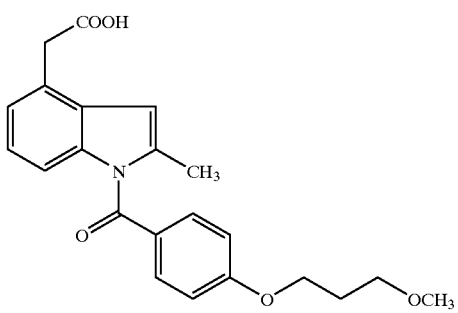

TLC: Rf 0.12 (ethyl acetate);

NMR (CDCl₃): δ 7.72–7.69 (m, 2H), 7.08–6.94 (m, 5H), 6.48 (s, 1H), 4.15 (t, J=6.5 Hz, 2H), 3.86 (s, 2H), 3.58 (t, J=6.0 Hz, 2H), 3.37 (s, 3H), 2.44 (s, 3H), 2.13–2.05 (m, 2H).

EXAMPLE 1(46)

1-(4-Methoxybenzoyl)-2-methylindole-4-acetic Acid

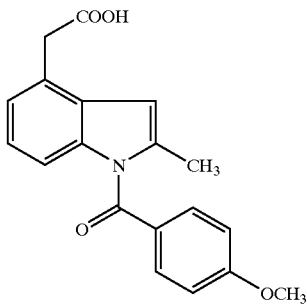

TLC: Rf 0.41 (chloroform:methanol=9:1);

NMR (CDCl₃): δ 7.72 (d, J=9.0 Hz, 2H), 7.08–6.92 (m, 5H), 6.50 (s, 1H), 3.90 (s, 3H), 3.88 (s, 2H), 2.45 (s, 3H).

EXAMPLE 1(47)

1-(4-(5-Methylfuran-2-yl)methoxybenzoyl)-2-methylindole-4-acetic Acid

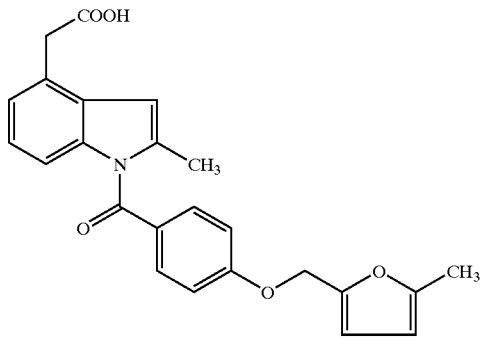

TLC: Rf 0.40 (chloroform:methanol=10:1);

NMR (CDCl₃): δ 7.72 (d, J=8.6 Hz, 2H), 7.07–6.95 (m, 5H), 6.49 (s, 1H), 6.36 (d, J=3.2 Hz, 1H), 5.99 (d, J=3.2 Hz, 1H), 5.02 (s, 2H), 3.86 (s, 2H), 2.44 (s, 3H), 2.32 (s, 3H).

EXAMPLE 1(48)

1-(4-(2-Methoxyethoxy)benzoyl)-2-methylindole-4-acetic Acid

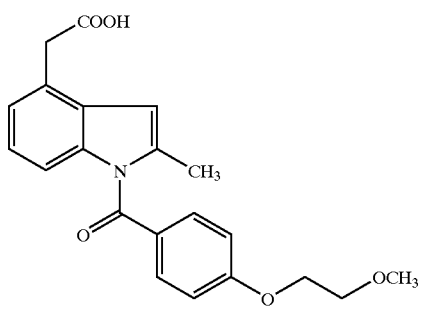

TLC: Rf 0.44 (chloroform:methanol=10:1);

NMR (CDCl₃): δ 7.70 (d, J=8.8 Hz, 2H), 7.03–6.93 (m, 5H), 6.48 (s, 1H), 4.21 (t, J=5.0 Hz, 2H), 3.85 (s, 2H), 3.79 (t, J=5.0 Hz, 2H), 3.47 (s, 3H), 2.44 (s, 3H).

EXAMPLE 1(49)

1-(4-(2-(3-Nitrophenyl)ethoxy)benzoyl)-2-methylindole-4-acetic Acid

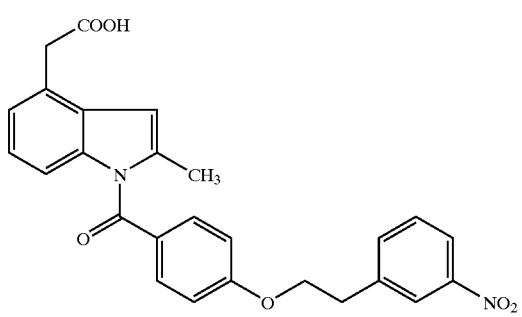

TLC: Rf 0.37 (chloroform:methanol=9:1);

NMR (CDCl₃): δ 8.22–8.16 (m, 1H), 8.16–8.10 (m, 1H), 7.74–7.62 (m, 3H), 7.52 (t, J=8.1 Hz, 1H), 7.08–6.90 (m, 5H), 6.49 (s, 1H), 4.31 (t, J=6.3 Hz, 2H), 3.87 (s, 2H), 3.26 (t, J=6.3 Hz, 2H), 2.43 (s, 3H).

EXAMPLE 1(50)
1-(4-(3-Phenylpropoxy)benzoyl)-2-methylindole-4-acetic Acid

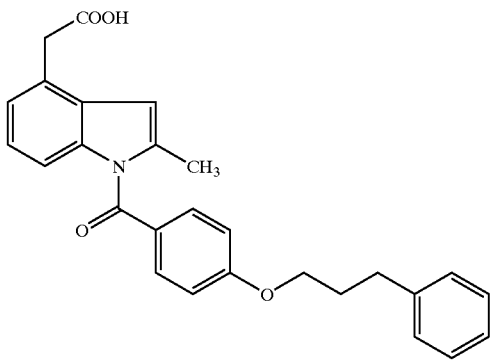

TLC: Rf 0.41 (chloroform:methanol=9:1);
NMR (CDCl$_3$): δ 7.70 (d, J=9.3 Hz, 2H), 7.34–7.16 (m, 5H), 7.08–6.88 (m, 5H), 6.50 (s, 1H), 4.05 (t, J=6.3 Hz, 2H), 3.88 (s, 2H), 2.84 (t, J=6.3 Hz, 2H), 2.45 (s, 3H), 2.20–2.10 (m, 2H).

EXAMPLE 1(51)
(+)-1-(4-(3-Phenyloxy-2-hydroxypropyloxy)benzoyl)-2-methylindole-4-acetic Acid

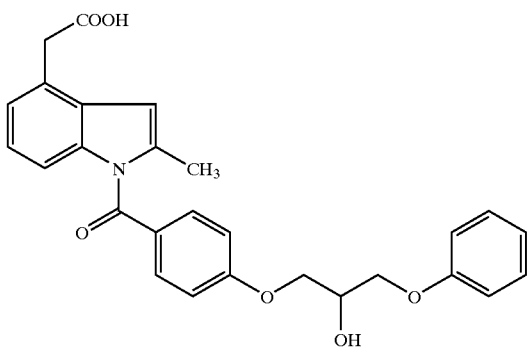

TLC: Rf 0.33 (chloroform:methanol=10:1);
NMR (CDCl$_3$): δ 7.69 (d, J=8.8 Hz, 2H), 7.33–7.23 (m, 2H), 7.06–6.90 (m, 8H), 6.47 (s, 1H), 4.43 (m, 1H), 4.24–4.15 (m, 4H), 3.83 (s, 2H), 2.42 (s, 3H).

EXAMPLE 1(52)
1-(4-Cyclohexyloxybenzoyl)-2-methylindole-4-acetic Acid

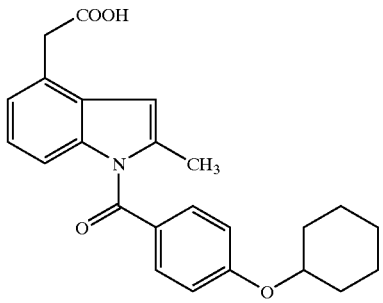

TLC: Rf 0.25 (ethyl acetate);
NMR (CDCl$_3$): δ 7.71–7.68 (m, 2H), 7.08–6.91 (m, 5H), 6.49 (s, 1H), 4.42–4.32 (m, 1H), 3.86 (s, 2H), 2.45(s, 3H), 2.08–1.96 (m, 2H), 1.88–1.78 (m, 2H), 1.64–1.32 (m, 6H).

EXAMPLE 1(53)
1-(4-Ethoxybenzoyl)-2-methylindole-4-acetic Acid

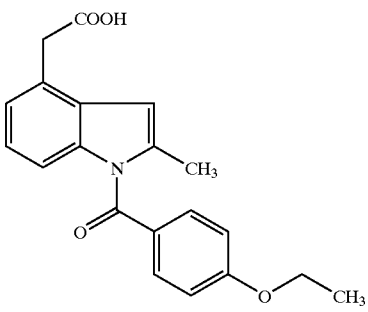

TLC: Rf 0.21 (ethyl acetate);
NMR (CDCl$_3$): δ 7.72–7.69 (m, 2H), 7.08–6.93 (m, 5H), 6.49 (s, 1H), 4.10 (q, J=7.0 Hz, 2H), 3.86 (s, 2H), 2.45 (s, 3H), 1.46 (t, J=7.0 Hz, 3H).

EXAMPLE 1(54)
1-(4-(3-Butenyloxy)benzoyl)-2-methylindole-4-acetic Acid

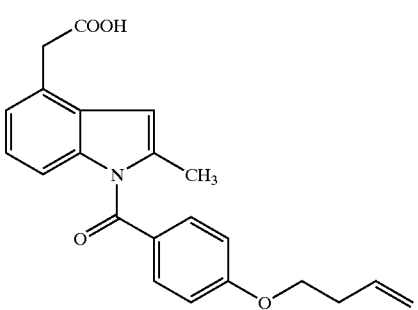

TLC: Rf 0.28 (ethyl acetate);
NMR (CDCl$_3$): δ 7.72–7.69 (m, 2H), 7.08–6.94 (m, 5H), 6.49 (s, 1H), 5.98–5.85 (m, 1H), 5.23–5.13 (m, 2H), 4.10 (t, J=6.5 Hz, 2H), 3.86 (s, 2H), 2.64–2.56 (m, 2H), 2.45 (s, 3H).

EXAMPLE 1(55)
1-(4-(2-(2,6-Dimethoxyphenyl)ethoxy)benzoyl)-2-methylindole-4-acetic Acid

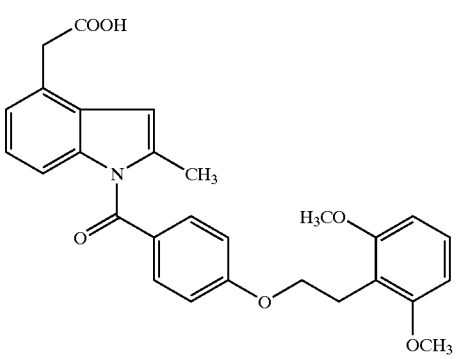

TLC: Rf 0.26 (ethyl acetate);
NMR (CDCl$_3$): δ 7.71–7.68 (m, 2H), 7.20 (t, J=8.5 Hz, 1H), 7.07–6.98 (m, 5H), 6.57 (d, J=8.5 Hz, 2H), 6.48 (s, 1H), 4.17–4.11 (m, 2H), 3.87 (s, 2H), 3.84 (s, 6H), 3.23–3.18 (m, 2H), 2.45 (s, 3H).

EXAMPLE 1(56)

1-(4-Butoxybenzoyl)-2,3-dimethylindole-4-acetic Acid

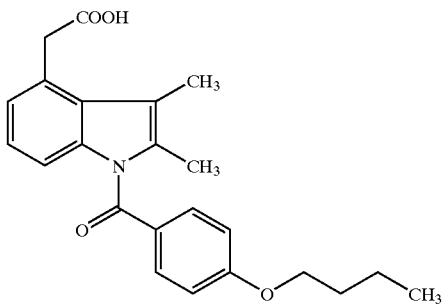

TLC: Rf 0.44 (chloroform:methanol=10:1);

NMR (CDCl$_3$): δ 7.72–7.65 (m, 2H), 7.07–6.90 (m, 5H), 4.07 (s, 2H), 4.04 (t, J=6.4 Hz, 2H), 2.39 (s, 3H), 2.30 (s, 3H), 1.87–1.74 (m, 2H), 1.60–1.41 (m, 2H), 0.99 (t, J=7.4 Hz, 3H).

EXAMPLE 1(57)

1-(3-Butoxybenzoyl)-2-methylindole-4-acetic Acid

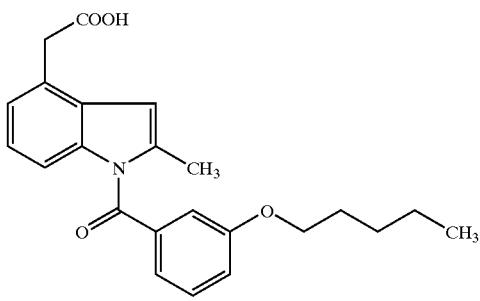

TLC: Rf 0.48 (chloroform:methanol=10:1);

NMR (CDCl$_3$): δ 7.36 (m, 1H), 7.24–6.99 (m, 6H), 6.48 (d, J=1.2 Hz, 1H), 3.98 (t, J=6.4 Hz, 2H), 3.85 (s, 2H), 2.41 (d, J=1.2 Hz, 3H), 1.84–1.70 (m, 2H), 1.58–1.38 (m, 2H), 0.96 (t, J=7.2 Hz, 3H).

EXAMPLE 1(58)

1-(3-Pentyloxybenzoyl)-2-methylindole-4-acetic Acid

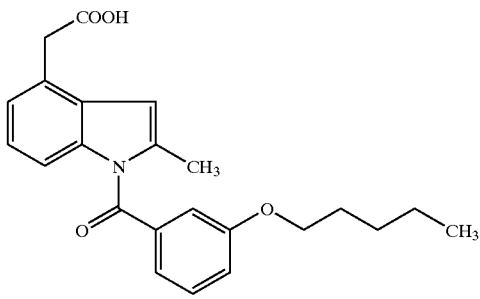

TLC: Rf 0.47 (chloroform:methanol=10:1);

NMR (CDCl$_3$): δ 7.35 (m, 1H), 7.24–6.99 (m, 6H), 6.48 (d, J=1.0 Hz, 1H), 3.97 (t, J=6.4 Hz, 2H), 3.85 (s, 2H), 2.41 (d, J=1.0 Hz, 3H), 1.84–1.72 (m, 2H), 1.50–1.32 (m, 4H), 0.92 (t, J=7.0 Hz, 3H).

EXAMPLE 1(59)

1-(3-Hexyloxybenzoyl)-2-methylindole-4-acetic Acid

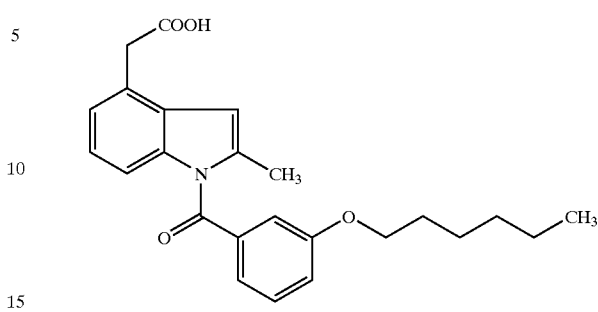

TLC: Rf 0.46 (chloroform:methanol=10:1);

NMR (CDCl$_3$): δ 7.35 (m, 1H), 7.24–6.98 (m, 6H), 6.48 (d, J=1.0 Hz, 1H), 3.97 (t, J=6.6 Hz, 2H), 3.85 (s, 2H), 2.41 (d, J=1.0 Hz, 3H), 1.85–1.69 (m, 2H), 1.53–1.28 (m, 6H), 0.90 (m, 3H).

EXAMPLE 1(60)

1-(3-Benzyloxybenzoyl)-2-methylindole-4-acetic Acid

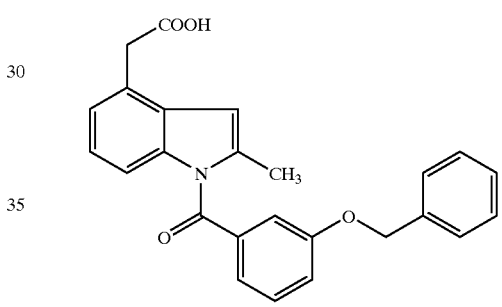

TLC: Rf 0.46 (chloroform:methanol=10:1);

NMR (CDCl$_3$): δ 7.44–7.18 (m, 9H), 7.10–6.99 (m, 3H), 6.48 (d, J=1.0 Hz, 1H), 5.08 (s, 2H), 3.85 (s, 2H), 2.36 (d, J=1.0 Hz, 3H).

EXAMPLE 1(61)

1-(3-Phenethyloxybenzoyl)-2-methylindole-4-acetic Acid

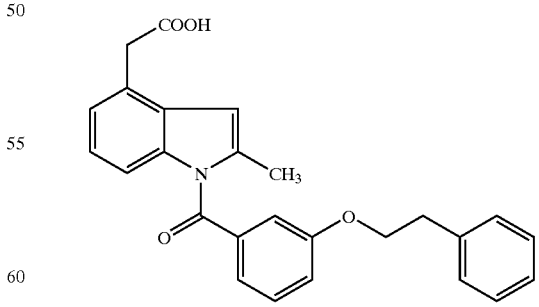

TLC: Rf 0.46 (chloroform methanol=10:1);

NMR (CDCl$_3$): δ 7.39–6.97 (m, 12H), 6.48 (d, J=1.2 Hz, 1H), 4.20 (t, J=7.0 Hz, 2H), 3.85 (s, 2H), 3.09 (t, J=7.0 Hz, 2H), 2.40 (d, J=1.2 Hz, 3H).

EXAMPLE 1(62)
1-(3-(3-Phenylpropyloxy)benzoyl)-2-methylindole-4-acetic Acid

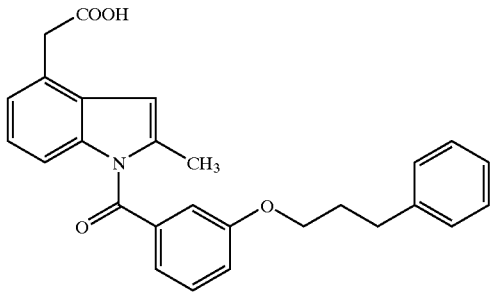

TLC: Rf 0.47 (chloroform:methanol=10:1);
NMR (CDCl$_3$): δ 7.40–6.98 (m, 12H), 6.48 (d, J=1.0 Hz, 1H), 3.98 (t, J=6.2 Hz, 2H), 3.85 (s, 2H), 2.80 (t, J=7.2 Hz, 2H), 2.41 (d, J=1.0 Hz, 3H), 2.17–2.03 (m, 2H).

EXAMPLE 1(63)
1-(4-(2-(2-Trifluoromethylphenyl)ethoxy)benzoyl)-2-methylindole-4-acetic Acid

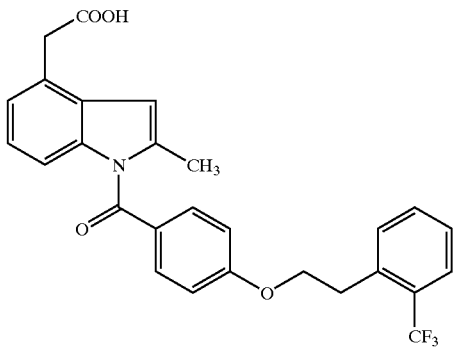

TLC: Rf 0.46 (chloroform:methanol=9:1);
NMR (CDCl$_3$): δ 7.73–7.65 (m, 3H), 7.56–7.45 (m, 2H), 7.42–7.33 (m, 1H), 7.08–6.90 (m, 5H), 6.49 (s, 1H), 4.27 (t, J=6.6 Hz, 2H), 3.87 (s, 2H), 3.34 (t, J=6.6 Hz, 2H), 2.44 (s, 3H).

EXAMPLE 1(64)
1-(4-(2-(2-Trifluoromethylphenyl)ethoxy)benzoyl)-2-methyl-3-methoxymethylindole-4-acetic Acid

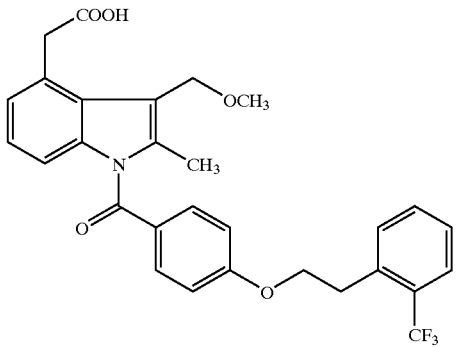

TLC: Rf 0.56 (chloroform:methanol=9:1);
NMR (CDCl$_3$): δ 7.74–7.65 (m, 3H), 7.57–7.45 (m, 2H), 7.42–7.30 (m, 1H), 7.14–7.10 (m, 1H), 7.05–6.80 (m, 1H), 6.98–6.90 (m, 3H), 4.71 (s, 2H), 4.27 (t, J=6.6 Hz, 2H), 4.09 (s, 2H), 3.47 (s, 3H), 3.34 (t, J=6.6 Hz, 2H), 2.46 (s, 3H).

EXAMPLE 1(65)
1-(4-(2-(3-Nitrophenyl)ethoxy)benzoyl)-2-methyl-3-methoxymethylindole-4-acetic Acid

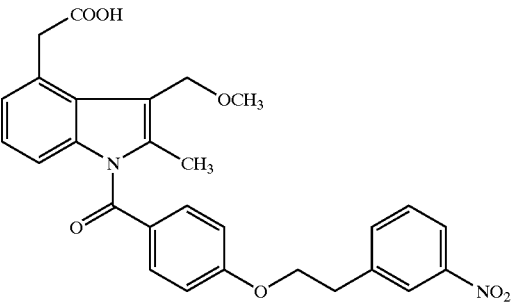

TLC: Rf 0.54 (chloroform:methanol=9:1);
NMR (CDCl$_3$): δ 8.22–8.18 (m, 1H), 8.16–8.11 (m, 1H), 7.71 (d, J=8.7 Hz, 2H), 7.68–7.60 (m, 1H), 7.52 (t, J=7.8 Hz, 1H), 7.14–7.09 (m, 1H), 7.00 (t, J=8.1 Hz, 1H), 6.97–6.90 (m, 3H), 4.70 (s, 2H), 4.32 (t, J=6.3 Hz, 2H), 4.09 (s, 2H), 3.46 (s, 3H), 3.26 (t, J=6.3 Hz, 2H), 2.45 (s, 3H).

EXAMPLE 1(66)
1-(4-(2-Phenoxyethyl)benzoyl)-2-methylindole-4-acetic Acid

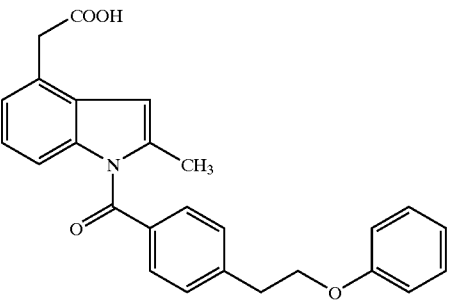

TLC: Rf 0.45 (chloroform:methanol=10:1);
NMR (CDCl$_3$): δ 7.64 (d, J=8.4 Hz, 2H), 7.36 (d, J=8.4 Hz, 2H), 7.24 (d, J=8.0 Hz, 2H), 7.03–6.85 (m, 6H), 6.47 (s, 1H), 4.20 (t, J=6.6 Hz, 2H), 3.81 (s, 2H), 3.15 (t, J=6.6 Hz, 2H), 2.39 (s, 3H).

EXAMPLE 1(67)
(+)-1-(4-(2-Phenyl-2-hydroxyethoxy)benzoyl)-2-methylindole-4-acetic Acid

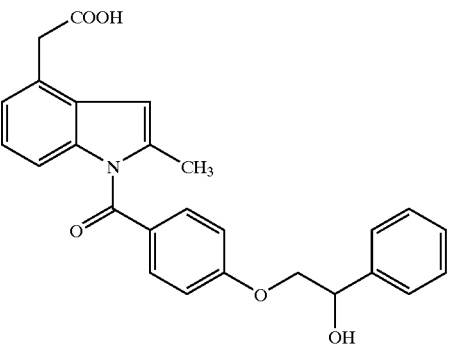

TLC: Rf 0.33 (chloroform:methanol=10:1);
NMR (CDCl$_3$): δ 7.57 (d, J=8.2 Hz, 2H), 7.32 (s, 5H), 6.99 (m, 1H), 6.93–6.86 (m, 4H), 6.44 (s, 1H), 5.34 (dd, J=8.0, 3.6 Hz, 1H), 3.97 (dd, J=12.2, 8.0 Hz, 1H), 3.86 (dd, J=12.2, 3.6 Hz, 1H), 3.81 (s, 2H), 2.37 (s, 3H).

EXAMPLE 1(68)
1-(4-(2-(3-Aminophenyl)ethoxy)benzoyl)-2-methylindole-4-acetic Acid

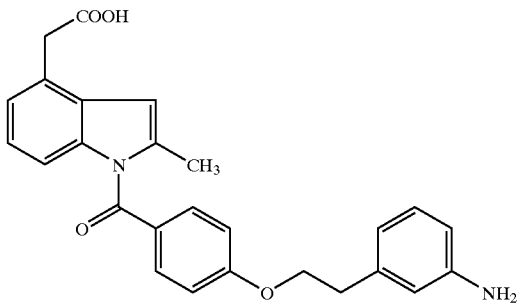

TLC: Rf 0.47 (chloroform:methanol=9:1);
NMR (CDCl$_3$): δ 7.70 (d, J=9.0 Hz, 2H), 7.16–6.90 (m, 6H), 6.72–6.67 (m, 1H), 6.65–6.56 (m, 2H), 6.49 (s, 1H), 4.23 (t, J=7.2 Hz, 2H), 3.87 (s, 2H), 3.05 (t, J=7.2 Hz, 2H), 2.45 (s, 3H).

EXAMPLE 1(69)
1-(4-(2-(3-Aminophenyl)ethoxy)benzoyl)-2-methyl-3-methoxymethylindole-4-acetic Acid

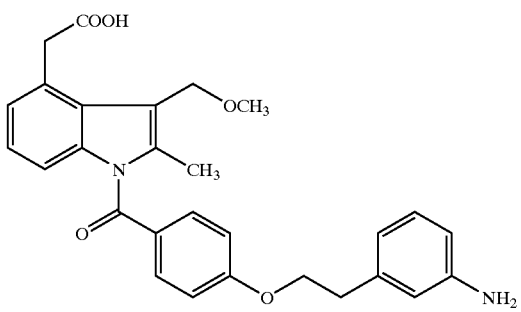

TLC: Rf 0.53 (chloroform:methanol=9:1);
NMR (CDCl$_3$): δ 7.70 (d, J=9.0 Hz, 2H), 7.16–7.08 (m, 2H), 7.01 (t, J=8.4 Hz, 1H), 6.97–6.90 (m, 3H), 6.71–6.66 (m, 1H), 6.64–6.56 (m, 2H), 4.70 (s, 2H), 4.23 (t, J=7.2 Hz, 2H), 4.09 (s, 2H), 3.46 (s, 3H), 3.05 (t, J=7.2 Hz, 2H), 2.46 (s, 3H).

EXAMPLE 1(70)
1-(4-Butoxybenzoyl)-2-ethylindole-4-acetic Acid

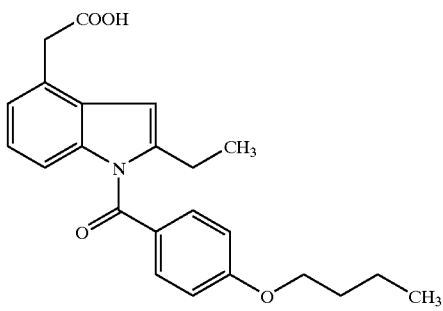

TLC: Rf 0.55 (chloroform:methanol=9:1);
NMR (CDCl$_3$): δ 7.71 (d, J=8.7 Hz, 2H), 7.07–6.86 (m, 5H), 6.53 (s, 1H), 4.05 (t, J=6.3 Hz, 2H), 3.89 (s, 2H), 2.87 (q, J=7.5 Hz, 2H), 1.90–1.35 (m, 4H), 1.24 (t, J=7.5 Hz, 3H), 0.97 (t, J=7.5 Hz, 3H).

EXAMPLE 1(71)
1-(4-(2-Phenoxyethoxy)benzoyl)-2-methylindole-4-acetic Acid

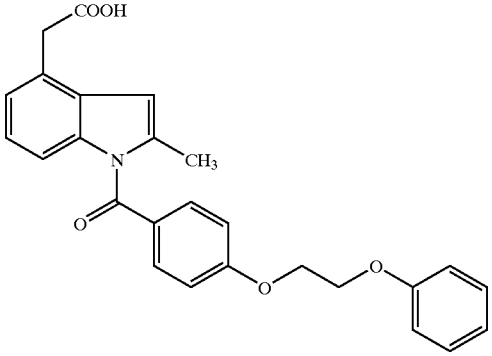

TLC: Rf 0.55 (chloroform:methanol=9:1);
NMR (CDCl$_3$): δ 7.72 (d, J=9.0 Hz, 2H), 7.32 (t, J=7.8 Hz, 2H), 7.08–6.92 (m, 8H), 6.49 (s, 1H), 4.46–4.34 (m, 4H), 3.87 (s, 2H), 2.45 (s, 3H).

EXAMPLE 1(72)
(±)-1-(4-(2-Methoxy-2-phenylethoxy)benzoyl)-2-methylindole-4-acetic Acid

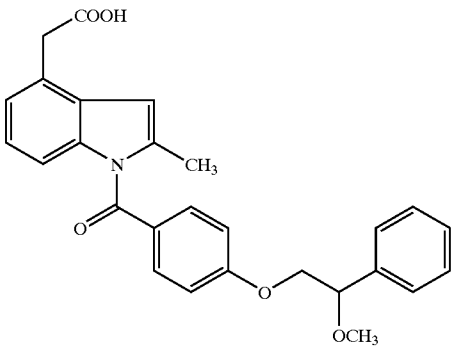

TLC: Rf 0.52 (chloroform:methanol=10:1);
NMR (CDCl$_3$): δ 7.59 (d, J=9.0 Hz, 2H), 7.38–7.30 (m, 5H), 7.04–6.80 (m, 5H), 6.44 (s, 1H), 5.44 (dd, J=8.0, 4.0 Hz, 1H), 3.84 (dd, J=10.8, 8.0 Hz, 1H), 3.83 (brs, 2H), 3.65 (dd, J=10.8, 4.0 Hz, 1H), 3.47 (s, 3H), 2.39 (s, 3H).

EXAMPLE 1(73)
1-(4-Phenylbenzoyl)-2-methylindole-4-acetic Acid

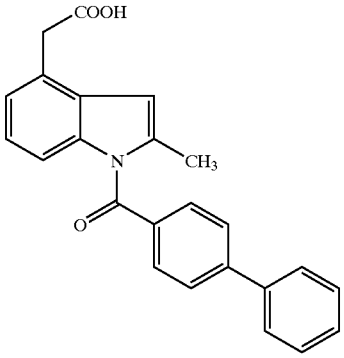

TLC: Rf 0.50 (chloroform:methanol=10:1);
NMR (CDCl$_3$): δ 7.84–7.78 (m, 2H), 7.74–7.66 (m, 4H), 7.52–7.38 (m, 3H), 7.10–6.98 (m, 3H), 6.52 (s, 1H), 3.87 (s, 2H), 2.46 (s, 3H).

EXAMPLE 1(74)
1-(4-Phenyldiazobenzoyl)-2-methylindole-4-acetic Acid

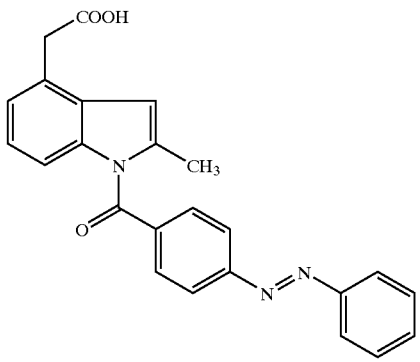

TLC: Rf 0.50 (chloroform:methanol=10:1);

NMR (CDCl₃) δ 8.04–7.96 (m, 4H), 7.90–7.86 (m, 2H), 7.60–7.52 (m, 3H), 7.10–7.00(m, 3H), 6.53 (s, 1H), 3.87 (s, 2H), 2.46 (s, 3H).

EXAMPLE 1(75)
1-(4-Butoxybenzoyl)-2,5-dimethylindole-4-acetic Acid

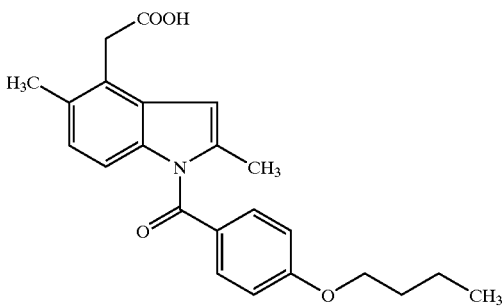

TLC: Rf 0.53 (chloroform:methanol=10:1);

NMR (CDCl₃): δ 7.68 (d, J=9.3 Hz, 2H), 6.93 (d, J=9.3 Hz, 2H), 6.85 (d, J=9.0 Hz, 1H), 6.82 (d, J=9.0 Hz, 1H), 6.44 (s, 1H), 4.04 (t, J=6.6 Hz, 2H), 3.86 (s, 2H), 2.43 (s, 3H), 2.37 (s, 3H), 1.80 (m, 2H), 1.53 (m, 2H), 0.99 (t, J=7.5 Hz, 3H).

REFERENCE EXAMPLE 9
2-Methylindole-4-carboxylic Acid Methyl Ester

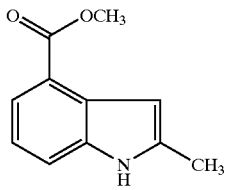

To a solution of 2-methyl-4-trifluoromethanesulfoxyindole (6.32 g; prepared in Reference Example 1) in methanol (33.43 ml)—N,N-dimethylformamide (200 ml) was added triethylamine (6.3 ml) and tetrakis(triphenylphosphine)palladium (2.6 g). The inside of the vessel was replaced with carbon monoxide and the mixture was stirred at 60° C. overnight. After the reaction was completed, to the mixture was added water and ethyl acetate and then the mixture was extracted. The aqueous layer was extracted with ethyl acetate. The combined organic layer was washed with water and a saturated aqueous solution of sodium chloride, successively, dried and concentrated under reduced pressure. The residue was purified by column chromatography on silica gel (n-hexane—ethyl acetate) to give the title compound (4.29 g) having the following physical data.

TLC: Rf 0.18 (toluene).

REFERENCE EXAMPLE 10
2-Methylindole-4-carboxylic Acid

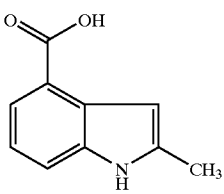

To a solution of 2-methylindole-4-carboxylic acid methyl ester (4.3 g; prepared in Reference Example 9) in methanol—dioxane (10 ml+10 ml) was added 5N aqueous solution of sodium hydroxide (10 ml), and the mixture was stirred at 60° C. overnight. To the reaction solution was added 2N hydrochloric acid, and then extracted with ethyl acetate. The aqueous layer was extracted with ethyl acetate. The combined organic layer was washed with water and a saturated aqueous solution of sodium chloride, successively, dried and concentrated under reduced pressure. The residue was purified by column chromatography on silica gel (chloroform-methanol) to give the title compound (1.6 g) having the following physical data.

TLC: Rf 0.48(chloroform:methanol=9:1);

NMR (CDCl₃): δ 8.14–8.04 (br, 1H), 7.93 (dd, 1H), 7.52 (m, 1H), 7.18 (dd, 1H), 6.94 (m, 1H), 3.71 (s, 3H).

REFERENCE EXAMPLE 11
2-Methylindole-4-carboxylic Acid Benzyl Ester

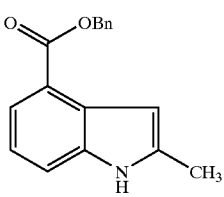

To a solution of 2-methylindole-4-carboxylic acid (690 mg; prepared in Reference Example 10) in N,N-dimethylformamide (10 ml) was added anhydrous potassium carbonate (815 mg) and benzyl bromide (0.7 ml) at room temperature, and the mixture was stirred at 80° C. for 2 hours. To the reaction solution was added water and ethyl acetate, and then extracted. The aqueous layer was extracted with ethyl acetate. The combined organic layer was washed with water and a saturated aqueous solution of sodium chloride, successively, dried and concentrated under reduced pressure. The residue was purified by column chromatography on silica gel (hexane—ethyl acetate) to give the title compound (610 mg) having the following physical data.

TLC: Rf 0.44(hexane:ethyl acetate=8:2);

NMR (CDCl₃): δ 8.05 (brs, 1H), 7.91 (d, 1H), 7.54–7.24 (m, 7H), 6.88 (m, 1H), 5.44 (s, 2H), 2.48 (s, 3H).

REFERENCE EXAMPLE 12

1-(4-Butoxybenzoyl)-2-methylindole-4-carboxylic Acid Benzyl Ester

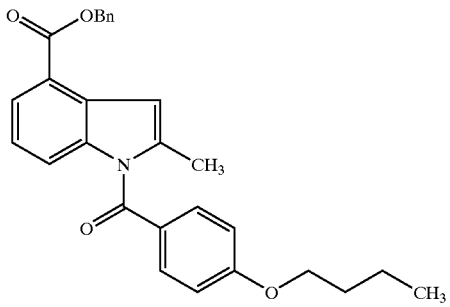

To a solution of 2-methylndole-4-carboxylic acid benzyl ester (690 mg; prepared in Reference Example 11) in N,N-dimethylformamide (8 ml) was added sodium hydride (114 mg; 60%) at 0° C., and the mixture was stirred at the same temperature for 30 minutes. To the reaction mixture was added 4-butoxybenzoyl chloride (0.54 ml), and the mixture was stirred at room temperature overnight. To the reaction mixture was added water and ethyl acetate, and then separated. The aqueous layer was extracted with ethyl acetate. The combined organic layer was washed with water and a saturated aqueous solution of sodium chloride, successively, dried and concentrated under reduced pressure. The residue was purified by column chromatography on silica gel (hexane—ethyl acetate) to give the title compound (1.02 g) having the following physical data.

TLC: Rf 0.61 (hexane:ethyl acetate=8:2);

NMR (CDCl$_3$): δ 8.10–6.90 (m, 13H), 5.45 (s, 2H), 4.05 (t, 2H), 2.44 (s, 3H), 1.86–1.74 (m, 2H), 1.60–1.45 (m, 2H), 0.99 (t, 3H).

EXAMPLE 2

(1) 1-(4-Butoxybenzoyl)-2-methylndole-4-carboxylic acid and (2) 1-(4-Butoxybenzoyl)-2-methyl-2,3-dihydroindole-4-carboxylic Acid

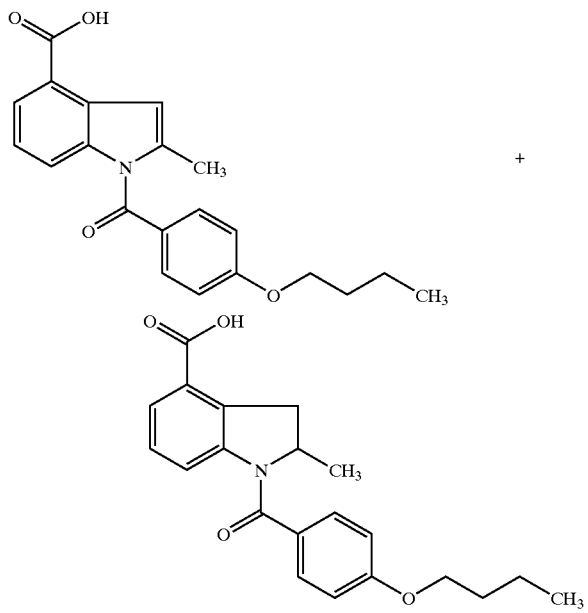

To a solution of 1-(4-butoxybenzoyl)-2-methylndole-4-carboxylic acid benzyl ester (1.02 g; prepared in Reference Example 12) in methanol (10 ml)—ethyl acetate (5 ml) was added palladium on activated carbon (100 mg). The inside of the vessel was replaced with hydrogen and the mixture was stirred at room temperature overnight. The reaction mixture was filtered through Celite (trademark). The filtrate and washing with chloroform were combined, and then concentrated under reduced pressure. The residue was purified by column chromatography on silica gel (chloroform—methanol) to give the title compound having the following physical data.

(1) indole

TLC: Rf 0.59 (chloroform:methanol=9:1);

NMR (CDCl$_3$): δ 7.99 (d, J=8.1 Hz, 1H), 7.70 (d, J=9.0 Hz, 2H), 7.36 (d, J=8.1 Hz, 1H), 7.21 (brs, 1H), 7.13 (t, J=8.1 Hz, 1H), 6.97 (d, J=9.0 Hz, 2H), 4.06 (t, J=6.6 Hz, 2H), 2.48 (s, 3H), 1.88–1.76 (m, 2H), 1.60–1.46 (m, 2H), 1.00 (t, J=7.5 Hz, 3H).

(2) indoline

TLC: Rf 0.53 chloroform:methanol=9:1);

NMR (CDCl$_3$): δ 7.74 (dd, 1H), 7.64–7.46 (br, 1H), 7.50 (d, 2H), 7.19 (t, 1H), 6.93 (d, 2H), 4.84–4.70 (m, 1H), 4.02 (t, 2H), 3.65 (dd, 1H), 3.22 (dd, 1H), 1.86–1.76 (m, 2H), 1.60–1.45 (m, 2H), 1.24 (d, 3H), 1.00 (t, 3H).

REFERENCE EXAMPLE 13

2-Methylindol-4-yloxyacetic Acid Methyl Ester

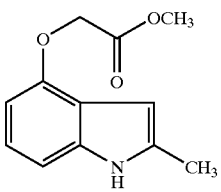

To a solution of 2-methyl-4-hydroxyindole (5 g) in N,N-dimethylformamide (50 ml) was added anhydrous potassium carbonate 11.7 g) and methyl bromoacetate (3.54 ml) at room temperature, and the mixture was stirred at 80° C. for 2 hours. To the reaction solution was added iced water to give the title compound (5.4 g) having the following physical data.

TLC: Rf 0.75 (benzene: ethyl acetate=4:1);

NMR (CDCl$_3$): δ 8.00–7.84 (br, 1H), 7.04–6.94 (m, 2H), 6.45–5.36 (m, 2H), 4.77 (s, 2H), 3.80 (s, 3H), 2.43 (s, 3H).

REFERENCE EXAMPLE 14

2-Methylindol-4-yloxyacetic Acid

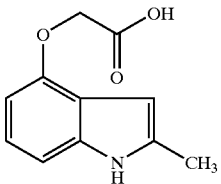

To a solution of 2-methylindol-4-yloxyacetic acid methyl ester (5.4 g) in methanol (18 ml)—dioxane (36 ml) was added 5N aqueous solution of sodium hydroxide (15 ml), and the mixture was stirred at room temperature for 1 hour. To the reaction solution was added 2N hydrochloric acid to give the title compound (3.5 g) having the following physical data.

TLC: Rf 0.20(chloroform:methanol=9:1).

REFERENCE EXAMPLE 15

2-Methylindol-4-yloxyacetic Acid Allyl Ester

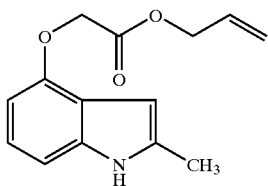

To a solution of 2-methylindol-4-yloxyacetic acid (2 g) in N,N-dimethylformamide (20 ml) was added anhydrous potassium carbonate (2.02 g) and allyl bromide (1.27 ml), and the mixture was stirred at 80° C. for 2 hours. To the reaction mixture was added water and ethyl acetate, then separated. The aqueous layer was extracted with ethyl acetate. The combined organic layer was washed with water and a saturated aqueous solution of sodium chloride, successively, dried and concentrated under reduced pressure. The residue was purified by column chromatography on silica gel (n-hexane—ethyl acetate) to give the title compound (1.88 g) having the following physical data.

TLC: Rf 0.50(n-hexane:ethyl acetate=7:3).

REFERENCE EXAMPLE 16

1-(4-Butoxybenzoyl)-2-methylindol-4-yloxyacetic Acid Allyl Ester

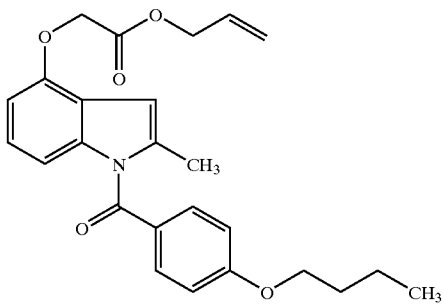

To a solution of 2-methylindol-4-yloxyacetic acid allyl ester (900 mg) in N,N-dimethylformamide (10 ml) was added sodium hydride (147 mg; 60%) at 0° C., and the mixture was stirred at the same temperature for 30 minutes. To the reaction mixture was added 4-butoxybenzoyl chloride (0.70 ml), and the mixture was stirred at room temperature overnight. To the reaction mixture was added water and ethyl acetate, and then separated. The aqueous layer was washed with ethyl acetate. The combined organic layer was washed with water and a saturated aqueous solution of sodium chloride, successively, dried and concentrated under reduced pressure. The residue was purified by column chromatography on silica gel (hexane—ethyl acetate) to give the title compound (800 mg) having the following physical data.

TLC: Rf 0.63(n-hexane:ethyl acetate=7:3);

NMR (CDCl$_3$): δ 7.69 (d, 2H), 7.00–6.85 (m, 3H), 6.68 (d, 1H), 6.67 (s, 1H), 6.47 (d, 1H), 6.00–5.87 (m, 1H), 5.40–5.30 (m, 1H), 5.30–5.24 (m, 1H), 4.78 (s, 2H), 4.75–4.68 (m, 2H), 4.05 (t, 2H), 2.42 (s, 3H), 1.87–1.75 (m, 2H), 1.60–1.45 (m, 2H), 1.00 (t, 3H).

EXAMPLE 3

1-(4-Butoxybenzoyl)-2-methylindol-4-yloxyacetic Acid

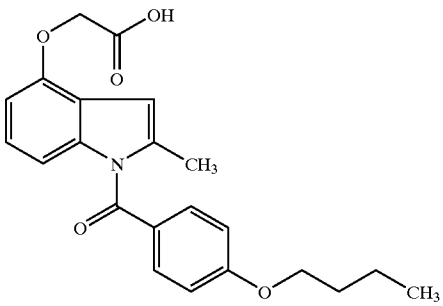

The compound of the present invention having the following physical data was obtained by the same procedure as Example 1, using the compound prepared in Reference Example 16.

TLC: Rf 0.38 (chloroform:methanol:acetic acid=90:9:1);

NMR (CDCl$_3$): δ 7.70 (d, J=9.0 Hz, 2H), 6.98–6.89 (m, 3H), 6.71 (d, J=8.4 Hz, 1H), 6.60–6.57 (m, 1H), 6.51 (d, J=8.4 Hz, 1H), 4.84 (s, 2H), 4.05 (t, J=6.6 Hz, 2H), 2.43 (s, 3H), 1.87–1.75 (m, 2H), 1.59–1.44 (m, 2H), 1.00 (t, J=7.5 Hz, 3H).

EXAMPLES 3(1) TO 3(6)

Each compound having the following physical data was obtained by the same procedures as a series of reactions of Reference Examples 13, 14, 15, 16 and Example 3.

EXAMPLE 3(1)

1-(4-(2-Ethoxyethoxy)benzoyl)-2-methylindolyl-4-oxyacetic Acid

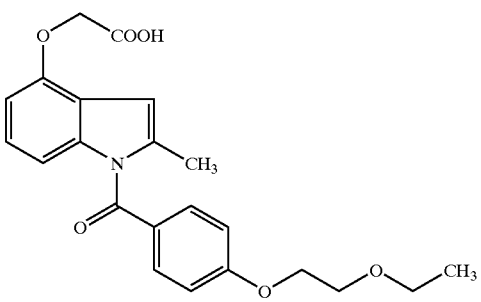

TLC: Rf 0.19 (methylene chloride:methanol=9:1);

NMR (CDCl$_3$): δ 7.68 (d, J=8.5 Hz, 2H), 6.97 (d, J=8.5 Hz, 2H), 6.91 (m, 1H), 6.66 (d, J=8.5 Hz, 1H), 6.58 (s, 1H), 6.49 (d, J=8.0 Hz, 1H), 4.77 (s, 2H), 4.20 (t, J=5.0 Hz, 2H), 3.83 (t, J=5.0 Hz, 2H), 3.62 (q, J=7.0 Hz, 2H), 2.41 (s, 3H), 1.26 (t, J=7.0 Hz, 3H).

EXAMPLE 3(2)
1-(4-Propyloxybenzoyl)-2-methylindolyl-4-oxyacetic Acid

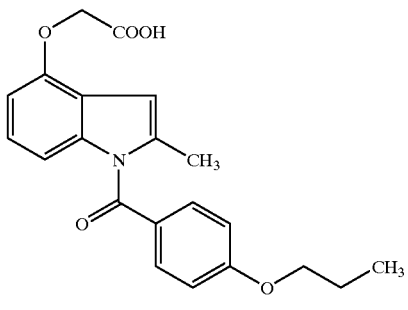

TLC: Rf 0.39 (chloroform:methanol=9:1);
NMR (CDCl$_3$): δ 7.73–7.67 (m, 2H), 6.97–6.90 (m, 3H), 6.72 (d, J=8.4 Hz, 1H), 6.59 (s, 1H), 6.52 (d, J=7.5 Hz, 1H), 4.80 (s, 2H), 4.01 (t, J=6.6 Hz, 2H), 2.43 (s, 3H), 1.86 (dt, J=7.5, 6.6 Hz, 2H), 1.07 (t, J=7.5 Hz, 3H).

EXAMPLE 3(3)
1-(4-Phenethyloxybenzoyl)-2-methylindolyl-4-oxyacetic Acid

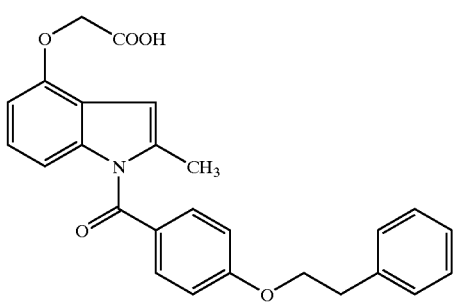

TLC: Rf 0.35 (chloroform:methanol=9:1);
NMR (CDCl$_3$): δ 7.71–7.67 (m, 2H), 7.37–7.25 (m, 5H), 6.97–6.89 (m, 3H), 6.70 (d, J=8.4 Hz, 1H), 6.58 (s, 1H), 6.52 (d, J=8.1 Hz, 1H), 4.80 (s, 2H), 4.26 (t, J=6.9 Hz, 2H), 3.14 (t, J=6.9 Hz, 2H), 2.43 (s, 3H).

EXAMPLE 3(4)
1-(4-Benzyloxybenzoyl)-2-methylindolyl-4-oxyacetic Acid

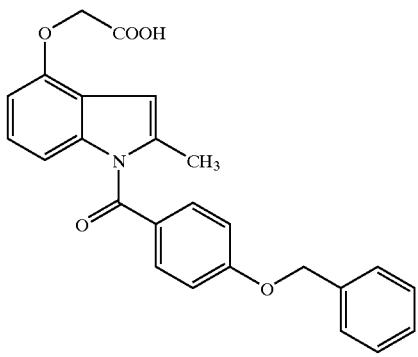

TLC: Rf 0.48 (chloroform:methanol=10:1);
NMR (DMSO-d$_6$): δ 7.65 (d, J=8.8 Hz, 2H), 7.51–7.33 (m, 5H), 7.17 (d, J=8.8 Hz, 2H), 6.93 (t, J=8.2 Hz, 1H), 6.59–6.52 (m, 3H), 5.21 (s, 2H), 4.77 (s, 2H), 2.32 (s, 3H).

EXAMPLE 3(5)
1-(4-(3-Methylbutoxy)benzoyl)-2-methylindolyl-4-oxyacetic Acid

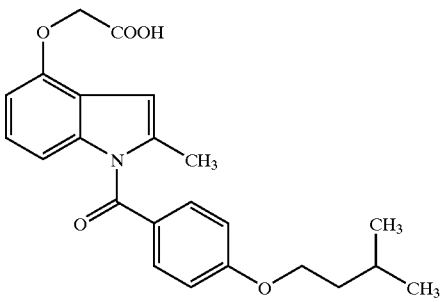

TLC: Rf 0.46 (chloroform:methanol=5:1);
NMR (CDCl$_3$): δ 7.64 (d, J=8.6 Hz, 2H), 6.92–6.84 (m, 3H), 6.70–6.45 (m, 3H), 4.72 (s, 2H), 4.05 (t, J=6.6 Hz, 2H), 2.37 (s, 3H), 1.83 (m, 1H), 1.72 (m, 2H), 0.97 (d, J=6.4 Hz, 6H).

EXAMPLE 3(6)
1-(4-Pentoxybenzoyl)-2-methylindolyl-4-oxyacetic Acid

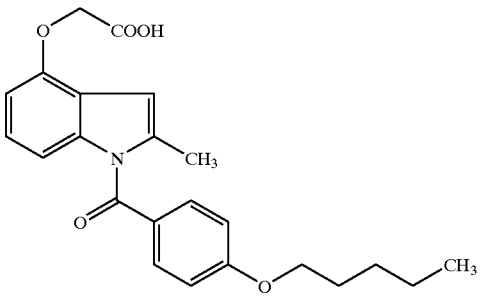

TLC: Rf 0.26 (chloroform:methanol=9:1);
NMR (CDCl$_3$): δ 7.70 (d, J=8.7 Hz, 2H), 6.98–6.90 (m, 3H), 6.72 (d, J=8.7 Hz, 1H), 6.58 (brs, 1H), 6.52 (d, J=8.1 Hz, 1H), 4.80 (s, 2H), 4.04 (t, J=6.6 Hz, 2H), 2.43 (s, 3H), 2.10–1.30 (m, 7H), 0.95 (t, J=6.9 Hz, 3H).

REFERENCE EXAMPLE 17
3-(2-Methylindol-4-yl)acrylic Acid Methyl Ester

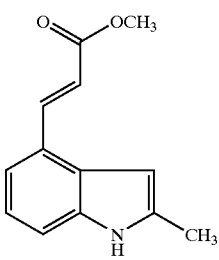

To a solution 2-methyl-4-trifluoromethylsulfoxyindole (3.2 g; prepared in Reference Example 2) in N,N-dimethylformamide (50 ml) was added acrylic acid methyl ester (2.24 ml), diisopropylethylamine (5.9 ml) and dichlorobis(triphenylphosphine)palladium(II) (238 mg), and the mixture was stirred at 95° C. for 2 days. To the reaction mixture was added water and ethyl acetate, then separated. The aqueous layer was extracted with ethyl acetate. The combined organic layer was washed with water and a saturated aqueous solution of sodium chloride, successively, dried and concentrated under reduced pressure. The residue was purified by column chromatography on silica gel (hexane—ethyl acetate) to give the title compound (950 mg) having the following physical data.
TLC: Rf 0.50 (hexane:ethyl acetate=8:2).

REFERENCE EXAMPLE 18
3-(2-Methylindol-4-yl)acrylic Acid

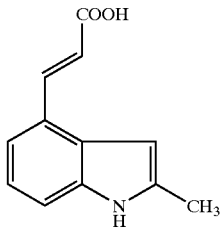

A title compound (700 mg) having the following physical data was obtained by the same procedure as Reference Example 14, using 3-(2-methylindol-4-yl)acrylic acid methyl ester (950 mg; prepared in Reference Example 17).
TLC: Rf 0.54(chloroform:methanol=9:1).

REFERENCE EXAMPLE 19
3-(2-Methylindol-4-yl)acrylic Acid Allyl Ester

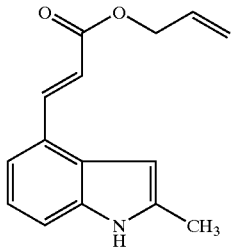

A title compound (240 mg) having the following physical data was obtained by the same procedure as Reference Example 15, using 3-(2-methylindol-4-yl)acrylic acid (300 mg; prepared in Reference Example 18).
TLC: Rf 0.43 (hexane:ethyl acetate=8:2).

REFERENCE EXAMPLE 20
3-(1-(4-Butoxybenzoyl)-2-methylindol-4-yl)acrylic Acid Allyl Ester

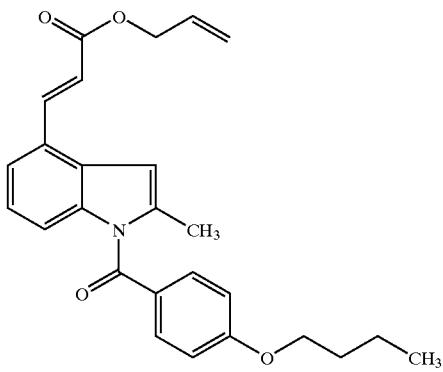

A title compound (545 mg) having the following physical data was obtained by the same procedure as Reference Example 16, using 3-(2-methylindol-4-yl)acrylic acid allyl ester (240 mg; prepared in Reference Example 19).
TLC: Rf 0.59 (hexane:ethyl acetate=8:2);
NMR (CDCl$_3$): δ 8.10–8.00 (m, 1H), 7.70 (d, 2H), 7.39 (d, 1H), 7.10–6.90 (m, 4H), 6.72 (s, 1H), 6.58 (d, 1H), 6.10–5.95 (m, 1H), 5.95–5.85 (m, 1H9, 5.82–5.75 (m, 1H), 4.80–4.70 (m, 2H), 4.10–4.00 (m, 2H), 2.47 (s, 3H), 1.90–1.70 (m, 2H), 1.70–1.40 (m, 2H), 1.10–0.95 (m, 3H).

EXAMPLE 4
3-(1-(4-Butoxybenzoyl)-2-methylindol-4-yl)acrylic Acid

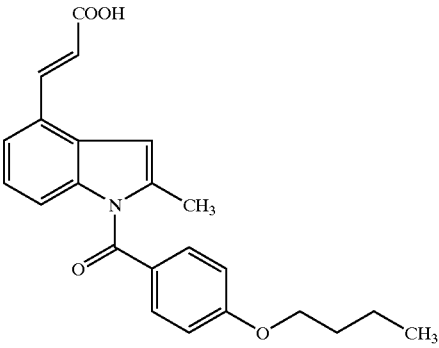

A title compound (374 mg) having the following physical data was obtained by the same procedure as Example 1, using 3-(1-(4-butoxybenzoyl)-2-methylindol-4-yl)acrylic acid allyl ester (413 mg; prepared in Reference Example 20).
TLC: Rf 0.53 (chloroform:methanol=9:1);
NMR (CDCl$_3$): δ 8.16 (d, J=16.2 Hz, 1H), 7.70 (d, J=9.0 Hz, 2H), 7.43 (brd, J=7.2 Hz, 1H), 7.15–7.03 (m, 2H), 6.96 (d, J=9.0 Hz, 2H), 6.74 (brs, 1H), 6.59 (d, J=16.2 Hz, 1H), 4.06 (t, J=6.3 Hz, 2H), 2.48 (s, 3H), 1.88–1.76 (m, 2H), 1.60–1.46 (m, 2H), 1.00 (t, J=7.2 Hz, 3H).

EXAMPLES 4(1) TO 4(7)

Each compound having the following physical data was obtained by the same procedures as a series of reactions of Reference Example 17, 18, 19, 20 and Example 4.

EXAMPLE 4(1)
3-(1-(4-Benzyloxybenzoyl)-2-methylindol-4-yl)-2-acrylic Acid

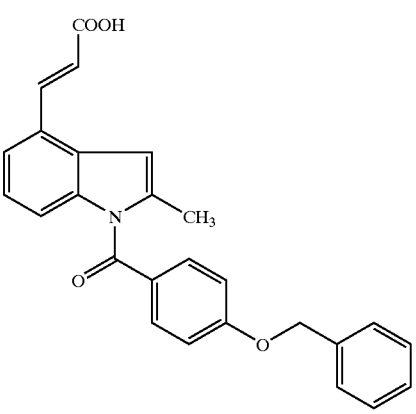

TLC: Rf 0.51 (chloroform:methanol=10:1);
NMR (DMSO-d$_6$): δ 7.90 (d, J=16 Hz, 1H), 7.65 (d, J=8.6 Hz, 2H), 7.60–7.30 (m, 6H), 7.17 (d, J=8.6 Hz, 2H), 7.16–7.05 (m, 2H), 6.90 (s, 1H), 6.60 (d, J=16 Hz, 1H), 5.21 (s, 2H), 2.36 (s, 3H).

EXAMPLE 4(2)
3-(1-(4-Pentyloxybenzoyl)-2-methylindol-4-yl)-2-acrylic Acid

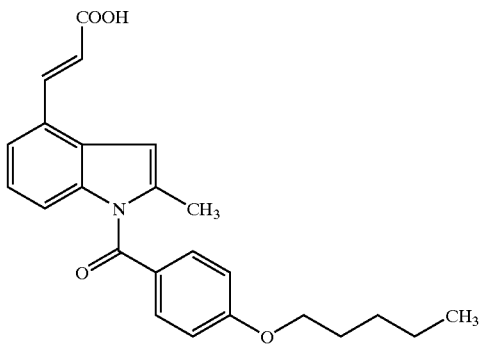

TLC: Rf 0.31 (chloroform:methanol=9:1);
NMR (CDCl₃): δ 8.15 (d, J=15.9 Hz, 1H), 7.70 (d, J=9.0 Hz, 2H), 7.43 (d, J=7.2 Hz, 1H), 7.15–7.02 (m, 2H), 6.96 (d, J=9.0 Hz, 2H), 6.74 (s, 1H), 6.58 (d, J=15.9 Hz, 1H), 4.05 (t, J=6.3 Hz, 2H), 2.48 (s, 3H), 2.00–1.30 (m, 7H), 0.95 (t, J=7.2 Hz, 3H).

EXAMPLE 4(3)
3-(1-(4-Phenethyloxybenzoyl)-2-methylindol-4-yl)-2-acrylic Acid

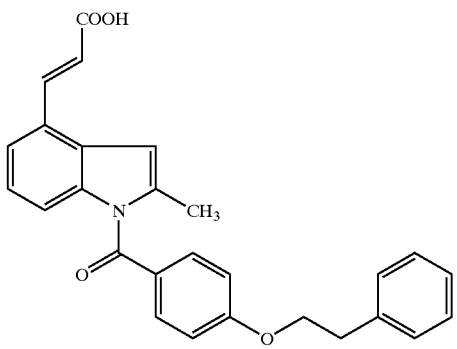

TLC: Rf 0.51 (chloroform:methanol=10:1);
NMR (CDCl₃): δ 8.16 (d, J=16 Hz, 1H), 7.68 (d, J=9.0 Hz, 2H), 7.44–7.26 (m, 6H), 7.09 (m, 2H), 6.96 (d, J=9.0 Hz, 2H), 6.74 (s, 1H), 6.58 (d, J=16 Hz, 1H), 4.27 (t, J=7.0 Hz, 2H), 3.15 (t, J=7.0 Hz, 2H), 2.47 (s, 3H).

EXAMPLE 4(4)
3-(1-(4-(3-Methylbutoxy)benzoyl)-2-methylindol-4-yl)-2-acrylic Acid

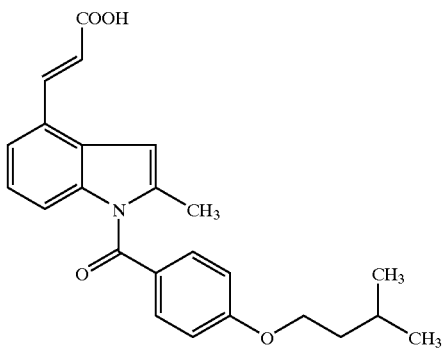

TLC: Rf 0.60 (chloroform:methanol=10:1);
NMR (DMSO-d₆): δ 12.4 (brs, 1H), 7.90 (d, J=16 Hz, 1H), 7.66–7.60 (m, 2H), 7.52 (brd, J=6.4 Hz, 2H), 7.11–7.05 (m, 4H), 6.90 (s, 1H), 6.59 (d, J=16 Hz, 1H), 4.09 (t, J=6.4 Hz, 2H), 2.36 (s, 3H), 1.90–1.50 (m, 3H), 0.92 (dd, J=6.4, 2.0 Hz, 6H).

EXAMPLE 4(5)
3-(1-(4-(2-Ethoxyethoxy)benzoyl)-2-methylindol-4-yl)-2-acrylic Acid

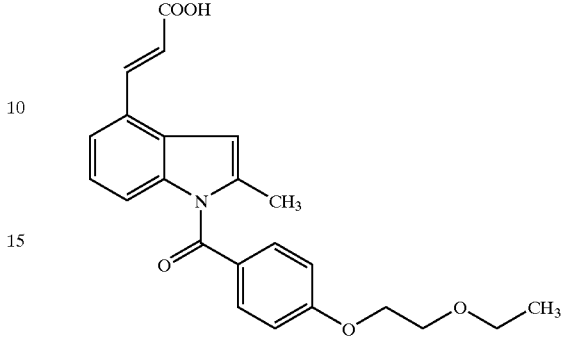

TLC: Rf 0.60 (ethyl acetate);
NMR (CDCl₃): δ 8.15 (d, J=15.9 Hz, 1H), 7.70 (d, J=9.0 Hz, 2H), 7.42 (m, 1H), 7.09–6.98 (m, 4H), 6.74 (s, 1H), 6.58 (d, J=15.9 Hz, 1H), 4.22 (t, J=4.6 Hz, 2H), 3.84 (t, J=4.6 Hz, 2H), 3.63 (q, J=7.0 Hz, 2H), 2.48 (d, J=1.0 Hz, 3H), 1.27 (t, J=7.0 Hz, 3H).

EXAMPLE 4(6)
3-(1-(4-Propyloxybenzoyl)-2-methylindol-4-yl)-2-acrylic Acid

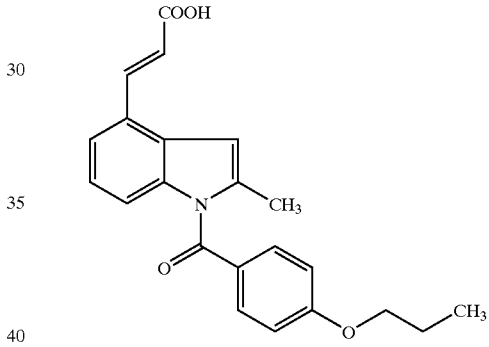

TLC: Rf 0.48 (chloroform:methanol=9:1);
NMR (CDCl₃): δ 8.15 (d, J=15.9 Hz, 1H), 7.71 (d, J=8.7 Hz, 2H), 7.43 (brd, J=7.2 Hz, 1H), 7.15–7.03 (m, 2H), 6.97 (d, J=8.7 Hz, 2H), 6.74 (s, 1H), 6.58 (d, J=15.9 Hz, 1H), 4.02 (t, J=6.6 Hz, 2H), 2.48 (s, 3H), 1.95–1.80 (m, 2H), 1.07 (t, J=7.5 Hz, 3H).

EXAMPLE 4(7)
3-(1-(4-(2-(Pyridin-2-yl)ethoxy)benzoyl)-2-methylindol-4-yl)-2-acrylic Acid

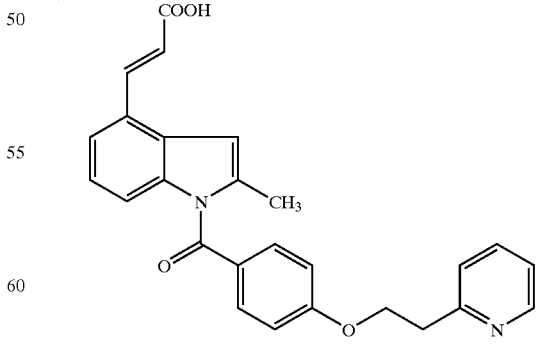

TLC: Rf 0.40 (chloroform:methanol=9:1);
NMR (CDCl₃): δ 8.61 (d, J=5.0 Hz, 1H), 8.13 (d, J=16.0 Hz, 1H), 7.71–6.95 (m, 10H), 6.72 (s, 1H), 6.58 (d, J=16.0 Hz, 1H), 4.19 (t, J=6.8 Hz, 2H), 3.34 (t, J=6.8 Hz, 2H), 2.45 (s, 3H).

EXAMPLE 5
3-(1-(4-Butoxybenzoyl)-2-methylindol-4-yl)propionic Acid

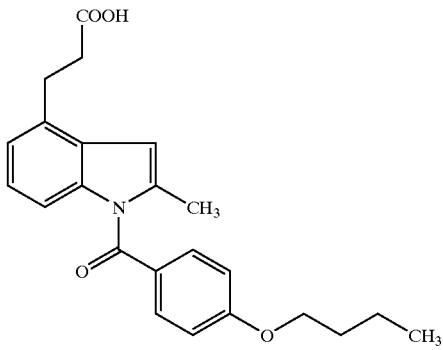

To a solution of 3-(1-(4-butoxybenzoyl)-2-methylindol-4-yl)acrylic acid (300 mg; prepared in Example 4) in methanol—ethyl acetate (5 ml+5 ml) was added palladium on activated carbon (100 mg) at room temperature. The inside of the vessel was replaced with hydrogen and the mixture was stirred at room temperature for 2 hours. The mixture was filtered through Celite (trademark). The filtrate and washing with chloroform were combined, and then concentrated under reduced pressure. The residue was purified by column chromatography on silica gel (chloroform—methanol) to give the title compound (25 mg) having the following physical data.

TLC: Rf 0.58 (chloroform:methanol=9:1);

NMR (CDCl$_3$): δ 7.70 (d, J=9.3 Hz, 2H), 7.00–6.86 (m, 5H), 6.48 (s, 1H), 4.05 (t, J=6.6 Hz, 2H), 3.75–3.65 (br, 1H), 3.19 (t, J=8.4 Hz, 2H), 2.79 (t, J=8.4 Hz, 2H), 2.45 (s, 3H), 1.87–1.72 (m, 2H), 1.60–1.40 (m, 2H), 1.00 (t, J=7.5 Hz, 3H).

REFERENCE EXAMPLE 21
4-(1-(4-Butoxybenzoyl)-2-methylindol-4-yl)butanoic Acid Benzyl Ester

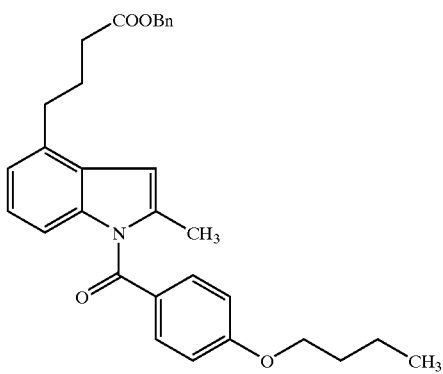

(1) To a solution of 3-(1-(4-butoxybenzoyl)-2-methylindol-4-yl)propionic acid (1.77 g; prepared in Example 5) in toluene (20 ml) was added oxalyl chloride (0.64 ml) and N,N-dimethylformamide (few drops) at room temperature, and the mixture was stirred at room temperature for 1 hour.

To a solution of the acid chloride prepared in (1) in tetrahydrofuran—acetonitrile (4 ml+4 ml) was added trimethylsilyidiazomethane (4.67 ml; 2M) at 0° C. The mixture was stirred at the same temperature for 1 hour and then concentrated under reduced pressure. To the residue was added benzyl alcohol (4 ml) and 2,4,6-collidine (4 ml), and the mixture was stirred at 180° C. for 30 minutes. After cooling to room temperature, the reaction mixture was purified by column chromatography on silica gel (hexane—ethyl acetate) to give the title compound (460 mg) having the following physical data.

TLC: Rf 0.51 (hexane:ethyl acetate=8:2).

EXAMPLE 6
4-(1-(4-Butoxybenzoyl)-2-methylindol-4-yl)butanoic Acid

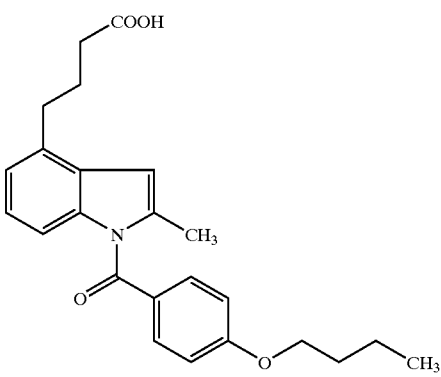

A title compound (170 mg) having the following physical data was obtained by the same procedure as Example 2, using 4-(1-(4-butoxybenzoyl)-2-methylindol-4-yl)butanoic acid benzyl ester (460 mg; prepared in Reference Example 21).

TLC: Rf 0.50 (chloroform:methanol=9:1);

NMR (CDCl$_3$): δ 7.71 (d, J=9.0 Hz, 2H), 7.00–6.86 (m, 5H), 6.48 (s, 1H), 4.05 (t, J=6.6 Hz, 2H), 2.90 (t, J=7.2 Hz, 2H), 2.48–2.38 (m, 5H), 2.14–2.00 (m, 2H), 2.00–1.40 (m, 5H), 1.00 (t, J=7.5 Hz, 3H).

EXAMPLES 7 TO EXAMPLE 7(228)

The compounds of the present invention having the following physical data were obtained by the same procedures as a series of reactions of Reference Example 7→Reference Example 8→Example 1. In Examples 7(37) and 7(151), hydroxy or amino group was protected by protective group, and the protective group was removed before the reaction corresponding Example 1.

EXAMPLE 7
1-(4-Butoxybenzoyl)-5-methoxy-2-methylindole-4-acetic Acid

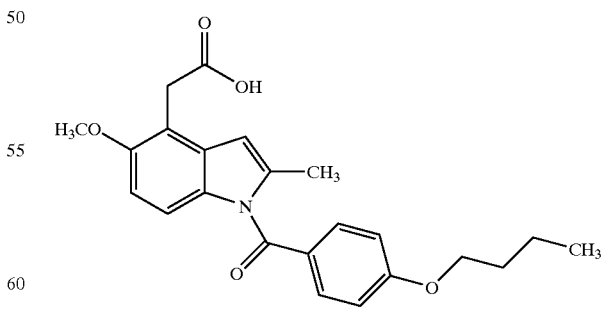

TLC: Rf 0.48 (chloroform:methanol=10:1);

MS: (MALDI, Pos.): 434 (M+K)$^+$, 418 (M+Na)$^+$, 396 (M+H)$^+$;

NMR (CDCl$_3$): δ 7.70–7.67 (m, 2H), 6.98–6.93 (m, 3H), 6.70 (d, J=9.3 Hz, 1H), 6.41 (s, 1H), 4.05 (t, J=6.5 Hz, 2H), 3.90 (s, 2H), 3.86 (s, 3H), 2.41 (s, 3H), 1.82 (m, 2H), 1.54 (m, 2H), 1.00 (t, J=7.5 Hz, 3H).

EXAMPLE 7(1)

1-(4-(2-Methylbutyloxy)benzoyl)-2-methylindole-4-acetic Acid

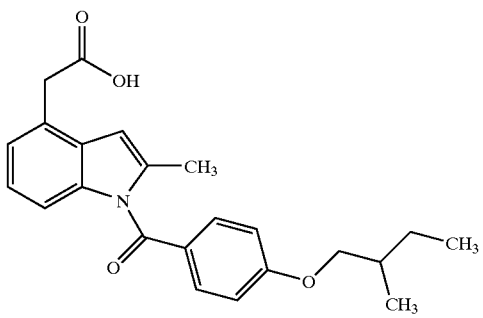

TLC: Rf 0.51 (chloroform:methanol=10:1);

MS: (MALDI, Pos.): 418 (M+K)$^+$, 402 (M+Na)$^+$.

EXAMPLE 7(2)

1-(4-Cyclopentyloxybenzoyl)-2-methylindole-4-acetic Acid

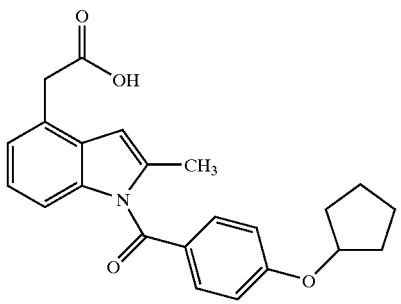

TLC: Rf 0.51 (chloroform:methanol=10:1);

MS: (APCI, Neg.): 376 (M−H)$^-$.

EXAMPLE 7(3)

1-(4-(1-Ethylpropyloxy)benzoyl)-2-methylindole-4-acetic Acid

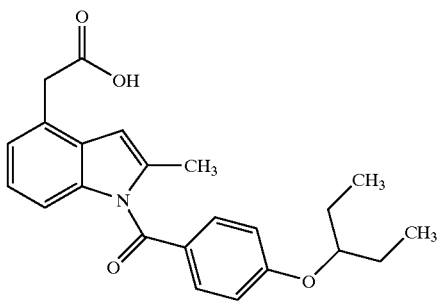

TLC: Rf 0.51 (chloroform:methanol=10:1);

MS: (APCI, Neg.): 378 (M−H)$^-$.

EXAMPLE 7(4)

1-(4-(Tetrahydrofuran-3-yloxy)benzoyl)-2-methylindole-4-acetic Acid

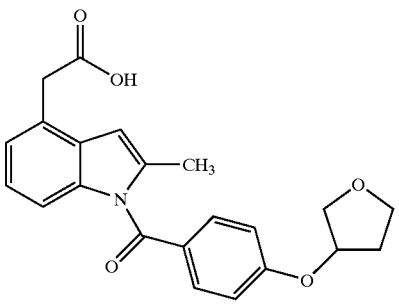

TLC: Rf 0.50 (chloroform:methanol=10:1);

MS: (APCI, Neg.): 378 (M−H)$^-$.

EXAMPLE 7(5)

1-(4-(1,2-Dimethylpropyloxy)benzoyl)-2-methylindole-4-acetic Acid

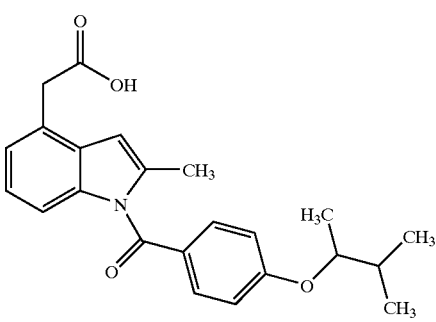

TLC: Rf 0.51 (chloroform:methanol=10:1);

MS: (MALDI, Pos.): 418 (M+K)$^+$, 402 (M+Na)$^+$.

EXAMPLE 7(6)

1-(4-Cyclobutyloxybenzoyl)-2-methylindole-4-acetic Acid

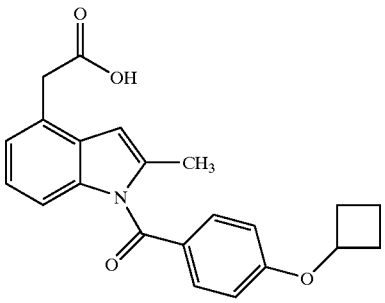

TLC: Rf 0.51 (chloroform:methanol=10:1);

MS: (MALDI, Pos.): 402 (M+K)$^+$, 386 (M+Na)$^+$.

EXAMPLE 7(7)

1-(4-(1-Methylcyclopropylmethyl)benzoyl)-2-methylindole-4-acetic Acid

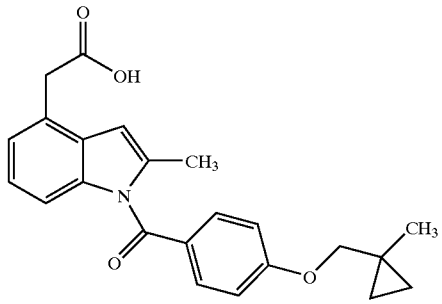

TLC: Rf 0.51 (chloroform:methanol=10:1);

MS: (MALDI, Pos.): 416 (M+K)$^+$, 400 (M+Na)$^+$.

EXAMPLE 7(8)

1-(4-Cyclobutylmethyloxybenzoyl)-2-methylindole-4-acetic Acid

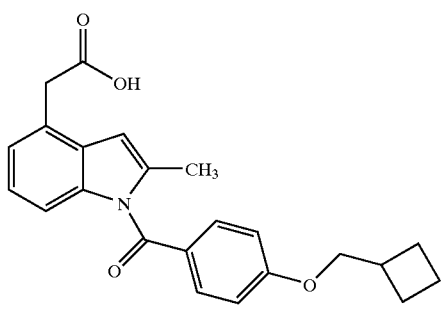

TLC: Rf 0.51 (chloroform:methanol=10:1);

MS: (MALDI, Pos.): 416 (M+K)$^+$, 400 (M+Na)$^+$.

EXAMPLE 7(9)

1-(4-(2-Benzyloxyethyloxy)benzoyl)-2-methylindole-4-acetic Acid

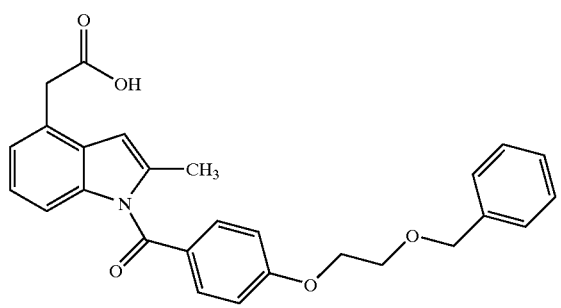

TLC: Rf 0.53 (chloroform:methanol=10:1);

MS: (APCI, Neg.): 442 (M−H)$^-$.

EXAMPLE 7(10)

1-(4-Cyclopropylmethyloxybenzoyl)-2-methylindole-4-acetic Acid

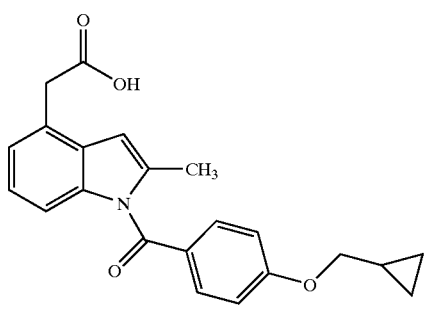

TLC: Rf 0.51 (chloroform:methanol=10:1);

MS: (MALDI, Pos.):402 (M+K)$^+$, 386 (M+Na)$^+$.

EXAMPLE 7(11)

1-(4-(3,7-Dimethyl-6-octen-1-yloxy)benzoyl)-2-methylindole-4-acetic Acid

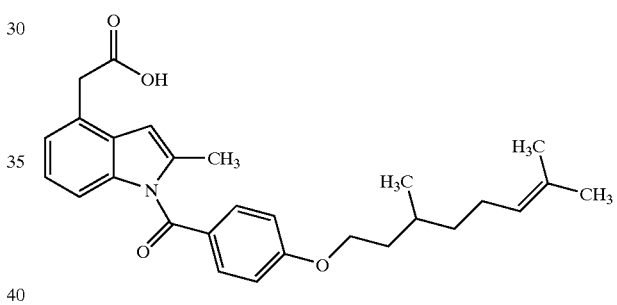

TLC: Rf 0.53 (chloroform:methanol=10:1);

MS: (MALDI, Pos.): 486 (M+K)$^+$, 470 (M+Na)$^+$.

EXAMPLE 7(12)

1-(4-(3-(3,4-Dimethoxyphenyl)propyloxy)benzoyl)-2-methylindole-4-acetic Acid

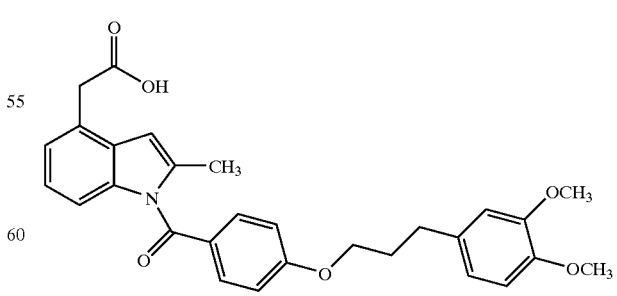

TLC: Rf 0.52 (chloroform:methanol=10:1);

MS: (MALDI, Pos.): 526 (M+K)$^+$, 510 (M+Na)$^+$.

EXAMPLE 7(13)

1-(4-(4-(4-Methoxyphenyl)butyloxy)benzoyl)-2-methylindole-4-acetic Acid

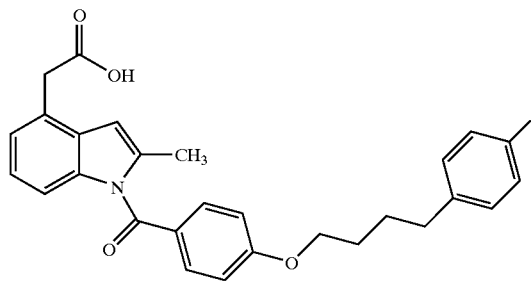

TLC: Rf 0.52 (chloroform:methanol=10:1);

MS: (MALDI, Pos.): 510 (M+K)$^+$, 494 (M+Na)$^+$.

EXAMPLE 7(14)

1-(4-(2,3,5,6-Tetrahydropyran-4-yloxy)benzoyl)-2-methylindole-4-acetic Acid

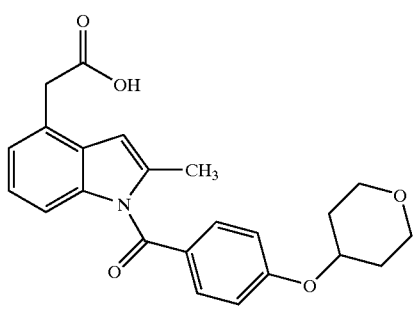

TLC: Rf 0.33 (chloroform:methanol=10:1);

MS: (MALDI, Pos.): 432 (M+K)$^+$, 416 (M+Na)$^+$, 393 (M)$^+$.

EXAMPLE 7(15)

1-(4-(1-Methylpropyloxy)benzoyl)-2-methylindole-4-acetic Acid

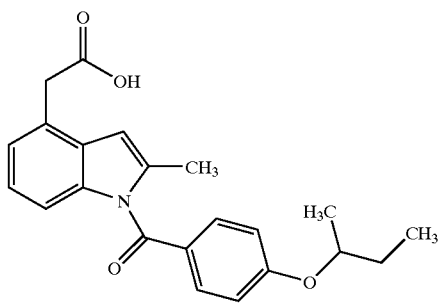

TLC: Rf 0.33 (chloroform:methanol=10:1);

MS: (MALDI, Pos.): 365 (M)$^+$.

EXAMPLE 7(16)

1-(4-(5-Chloropentyloxy)benzoyl)-2-methylindole-4-acetic Acid

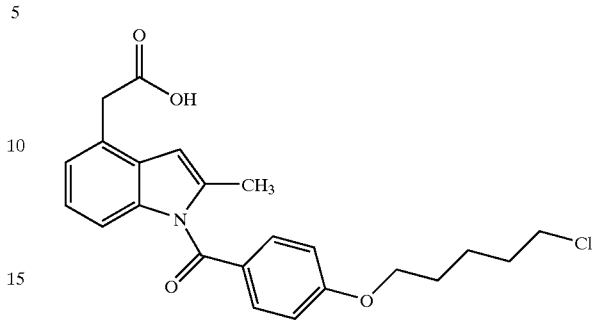

TLC: Rf 0.28 (chloroform:methanol=10:1);

MS: (MALDI, Pos.): 436 (M+Na)$^+$, 413 (M)$^+$.

EXAMPLE 7(17)

1-(4-(2,3,4,5-Tetrahydrofuran-2-ylmethyloxy)benzoyl)-2-methylindole-4-acetic Acid

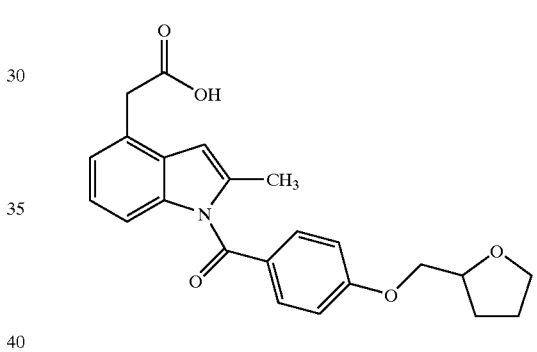

TLC: Rf 0.27 (chloroform:methanol=10:1);

MS: (MALDI, Pos.): 432 (M+K)$^+$, 416 (M+Na)$^+$, 394 (M+H)$^+$, 393 (M)$^+$.

EXAMPLE 7(18)

1-(4-(2-(N,N-Diethylamino)ethyloxy)benzoyl)-2-methylindole-4-acetic Acid

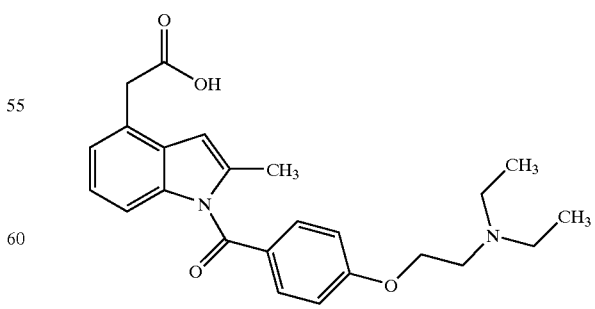

TLC: Rf 0.08 (chloroform:methanol=2:1);

MS: (MALDI, Pos.): 409 (M+H)$^+$.

EXAMPLE 7(19)

1-(4-(2-(Piperidin-1-yl)ethyloxy)benzoyl)-2-methylindole-4-acetic Acid

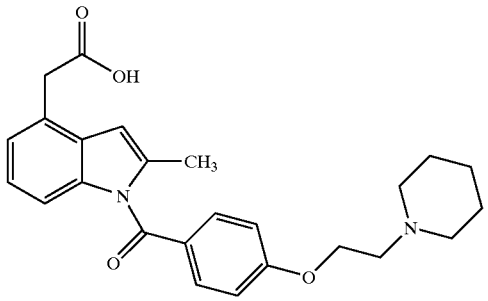

TLC: Rf 0.16 (chloroform:methanol=2:1);

MS: (MALDI, Pos.): 443 (M+Na)+, 421 (M+H)+.

EXAMPLE 7(20)

1-(4-(2-Cyclopentylethyloxy)benzoyl)-2-methylindole-4-acetic Acid

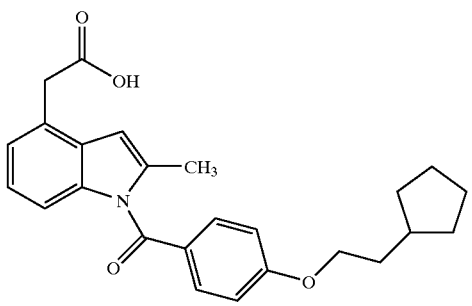

TLC: Rf 0.33 (chloroform:methanol=10:1);

MS: (MALDI, Pos.):428 (M+Na)+, 406 (M+H)+.

EXAMPLE 7(21)

1-(4-(3-Methoxy-3-methylbutyloxy)benzoyl)-2-methylindole-4-acetic Acid

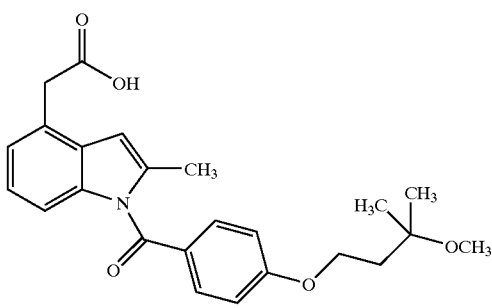

TLC: Rf 0.34 (chloroform:methanol=10:1);

MS: (MALDI, Pos.): 448 (M+Na)+, 432 (M+H)+.

EXAMPLE 7(22)

1-(4-(2-(3,5-Dimethylpyrazol-1-yl)ethyloxy)benzoyl)-2-methylindole-4-acetic Acid

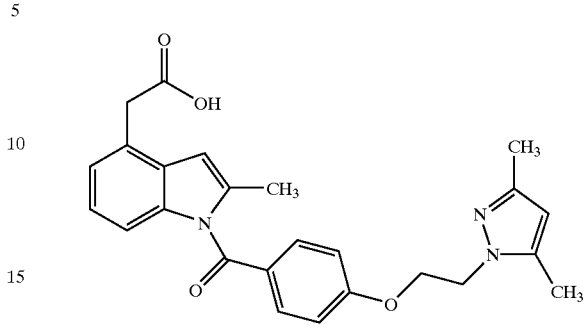

TLC: Rf 0.33 (chloroform:methanol=10:1);

MS: (APCI, Neg.): 430 (M−H)−.

EXAMPLE 7(23)

1-(4-(2-(N,N-Diallylamino)ethyloxy)benzoyl)-2-methylindole-4-acetic Acid

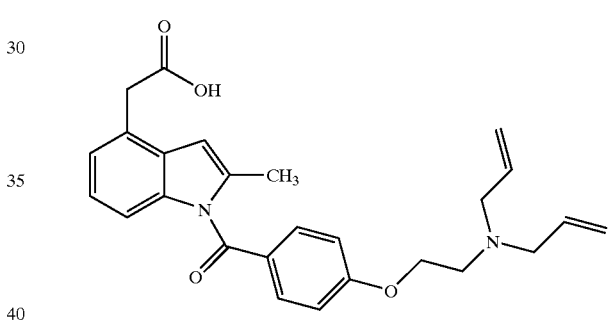

TLC: Rf 0.31 (chloroform:methanol=10:1);

MS: (APCI, Neg.): 431 (M−H)−.

EXAMPLE 7(24)

1-(4-(6-(N,N-Dimethylamino)hexyloxy)benzoyl)-2-methylindole-4-acetic Acid

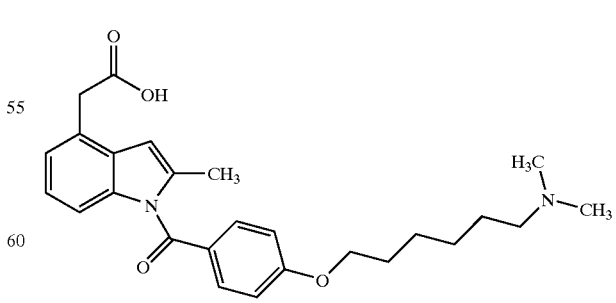

TLC: Rf 0.53 (chloroform:methanol=10:1);

MS: (APCI, Neg.): 435 (M−H)−.

EXAMPLE 7(25)

1-(4-(3-Butyn-1-yloxy)benzoyl)-2-methylindole-4-acetic Acid

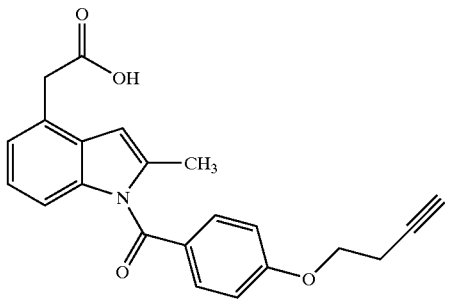

TLC: Rf 0.51 (chloroform:methanol=10:1);

MS: (APCI, Neg.): 360 (M−H)⁻.

EXAMPLE 7(26)

1-(4-Cyclohexylmethyloxybenzoyl)-2-methylindole-4-acetic Acid

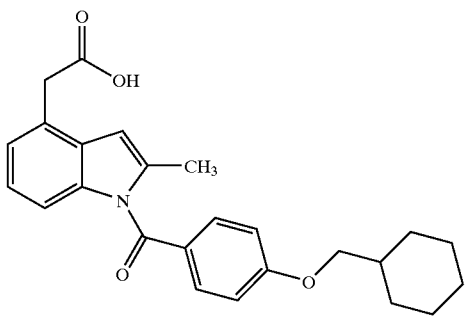

TLC: Rf 0.51 (chloroform:methanol=10:1);

MS: (MALDI, Pos.): 444 (M+K)⁺, 428 (M+Na)⁺.

EXAMPLE 7(27)

1-(4-(2-(Pyrrol-1-yl)ethyloxy)benzoyl)-2-methylindole-4-acetic Acid

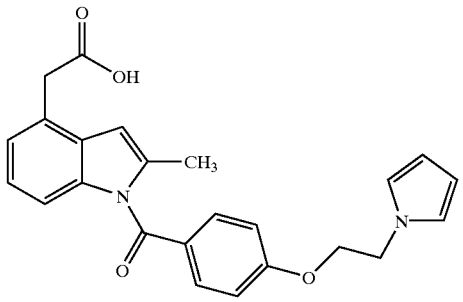

TLC: Rf 0.53 (chloroform:methanol=10:1);

MS: (MALDI, Pos.): 441 (M+K)⁺, 425 (M+Na)⁺.

EXAMPLE 7(28)

1-(4-(2-(3,4-Dimethoxyphenyl)ethyloxy)benzoyl)-2-methylindole-4-acetic Acid

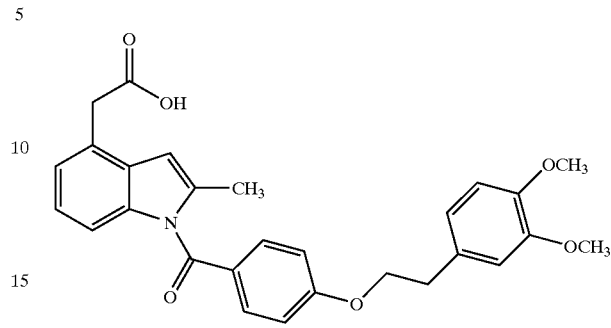

TLC: Rf 0.51 (chloroform:methanol=10:1);

MS: (MALDI, Pos.): 512 (M+K)⁺, 496 (M+Na)⁺.

EXAMPLE 7(29)

1-(4-(3-Pentyn-1-yloxy)benzoyl)-2-methylindole-4-acetic Acid

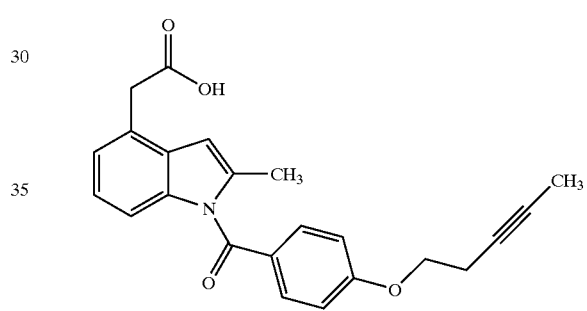

TLC: Rf 0.51 (chloroform:methanol=10:1);

MS: (MALDI, Pos.): 414 (M+K)⁺, 398 (M+Na)⁺.

EXAMPLE 7(30)

1-(4-Phenylbuthyloxybenzoyl)-2-methylindole-4-acetic Acid

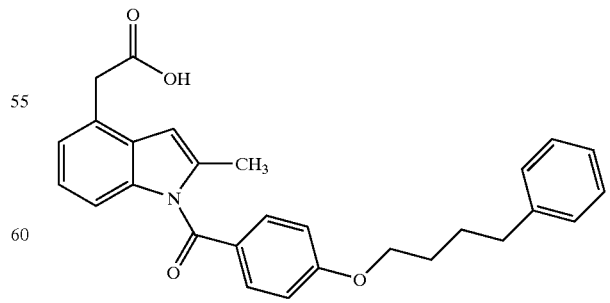

TLC: Rf 0.55 (chloroform:methanol=10:1);

MS: (MALDI, Pos.): 480 (M+K)⁺, 464 (M+Na)⁺.

EXAMPLE 7(31)

1-(4-(4-Methylthiobutyloxy)benzoyl)-2-methylindole-4-acetic Acid

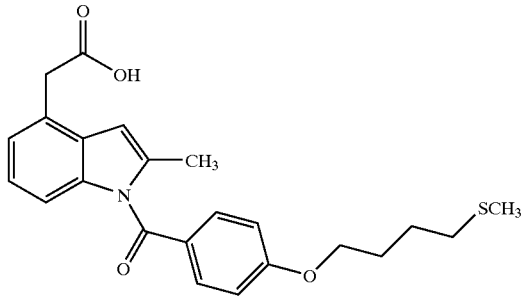

TLC: Rf 0.51 (chloroform:methanol=10:1);

MS: (MALDI, Pos.): 450 (M+K)$^+$, 434 (M+Na)$^+$.

EXAMPLE 7(32)

1-(4-(4-Pentyn-1-yloxy)benzoyl)-2-methylindole-4-acetic Acid

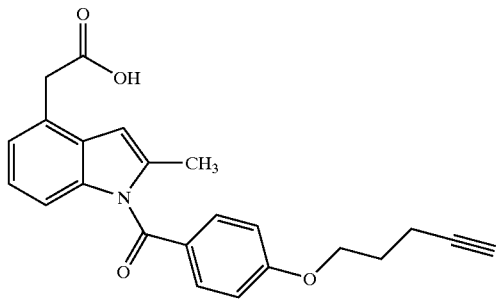

TLC: Rf 0.51 (chloroform:methanol=10:1);

MS: (MALDI, Pos.): 414 (M+K)$^+$, 398 (M+Na)$^+$.

EXAMPLE 7(33)

1-(4-(2-Phenylthioethyloxy)benzoyl)-2-methylindole-4-acetic Acid

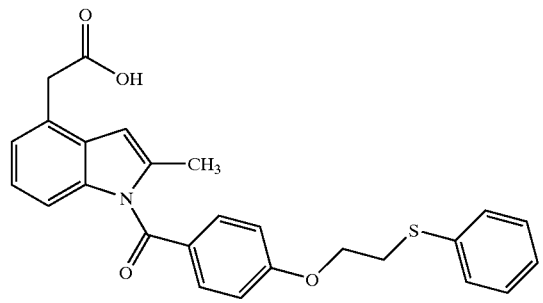

TLC: Rf 0.51 (chloroform:methanol=10:1);

MS: (MALDI, Pos.): 484 (M+K)$^+$, 468 (M+Na)$^+$.

EXAMPLE 7(34)

1-(4-(4-Penten-1-yloxy)benzoyl)-2-methylindole-4-acetic Acid

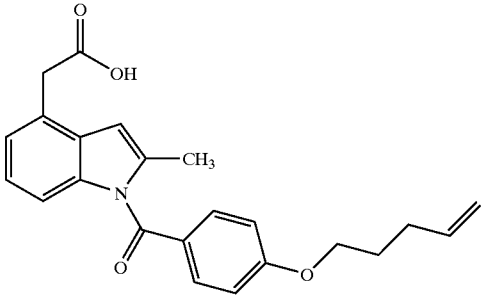

TLC: Rf 0.51 (chloroform:methanol=10:1);

MS: (MALDI, Pos.):416 (M+K)$^+$, 400 (M+Na)$^+$.

EXAMPLE 7(35)

1-(4-(5-Hexen-1-yloxy)benzoyl)-2-methylindole-4-acetic Acid

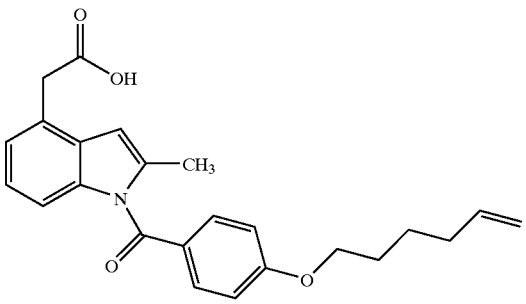

TLC: Rf 0.51 (chloroform:methanol=10:1);

MS: (MALDI, Pos.): 430 (M+K)$^+$, 414 (M+Na)$^+$.

EXAMPLE 7(36)

1-(4-(2-Benzylthioethyloxy)benzoyl)-2-methylindole-4-acetic Acid

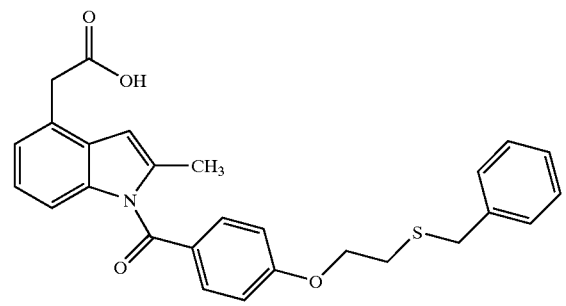

TLC: Rf 0.53 (chloroform:methanol=10:1);

MS: (MALDI, Pos.): 498 (M+K)$^+$, 482 (M+Na)$^+$.

EXAMPLE 7(37)

1-(4-(6-Hydroxyhexyloxy)benzoyl)-2-methylindole-4-acetic Acid

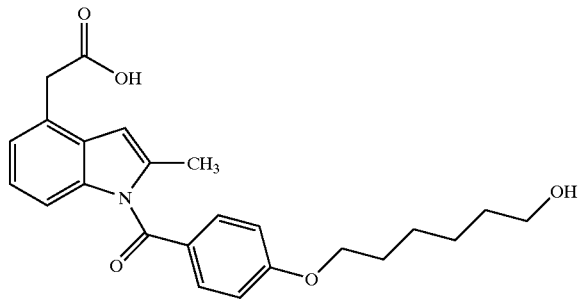

TLC: Rf 0.47 (chloroform:methanol=10:1);

MS: (MALDI, Pos.): 508 (M+K)$^+$, 492 (M+Na)$^+$.

EXAMPLE 7(38)

1-(4-(2-(4-Ethoxyphenyl)ethyloxy)benzoyl)-2-methylindole-4-acetic Acid

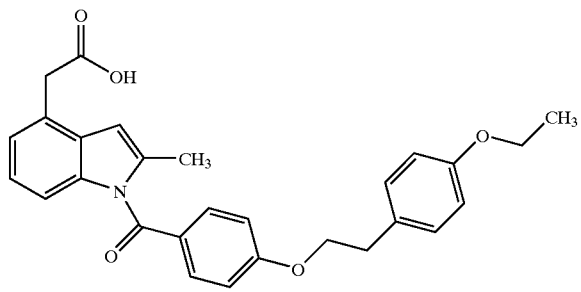

TLC: Rf 0.53 (chloroform:methanol=10:1);

MS: (MALDI, Pos.): 496 (M+K)$^+$, 480 (M+Na)$^+$.

EXAMPLE 7(39)

1-(4-(2-Butoxyethyloxy)benzoyl)-2-methylindole-4-acetic Acid

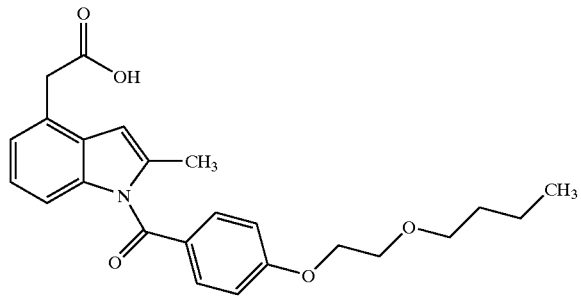

TLC: Rf 0.51 (chloroform:methanol=10:1);

MS: (APCI, Neg.): 408 (M−H)$^−$.

EXAMPLE 7(40)

1-(4-(3-Methyloxetan-3-ylmethyloxy)benzoyl)-2-methylindole-4-acetic Acid

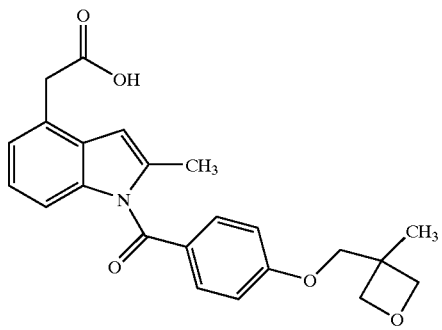

TLC: Rf 0.51 (chloroform:methanol=10:1);

MS: (APCI, Neg.): 392 (M−H)$^−$.

EXAMPLE 7(41)

1-(4-(2-(N-Ethyl-N-(3-methylphenyl)amino)ethyloxy)benzoyl)-2-methylindole-4-acetic Acid

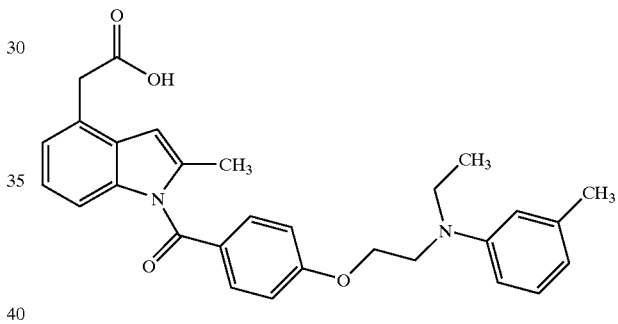

TLC: Rf 0.55 (chloroform:methanol=10:1);

MS: (MALDI, Pos.): 471 (M+H)$^+$.

EXAMPLE 7(42)

1-(4-(2-(N-Methyl-N-phenylamino)ethyloxy)benzoyl)-2-methylindole-4-acetic Acid

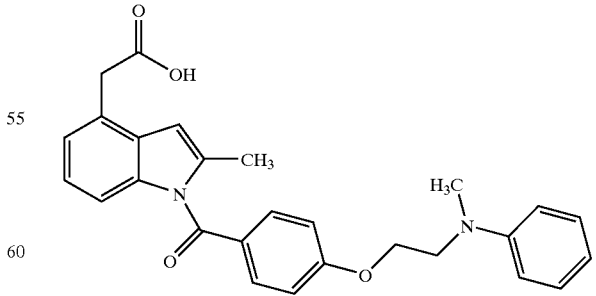

TLC: Rf 0.55 (chloroform:methanol=10:1);

MS: (MALDI, Pos.): 481 (M+K)$^+$, 465 (M+Na)$^+$, 443 (M+H)$^+$.

EXAMPLE 7(43)

1-(4-(3-(4-Methoxyphenyl)propyloxy)benzoyl)-2-methylindole-4-acetic Acid

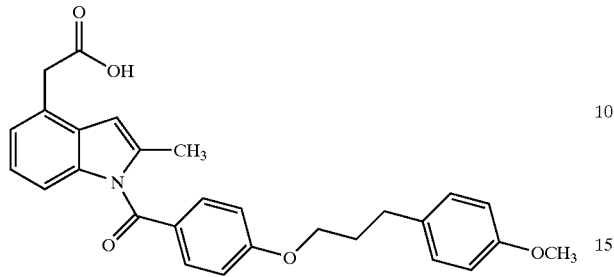

TLC: Rf 0.51 (chloroform:methanol=10:1);

MS: (MALDI, Pos.): 496 (M+K)$^+$, 480 (M+Na)$^+$.

EXAMPLE 7(44)

1-(4-(3-Nonyn-1-yloxy)benzoyl)-2-methylindole-4-acetic Acid

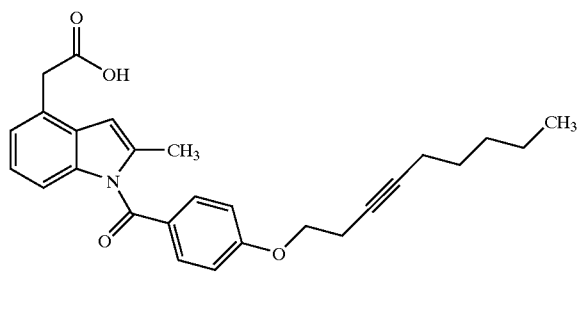

TLC: Rf 0.51 (chloroform:methanol=10:1);

MS: (MALDI, Pos.): 470 (M+K)$^+$, 454 (M+Na)$^+$.

EXAMPLE 7(45)

1-(4-(2-(4-Chlorophenylthio)ethyloxy)benzoyl)-2-methylindole-4-acetic Acid

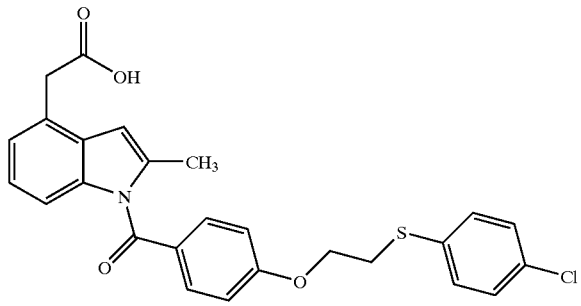

TLC: Rf 0.53 (chloroform:methanol=10:1);

MS: (MALDI, Pos.):518 (M+K)$^+$, 502 (M+Na)$^+$.

EXAMPLE 7(46)

1-(4-(2-Phenylaminoethyloxy)benzoyl)-2-methylindole-4-acetic Acid

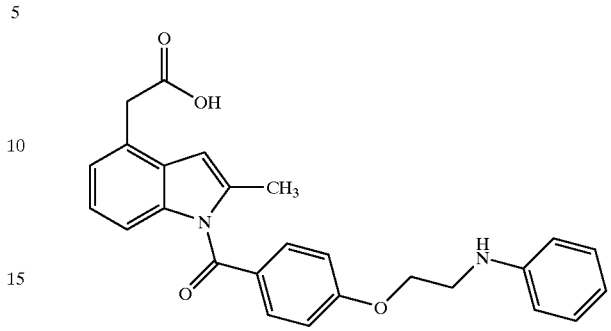

TLC: Rf 0.55 (chloroform:methanol=10:1);

MS: (APCI, Neg.): 427 (M−H)$^−$.

EXAMPLE 7(47)

1-(4-(3-(Pyridin-3-yl)propyloxy)benzoyl)-2-methylindole-4-acetic Acid

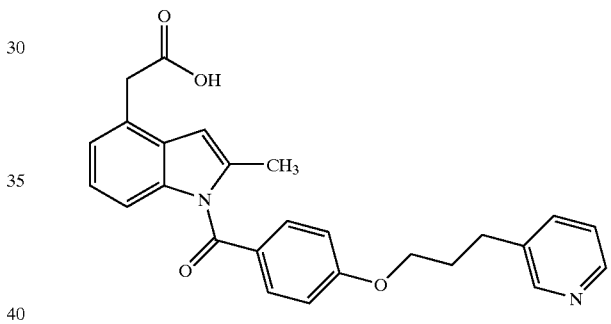

TLC: Rf 0.57 (chloroform:methanol=10:1);

MS: (MALDI, Pos.): 467 (M+K)$^+$, 451 (M+Na)$^+$.

EXAMPLE 7(48)

1-(4-(2-(3-Trifluoromethylphenyl)ethyloxy)benzoyl)-2-methylindole-4-acetic Acid

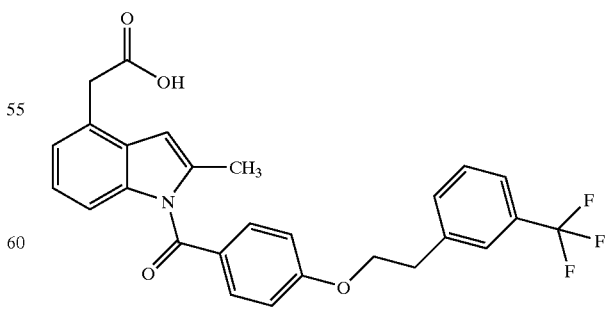

TLC: Rf 0.60 (chloroform:methanol 10:1);

MS: (MALDI, Pos.): 520 (M+K)$^+$, 504 (M+Na)$^+$.

EXAMPLE 7(49)

1-(4-(2-(2-Chlorophenyloxy)ethyloxy)benzoyl)-2-methylindole-4-acetic Acid

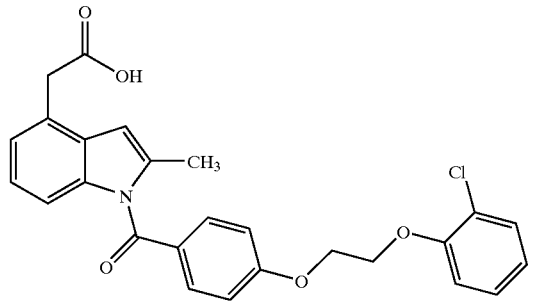

TLC: Rf 0.61 (chloroform:methanol=10:1);
MS: (MALDI, Pos.): 504 (M+K)$^+$, 488 (M+Na)$^+$.

EXAMPLE 7(50)

1-(4-(2-(3-Methylphenyloxy)ethyloxy)benzoyl)-2-methylindole-4-acetic Acid

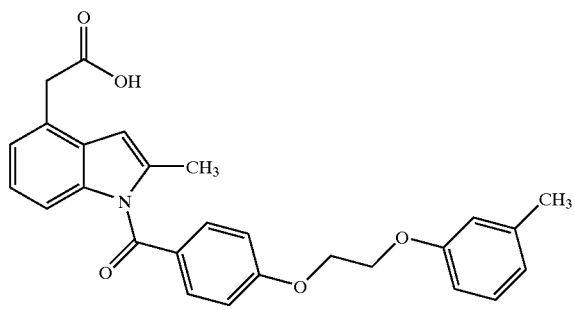

TLC: Rf 0.65 (chloroform:methanol=10:1);
MS: (MALDI, Pos.): 482 (M+K)$^+$, 466 (M+Na)$^+$.

EXAMPLE 7(51)

1-(4-Butoxybenzoyl)-6-methoxy-2-methylindole-4-acetic Acid

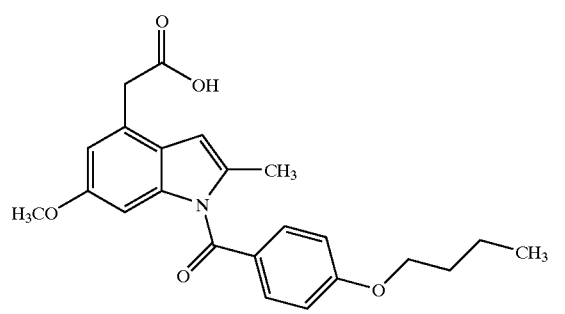

TLC: Rf 0.44 (chloroform:methanol=10:1);
MS: (MALDI, Pos.): 434 (M+K)$^+$, 418 (M+Na)$^+$, 395 (M)$^+$;
NMR (CDCl$_3$): δ 7.70 (m, 2H), 6.95 (m, 2H), 6.73 (d, J=2.1 Hz, 1H), 6.68 (d, J=2.1 Hz, 1H), 6.38 (s, 1H), 4.04 (t, J=6.6 Hz, 2H), 3.81 (s, 2H), 3.65 (s, 3H), 2.34 (s, 3H), 1.81 (m, 2H), 1.51 (m, 2H), 0.99 (t, J=7.5 Hz, 3H).

EXAMPLE 7(52)

1-(4-(Thiophen-2-ylmethyloxy)benzoyl)-2-methylindole-4-acetic Acid

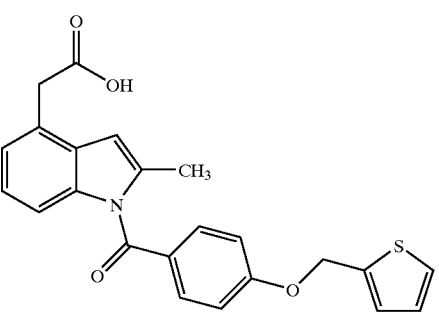

TLC: Rf 0.51 (chloroform:methanol=10:1);
MS: (APCI, Neg.): 404 (M−H)$^-$.

EXAMPLE 7(53)

1-(4-(2-(2-Chloroethyloxy)ethyloxy)benzoyl)-2-methylindole-4-acetic Acid

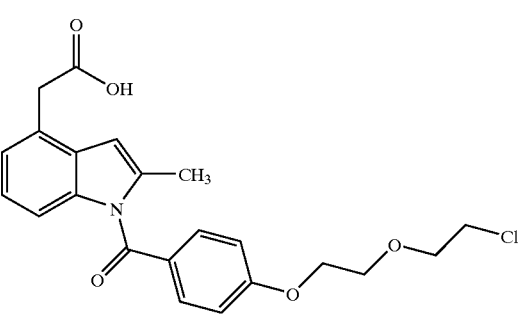

TLC: Rf 0.53 (chloroform:methanol=10:1);
MS: (APCI, Neg.): 414 (M−H)$^-$.

EXAMPLE 7(54)

1-(4-(2-(Morpholin-4-yl)ethyloxy)benzoyl)-2-methylindole-4-acetic Acid

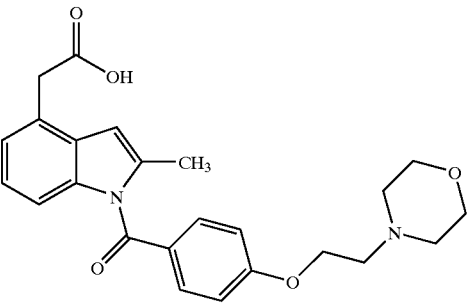

TLC: Rf 0.33 (chloroform methanol=10:1);
MS: (APCI, Neg.): 421 (M−H)$^-$.

EXAMPLE 7(55)

1-(4-(5-Hexyn-1-yloxy)benzoyl)-2-methylindole-4-acetic Acid

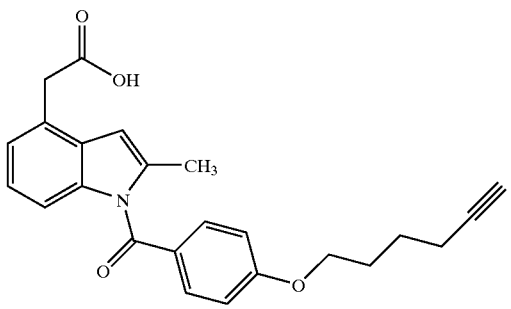

TLC: Rf 0.52 (chloroform:methanol=10:1);

MS: (APCI, Neg.): 388 (M−H)⁻.

EXAMPLE 7(56)

1-(4-(4-Methyl-3-penten-1-yloxy)benzoyl)-2-methylindole-4-acetic Acid

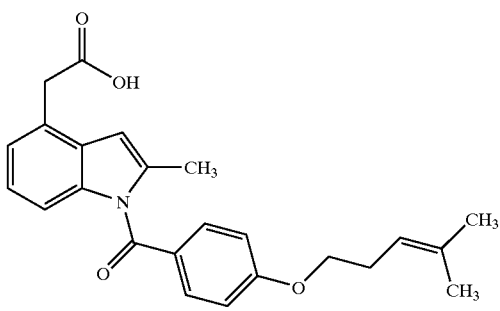

TLC: Rf 0.51 (chloroform:methanol=10:1);

MS: (APCI, Neg.): 390 (M−H)⁻.

EXAMPLE 7(57)

1-(4-(2-(5-Methylfuran-2-yl)ethyloxy)benzoyl)-2-methylindole-4-acetic Acid

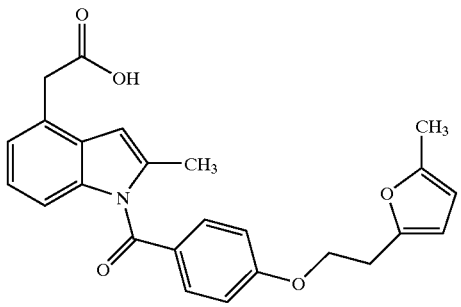

TLC: Rf 0.51 (chloroform:methanol=10:1);

MS: (APCI, Neg.): 416 (M−H)⁻.

EXAMPLE 7(58)

1-(4-(2-(Furan-2-yl)ethyloxy)benzoyl)-2-methylindole-4-acetic Acid

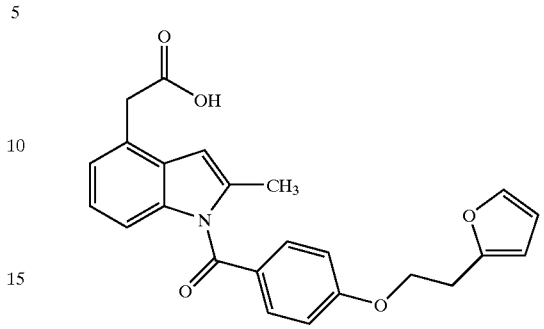

TLC: Rf 0.51 (chloroform:methanol=10:1);

MS: (APCI, Neg.): 402 (M−H)⁻.

EXAMPLE 7(59)

1-(4-(2-Cyclobutyloxyethyloxy)benzoyl)-2-methylindole-4-acetic Acid

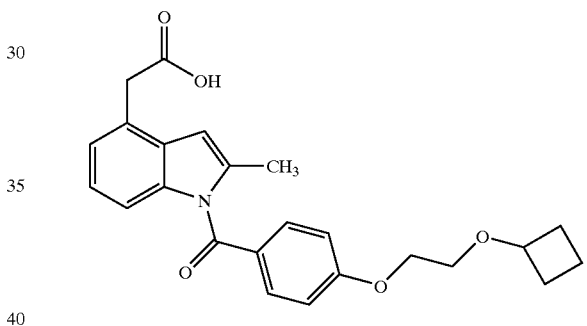

TLC: Rf 0.51 (chloroform:methanol=10:1);

MS: (APCI, Neg.): 406 (M−H)⁻.

EXAMPLE 7(60)

1-(4-(2-(2,4-Difluorophenyl)ethyloxy)benzoyl)-2-methylindole-4-acetic Acid

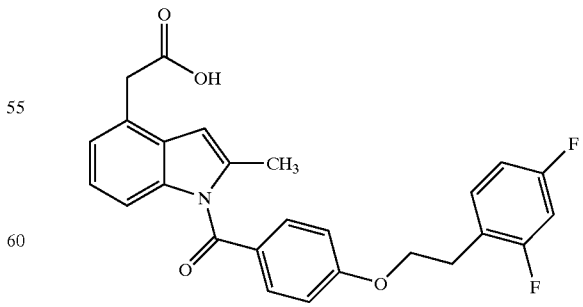

TLC: Rf 0.51 (chloroform:methanol=10:1);

MS: (APCI, Neg.): 448 (M−H)⁻.

EXAMPLE 7(61)

1-(4-(2-(2,5-Difluorophenyl)ethyloxy)benzoyl)-2-methylindole-4-acetic Acid

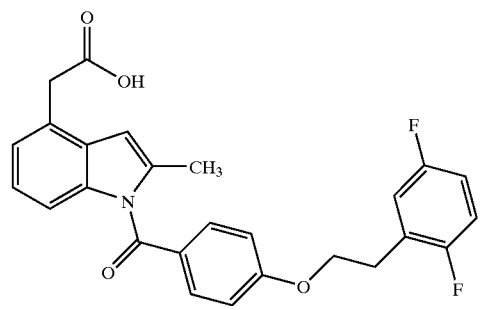

TLC: Rf 0.51 (chloroform:methanol=10:1);

MS: (APCI, Neg.): 448 (M−H)⁻.

EXAMPLE 7(62)

1-(4-(2-(2-Ethoxyphenyl)ethyloxy)benzoyl)-2-methylindole-4-acetic Acid

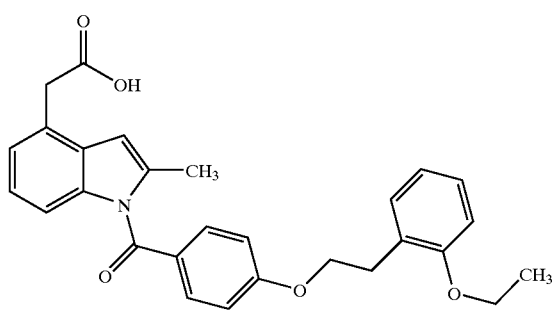

TLC: Rf 0.53 (chloroform:methanol=10:1);

MS: (APCI, Neg.): 456 (M−H)⁻.

EXAMPLE 7(63)

1-(4-(2-(2-Methylpropyloxy)ethyloxy)benzoyl)-2-methylindole-4-acetic Acid

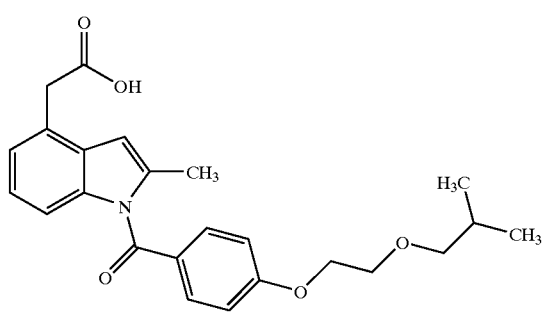

TLC: Rf 0.51 (chloroform methanol=10:1);

MS: (APCI, Neg.): 408 (M−H)⁻.

EXAMPLE 7(64)

1-(4-(4-Methoxybutyloxy)benzoyl)-2-methylindole-4-acetic Acid

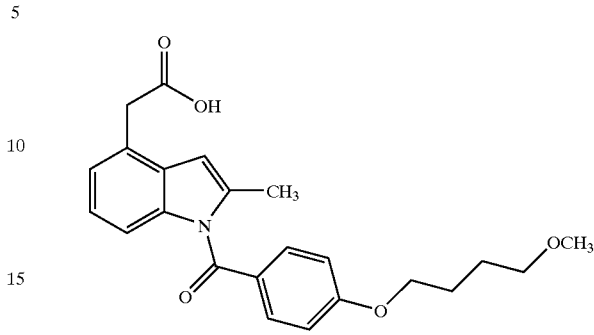

TLC: Rf 0.51 (chloroform:methanol=10:1);

MS: (APCI, Neg.): 394 (M−H)⁻.

EXAMPLE 7(65)

1-(4-(2-(2,5-Dimethylphenyl)ethyloxy)benzoyl)-2-methylindole-4-acetic Acid

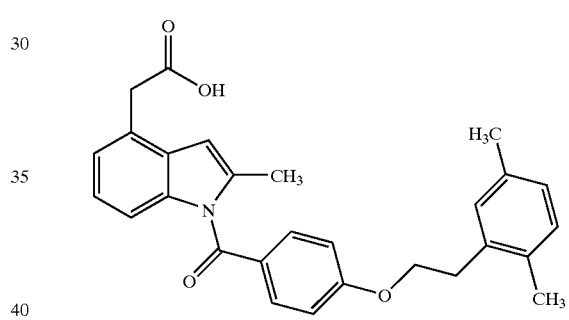

TLC: Rf 0.51 (chloroform:methanol=10:1);

MS: (APCI, Neg.): 440 (M−H)⁻.

EXAMPLE 7(66)

1-(4-(2-(2-(2-Methoxyethyloxy)ethyloxy)ethyloxy)benzoyl)-2-methylindole-4-acetic Acid

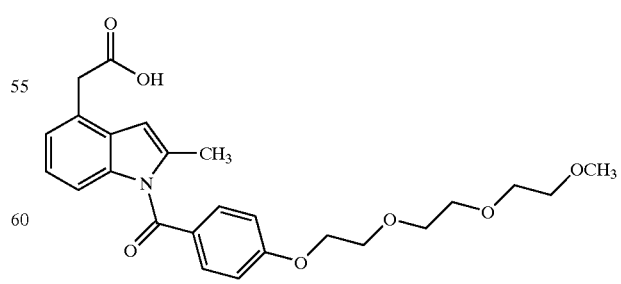

TLC: Rf 0.55 (chloroform:methanol=10:1);

MS: (APCI, Neg.): 454 (M−H)⁻.

EXAMPLE 7(67)

1-(4-(2-(2,4-Dimethoxyphenyl)ethyloxy)benzoyl)-2-methylindole-4-acetic Acid

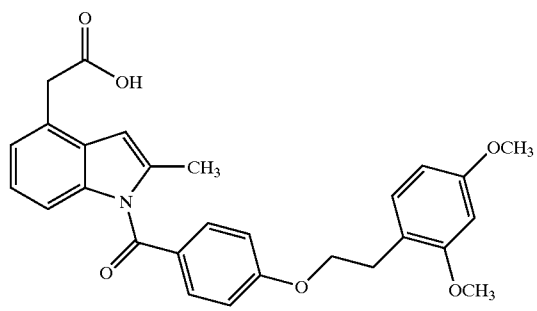

TLC: Rf 0.52 (chloroform:methanol=10:1);

MS: (APCI, Neg.): 472 (M−H)⁻.

EXAMPLE 7(68)

1-(4-(2-(2,3-Difluorophenyl)ethyloxy)benzoyl)-2-methylindole-4-acetic Acid

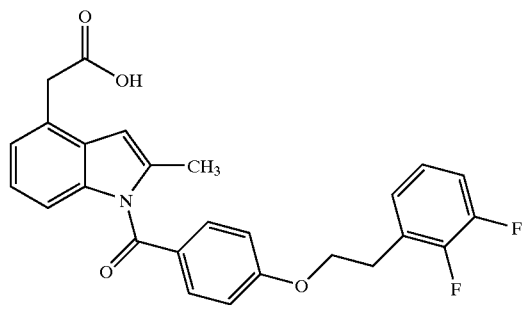

TLC: Rf 0.53 (chloroform:methanol=10:1);

MS: (APCI, Neg.): 448 (M−H)⁻.

EXAMPLE 7(69)

1-(4-(1-Phenylcyclopropylmethyloxy)benzoyl)-2-methylindole-4-acetic Acid

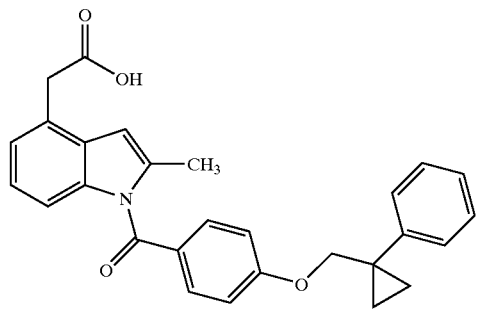

TLC: Rf 0.53 (chloroform:methanol=10:1);

MS: (APCI, Neg.): 438 (M−H)⁻.

EXAMPLE 7(70)

1-(4-(2-(3-Methoxymethylphenyl)ethyloxy)benzoyl)-2-methylindole-4-acetic Acid

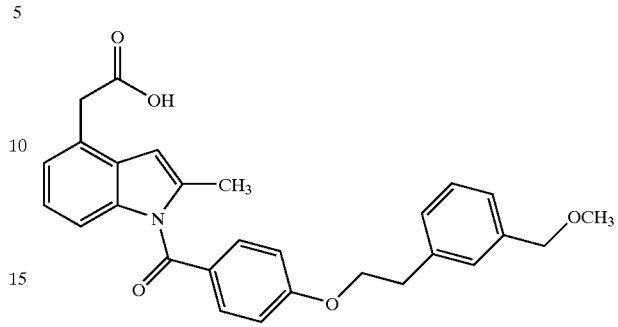

TLC: Rf 0.53 (chloroform:methanol=10:1);

MS: (APCI, Neg.): 456 (M−H)⁻.

EXAMPLE 7(71)

1-(4-(Furan-2-ylmethyloxy)benzoyl)-2-methylindole-4-acetic Acid

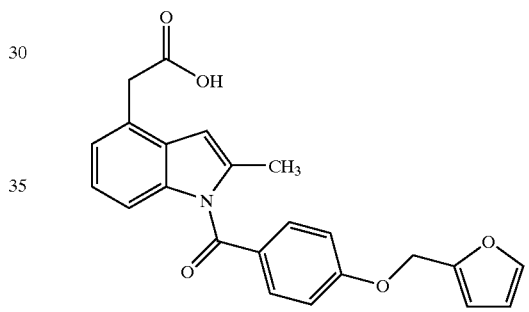

TLC: Rf 0.51 (chloroform:methanol=10:1);

MS: (APCI, Neg.): 388 (M−H)⁻.

EXAMPLE 7(72)

1-(4-(2-(N-Benzyl-N-methylamino)ethyloxy)benzoyl)-2-methylindole-4-acetic Acid

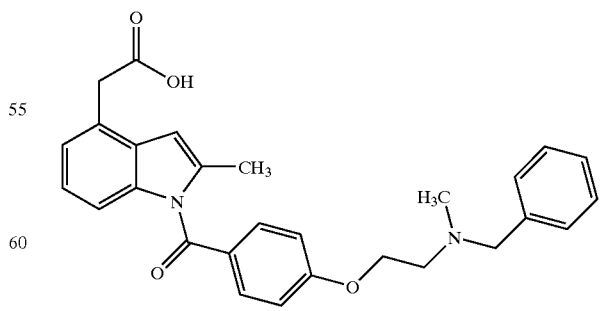

TLC: Rf 0.35 (chloroform:methanol=10:1);

MS: (APCI, Neg.): 455 (M−H)⁻.

EXAMPLE 7(73)

1-(4-(2-(2-Butoxyethyloxy)ethyloxy)benzoyl)-2-methylindole-4-acetic Acid

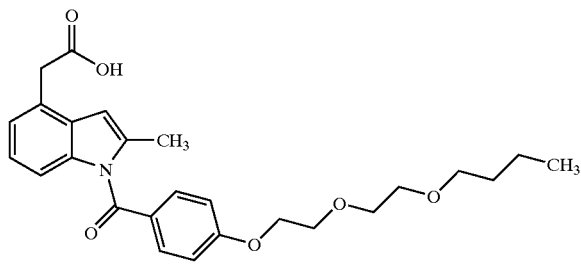

TLC: Rf 0.55 (chloroform:methanol=10:1);

MS: (APCI, Neg.): 452 (M−H)⁻.

EXAMPLE 7(74)

1-(4-(2-Methoxy-3-phenoxypropyloxy)benzoyl)-2-methylindole-4-acetic Acid

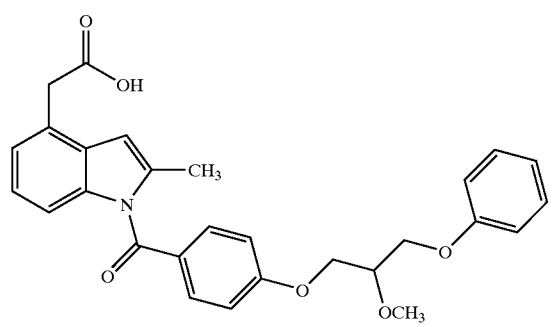

TLC: Rf 0.53 (chloroform:methanol=10:1);

MS: (APCI, Neg.): 472 (M−H)⁻.

EXAMPLE 7(75)

1-(4-(2-(4-Methylphenyloxy)ethyloxy)benzoyl)-2-methylindole-4-acetic Acid

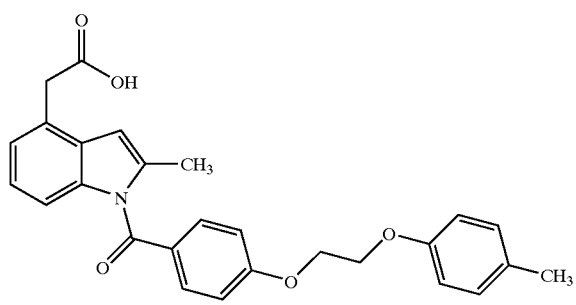

TLC: Rf 0.44 (chloroform:methanol=10:1);

MS: (APCI, Neg.): 442 (M−H)⁻.

EXAMPLE 7(76)

1-(4-(2-(2-(2-Ethoxyethyloxy)ethyloxy)ethyloxy)benzoyl)-2-methylindole-4-acetic Acid

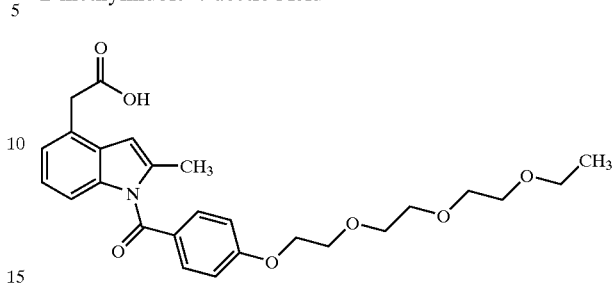

TLC: Rf 0.36 (chloroform:methanol=10:1);

MS: (APCI, Neg.): 468 (M−H)⁻.

EXAMPLE 7(77)

1-(4-(2-(Naphthalen-1-ylamino)ethyloxy)benzoyl)-2-methylindole-4-acetic Acid

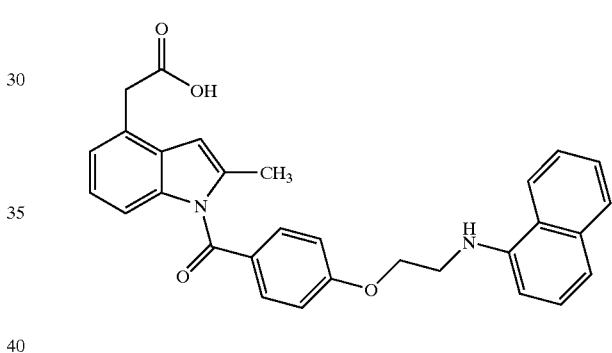

TLC: Rf 0.33 (chloroform:methanol=10:1);

MS: (APCI, Neg.): 477 (M−H)⁻.

EXAMPLE 7(78)

1-(4-(2-(Naphthalen-1-yloxy)ethyloxy)benzoyl)-2-methylindole-4-acetic Acid

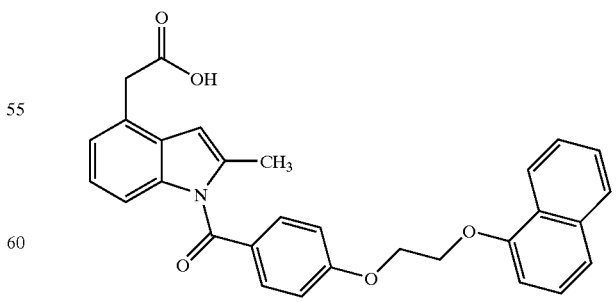

TLC: Rf 0.37 (chloroform:methanol=10:1);

MS: (APCI, Neg.): 478 (M−H)⁻.

EXAMPLE 7(79)

1-(4-(2-(Pyrazol-1-yl)ethyloxy)benzoyl)-2-methylindole-4-acetic Acid

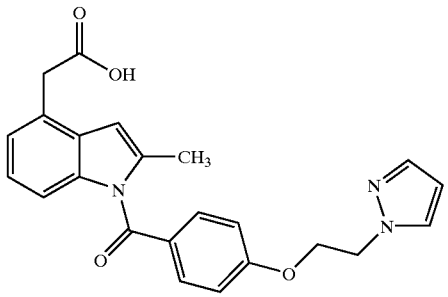

TLC: Rf 0.32 (chloroform:methanol=10:1);

MS: (APCI, Neg.): 402 (M−H)−.

EXAMPLE 7(80)

1-(4-(2-(2-Propen-1-yloxy)ethyloxy)benzoyl)-2-methylindole-4-acetic Acid

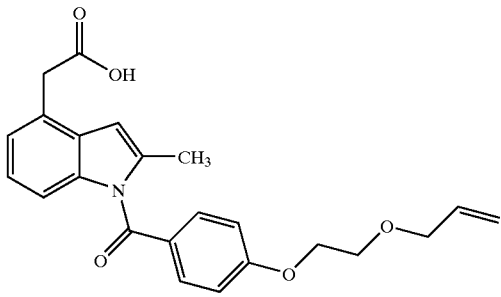

TLC: Rf 0.33 (chloroform:methanol=10:1);

MS: (APCI, Neg.): 392 (M−H)−.

EXAMPLE 7(81)

1-(4-(4,4,4-Trifluorobutyloxy)benzoyl)-2-methylindole-4-acetic Acid

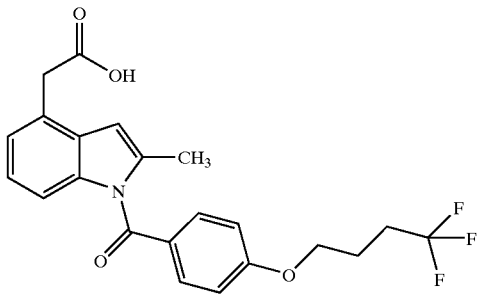

TLC: Rf 0.40 (chloroform:methanol=10:1);

MS: (APCI, Neg.): 418 (M−H)−.

EXAMPLE 7(82)

1-(4-(Indan-2-yloxy)benzoyl)-2-methylindole-4-acetic Acid

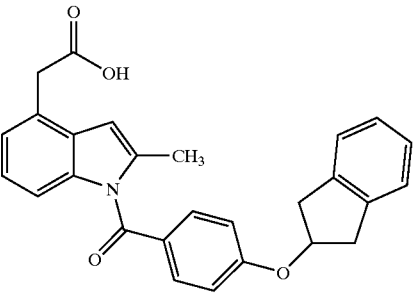

TLC: Rf 0.36 (chloroform:methanol=10:1);

MS: (APCI, Neg.): 424 (M−H)−.

EXAMPLE 7(83)

1-(4-(2-(2-Methylphenyloxy)ethyloxy)benzoyl)-2-methylindole-4-acetic Acid

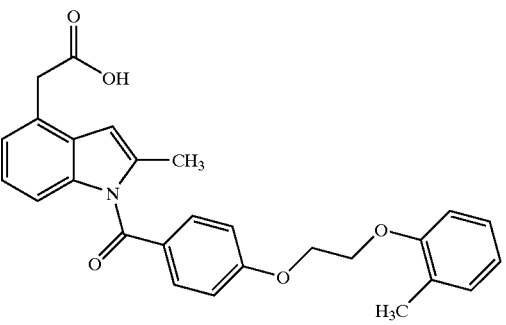

TLC: Rf 0.38 (chloroform:methanol=10:1);

MS: (APCI, Neg.): 442 (M−H)−.

EXAMPLE 7(84)

1-(4-(1,4-Benzodioxan-2-ylmethyloxy)benzoyl)-2-methylindole-4-acetic Acid

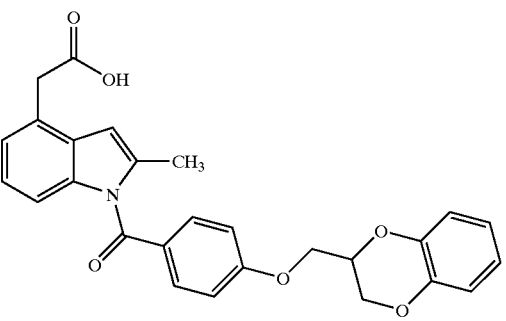

TLC: Rf 0.34 (chloroform:methanol=10:1);

MS: (FAB, Pos.): 458 (M+H)+;

NMR (CDCl$_3$): δ 7.71 (d, J=8.8 Hz, 2H), 7.09–6.82 (m, 9H), 6.48 (s, 1H), 4.61 (m, 2H), 4.42 (dd, J=11.8, 2.6 Hz, 1H), 4.38–4.18 (m, 3H), 3.84 (s, 2H), 2.43 (s, 3H).

EXAMPLE 7(85)

1-(4-(2-(2-Chlorophenyl)ethyloxy)benzoyl)-2-methylindole-4-acetic Acid

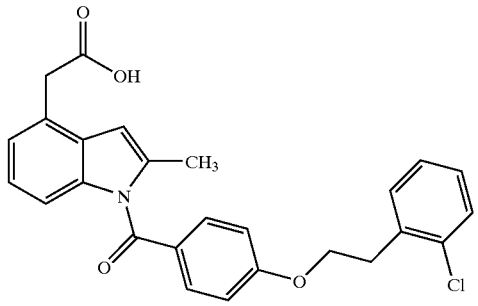

TLC: Rf 0.39 (chloroform:methanol=10:1);

MS: (APCI, Neg.): 446 (M−H)⁻.

EXAMPLE 7(86)

1-(4-(2-(2-Ethoxyethyloxy)ethyloxy)benzoyl)-2-methylindole-4-acetic Acid

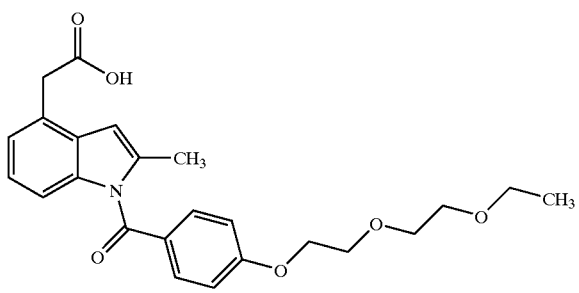

TLC: Rf 0.37 (chloroform:methanol=10:1);

MS: (APCI, Neg.): 424 (M−H)⁻.

EXAMPLE 7(87)

1-(4-(5-Ethoxypentyloxy)benzoyl)-2-methylindole-4-acetic Acid

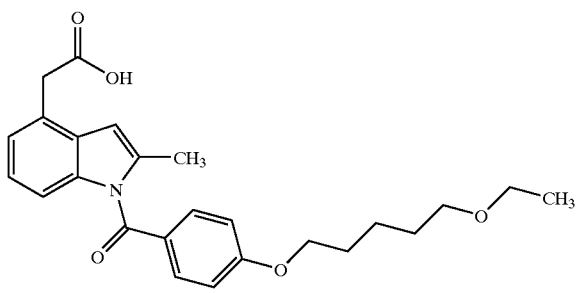

TLC: Rf 0.35 (chloroform:methanol=10:1);

MS: (APCI, Neg.): 422 (M−H)⁻.

EXAMPLE 7(88)

1-(4-(5-Methoxypentyloxy)benzoyl)-2-methylindole-4-acetic Acid

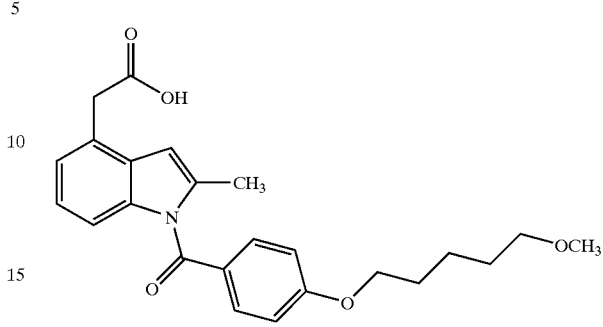

TLC: Rf 0.33 (chloroform:methanol=10:1);

MS: (APCI, Neg.): 408 (M−H)⁻.

EXAMPLE 7(89)

1-(4-((3E)-4-Phenyl-3-buten-1-yloxy)benzoyl)-2-methylindole-4-acetic Acid

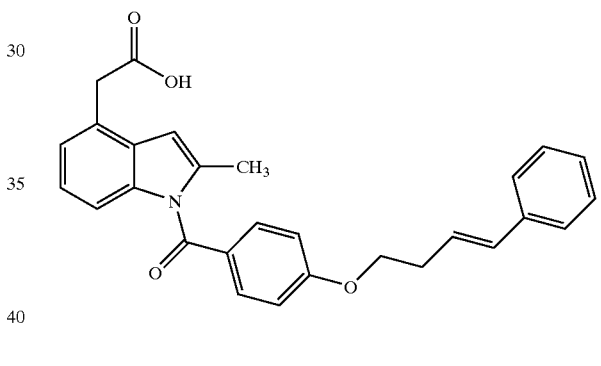

TLC: Rf 0.29 (chloroform:methanol=10:1);

MS: (APCI, Neg.): 438 (M−H)⁻.

EXAMPLE 7(90)

1-(4-(2-(N-Benzoyl-N-methylamino)ethyloxy)benzoyl)-2-methylindole-4-acetic Acid

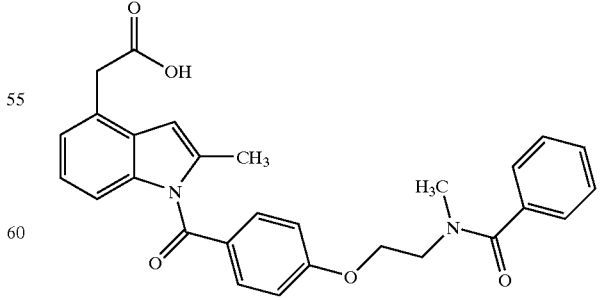

TLC: Rf 0.30 (chloroform:methanol=10:1);

MS: (APCI, Neg.): 469 (M−H)⁻.

EXAMPLE 7(91)

1-(4-(4-Ethoxybutyloxy)benzoyl)-2-methylindole-4-acetic Acid

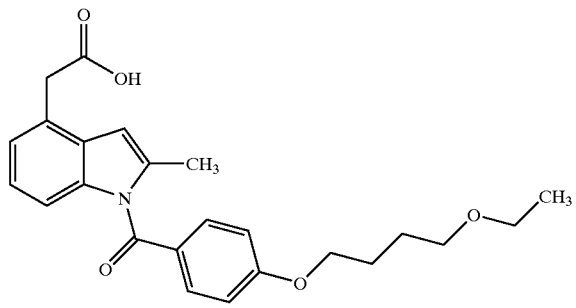

TLC: Rf 0.34 (chloroform methanol=10:1);

MS: (APCI, Neg.): 408 (M–H)⁻.

EXAMPLE 7(92)

1-(4-(3-(Pyrrol-1-yl)propyloxy)benzoyl)-2-methylindole-4-acetic Acid

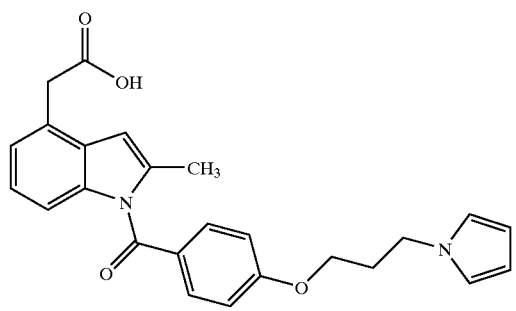

TLC: Rf 0.43 (chloroform:methanol=10:1);

MS: (APCI, Neg.): 415 (M–H)⁻.

EXAMPLE 7(93)

1-(4-(2-(Naphthalen-2-yloxy)ethyloxy)benzoyl)-2-methylindole-4-acetic Acid

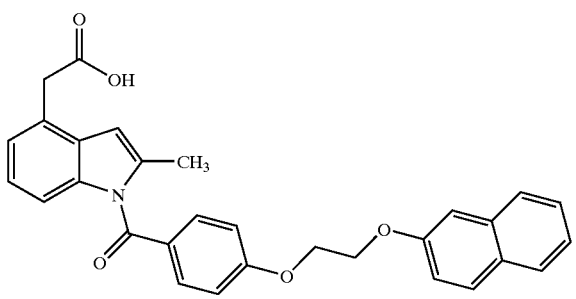

TLC: Rf 0.40 (chloroform methanol=10:1);

MS: (APCI, Neg.): 478 (M–H)⁻.

EXAMPLE 7(94)

1-(4-(2-(2,4,6-Trimethylphenyl)ethyloxy)benzoyl)-2-methylindole-4-acetic Acid

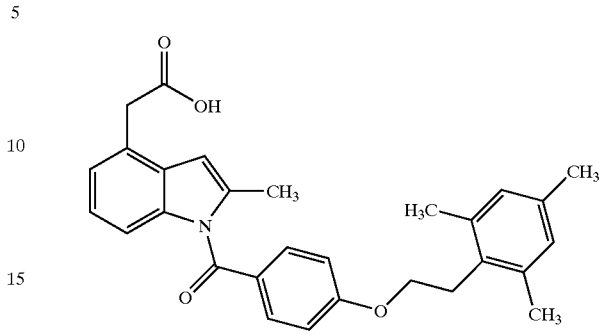

TLC: Rf 0.40 (chloroform:methanol=10:1);

MS: (APCI, Neg.): 454 (M–H)⁻.

EXAMPLE 7(95)

1-(4-(3-Benzyloxypropyloxy)benzoyl)-2-methylindole-4-acetic Acid

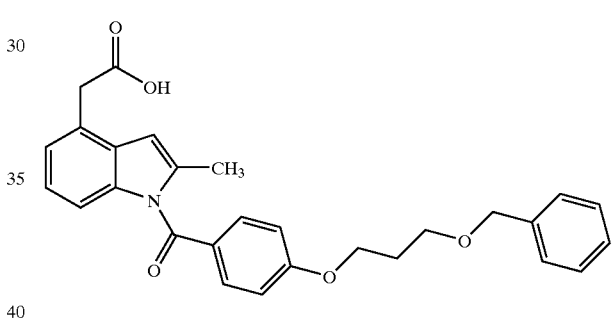

TLC: Rf 0.41 (chloroform:methanol=10:1);

MS: (APCI, Neg.): 456 (M–H)⁻.

EXAMPLE 7(96)

1-(4-(3,3,4,4,5,5,6,6,6-Nonafluorohexyloxy)benzoyl)-2-methylindole-4-acetic Acid

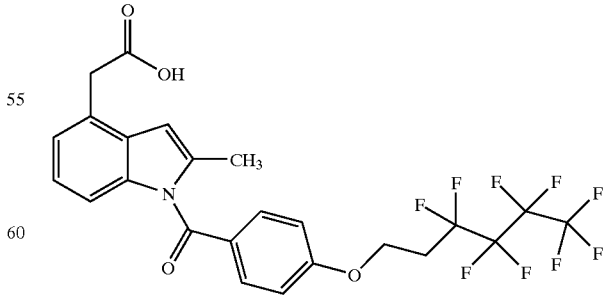

TLC: Rf 0.42 (chloroform:methanol=10:1);

MS: (APCI, Neg.): 554 (M–H)⁻.

EXAMPLE 7(97)

1-(4-(3-Phenoxypropyloxy)benzoyl)-2-methylindole-4-acetic Acid

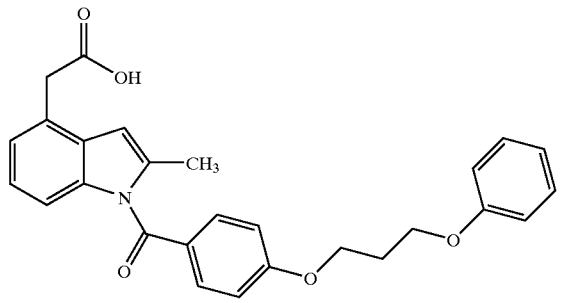

TLC: Rf 0.44 (chloroform:methanol=10:1);

MS: (APCI, Neg.): 442 (M–H)⁻.

EXAMPLE 7(98)

1-(4-(3-(2-Fluoroethyloxy)propyloxy)benzoyl)-2-methylindole-4-acetic Acid

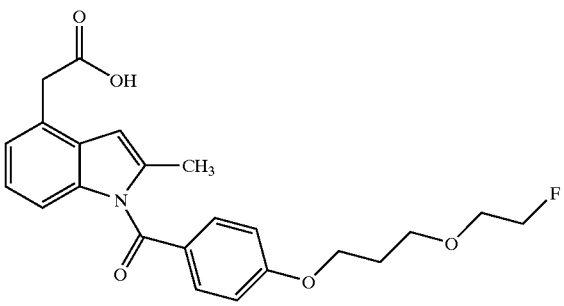

TLC: Rf 0.35 (chloroform:methanol=10:1);

MS: (APCI, Neg.): 412 (M–H)⁻.

EXAMPLE 7(99)

1-(4-(2-Cyclopentyloxyethyloxy)benzoyl)-2-methylindole-4-acetic Acid

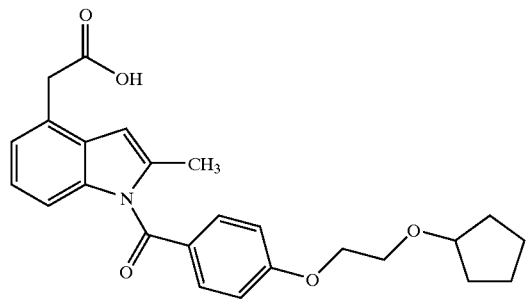

TLC: Rf 0.36 (chloroform:methanol=10:1);

MS: (APCI, Neg.): 420 (M–H)⁻.

EXAMPLE 7(100)

1-(4-(3-(2,2,2-Trifluoroethyloxy)propyloxy)benzoyl)-2-methylindole-4-acetic Acid

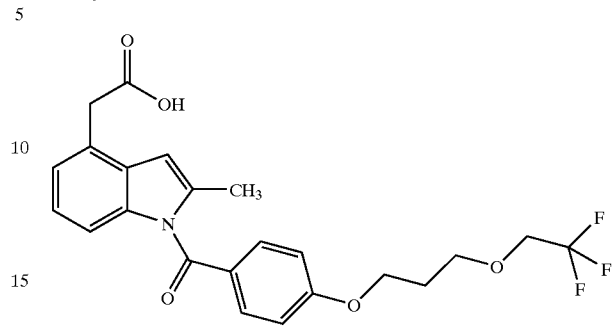

TLC: Rf 0.41 (chloroform:methanol=10:1);

MS: (APCI, Neg.): 448 (M–H)⁻.

EXAMPLE 7(101)

1-(4-(2-Cyclopropylmethyloxyethyloxy)benzoyl)-2-methylindole-4-acetic Acid

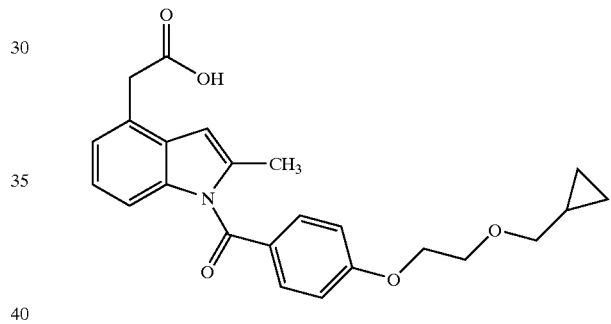

TLC: Rf 0.47 (chloroform:methanol=10:1);

MS: (APCI, Neg.): 406 (M–H)⁻.

EXAMPLE 7(102)

1-(4-(2-(3,3,3-Trifluoropropyloxy)ethyloxy)benzoyl)-2-methylindole-4-acetic Acid

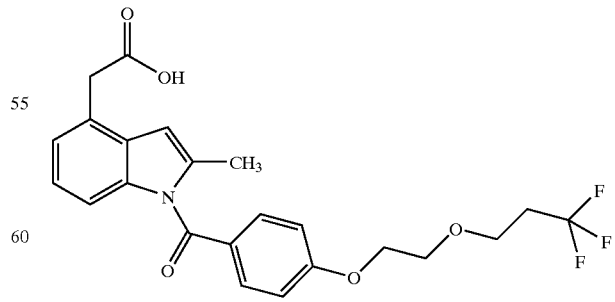

TLC: Rf 0.39 (chloroform:methanol=10:1);

MS: (APCI, Neg.): 448 (M–H)⁻.

EXAMPLE 7(103)

1-(4-(2-(2,2,2-Trifluoroethyloxy)ethyloxy)benzoyl)-2-methylindole-4-acetic Acid

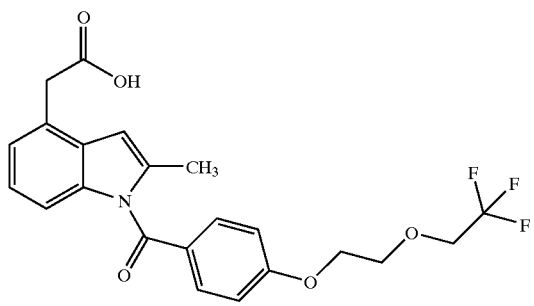

TLC: Rf 0.39 (chloroform:methanol=10:1);

MS: (APCI, Neg.): 434 (M–H)⁻.

EXAMPLE 7(104)

1-(4-(2-(2-Fluoroethyloxy)ethyloxy)benzoyl)-2-methylindole-4-acetic Acid

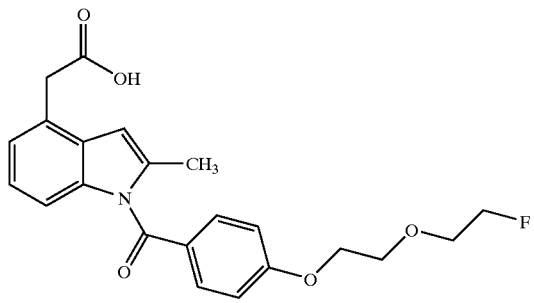

TLC: Rf 0.38 (chloroform:methanol=10:1);

MS: (APCI, Neg.): 398 (M–H)⁻.

EXAMPLE 7(105)

1-(4-(2-(2,4-Dichlorophenyl)ethyloxy)benzoyl)-2-methylindole-4-acetic Acid

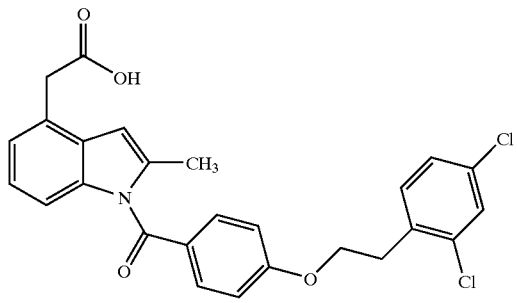

TLC: Rf 0.44 (chloroform:methanol=10:1);

MS: (APCI, Neg.): 480 (M–H)⁻.

EXAMPLE 7(106)

1-(4-(2-(2,3,4,5,6-Pentamethylphenyl)ethyloxy)benzoyl)-2-methylindole-4-acetic Acid

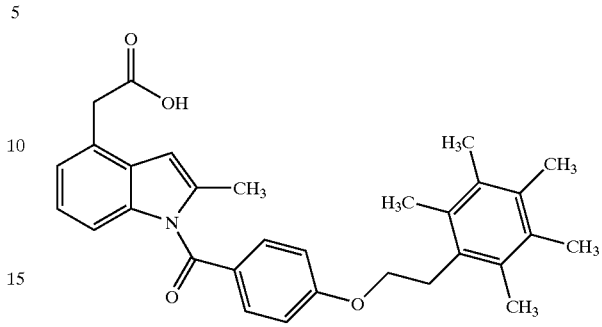

TLC: Rf 0.50 (chloroform:methanol=10:1);

MS: (APCI, Neg.):482 (M–H)⁻.

EXAMPLE 7(107)

1-(4-(3,3,3-Trifluoropropyloxy)benzoyl)-2-methylindole-4-acetic Acid

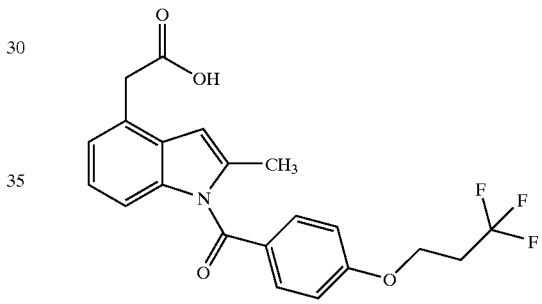

TLC: Rf 0.32 (chloroform:methanol=10:1);

MS: (APCI, Neg.): 404 (M–H)⁻.

EXAMPLE 7(108)

1-(4-(2-(4-Methyl-1,3-thiazol-5-yl)ethyloxy)benzoyl)-2-methylindole-4-acetic Acid

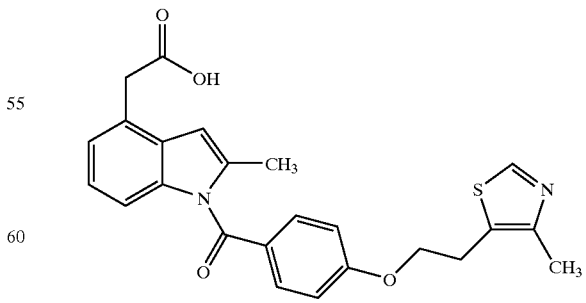

TLC: Rf 0.28 (chloroform:methanol=10:1);

MS: (APCI, Neg.): 433 (M–H)⁻.

EXAMPLE 7(109)

1-(4-(2-(Imidazol-1-yl)ethyloxy)benzoyl)-2-methylindole-4-acetic Acid

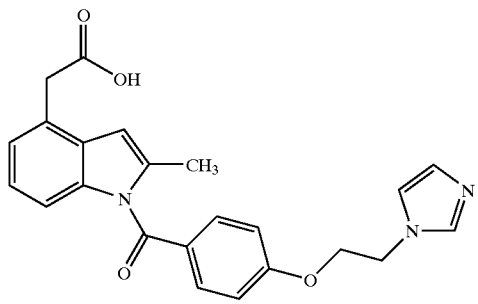

TLC: Rf 0.45 (chloroform:methanol=2:1);

MS: (FAB, Pos.): 404 (M+H)$^+$.

EXAMPLE 7(110)

1-(4-(2-(2-Methylimidazol-1-yl)ethyloxy)benzoyl)-2-methylindole-4-acetic Acid

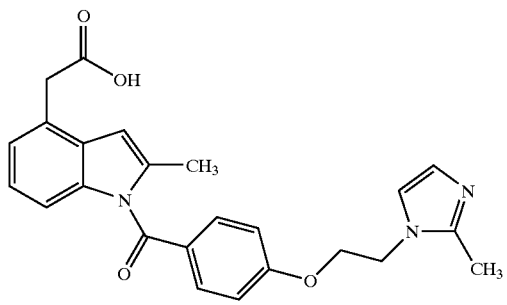

TLC: Rf 0.28 (chloroform:methanol=2:1);

MS: (APCI, Neg.): 416 (M−H)$^-$.

EXAMPLE 7(111)

1-(4-(1,3-Dioxaindan-4-ylmethyloxy)benzoyl)-2-methylindole-4-acetic Acid

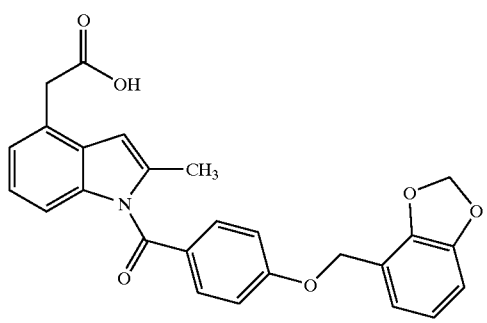

TLC: Rf 0.45 (chloroform:methanol=9:1);

MS: (APCI, Neg.): 442 (M−H)$^-$.

EXAMPLE 7(112)

1-(4-(Naphthalen-1-ylmethyloxy)benzoyl)-2-methylindole-4-acetic Acid

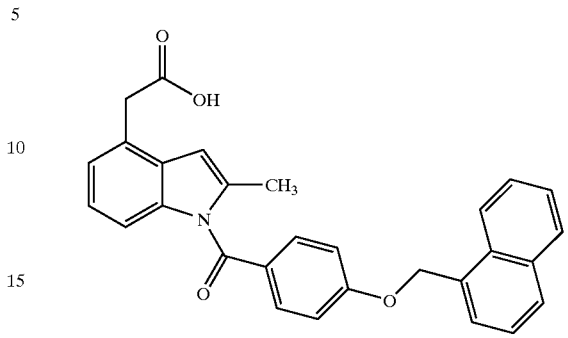

TLC: Rf 0.43 (chloroform:methanol=9:1);

MS: (APCI, Neg.): 448 (M−H)$^-$.

EXAMPLE 7(113)

1-(4-(3-(2-Pyrrolidinon-1-ylpropyloxy)benzoyl)-2-methylindole-4-acetic Acid

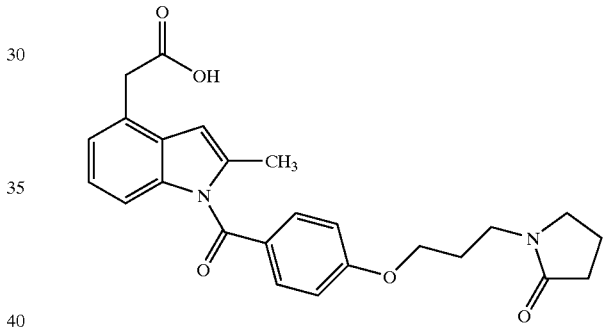

TLC: Rf 0.38 (chloroform:methanol=9:1);

MS: (APCI, Neg.20 V): 433 (M−H)$^-$.

EXAMPLE 7(114)

1-(4-(Pyridin-2-ylmethyloxy)benzoyl)-2-methylindole-4-acetic Acid

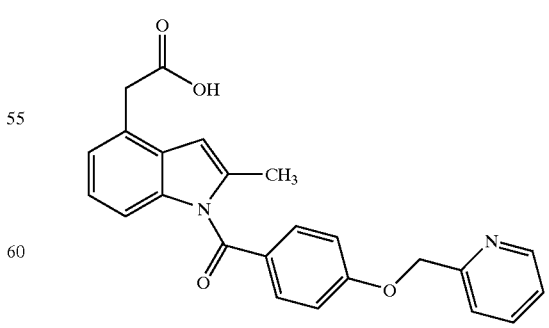

TLC: Rf 0.42 (chloroform:methanol=9:1);

MS: (APCI, Neg.): 399 (M−H)$^-$.

EXAMPLE 7(115)

1-(4-(1-Benzylethyloxy)benzoyl)-2-methylindole-4-acetic Acid

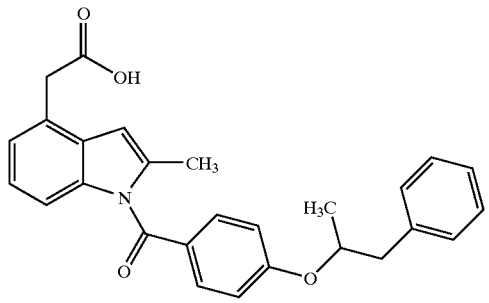

TLC: Rf 0.45 (chloroform:methanol=9:1);

MS: (APCI, Neg.): 426 (M–H)⁻.

EXAMPLE 7(116)

1-(4-((3Z)-3-Octen-1-yloxy)benzoyl)-2-methylindole-4-acetic Acid

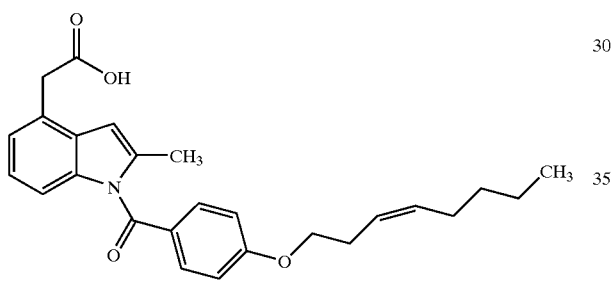

TLC: Rf 0.50 (chloroform:methanol=9:1);

MS: (APCI, Neg.): 418 (M–H)⁻.

EXAMPLE 7(117)

1-(4-(2-Phenylpropyloxy)benzoyl)-2-methylindole-4-acetic Acid

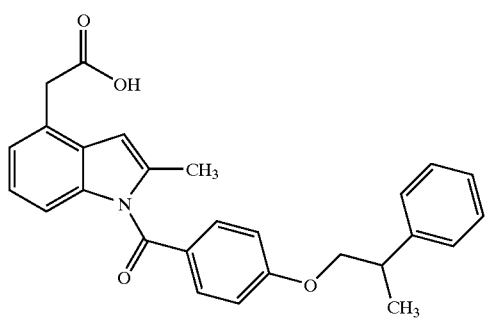

TLC: Rf 0.48 (chloroform:methanol=9:1);

MS: (APCI, Neg.): 426 (M–H)⁻.

EXAMPLE 7(118)

1-(4-(Naphthalen-2-ylmethyloxy)benzoyl)-2-methylindole-4-acetic Acid

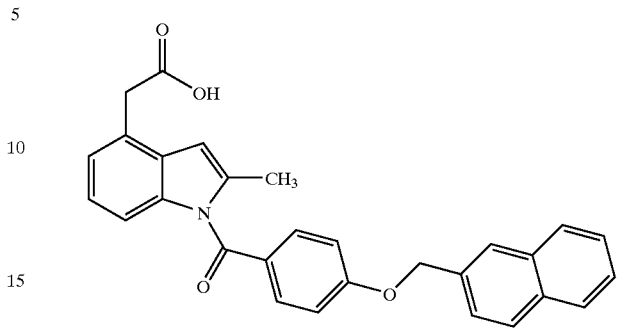

TLC: Rf 0.45 (chloroform:methanol=9:1);

MS: (APCI, Neg.: 448 (M–H)⁻.

EXAMPLE 7(119)

1-(4-(3-Chloropropyloxy)benzoyl)-2-methylindole-4-acetic Acid

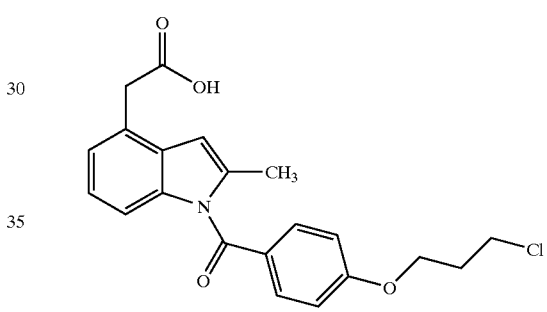

TLC: Rf 0.43 (chloroform:methanol=9:1);

MS: (APCI, Neg.): 384 (M–H)⁻.

EXAMPLE 7(120)

1-(4-(2-(2,3-Dimethylphenyl)ethyloxy)benzoyl)-2-methylindole-4-acetic Acid

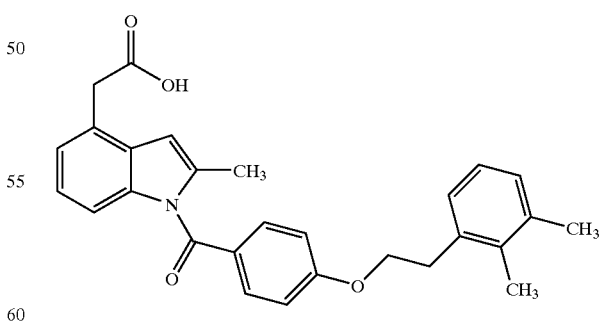

TLC: Rf 0.47 (chloroform:methanol=9:1);

MS: (APCI, Neg.): 440 (M–H)⁻;

NMR (CDCl$_3$): δ 7.70 (d, J=8.7 Hz, 2H), 7.12–6.90 (m, 8H), 6.49 (s, 1H), 4.21 (t, J=7.5 Hz, 2H), 3.87 (s, 2H), 3.19 (t, J=7.5 Hz, 2H), 2.45 (s, 3H), 2.31 (s, 3H), 2.30 (s, 3H).

EXAMPLE 7(121)
1-(4-(2-(4-Methoxymethylphenyl)ethyloxy)benzoyl)-2-methylindole-4-acetic Acid

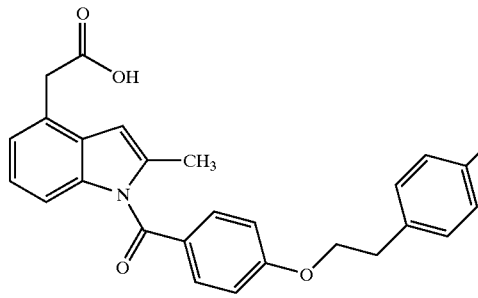

TLC: Rf 0.48 (chloroform:methanol=9:1);
MS: (APCI, Neg.): 456 (M−H)⁻;
NMR (CDCl$_3$): δ 7.69 (d, J=9.0 Hz, 2H), 7.34–7.24 (m, 3H), 7.10–6.85 (m, 6H), 6.48 (s, 1H), 4.45 (s, 2H), 4.24 (t, J=6.9 Hz, 2H), 3.86 (s, 2H), 3.40 (s, 3H), 3.13 (t, J=6.9 Hz, 2H), 2.44 (s, 3H).

EXAMPLE 7(122)
1-(4-(2,2,3,3,3-Pentafluoropropyloxy)benzoyl)-2-methylindole-4-acetic Acid

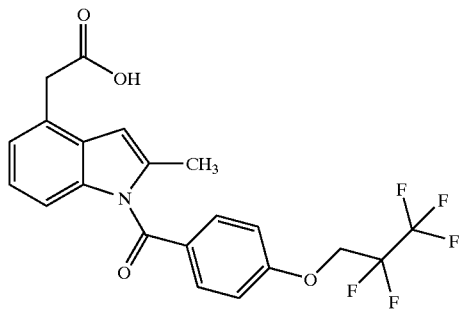

TLC: Rf 0.48 (chloroform:methanol=9:1);
MS: (APCI, Neg.): 440 (M−H)⁻;
NMR (CDCl$_3$): δ 7.72 (d, J=9.0 Hz, 2H), 7.08–6.92 (m, 5H), 6.49 (s, 1H), 3.90 (s, 2H), 3.86 (s, 2H), 2.45 (s, 3H).

EXAMPLE 7(123)
1-(4-(2-(2,6-Difluorophenyl)ethyloxy)benzoyl)-2-methylindole-4-acetic Acid

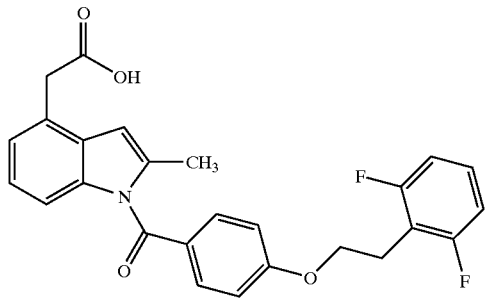

TLC: Rf 0.48 (chloroform:methanol=9:1);
MS: (APCI, Neg.): 448 (M−H)⁻;
NMR (CDCl$_3$): δ 7.69 (d, J=9.0 Hz, 2H), 7.08–6.85 (m, 8H), 6.49 (s, 1H), 4.25 (t, J=6.6 Hz, 2H), 3.87 (s, 2H), 3.26–3.16 (m, 2H), 2.44 (s, 3H).

EXAMPLE 7(124)
1-(4-(3-Phenoxybenzyloxy)benzoyl)-2-methylindole-4-acetic Acid

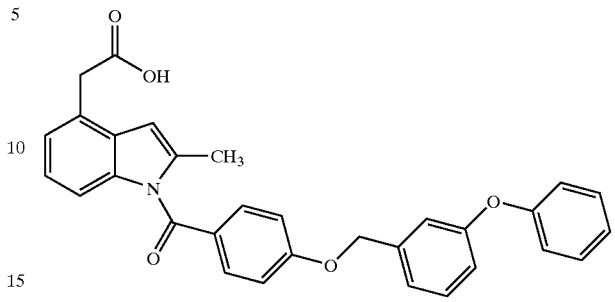

TLC: Rf 0.55 (chloroform:methanol=9:1);
MS: (APCI, Neg.): 490 (M−H)⁻;
NMR (CDCl$_3$): δ 7.71 (d, J=8.7 Hz, 2H), 7.40–6.85 (m, 14H), 6.49 (s, 1H), 5.12 (s, 2H), 3.87 (s, 2H), 2.44 (s, 3H).

EXAMPLE 7(125)
1-(4-Methoxymethyloxybenzoyl)-2-methylindole-4-acetic Acid

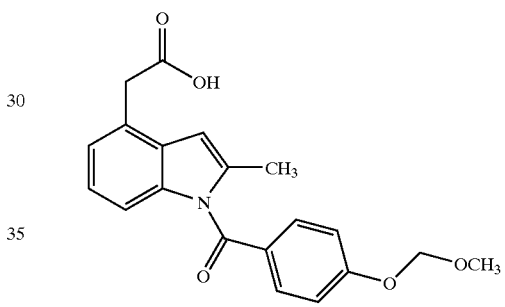

TLC: Rf 0.45 (chloroform:methanol=10:1);
MS: (APCI, Neg.): 352 (M−H)⁻;
NMR (CDCl$_3$): δ 7.70 (d, J=9.0 Hz, 2H), 7.09 (d, J=9.0 Hz, 2H), 7.08–6.97 (m, 3H), 6.48 (s, 1H), 5.26 (s, 2H), 3.85 (s, 2H), 3.51 (s, 3H), 2.43 (s, 3H).

EXAMPLE 7(126)
1-(4-(2-(2,5-Dimethyloxazol-4-yl)ethyloxy)benzoyl)-2-methylindole-4-acetic Acid

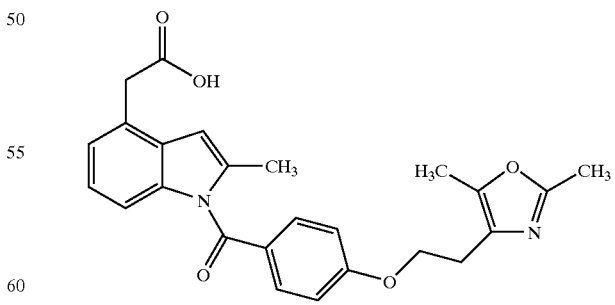

TLC: Rf 0.33 (chloroform:methanol 9:1);
MS: (APCI, Neg.): 431 (M−H)⁻;
NMR (CDCl$_3$): δ 7.67 (d, J=8.7 Hz, 2H), 7.08–6.86 (m, 5H), 6.50 (s, 1H), 4.22 (t, J=6.6 Hz, 2H), 3.86 (s, 2H), 2.90 (t, J=6.6 Hz, 2H), 2.44 (s, 3H), 2.39 (s, 3H), 2.26 (s, 3H).

EXAMPLE 7(127)
1-(4-(2-(4-Methoxy-3-methylphenyl)ethyloxy)benzoyl)-2-methylindole-4-acetic Acid

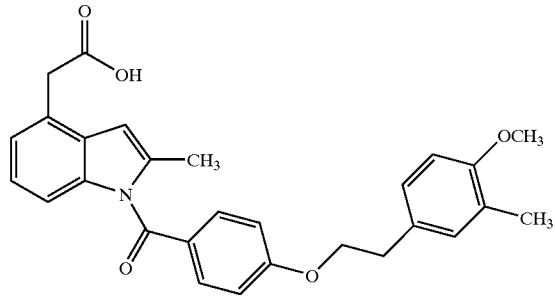

TLC: Rf 0.58 (chloroform:methanol=9:1);
MS: (APCI, Neg.): 456 (M–H)⁻;
NMR (CDCl₃): δ 7.69 (d, J=9.3 Hz, 2H), 7.11–6.87 (m, 7H), 6.79 (d, J=8.1 Hz, 1H), 6.48 (s, 1H), 4.21 (t, J=7.2 Hz, 2H), 3.86 (s, 2H), 3.82 (s, 3H), 3.05 (t, J=7.2 Hz, 2H), 2.44 (s, 3H), 2.22 (s, 3H).

EXAMPLE 7(128)
1-(4-(2-(3-Ethoxyphenyl)ethyloxy)benzoyl)-2-methylindole-4-acetic Acid

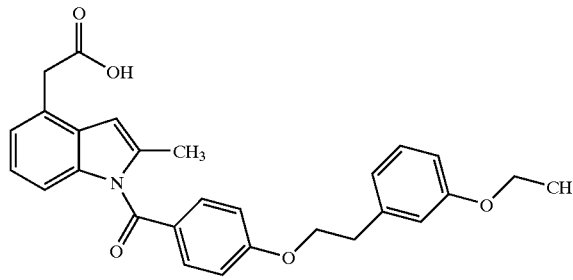

TLC: Rf 0.56 (chloroform:methanol=9:1);
MS: (APCI, Neg.): 456 (M–H)⁻;
NMR (CDCl₃): δ 7.70 (d, J=8.7 Hz, 2H), 7.26–7.20 (m, 1H), 7.08–6.76 (m, 8H), 6.49 (s, 1H), 4.25 (t, J=7.2 Hz, 2H), 4.04 (q, J=7.2 Hz, 2H), 3.87 (s, 2H), 3.11 (t, J=7.2 Hz, 2H), 2.45 (s, 3H), 1.42 (t, J=7.2 Hz, 3H).

EXAMPLE 7(129)
1-(4-(2-(1,3-Dihydrobenzo[c]furan-5-yl)ethyloxy)benzoyl)-2-methylindole-4-acetic Acid

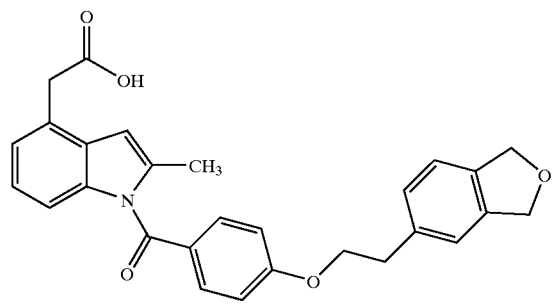

TLC: Rf 0.53 (chloroform:methanol=9:1);
MS: (APCI, Neg.): 454 (M–H)⁻;
NMR (CDCl₃): δ 7.70 (d, J=8.7 Hz, 2H), 7.22–7.15 (m, 2H), 7.07–6.86 (m, 6H), 6.49 (s, 1H), 5.11 (s, 4H), 4.25 (t, J=6.9 Hz, 2H), 3.87 (s, 2H), 3.16 (t, J=6.9 Hz, 2H), 2.44 (s, 3H).

EXAMPLE 7(130)
1-(4-(2-Buten-1-yloxy)benzoyl)-2-methylindole-4-acetic Acid (Mixture of EZ Form)

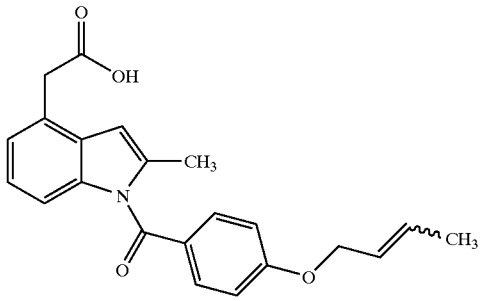

TLC: Rf 0.53 (chloroform:methanol=9:1);
MS: (APCI, Neg.): 362 (M–H)⁻;
NMR (CDCl₃): δ 7.70 (d, J=9.0 Hz, 2H), 7.10–6.90 (m, 5H), 6.49 (s, 1H), 6.00–5.83 (m, 1H), 5.80–5.70 (m, 1H), 4.55 (d, J=6.0 Hz, 2H), 3.87 (s, 2H), 2.45 (s, 3H), 1.78 (d, J=7.8 Hz, 3H).

EXAMPLE 7(131)
1-(4-(2-(6-Methylpyridin-2-yl)ethyloxy)benzoyl)-2-methylindole-4-acetic Acid

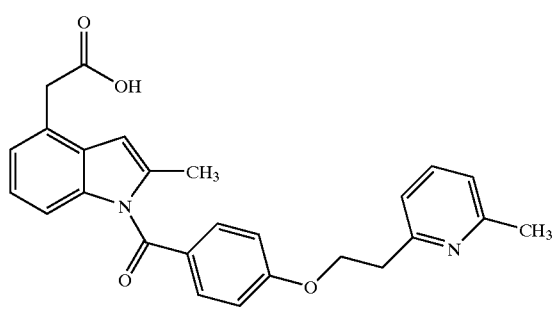

TLC: Rf 0.31 (chloroform methanol=10:1);
MS: (EI, Pos.): 428 (M)⁺;
NMR (CDCl₃): δ 7.68–7.63 (m, 2H), 7.55 (dd, J=6.6, 6.6 Hz, 1H), 7.11–7.04 (m, 3H), 6.98–6.87 (m, 4H), 6.51 (s, 1H), 4.33 (t, J=6.6 Hz, 2H), 3.86 (s, 2H), 3.26 (t, J=6.6 Hz, 2H), 2.56 (s, 3H), 2.43 (s, 3H).

EXAMPLE 7(132)
1-(4-(2-(3-Methylpyridin-2-yl)ethyloxy)benzoyl)-2-methylindole-4-acetic Acid

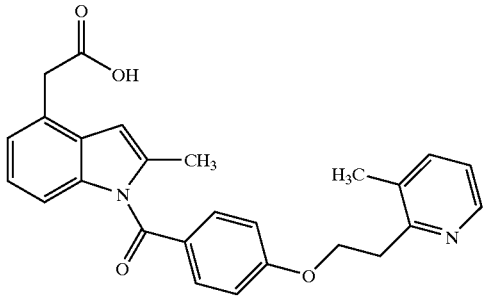

TLC: Rf 0.32 (chloroform:methanol=10:1);
MS: (EI, Pos.): 428 (M)⁺;
NMR (CDCl₃): δ 8.43 (dd, J=5.1, 1.2 Hz, 1H), 7.66–7.61 (m, 2H), 7.51 (dd, J=7.5, 1.2 Hz, 1H), 7.13 (dd, J=7.5, 5.1

Hz, 1H), 7.06 (dd, J=7.2, 1.2 Hz, 1H), 6.95 (dd, J=8.1, 7.2 Hz, 1H), 6.91–6.86 (m, 3H), 6.52 (s, 1H), 4.40 (t, J=6.6 Hz, 2H), 3.86 (s, 2H), 3.32 (t, J=6.6 Hz, 2H), 2.42 (s, 3H), 2.41 (s, 3H).

EXAMPLE 7(133)
1-(4-(2-Chloroethyloxy)benzoyl)-2-methylindole-4-acetic Acid

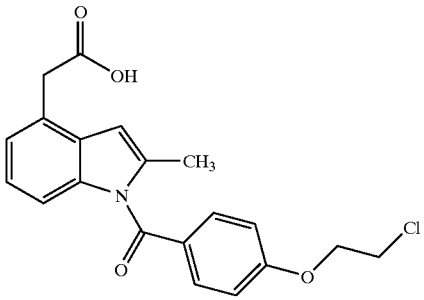

TLC: Rf 0.53 (chloroform:methanol=9:1);
MS: (APCI, Neg.): 370 (M−H)⁻;
NMR (CDCl₃): δ 7.72 (d, J=9.3 Hz, 2H), 7.08–6.88 (m, 5H), 6.50 (s, 1H), 4.32 (t, J=6.0 Hz, 2H), 3.90–3.84 (m, 4H), 2.45 (s, 3H).

EXAMPLE 7(134)
1-(4-(2-(Benzo[b]thiophen-3-yl)ethyloxy)benzoyl)-2-methylindole-4-acetic Acid

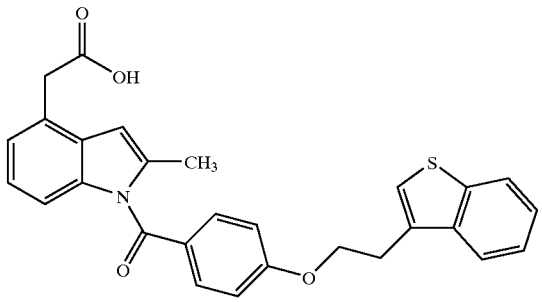

TLC: Rf 0.50 (chloroform:methanol=9:1);
MS: (APCI, Neg.): 468 (M−H)⁻;
NMR (CDCl₃): δ 7.91–7.80 (m, 2H), 7.70 (d, J=8.7 Hz, 2H), 7.46–7.30 (m, 2H), 7.30–7.24 (m, 1H), 7.08–6.88 (m, 5H), 6.48 (s, 1H), 4.38 (t, J=6.9 Hz, 2H), 3.87 (s, 2H), 3.40 (t, J=6.9 Hz, 2H), 2.44 (s, 3H).

EXAMPLE 7(135)
1-(4-Ethoxymethyloxybenzoyl)-2-methylindole-4-acetic Acid

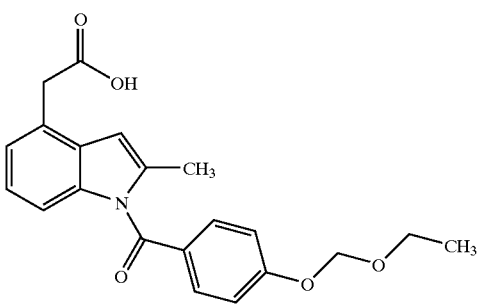

TLC: Rf 0.45 (chloroform:methanol=10:1);
MS: (APCI, Neg.): 366 (M−H)⁻;
NMR (CDCl₃): δ 7.63 (d, J=8.8 Hz, 2H), 7.05–6.90 (m, 5H), 6.41 (d, J=0.8 Hz, 1H), 5.24 (s, 2H), 3.79 (s, 2H), 3.67 (q, J=7.2 Hz, 2H), 2.36 (d, J=0.8 Hz, 3H), 1.16 (t, J=7.2 Hz, 3H).

EXAMPLE 7(136)
1-(4-Acetyloxybenzoyl)-2-methylindole-4-acetic Acid

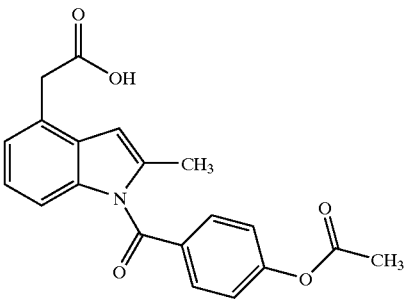

TLC: Rf 0.53 (chloroform:methanol=9:1);
MS: (APCI, Neg.): 350 (M−H)⁻;
NMR (CDCl₃): δ 7.77 (d, J=8.7 Hz, 2H), 7.28–7.17 (m, 2H), 7.10–6.94 (m, 3H), 6.51 (s, 1H), 3.87 (s, 2H), 2.43 (s, 3H), 2.35 (s, 3H).

EXAMPLE 7(137)
1-(4-(2-Propyn-1-yloxy)benzoyl)-2-methylindole-4-acetic Acid

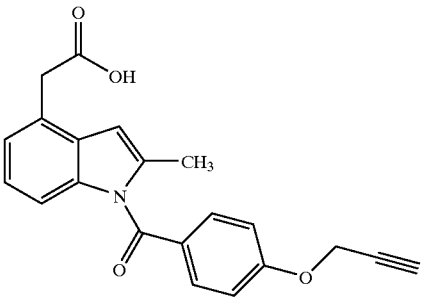

TLC: Rf 0.59 (chloroform:methanol=9:1);
MS: (APCI, Neg.): 346 (M−H)⁻;
NMR (CDCl₃): δ 7.73 (d, J=9.0 Hz, 2H), 7.09–6.90 (m, 5H), 6.50 (s, 1H), 4.79 (d, J=2.4 Hz, 2H), 3.87 (s, 2H), 2.58 (t, J=2.4 Hz, 1H), 2.45 (s, 3H).

EXAMPLE 7(138)
1-(4-(2-Propen-1-yloxy)benzoyl)-2-methylindole-4-acetic Acid

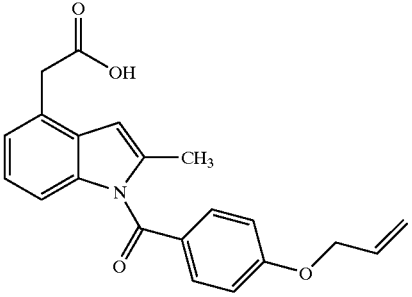

TLC: Rf 0.45 (chloroform:methanol=9:1);
MS: (APCI, Neg.): 348 (M−H)⁻;
NMR (CDCl₃): δ 7.71 (d, J=8.7 Hz, 2H), 7.10–6.90 (m, 5H), 6.49 (s, 1H), 6.15–6.00 (m, 1H), 5.50–5.40 (m, 1H), 5.40–5.30 (m, 1H), 4.65–4.60 (m, 2H), 3.87 (s, 2H), 2.45 (s, 3H).

EXAMPLE 7(139)
1-(4-(2-Butyn-1-yloxy)benzoyl)-2-methylindole-4-acetic Acid

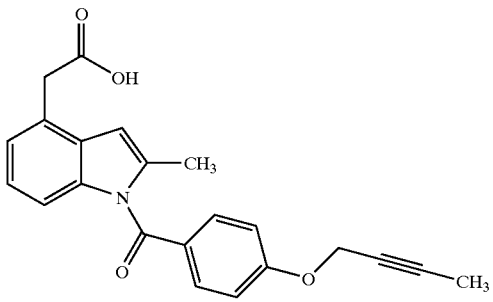

TLC: Rf 0.50 (chloroform:methanol=9:1);
MS: (APCI, Neg.): 360 (M–H)⁻;
NMR (CDCl₃): δ 7.72 (d, J=9.0 Hz, 2H), 7.08–6.92 (m, 5H), 6.49 (s, 1H), 4.78–4.70 (m, 2H), 3.87 (s, 2H), 2.45 (s, 3H), 1.88 (t, J=2.4 Hz, 3H).

EXAMPLE 7(140)
1-(4-(3-Penten-1-yloxy)benzoyl)-2-methylindole-4-acetic Acid

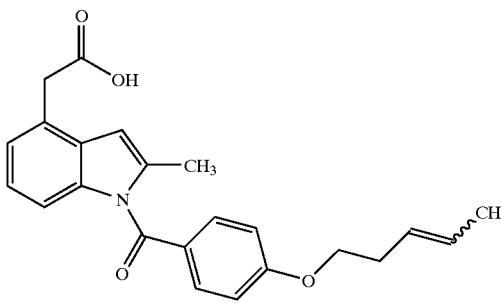

TLC: Rf 0.51 (chloroform:methanol=10:1);
MS: (APCI, Neg.): 376 (M–H)⁻;
NMR (CDCl₃): δ 7.70 (dd, J=6.9, 2.4 Hz, 2H), 7.05–6.92 (m, 5H), 6.48 (d, J=0.6 Hz, 1H), 5.70–5.40 (m, 2H), 4.05 (t, J=6.6 Hz, 2H), 3.86 (s, 2H), 2.52 (m, 2H), 2.44 (d, J=0.6 Hz, 3H), 1.69 (m, 3H).

EXAMPLE 7(141)
1-(4-(2-(1-Methylindol-3-yl)ethyloxy)benzoyl)-2-methylindole-4-acetic Acid

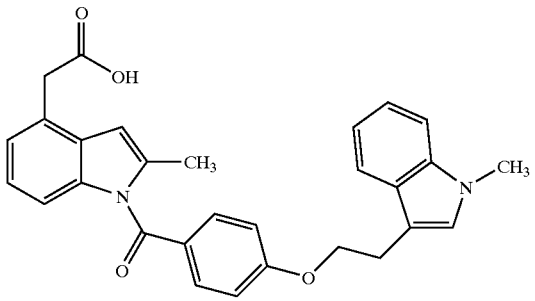

TLC: Rf 0.53 (chloroform:methanol=10:1);
MS: (APCI, Neg.): 465 (M–H)⁻;
NMR (CDCl₃): δ 7.70–7.63 (m, 3H), 7.35–7.20 (m, 2H), 7.14 (m, 1H), 7.03 (m, 1H), 7.05–6.93 (m, 5H), 6.47 (d, J=1.2 Hz, 1H), 4.29 (t, J=6.9 Hz, 2H), 3.85 (s, 2H), 3.77 (s, 3H), 3.28 (t, J=6.9 Hz, 2H), 2.43 (d, J=1.2 Hz, 3H).

EXAMPLE 7(142)
1-(4-(2-(1,2,3,4-Tetrahydronaphthalen-2-yl)ethyloxy)benzoyl)-2-methylindole-4-acetic Acid

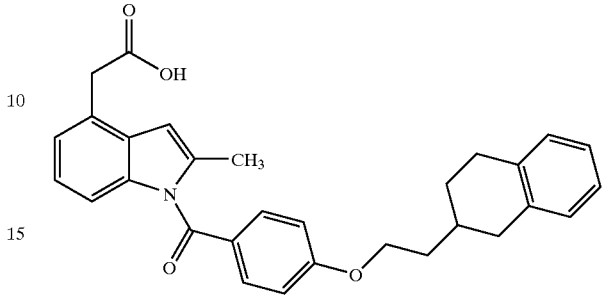

TLC: Rf 0.53 (chloroform:methanol=10:1);
MS: (APCI, Neg.): 452 (M–H)⁻;
NMR (CDCl₃): δ 7.72 (dd, J=6.9, 1.8 Hz, 2H), 7.12–7.10 (m, 4H), 7.04 (m, 1H), 7.03–6.95 (m, 4H), 6.49 (s, 1H), 4.02 (d, J=6.3 Hz, 2H), 3.87 (s, 2H), 3.01 (dd, J=14, 4.2 Hz, 1H), 2.92–2.87 (m, 2H), 2.68 (dd, J=14, 10.5 Hz, 1H), 2.45 (s, 3H), 2.35 (m, 1H), 2.10 (m, 1H), 1.65 (m, 1H).

EXAMPLE 7(143)
1-(4-(2-(1,2,3,4-Tetrahydroquinolin-1-yl)ethyloxy)benzoyl)-2-methylindole-4-acetic Acid

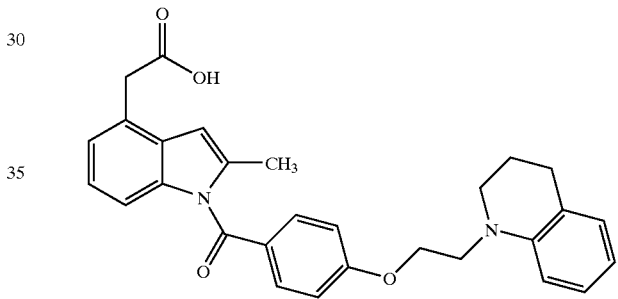

TLC: Rf 0.51 (chloroform:methanol=10:1);
MS: (APCI, Neg.): 467 (M–H)⁻;
NMR (CDCl₃): δ 7.70 (d, J=8.7 Hz, 2H), 7.15–6.90 (m, 7H), 6.65–6.55 (m, 2H), 6.47 (s, 1H), 4.22 (t, J=5.7 Hz, 2H), 3.84 (s, 2H), 3.73 (t, J=5.7 Hz, 2H), 3.44 (t, J=5.7 Hz, 2H), 2.76 (t, J=5.7 Hz, 2H), 2.43 (s, 3H), 2.00–1.90 (m, 2H).

EXAMPLE 7(144)
1-(4-(2-Hydroxy-(1-hydroxymethyl)ethyloxy)benzoyl)-2-methylindole-4-acetic Acid

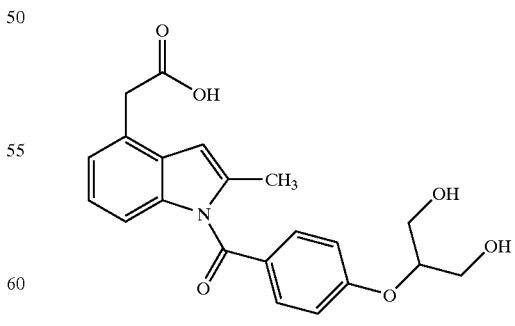

TLC: Rf 0.12 (chloroform methanol=9:1);
MS: (APCI, Neg.): 382 (M–H)⁻;
NMR (CDCl₃): δ 7.70 (d, J=8.7 Hz, 2H), 7.10–6.90 (m, 5H), 6.52 (s, 1H), 4.58–4.48 (m, 1H), 3.90 (d, J=6.0 Hz, 4H), 3.83 (s, 2H), 2.44 (s, 3H).

EXAMPLE 7(145)
1-(4-(2-(2-Ethylphenyl)ethyloxy)benzoyl)-2-methylindole-4-acetic Acid

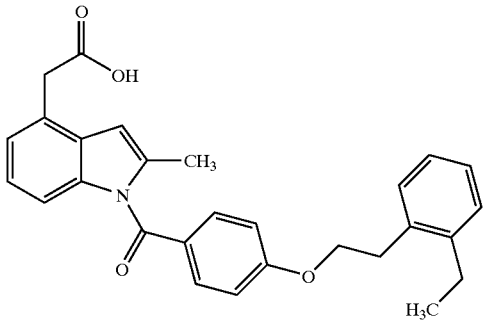

TLC: Rf 0.35 (chloroform:methanol=10:1);
MS: (APCI, Neg.): 440 (M−H)⁻;
NMR (CDCl₃): δ 7.72–7.67 (m, 2H), 7.26–7.15 (m, 3H), 7.06–6.90 (m, 6H), 6.49 (d, J=0.9 Hz, 1H), 4.23 (t, J=7.5 Hz, 2H), 3.87 (s, 2H), 3.18 (t, J=7.5 Hz, 2H), 2.74 (q, J=7.5 Hz, 2H), 2.44 (d, J=0.9 Hz, 3H), 1.27 (t, J=7.5 Hz, 3H).

EXAMPLE 7(146)
1-(4-(2-(2-Methoxymethylphenyl)ethyloxy)benzoyl)-2-methylindole-4-acetic Acid

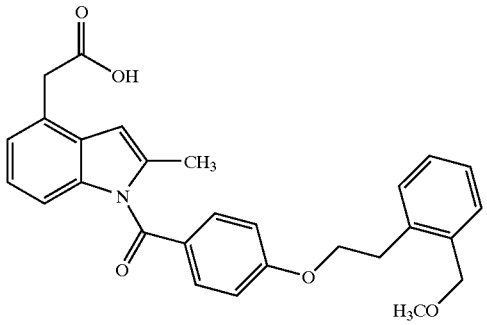

TLC: Rf 0.34 (chloroform:methanol=10:1);
MS: (FAB, Pos.): 458 (M+H)⁺;
NMR (CDCl₃): δ 7.71–7.67 (m, 2H), 7.37–7.23 (m, 3H), 7.06–6.93 (m, 6H), 6.48 (s, 1H), 4.54 (s, 2H), 4.27 (t, J=7.5 Hz, 2H), 3.86 (s, 2H), 3.41 (s, 3H), 3.21 (t, J=7.5 Hz, 2H), 2.44 (d, J=0.6 Hz, 3H).

EXAMPLE 7(147)
1-(4-(3,4-Dihydro-2H-benzo[b]pyran-3-ylmethyloxy)benzoyl)-2-methylindole-4-acetic Acid

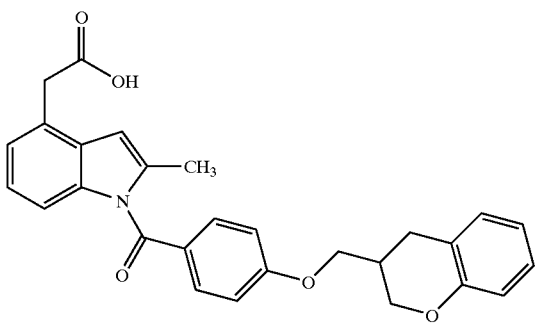

TLC: Rf 0.34 (chloroform:methanol=10:1);
MS: (APCI, Neg.): 454 (M−H)⁻;
NMR (CDCl₃): δ 7.72–7.43 (m, 5H), 7.15–6.82 (m, 6H), 6.49 (s, 1H), 4.36 (m, 1H), 4.17 (m, 1H), 4.08 (d, J=6.9 Hz, 2H), 3.87 (s, 2H), 3.04 (dd, J=16.5, 6.0 Hz, 1H), 2.78 (dd, J=16.5, 7.2 Hz, 1H), 2.63 (m, 1H), 2.44 (d, J=1.2 Hz, 3H).

EXAMPLE 7(148)
1-(4-(Indan-2-ylmethyloxy)benzoyl)-2-methylindole-4-acetic Acid

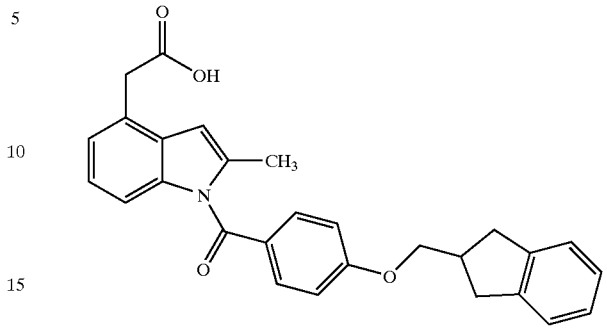

TLC: Rf 0.35 (chloroform methanol=10:1);
MS: (FAB, Pos.):440 (M+H)⁺;
NMR (CDCl₃): δ 7.73–7.68 (m, 2H), 7.26–6.93 (m, 9H), 6.49 (s, 1H), 4.04 (d, J=6.9 Hz, 2H), 3.87 (s, 2H), 3.19 (dd, J=16.5, 7.5 Hz, 2H), 3.02 (m, 1H), 2.89 (dd, J=16.5, 6.0 Hz, 2H), 2.44 (d, J=1.2 Hz, 3H).

EXAMPLE 7(149)
1-(4-(2-(1,4-Benzodioxan-2-yl)ethyloxy)benzoyl)-2-methylindole-4-acetic Acid

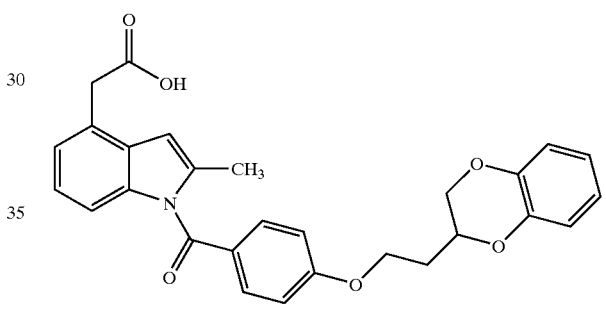

TLC: Rf 0.44 (chloroform:methanol=9:1);
MS: (APCI, Neg.): 470 (M−H)⁻;
NMR (CDCl₃): δ 7.71 (d, J=8.7 Hz, 2H), 7.10–6.80 (m, 9H), 6.49 (s, 1H), 4.50–4.40 (m, 1H), 4.38–4.17 (m, 3H), 4.01 (dd, J=11.4, 7.2 Hz, 1H), 3.86 (s, 2H), 2.44 (s, 3H), 2.17 (q, J=6.0 Hz, 2H).

EXAMPLE 7(150)
1-(4-(3,4-Dihydro-2H-benzo[b]pyran-2-ylmethyloxy)benzoyl)-2-methylindole-4-acetic Acid

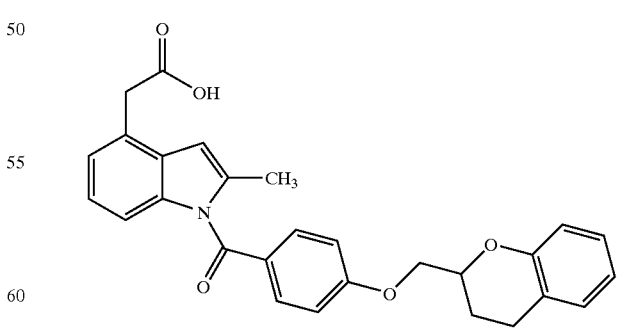

TLC: Rf 0.49 (chloroform:methanol=10:1);
MS: (APCI, Neg.): 454 (M−H)⁻;
NMR (CDCl₃): δ 7.74–7.67 (m, 2H), 7.06–6.87 (m, 9H), 6.49 (s, 1H), 4.45 (m, 1H), 4.38–4.15 (m, 2H), 3.86 (s, 2H), 3.00–2.80 (m, 2H), 2.44 (s, 3H), 2.30–1.90 (m, 2H).

EXAMPLE 7(151)

1-(4-(3,4-Dihydro-2H-1,4-benzoxazin-2-ylmethyloxy)benzoyl)-2-methylindole-4-acetic Acid

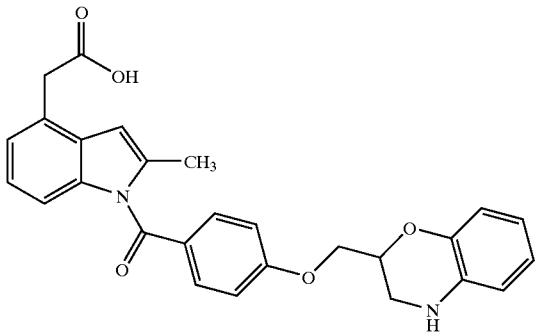

TLC: Rf 0.25 (chloroform:methanol=10:1);

MS: (APCI, Neg.): 455 (M−H)⁻;

NMR (CDCl$_3$): δ 7.76–7.40 (m, 3H), 7.10–6.89 (m, 4H), 6.89–6.60 (m, 4H), 6.49 (s, 1H), 4.60 (m, 1H), 4.31 (dd, J=9.8, 5.0 Hz, 1H), 4.24 (dd, J=9.8, 6.2 Hz, 1H), 3.86 (s, 2H), 3.58 (dd, J=11.8, 3.0 Hz, 1H), 3.42 (dd, J=11.8, 6.6 Hz, 1H), 2.44 (s, 3H).

EXAMPLE 7(152)

1-(4-(4-Methyl-3,4-dihydro-2H-1,4-benzoxazin-2-ylmethyloxy)benzoyl)-2-methylindole-4-acetic Acid

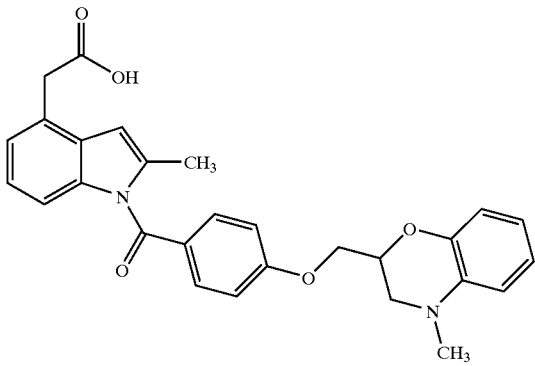

TLC: Rf 0.26 (chloroform:methanol=10:1);

MS: (APCI, Neg.): 469 (M−H)⁻;

NMR (CDCl$_3$): δ 7.78–7.40 (m, 3H), 7.10–6.78 (m, 6H), 6.73 (d, J=8.0 Hz, 2H), 6.49 (s, 1H), 4.68 (m, 1H), 4.31 (dd, J=10.0, 5.2 Hz, 1H), 4.20 (dd, J=10.0, 6.4 Hz, 1H), 3.86 (s, 2H), 3.41 (dd, J=11.6, 2.8 Hz, 1H), 3.27 (dd, J=11.6, 6.6 Hz, 1H), 2.92 (s, 3H), 2.44 (s, 3H).

EXAMPLE 7(153)

1-(4-(1,3-Dioxaindan-2-ylmethyloxy)benzoyl)-2-methylindole-4-acetic Acid

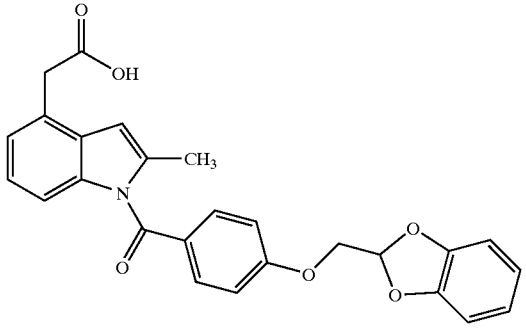

TLC: Rf 0.33 (chloroform:methanol=10:1);
MS: (FAB, Pos.): 444 (M+H)⁺;
NMR (CDCl$_3$): δ 7.74–7.69 (m, 2H), 7.06–6.85 (m, 9H), 6.50–6.47 (m, 2H), 4.35 (d, J=4.2 Hz, 2H), 3.85 (s, 2H), 2.43 (d, J=0.9 Hz, 3H).

EXAMPLE 7(154)

1-(4-(Benzo[b]furan-2-ylmethyloxy)benzoyl)-2-methylindole-4-acetic Acid

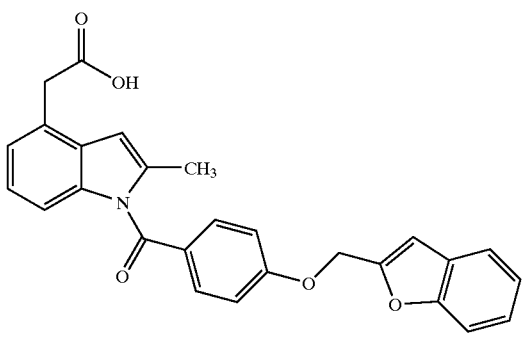

TLC: Rf 0.38 (chloroform:methanol=10:1);
MS: (FAB, Pos.): 440 (M+H)⁺;
NMR (CDCl$_3$): δ 7.76–7.71 (m, 2H), 7.59 (m, 1H), 7.51 (m, 1H), 7.32 (m, 1H), 7.25 (m, 1H), 7.11–6.92 (m, 5H), 6.84 (d, J=0.6 Hz, 1H), 6.49 (m, 1H), 5.26 (s, 2H), 3.87 (s, 2H), 2.45 (d, J=1.2 Hz, 3H).

EXAMPLE 7(155)

1-(4-(2,3-Dihydrobenzo[b]furan-2-ylmethyloxy)benzoyl)-2-methylindole-4-acetic Acid

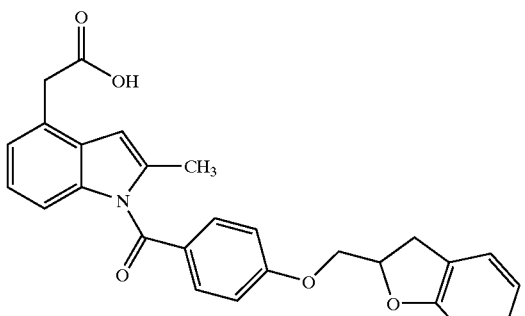

TLC: Rf 0.34 (chloroform:methanol=10:1);
MS: (El, Pos.): 441 (M)⁺;
NMR (CDCl$_3$): δ 7.73–7.69 (m, 2H), 7.23–7.12 (m, 2H), 7.06–6.82 (m, 7H), 6.49 (d, J=1.2 Hz, 1H), 5.20 (m, 1H), 4.29 (dd, J=9.9, 6.3 Hz, 1H), 4.20 (dd, J=9.9, 4.2 Hz, 1H), 3.86 (s, 2H), 3.42 (dd, J=15.9, 9.6 Hz, 1H), 3.17 (dd, J=15.9, 8.4 Hz, 1H), 2.44 (d, J=1.2 Hz, 3H).

EXAMPLE 7(156)

1-(4-(2-(2,5-Dimethoxyphenyl)ethyloxy)benzoyl)-2-methylindole-4-acetic Acid

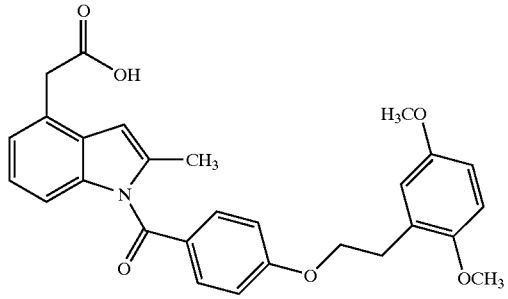

TLC: Rf 0.50 (chloroform:methanol=10:1);

MS: (FAB, Pos.): 474 (M+H)$^+$;

NMR (CDCl$_3$): δ 7.69 (m, 2H), 7.08–6.92 (m, 5H), 6.86–6.72 (m, 3H), 6.48 (s, 1H), 4.24 (t, J=6.8 Hz, 2H), 3.86 (s, 2H), 3.81 (s, 3H), 3.77 (s, 3H), 3.12 (t, J=6.8 Hz, 2H), 2.44 (s, 3H).

EXAMPLE 7(157)

1-(4-(2,3-Dihydrobenzo[b]furan-3-ylmethyloxy)benzoyl)-2-methylindole-4-acetic Acid

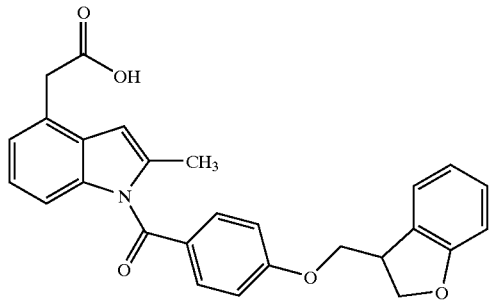

TLC: Rf 0.45 (chloroform:methanol=10:1);

MS: (FAB, Pos.): 442 (M+H)$^+$;

NMR (CDCl$_3$): δ 7.70 (m, 2H), 7.31 (d, J=7.4 Hz, 1H), 7.21 (m, 1H), 7.10–6.82 (m, 7H), 6.49 (s, 1H), 4.73 (t, J=9.6 Hz, 1H), 4.55 (dd, J=9.6, 4.6 Hz, 1H), 4.29–3.88 (m, 3H), 3.86 (s, 2H), 2.44 (s, 3H).

EXAMPLE 7(158)

1-(4-(2-Cyclopropyloxyethyloxy)benzoyl)-2-methylindole-4-acetic Acid

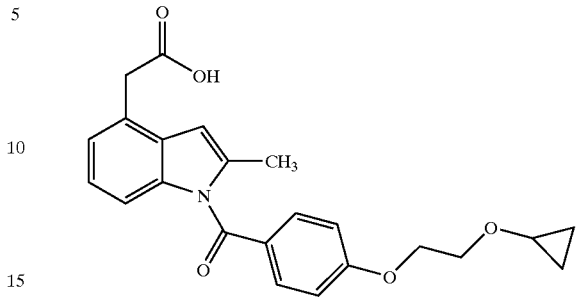

TLC: Rf 0.42 (chloroform:methanol=10:1);

MS: (FAB, Pos.): 394 (M+H)$^+$;

NMR (CDCl$_3$): δ 7.71 (m, 2H), 7.12–6.88 (m, 5H), 6.49 (s, 1H), 4.19 (t, J=4.6 Hz, 2H), 3.97–3.82 (m, 4H), 3.42 (m, 1H), 2.44 (s, 3H), 0.72–0.58 (m, 2H), 0.58–0.46 (m, 2H).

EXAMPLE 7(159)

1-(4-(2-(2,4-Dimethylphenyl)ethyloxy)benzoyl)-2-methylindole-4-acetic Acid

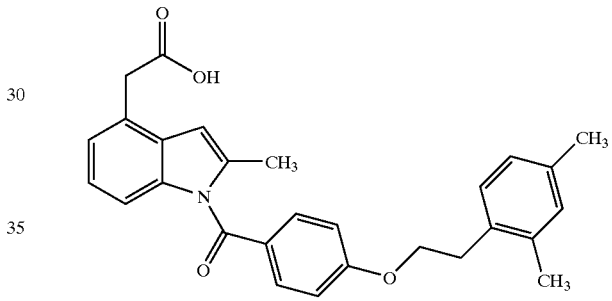

TLC: Rf 0.50 (chloroform:methanol=9:1);

MS: (APCI, Neg.): 440 (M−H)$^-$;

NMR (CDCl$_3$): δ 7.69 (d, J=9.0 Hz, 2H), 7.12 (d, J=7.5 Hz, 1H), 7.08–6.90 (m, 7H), 6.49 (s, 1H), 4.20 (t, J=7.5 Hz, 2H), 3.87 (s, 2H), 3.12 (t, J=7.5 Hz, 2H), 2.45 (s, 3H), 2.36 (s, 3H), 2.31 (s, 3H).

EXAMPLE 7(160)

1-(4-(2-(2,6-Dimethylphenyl)ethyloxy)benzoyl)-2-methylindole-4-acetic Acid

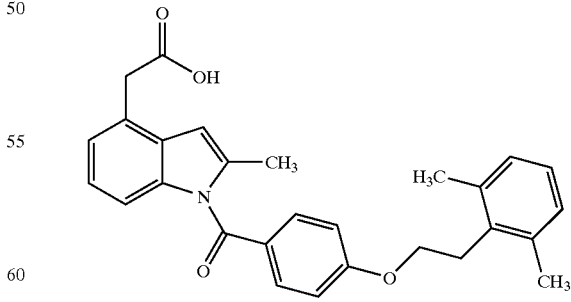

TLC: Rf 0.59 (chloroform:methanol=9:1);

MS: (APCI, Neg.): 440 (M−H)$^-$;

NMR (CDCl$_3$): δ 7.70 (d, J=9.0 Hz, 2H), 7.09–6.90 (m, 8H), 6.49 (s, 1H), 4.13 (t, J=7.2 Hz, 2H), 3.88 (s, 2H), 3.22 (t, J=7.2 Hz, 2H), 2.45 (s, 3H), 2.41 (s, 6H).

EXAMPLE 7(161)

1-(4-(2-(Benzo[b]thiophen-2-yl)ethyloxy)benzoyl)-2-methylindole-4-acetic Acid

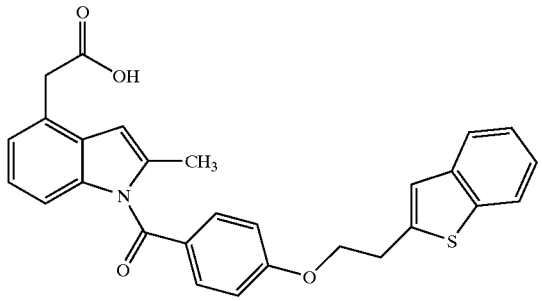

TLC: Rf 0.61 (chloroform:methanol=9:1);
MS: (APCI, Neg.): 468 (M−H)⁻;
NMR (CDCl₃): δ 7.82–7.76 (m, 1H), 7.75–7.68 (m, 3H), 7.37–7.24 (m, 2H), 7.16 (s, 1H), 7.08–6.92 (m, 5H), 6.49 (s, 1H), 4.36 (t, J=6.3 Hz, 2H), 3.87 (s, 2H), 3.43 (t, J=6.3 Hz, 2H), 2.44 (s, 3H).

EXAMPLE 7(162)

1-(4-(2-(2-Methoxyphenyloxy)ethyloxy)benzoyl)-2-methylindole-4-acetic Acid

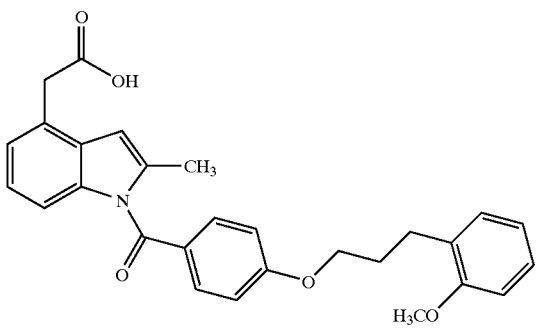

TLC: Rf 0.52 (chloroform:methanol=10:1);
MS: (APCI, Neg.): 458 (M−H)⁻;
NMR (CDCl₃): δ 7.70 (d, J=9.0 Hz, 2H), 7.03–6.92 (m, 9H), 6.48 (d, J=0.9 Hz, 1H), 4.42 (s, 4H), 3.85 (s, 3H), 3.84 (s, 2H), 2.44 (d, J=0.9 Hz, 3H).

EXAMPLE 7(163)

1-(4-(2-(N-Ethyl-N-phenylamino)ethyloxy)benzoyl)-2-methylindole-4-acetic Acid Acetate

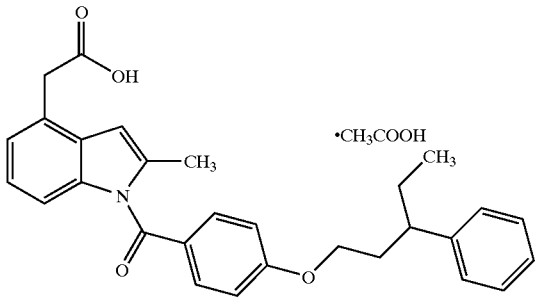

TLC: Rf 0.50 (chloroform:methanol 10:1);
MS: (APCI, Neg.): 455 (M−H)⁻;
NMR (CDCl₃): δ 7.67 (d, J=9.0 Hz, 2H), 7.26–7.20 (m, 2H), 7.04–6.88 (m, 5H), 6.76–6.66 (m, 3H), 6.45 (d, J=0.9 Hz, 1H), 4.17 (d, J=6.8 Hz, 2H), 3.83 (s, 2H), 3.74 (t, J=6.8 Hz, 2H), 3.47 (q, J=7.2 Hz, 2H), 2.42 (d, J=0.9 Hz, 3H), 2.06 (s, 3H), 1.19 (t, J=7.2 Hz, 3H).

EXAMPLE 7(164)

1-(4-(2-(Indol-1-yl)ethyloxy)benzoyl)-2-methylindole-4-acetic Acid

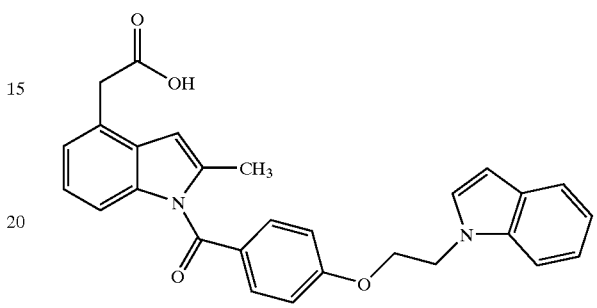

TLC: Rf 0.50 (chloroform:methanol=10:1);

MS: (APCI, Neg.): 451 (M−H)⁻;

NMR (CDCl₃): δ 7.68–7.63 (m, 3H), 7.41 (d, J=8.0 Hz, 1H), 7.26–7.21 (m, 2H), 7.14–6.86 (m, 8H), 6.54 (dd, J=3.0, 0.6 Hz, 1H), 6.48 (s, 1H), 4.58 (t, J=5.4 Hz, 2H), 4.36 (t, J=5.4 Hz, 2H), 3.86 (s, 2H), 2.42 (s, 3H).

EXAMPLE 7(165)

1-(4-(2-(3-Methylpyridin-2-yl)ethyloxy)benzoyl)-2-methylindole-4-acetic Acid

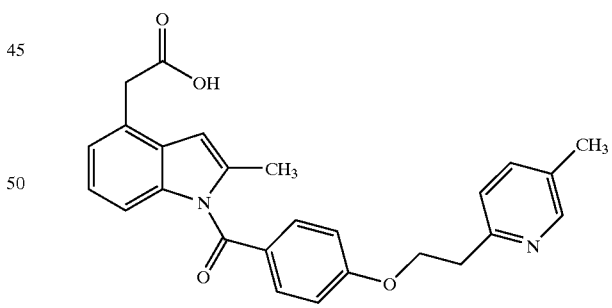

TLC: Rf 0.44 (chloroform:methanol=10:1);

MS: (APCI, Neg.): 427 (M−H)⁻;

NMR (CDCl₃): δ 8.43 (m, 1H), 7.64 (d, J=6.9 Hz, 2H), 7.49 (m, 1H), 7.21 (d, J=8.1 Hz, 1H), 7.05 (d, J=8.1 Hz, 1H), 7.00–6.85 (m, 4H), 6.53 (d, J=0.9 Hz, 1H), 4.33 (t, J=6.6 Hz, 2H), 3.85 (s, 2H), 3.26 (t, J=6.6 Hz, 2H), 2.41 (d, J=0.9 Hz, 3H), 2.31 (s, 3H).

EXAMPLE 7(166)

1-(4-(2-(Benzo[b]furan-2-yl)ethyloxy)benzoyl)-2-methylindole-4-acetic Acid

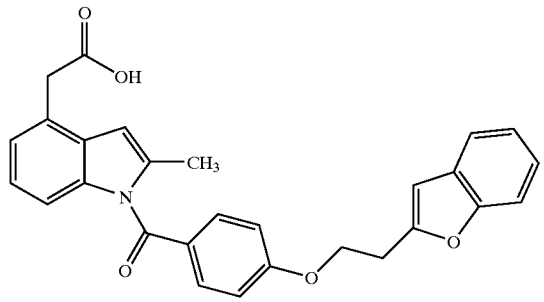

TLC: Rf 0.50 (chloroform:methanol=9:1);
MS: (APCI, Neg.): 452 (M−H)⁻;
NMR (CDCl₃): δ 7.76–7.42 (m, 4H), 7.30–7.17 (m, 2H), 7.10–6.90 (m, 5H), 6.57 (s, 1H), 6.49 (s, 1H), 4.42 (t, J=6.6 Hz, 2H), 3.87 (s, 2H), 3.32 (t, J=6.6 Hz, 2H), 2.44 (s, 3H).

EXAMPLE 7(167)

1-(4-(4-Methyl-3,4-dihydro-2H-1,4-benzoxazin-3-ylmethyloxy)benzoyl)-2-methylindole-4-acetic Acid

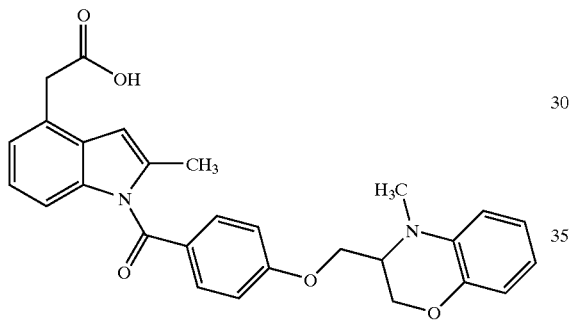

TLC: Rf 0.37 (chloroform:methanol=10:1);
MS: (APCI, Neg.): 469 (M−H)⁻;
NMR (CDCl₃): δ 7.72–7.67 (m, 2H), 7.06–6.81 (m, 7H), 6.69–6.62 (m, 2H), 6.49 (m, 1H), 4.48 (dd, J=11.1, 1.8 Hz, 1H), 4.14 (d, J=7.5 Hz, 2H), 4.13 (dd, J=11.1, 2.4 Hz, 1H), 3.86 (s, 2H), 3.74 (m, 1H), 3.08 (s, 3H), 2.44 (d, J=1.2 Hz, 3H).

EXAMPLE 7(168)

1-(4-(2-(2,4-Dimethoxyphenyloxy)ethyloxy)benzoyl)-2-methylindole-4-acetic Acid

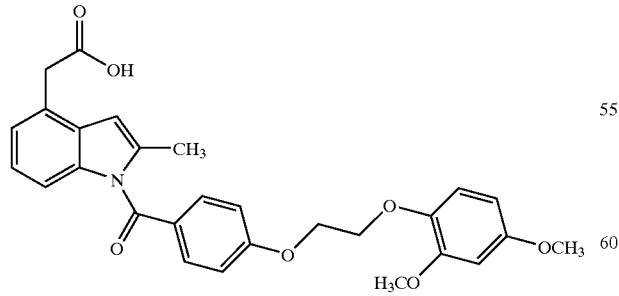

TLC: Rf 0.52 (chloroform:methanol 10:1);
MS: (APCI, Neg.): 488 (M−H)⁻;
NMR (CDCl₃): δ 7.72–7.62 (m, 3H), 7.58–7.50 (m, 1H), 7.49–7.41 (m, 1H), 7.06–6.85 (m, 4H), 6.53–6.48 (m, 2H), 6.39 (dd, J=8.7, 2.7 Hz, 1H), 4.45–4.30 (m, 4H), 3.85 (s, 2H), 3.83 (s, 3H), 3.78 (s, 3H), 2.44 (d, J=0.9 Hz, 3H).

EXAMPLE 7(169)

1-(4-(2-(4-Methylpyridin-2-yl)ethyloxy)benzoyl)-2-methylindole-4-acetic Acid

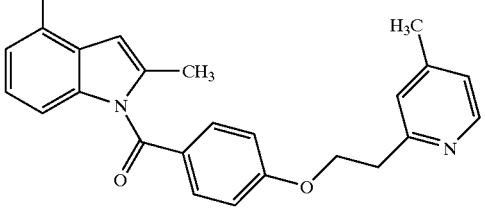

TLC: Rf 0.44 (chloroform:methanol=10:1);

MS: (APCI, Neg.): 427 (M−H)⁻;

NMR (CDCl₃): δ 8.44 (d, J=6.6 Hz, 1H), 7.64 (d, J=8.7 Hz, 2H), 7.13–6.86 (m, 7H), 6.52 (d, J=0.8 Hz, 1H), 4.34 (t, J=6.2 Hz, 2H), 3.85 (s, 2H), 3.26 (t, J=6.2 Hz, 2H), 2.41 (d, J=0.8 Hz, 3H), 2.31 (s, 3H).

EXAMPLE 7(170)

1-(4-(4-Ethyl-3,4-dihydro-2H-1,4-benzoxazin-3-ylmethyloxy)benzoyl)-2-methylindole-4-acetic Acid

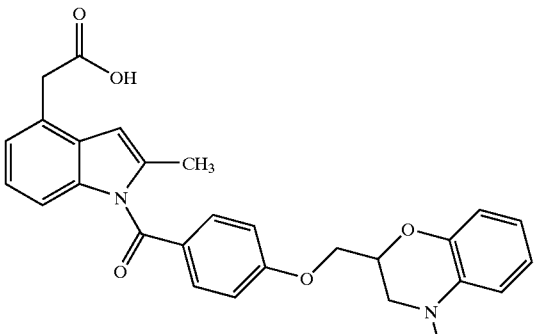

TLC: Rf 0.28 (chloroform:methanol=10:1);

MS: (APCI, Neg.): 483 (M−H)⁻;

NMR (CDCl₃): δ 7.80–7.57 (m, 2H), 7.10–6.79 (m, 7H), 6.79–6.56 (m, 2H), 6.49 (s, 1H), 4.68–4.50 (m, 1H), 4.31 (dd, J=9.6, 5.2 Hz, 1H), 4.21 (dd, J=9.6, 6.2 Hz, 1H), 3.86 (s, 2H), 3.57–3.20 (m, 4H), 2.44 (s, 3H), 1.17 (t, J=7.4 Hz, 3H).

EXAMPLE 7(171)
1-(4-(2-(N-Methyl-N-(3-methylphenyl)amino)ethyloxy) benzoyl)-2-methylindole-4-acetic Acid

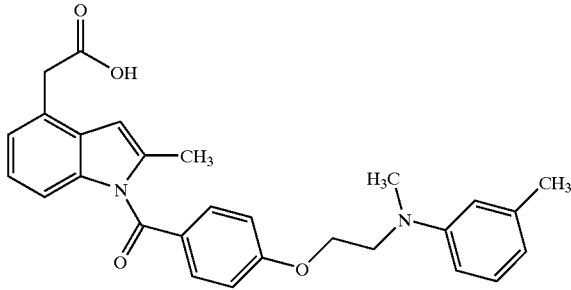

TLC: Rf 0.27 (chloroform:methanol=10:1);
MS: (APCI, Neg.): 455 (M–H)⁻;
NMR (CDCl$_3$): δ 7.68 (d, J=8.8 Hz, 2H), 7.21–6.87 (m, 6H), 6.63–6.52 (m, 3H), 6.48 (s, 1H), 4.22 (t, J=6.0 Hz, 2H), 3.85 (s, 2H), 3.79 (t, J=6.0 Hz, 2H), 3.06 (s, 3H), 2.43 (s, 3H), 2.32 (s, 3H).

EXAMPLE 7(172)
1-(4-(3,4-Dihydro-2H-1,5-benzodioxepin-3-yloxy) benzoyl)-2-methylindole-4-acetic Acid

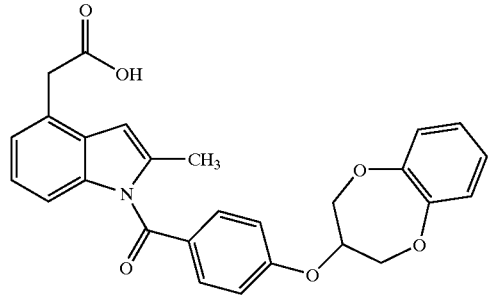

TLC: Rf 0.54 (chloroform:methanol=9:1);
MS: (APCI, Neg.): 456 (M–H)⁻;
NMR (CDCl$_3$): δ 7.78–7.42 (m, 6H), 7.10–6.90 (m, 5H), 6.50 (s, 1H), 5.08–4.96 (m, 1H), 4.57 (dd, J=12.6, 4.2 Hz, 2H), 4.47 (dd, J=12.6, 4.2 Hz, 2H), 3.87 (s, 2H), 2.45 (s, 3H).

EXAMPLE 7(173)
1-(4-(3,4-Dihydro-2H-1,5-benzodioxepin-3-ylmethyloxy) benzoyl)-2-methylindole-4-acetic Acid

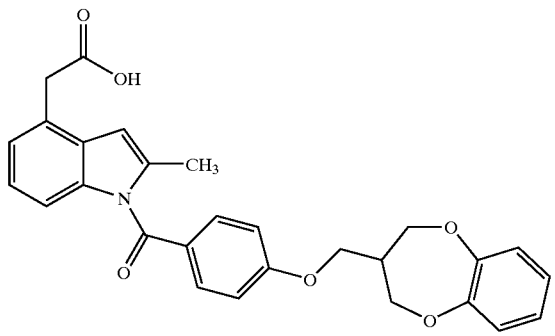

TLC: Rf 0.50 (chloroform:methanol=9:1);
MS: (APCI, Neg.): 470 (M–H)⁻;
NMR (CDCl$_3$): δ 7.78–7.42 (m, 5H), 7.10–6.90 (m, 6H), 6.50 (s, 1H), 4.40–4.28 (m, 4H), 4.26 (d, J=6.9 Hz, 2H), 3.87 (s, 2H), 2.80–2.70 (m,1H), 2.45 (s, 3H).

EXAMPLE 7(174)
1-(4-(1,4-Benzodioxan-6-ylmethyloxy)benzoyl)-2-methylindole-4-acetic Acid

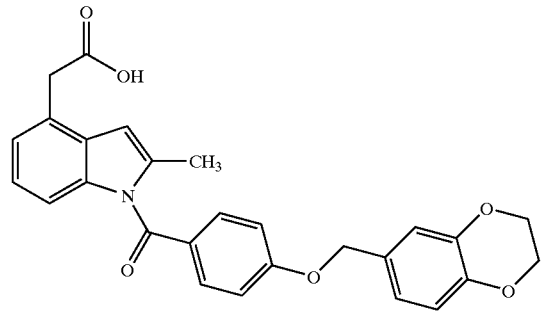

TLC: Rf 0.40 (chloroform:methanol=10:1);
MS: (EI, Pos.): 457 (M)⁺;
NMR (CDCl$_3$): δ 7.73–7.68 (m, 2H), 7.07–6.90 (m, 8H), 6.49 (s, 1H), 5.03 (s, 2H), 4.27 (s, 4H), 3.87 (s, 2H), 2.45 (d, J=0.9 Hz, 3H).

EXAMPLE 7(175)
1-(4-(2-(4-Methoxy-2-methylphenyl)ethyloxy)benzoyl)-2-methylindole-4-acetic Acid

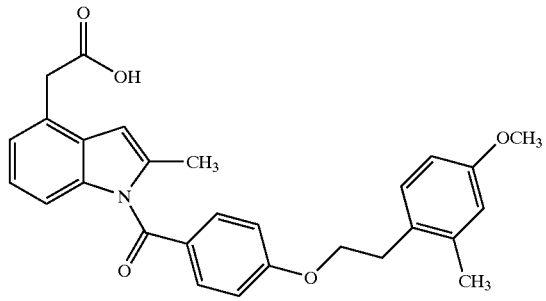

TLC: Rf 0.37 (chloroform:methanol=10:1);
MS: (EI, Pos.): 457 (M)⁺;
NMR (CDCl$_3$): δ 7.72–7.67 (m, 2H), 7.15 (d, J=8.1 Hz, 1H), 7.06–6.91 (m, 5H), 6.76–6.71 (m, 2H), 6.49 (s, 1H), 4.18 (t, J=7.2 Hz, 2H), 3.86 (s, 2H), 3.79 (s, 3H), 3.09 (t, J=7.2 Hz, 2H), 2.44 (d, J=0.9 Hz, 3H) 2.37 (s, 3H).

EXAMPLE 7(176)
1-(4-(1-Methyl-1,2,3,4-tetrahydroquinolin-2-ylmethyloxy) benzoyl)-2-methylindole-4-acetic Acid

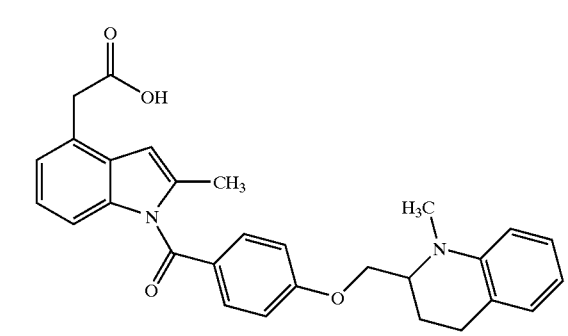

TLC: Rf 0.39 (chloroform:methanol=10:1);
MS: (EI, Pos.): 468 (M)⁺;
NMR (CDCl$_3$): δ 7.72–7.67 (m, 2H), 7.12 (m, 1H), 7.06–6.91 (m, 6H), 6.68–6.58 (m, 2H), 6.49 (m, 1H), 4.13

(dd, J=9.3, 5.7 Hz, 1H), 4.00 (dd, J=9.3, 7.5 Hz, 1H), 3.86 (s, 2H), 3.79 (m, 1H), 3.07 (s, 3H), 2.89–2.70 (m, 2H), 2.44 (d, J=0.9 Hz, 3H) 2.19 (m, 1H), 2.02 (m, 1H).

EXAMPLE 7(177)

1-(4-(2-(2,3-Dihydrobenzo[b]furan-2-yl)ethyloxy)benzoyl)-2-methylindole-4-acetic Acid

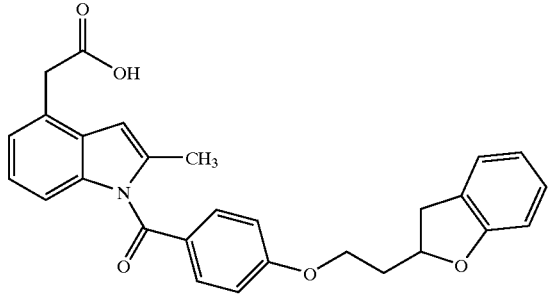

TLC: Rf 0.50 (chloroform:methanol=9:1);

MS: (APCI, Neg.): 454 (M–H)$^-$;

NMR (CDCl$_3$): δ 7.72 (d, J=8.7 Hz, 2H), 7.22–6.76 (m, 9H), 6.50 (s, 1H), 5.10–5.00 (m, 1H), 4.40–4.20 (m, 2H), 3.88 (s, 2H), 3.41 (dd, J=15.6, 8.4 Hz, 1H), 2.97 (dd, J=15.6, 7.5 Hz, 1H), 2.46 (s, 3H), 2.35–2.15 (m, 2H).

EXAMPLE 7(178)

1-(4-(4,7-Dimethyl-3,4-dihydro-2H-1,4-benzoxazin-2-ylmethyloxy)benzoyl)-2-methylindole-4-acetic Acid

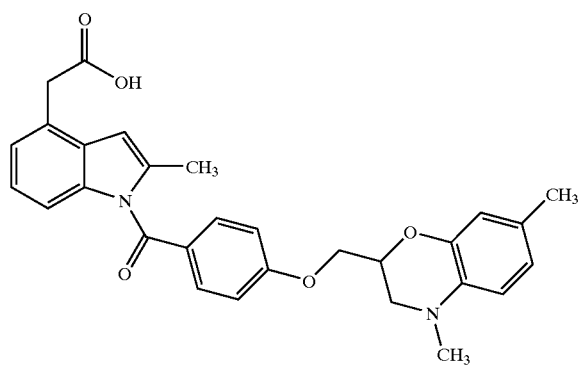

TLC: Rf 0.48 (chloroform:methanol=10:1);

MS: (APCI, Neg.): 483 (M–H)$^-$;

NMR (CDCl$_3$): δ 7.69 (dd, J=8.8, 2.2 Hz, 2H), 7.04–6.90 (m, 6H), 6.70–6.63 (m, 2H), 6.48 (s, 1H), 4.65 (m, 1H), 4.28 (dd, J=7.2, 5.1 Hz, 1H), 4.23 (dd, J=7.2, 2.5 Hz, 1H), 3.85 (s, 2H), 3.32 (dd, J=12.4, 2.6 Hz, 1H), 3.20 (dd, J=12.4, 6.6 Hz, 1H), 2.87 (s, 3H), 2.44 (s, 3H), 2.23 (s, 3H).

EXAMPLE 7(179)

1-(4-(4,6-Dimethyl-3,4-dihydro-2H-1,4-benzoxazin-2-ylmethyloxy)benzoyl)-2-methylindole-4-acetic Acid

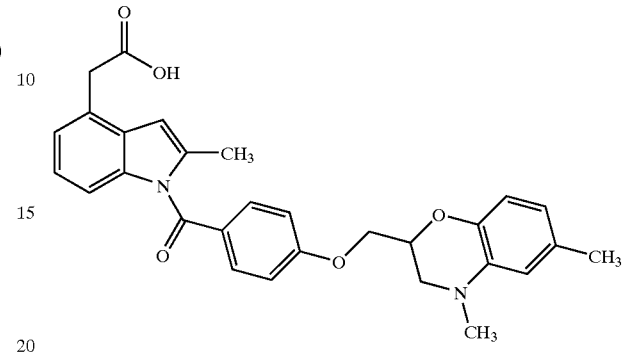

TLC: Rf 0.48 (chloroform:methanol=10:1);

MS: (APCI, Neg.): 483 (M–H)$^-$;

NMR (CDCl$_3$): δ 7.69 (m, 2H), 7.04–6.90 (m, 6H), 6.73 (d, J=8.0 Hz, 1H), 6.53 (s, 1H), 6.48 (s, 1H), 4.65 (m, 1H), 4.28 (dd, J=7.2, 5.1 Hz, 1H), 4.22 (dd, J=7.2, 2.5 Hz, 1H), 3.85 (s, 2H), 3.35 (dd, J=12.2, 3.0 Hz, 1H), 3.25 (dd, J=12.2, 6.2 Hz, 1H), 2.90 (s, 3H), 2.44 (s, 3H), 2.27 (s, 3H).

EXAMPLE 7(180)

1-(4-(1-Methylindolin-2-ylmethyloxy)benzoyl)-2-methylindole-4-acetic Acid

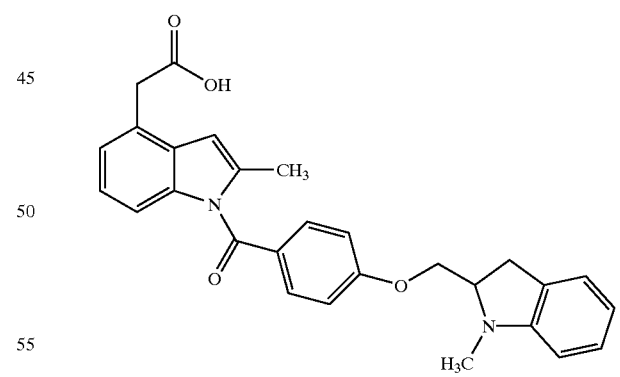

TLC: Rf 0.49 (chloroform:methanol=9:1);

MS: (APCI, Neg.): 453 (M–H)$^-$;

NMR (CDCl$_3$): δ 7.76–7.66 (m, 2H), 7.20–6.46 (m, 10H), 5.00–2.80 (m, 5H), 3.87 (s, 2H), 2.94 and 2.91 (each s, total 3H), 2.45 (s, 3H).

EXAMPLE 7(181)

1-(4-(4,5-Dimethyl-3,4-dihydro-2H-1,4-benzoxazin-2-ylmethyloxy)benzoyl)-2-methylindole-4-acetic Acid

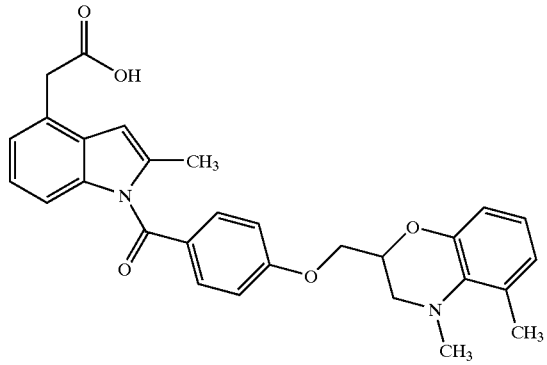

TLC: Rf 0.51 (chloroform:methanol=9:1);

MS: (APCI, Neg.): 483 (M−H)⁻;

NMR (CDCl$_3$): δ 7.74 (d, J=9.0 Hz, 2H), 7.08–6.84 (m, 6H), 6.82–6.75 (m, 2H), 6.50 (s, 1H), 4.55–4.45 (m, 1H), 4.36 (dd, J=9.9, 4.5 Hz, 1H), 4.22 (dd, J=9.9, 4.5 Hz, 1H), 3.87 (s, 2H), 3.27 (dd, J=13.8, 2.4 Hz, 1H), 3.08 (dd, J=13.8, 9.9 Hz, 1H), 2.78 (s, 3H), 2.45 (s, 3H), 2.33 (s, 3H).

EXAMPLE 7(182)

1-(4-(4-Acetyl-3,4-dihydro-2H-1,4-benzoxazin-2-ylmethyloxy)benzoyl)-2-methylindole-4-acetic Acid

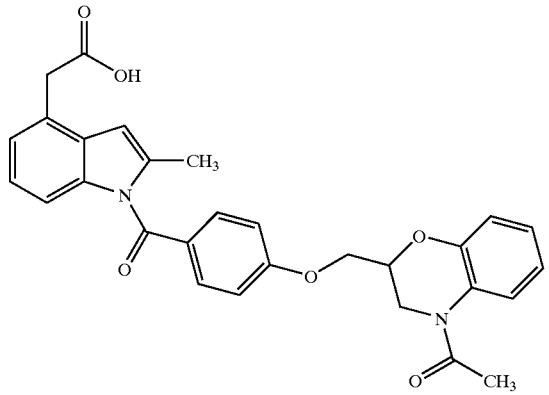

TLC: Rf 0.50 (chloroform:methanol=10:1);

MS: (APCI, Neg.): 497 (M−H)⁻;

NMR (CDCl$_3$): δ 7.75–7.62 (m, 4H), 7.15–6.90 (m, 7H), 6.49 (s, 1H), 4.64 (brs, 2H), 4.25 (m, 2H), 3.86 (s, 2H), 3.60 (brs 1H), 2.44 (s, 3H), 2.35 (s, 3H).

EXAMPLE 7(183)

1-(4-(3-Acetyl-2,3-dihydro-1,3-benzoxazol-2-ylmethyloxy)benzoyl)-2-methylindole-4-acetic Acid

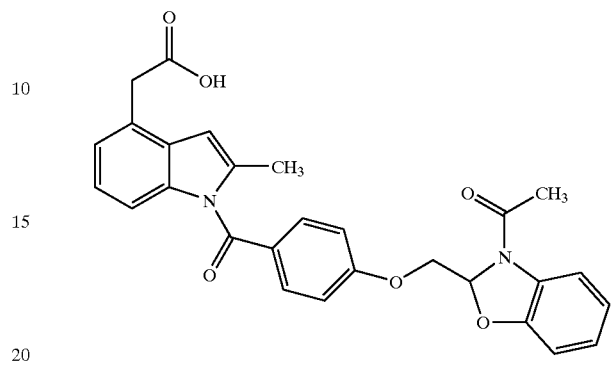

TLC: Rf 0.34 (chloroform:methanol=10:1);

MS: (FAB, Pos.):485 (M+H)⁺;

NMR (CDCl$_3$): δ 7.67 (d, J=9.3 Hz, 2H), 7.10–6.90 (m, 9H), 6.66 (brs, 1H), 6.48 (s, 1H), 4.40 (brs, 2H), 3.86 (s, 2H), 2.43 (s, 3H), 2.43 (d, J=0.9 Hz, 3H).

EXAMPLE 7(184)

1-(4-(4,6,8-Trimethyl-3,4-dihydro-2H-1,4-benzoxazin-2-ylmethyloxy)benzoyl)-2-methylindole-4-acetic Acid

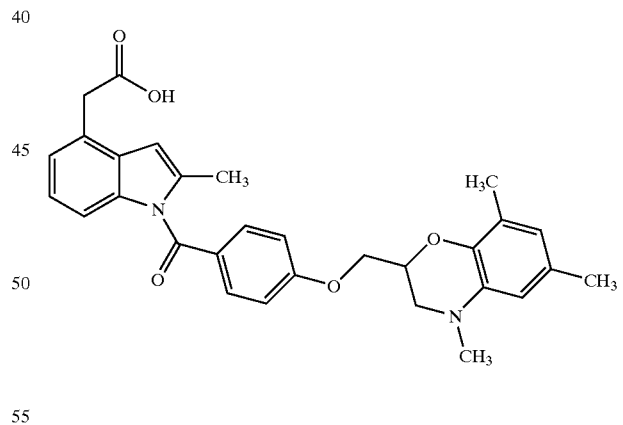

TLC: Rf 0.36 (chloroform:methanol=10:1);

MS: (APCI, Neg.): 497 (M−H)⁻;

NMR (CDCl$_3$): δ 7.74–7.69 (m, 2H), 7.07–6.93 (m, 5H), 6.49 (s, 1H), 6.40 (s, 1H), 6.40 (s, 1H), 4.65 (m, 1H), 4.31 (dd, J=9.9, 4.8 Hz, 1H), 4.21 (dd, J=9.9, 6.3 Hz, 1H), 3.87 (s, 2H), 3.39 (dd, J=11.7, 2.7 Hz, 1H), 3.24 (dd, J=11.7, 6.0 Hz, 1H), 2.89 (s, 3H), 2.45 (d, J=0.6 Hz, 3H), 2.24 (s, 3H), 2.14 (s, 3H).

EXAMPLE 7(185)
1-(4-((3Z)-3-Hexen-1-yloxy)benzoyl)-2-methylindole-4-acetic Acid

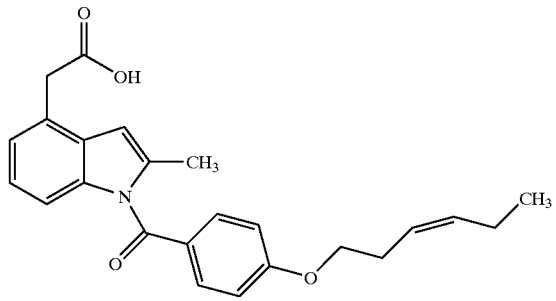

TLC: Rf 0.52 (chloroform:methanol=10:1);
MS: (APCI, Neg.): 390 (M−H)⁻;
NMR (CDCl₃): δ 7.70 (dd, J=6.9, 2.1 Hz, 2H), 7.06–6.92 (m, 5H), 6.48 (d, J=0.9 Hz, 1H), 5.56 (m, 1H), 5.40 (m, 1H), 4.05 (t, J=6.9 Hz, 2H), 3.86 (s, 2H), 2.57 (m, 2H), 2.44 (d, J=0.9 Hz, 3H), 2.11 (m, 2H), 1.00 (t, J=7.2 Hz, 3H).

EXAMPLE 7(186)
1-(4-(4-Methyl-1,3-dioxaindan-2-ylmethyloxy)benzoyl)-2-methylindole-4-acetic Acid

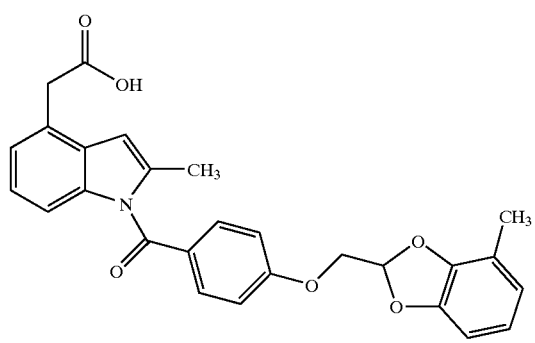

TLC: Rf 0.52 (chloroform:methanol=10:1);
MS: (APCI, Neg.): 456 (M−H)⁻;
NMR (CDCl₃): δ 7.71 (dd, J=6.9, 2.1 Hz, 2H), 7.04–6.95 (m, 5H), 6.80–6.67 (m, 2H), 6.48–6.44 (m, 2H), 4.35 (d, J=4.2 Hz, 2H), 3.85 (s, 2H), 2.44 (d, J=0.9 Hz, 3H), 2.23 (s, 3H).

EXAMPLE 7(187)
1-(4-(5-Methyl-1,3-dioxaindan-2-ylmethyloxy)benzoyl)-2-methylindole-4-acetic Acid

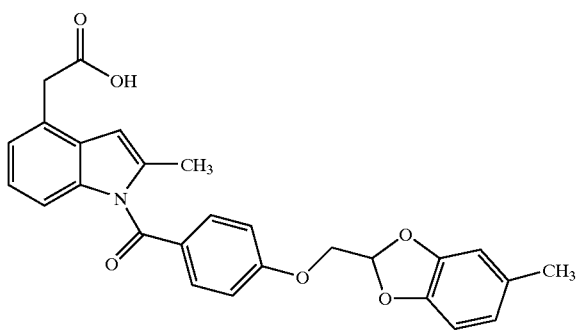

TLC: Rf 0.52 (chloroform:methanol=10:1);
MS: (APCI, Neg.): 456 (M−H)⁻;
NMR (CDCl₃): δ 7.71 (m, 2H), 7.06–6.92 (m, 6H), 6.75–6.65 (m, 2H), 6.49–6.44 (m, 2H), 4.32 (d, J=4.2 Hz, 2H), 3.86 (s, 2H), 2.44 (d, J=0.9 Hz, 3H), 2.29 (s, 3H).

EXAMPLE 7(188)
1-(4-((4E)-4-Hexen-1-yloxy)benzoyl)-2-methylindole-4-acetic Acid

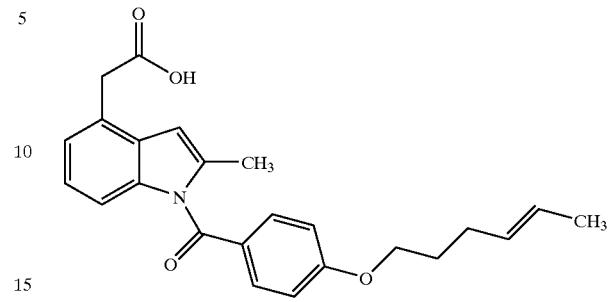

TLC: Rf 0.40 (chloroform:methanol=10:1);
MS: (APCI, Neg.): 390 (M−H)⁻;
NMR (CDCl₃): δ 7.72–7.67 (m, 2H), 7.05–6.92 (m, 5H), 6.48 (s, 1H), 5.56–5.40 (m, 2H), 4.04 (t, J=6.6 Hz, 2H), 3.85 (s, 2H), 2.44 (d, J=0.9 Hz, 3H), 2.22–2.14 (m, 2H), 1.92–1.83 (m, 2H), 1.67–1.65 (m, 3H).

EXAMPLE 7(189)
1-(4-((3E)-3-Hexen-1-yloxy)benzoyl)-2-methylindole-4-acetic Acid

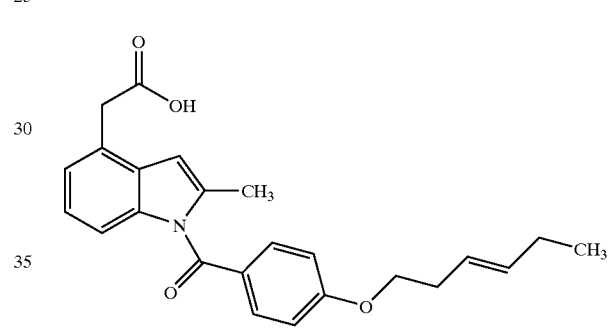

TLC: Rf 0.38 (chloroform:methanol=10:1);
MS: (APCI, Neg.): 390 (M−H)⁻;
NMR (CDCl₃): δ 7.72–7.68 (m, 2H), 7.06–6.93 (m, 5H), 6.48 (s, 1H), 5.64 (dt, J=15.3, 6.0 Hz, 1H), 5.48 (dt, J=15.3, 6.6 Hz, 1H), 4.05 (t, J=6.9 Hz, 2H), 3.86 (s, 2H), 2.52 (dt, J=6.6, 6.9 Hz, 2H), 2.44 (d, J=0.9 Hz, 3H), 2.05 (dq, J=6.0, 7.5 Hz, 2H), 0.99 (t, J=7.5 Hz, 3H).

EXAMPLE 7(190)
1-(4-(3-(N-Methyl-N-phenylamino)propyloxybenzoyl)-5-methylindole-4-acetic Acid

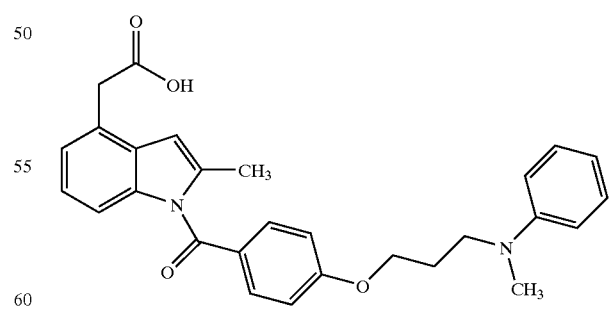

TLC: Rf 0.44 (chloroform:methanol=9:1):
MS: (APCI, Neg.): 455 (M−H)⁻;
NMR (CDCl₃): δ 7.71 (d, J=9.0 Hz, 2H), 7.26–7.16 (m, 2H), 7.08–6.92 (m, 5H), 6.79–6.66 (m, 3H), 6.49 (s, 1H), 4.09 (t, J=5.7 Hz, 2H), 3.87 (s, 2H), 3.57 (t, J=6.9 Hz, 2H), 2.60 (s, 3H), 2.45 (s, 3H), 2.20–2.00 (m, 2H).

EXAMPLE 7(191)

1-(4-(4-Methanesulfonyl-3,4-dihydro-2H-1,4-benzoxazin-2-ylmethyloxy)benzoyl)-2-methylindole-4-acetic Acid

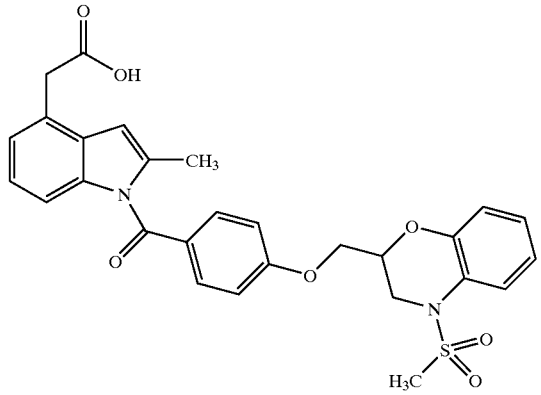

TLC: Rf 0.50 (chloroform:methanol=10:1);

MS: (APCI, Neg.): 533 (M−H)⁻;

NMR (CDCl$_3$): δ 7.72 (m, 3H), 7.12–6.91 (m, 8H), 6.50 (s, 1H), 4.56 (brs, 1H), 4.46–4.26 (m, 3H), 3.88 (s, 2H), 3.57 (dd, J=13.8, 9.3 Hz, 1H), 3.02 (s, 3H) 2.45 (s, 3H).

EXAMPLE 7(192)

1-(4-(4-Methyl-7-methoxy-3,4-dihydro-2H-1,4-benzoxazin-2-ylmethyloxy)benzoyl)-2-methylindole-4-acetic Acid

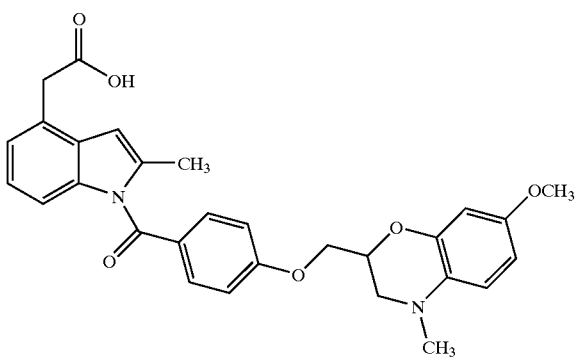

TLC: Rf 0.40 (chloroform:methanol=10:1);

MS: (APCI, Neg.): 499 (M−H)⁻;

NMR (CDCl$_3$): δ 7.75–7.62 (m, 4H), 7.04–6.90 (m, 4H), 6.66 (d, J=9.0 Hz, 1H), 6.49 (s, 1H), 6.48 (d, J=9.0 Hz, 1H), 4.70 (m, 1H), 4.30 (dd, J=12.0, 5.4 Hz, 1H), 4.24 (m, 1H), 3.87 (s, 2H), 3.74 (s, 3H), 3.33 (dd, J=11.4, 2.7 Hz, 1H), 3.18 (dd, J=11.7, 6.6, 1H), 2.86 (s, 3H), 2.45 (s, 3H).

EXAMPLE 7(193)

1-(4-(2,2-Dimethyl-1,3-dioxolan-4-ylmethyloxy)benzoyl)-2-methylindole-4-acetic Acid

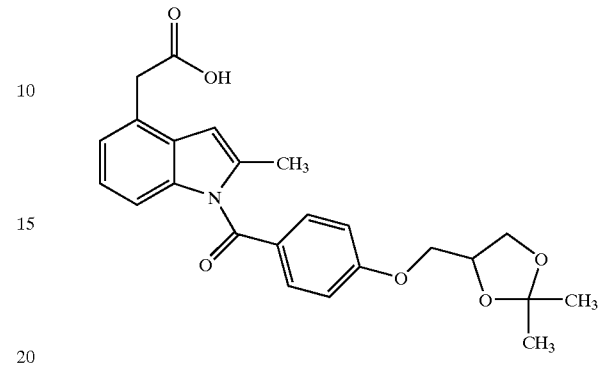

TLC: Rf 0.38 (chloroform:methanol=10:1);

NMR (FAB, Pos.): 424 (M+H)⁺;

NMR (CDCl$_3$): δ 7.73–7.68 (m, 2H), 7.06–6.92 (m, 5H), 6.48 (s, 1H), 4.52 (m, 1H), 4.20 (dd, J=8.4, 6.6 Hz, 1H), 4.13 (dd, J=9.6, 5.7 Hz, 1H), 4.04 (dd, J=9.6, 5.7 Hz, 1H), 3.94 (dd, J=8.4, 5.7 Hz, 1H), 3.86 (s, 2H), 2.44 (s, 3H), 1.48 (s, 3H), 1.42 (s, 3H).

EXAMPLE 7(194)

1-(4-(6-Fluoro-4-methyl-3,4-dihydro-2H-1,4-benzoxazin-2-ylmethyloxy)benzoyl)-2-methylindole-4-acetic Acid

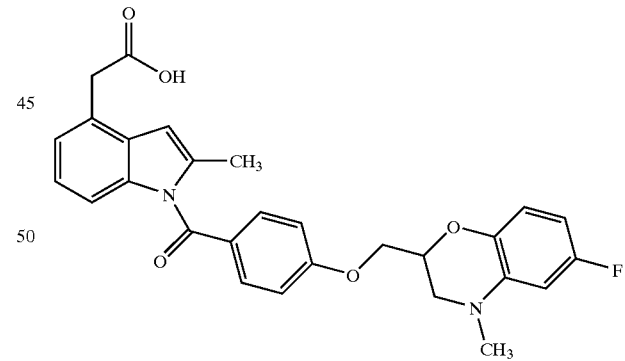

TLC: Rf 0.50 (chloroform:methanol=10:1);

MS: (APCI, Pos.): 489 (M+H)⁺;

NMR (CDCl$_3$): δ 7.72 (d, J=8.7 Hz, 2H), 7.08–6.90 (m, 5H), 6.74 (dd, J=8.7, 5.4 Hz, 1H), 6.50 (s, 1H), 6.35 (m, 2H), 4.60 (m, 1H), 4.30 (dd, J=9.9, 5.1 Hz, 1H), 4.19 (dd, J=9.9, 6.3 Hz, 1H), 3.87 (s, 2H), 3.41 (dd, J=11.7, 3.6 Hz, 1H), 3.30 (dd, J=11.7, 6.6 Hz, 1H), 2.91 (s, 3H), 2.45 (s, 3H).

EXAMPLE 7(195)

1-(4-(4,5-Dimethyl-1,3-dioxolan-2-ylmethyloxy)benzoyl)-2-methylindole-4-acetic Acid

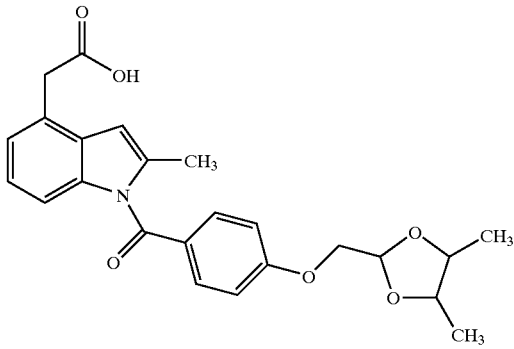

TLC: Rf 0.35 (chloroform:methanol=10:1);

MS: (EI, Pos.): 423 (M)+;

NMR (CDCl₃): δ 7.72–7.67 (m, 2H), 7.05–6.90 (m, 5H), 6.48 (s, 1H), 5.54 and 5.44 and 5.27 (each t, J=4.2 Hz, total 1H), 4.36–4.31 and 4.28–4.23 and 3.74–3.69 (each m, total 2H), 4.14 and 4.09 and 4.03 (each d, J=4.2 Hz, total 2H), 3.85 (s, 2H), 2.44 (d, J=0.6 Hz, 3H), 1.38–1.17 (m, 6H).

EXAMPLE 7(196)

1-(4-((3Z)-3-Penten-1-yloxy)benzoyl)-2-methylindole-4-acetic Acid

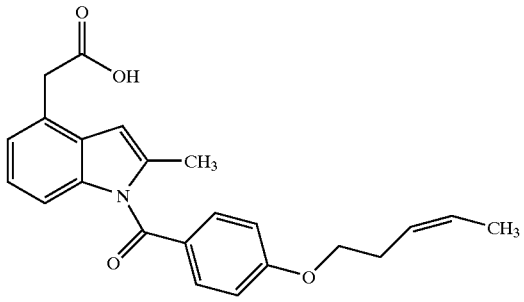

TLC: Rf 0.51 (chloroform:methanol=10:1);

MS: (APCI, Neg.):376 (M–H)⁻;

NMR (CDCl₃): δ 7.69 (m, 2H), 7.08–6.93 (m, 5H), 6.49 (d, J=1.2 Hz, 1H), 5.64–5.40 (m, 2H), 4.06 (t, J=7.0 Hz, 2H), 3.86 (s, 2H), 2.60 (m, 2H), 2.44 (d, J=1.2 Hz, 3H), 1.70 (m, 3H).

EXAMPLE 7(197)

1-(4-(1,3-Benzoxathiolan-2-ylmethyloxy)benzoyl)-2-methylindole-4-acetic Acid

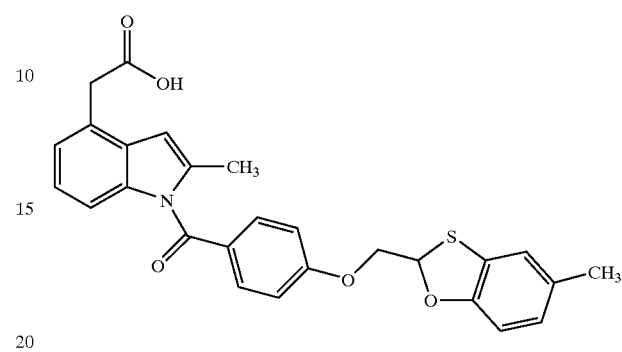

TLC: Rf 0.51 (chloroform:methanol=10:1);

MS: (APCI, Neg.): 458 (M–H)⁻;

NMR (CDCl₃): δ 7.70 (m, 2H), 7.25–7.20 (m, 2H), 7.19–7.10 (m, 1H), 7.08–6.82 (m, 6H), 6.48 (s, 1H), 6.36 (dd, J=6.9, 4.5 Hz, ⅘H), 6.13 (dd, J=4.2, 2.1 Hz, ⅕H), 4.45 (dd, J=10.5, 6.9 Hz, ⅘H), 4.17 (dd, J=10.5, 4.5 Hz, ⅕H), 3.84 (s, 2H), 3.34 (dd, J=13.2, 2.1 Hz, ⅕H), 3.23 (dd, J=13.2, 4.2 Hz, ⅕H), 2.43 (s, 3H).

EXAMPLE 7(198)

1-(4-(1,4-Benzodioxan-5-ylmethyloxy)benzoyl)-2-methylindole-4-acetic Acid

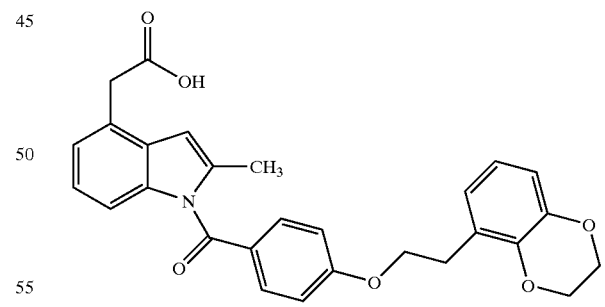

TLC: Rf 0.50 (chloroform:methanol=10:1);

MS: (APCI, Pos.): 471 (M+H)+;

NMR (CDCl₃): δ 7.69 (d, J=8.7 Hz, 2H), 7.10–6.90 (m, 5H), 6.80 (s, J=8.7, 3H), 6.48 (s, 1H), 4.34–4.18 (m, 6H), 3.86 (s, 2H), 3.12 (t, J=7.2 Hz, 2H), 2.44 (s, 3H).

EXAMPLE 7(199)

1-(4-(1,4-Benzoxathian-2-ylmethyloxy)benzoyl)-2-methylindole-4-acetic Acid

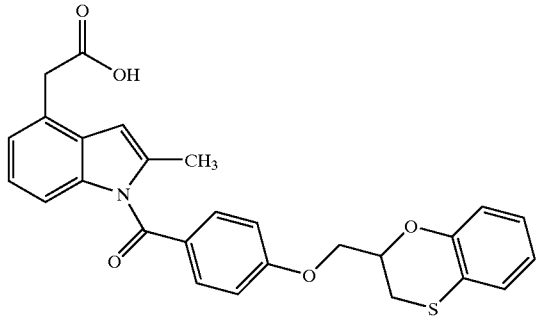

TLC: Rf 0.25 (chloroform:methanol=10:1);

MS: (FAB, Pos.): 474 (M+H)+;

NMR (CDCl$_3$): δ 7.73 (d, J=8.7 Hz, 2H), 7.12–6.83 (m, 9H), 6.49 (s, 1H), 4.68 (m, 1H), 4.37 (dd, J=9.6, 4.8 Hz, 1H), 4.26 (dd, J=9.6, 6.3 Hz, 1H), 3.86 (s, 2H), 3.26–3.15 (m, 2H), 2.45 (s, 3H).

EXAMPLE 7(200)

1-(4-(1,4-Benzoxathian-S, S-dioxide-2-ylmethyloxy)benzoyl)-2-methylindole-4-acetic Acid

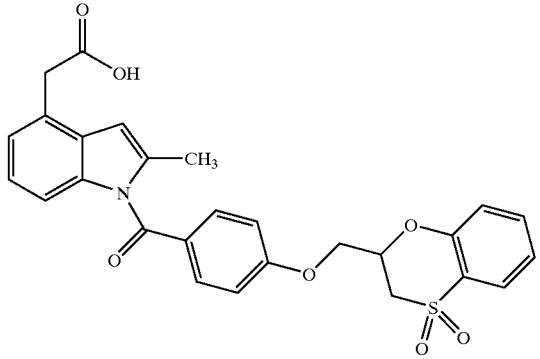

TLC: Rf 0.15 (chloroform:methanol=10:1);

MS: (FAB, Pos.): 506 (M+H)+;

NMR (CDCl$_3$): δ 7.88–7.60 (m, 4H), 7.60–7.40 (m, 3H), 7.23–7.10 (m, 1H), 7.10–6.85. (m, 3H), 6.50 (s, 1H), 5.25 (m, 1H), 4.48 (dd, J=10.2, 4.2 Hz, 1H), 4.40 (dd, J=10.2, 4.2 Hz, 1H), 3.86 (s, 2H), 3.76 (dd, J=13.8, 12.0 Hz, 1H), 3.58 (dd, J=13.8, 1.5 Hz, 1H), 2.45 (s, 3H).

EXAMPLE 7(201)

1-(4-(Pyrazin-2-ylmethyloxy)benzoyl)-2-methylindole-4-acetic Acid

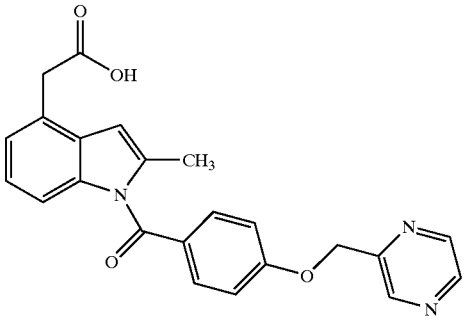

TLC: Rf 0.50 (chloroform:methanol=9:1);
MS: (APCI, Neg.): 400 (M−H)−;
NMR (CDCl$_3$): δ 8.86 (s, 1H), 8.65–8.55 (m, 2H), 7.74 (d, J=8.7 Hz, 2H), 7.13–6.90 (m, 5H), 6.50 (s, 1H), 5.33 (s, 2H), 3.87 (s, 2H), 2.45 (s, 3H).

EXAMPLE 7(202)

1-(4-(2,3-Dihydro-1-ethylindol-2-ylmethyloxy)benzoyl)-2-methylindole-4-acetic Acid

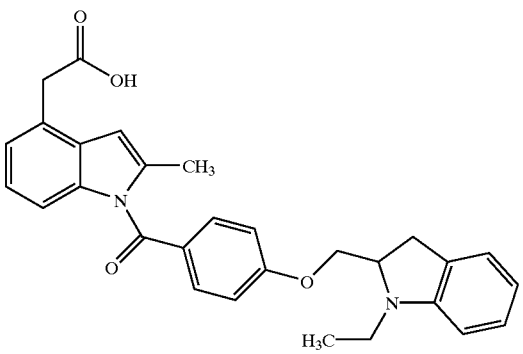

TLC: Rf 0.45 (chloroform:methanol=9:1);
MS: (APCI, Neg.): 467 (M−H)−;
NMR (CDCl$_3$): δ 7.76–7.68 (m, 2H), 7.16–6.44 (m, 10H), 5.00–2.80 (m, 7H), 3.87 (s, 2H), 2.45 (s, 3H), 1.20–1.10 (m, 3H).

EXAMPLE 7(203)

1-(4-(2,3,4,5-Tetrahydrofuran-3-ylmethyloxy)benzoyl)-2-methylindole-4-acetic Acid

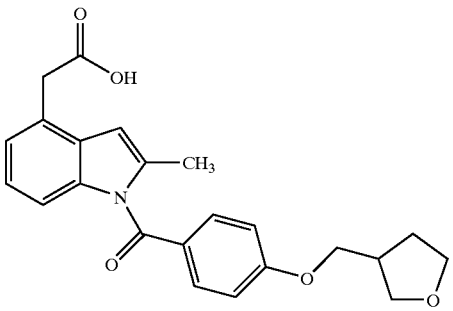

TLC: Rf 0.33 (chloroform:methanol=9:1);
MS: (MALDI, Pos.): 393 (M+H)+, 416 (M+Na)+;
NMR (CDCl$_3$): δ 7.71 (d, J=8.7 Hz, 2H), 7.08–6.98 (m, 3H), 6.95 (d, J=8.7 Hz, 2H), 6.49 (s, 1H), 4.05–3.70 (m, 8H), 2.85–2.72 (m, 1H), 2.44 (s, 3H), 2.22–2.08 (m, 1H), 1.82–1.70 (m, 1H).

EXAMPLE 7(204)

1-(4-(2-(2-Phenyl-5-methyloxazol-4-yl)ethyloxy)benzoyl)-2-methylindole-4-acetic Acid

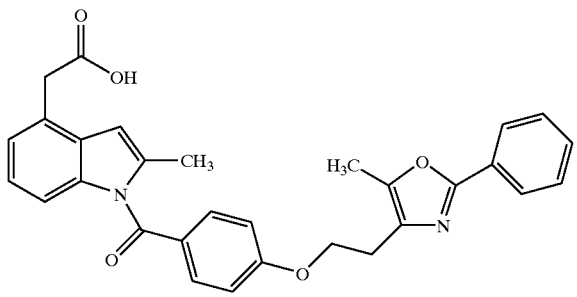

TLC: Rf 0.47 (chloroform:methanol=9:1);
MS: (FAB, Pos.): 495 (M+H)⁺.

EXAMPLE 7(205)

1-(4-(2-(2,3-Dimethoxyphenyl)ethyloxy)benzoyl)-2-methylindole-4-acetic Acid

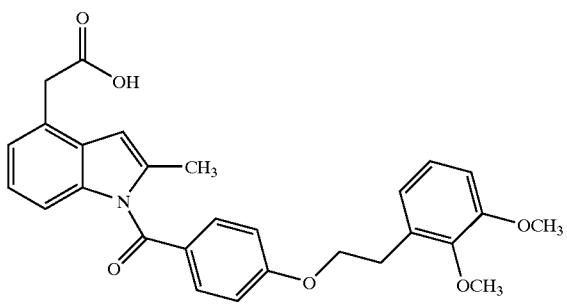

TLC: Rf 0.5 (chloroform:methanol=10:1);
MS: (APCI, Pos.): 474 (M+H)⁺;
NMR (CDCl$_3$): δ 7.69 (d, J=9.0 Hz, 2H), 7.08–6.92 (m, 6H), 6.86 (m, 2H), 6.48 (s, 1H), 4.25 (t, J=7.5 Hz, 2H), 3.88 (s, 6H), 3.84(s, 2H), 3.15 (t, J=7.5 Hz, 2H), 2.44 (s, 3H).

EXAMPLE 7(206)

1-(4-(4-Methyl-6-trifluoromethylbenzoxazin-2-ylmethyloxy)benzoyl)-2-methylindole-4-acetic Acid

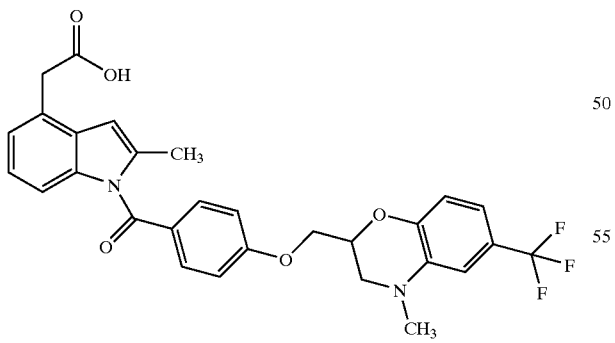

TLC: Rf 0.5 (chloroform:methanol=10:1);
MS: (APCI, Pos.): 539 (M+H)⁺;
NMR (CDCl$_3$): δ 7.73 (d, J=9.0 Hz, 2H), 7.06–6.86 (m, 8H), 6.50 (s, 1H), 4.70 (m, 1H), 4.31 (dd, J=9.9, 4.8 Hz, 1H), 4.21 (dd, J=9.9, 6.3 Hz, 1H), 3.87 (s, 2H), 3.45 (dd, J=11.7, 2.7 Hz, 1H), 3.33 (dd, J=11.7, 6.6 Hz, 1H), 2.96 (s, 3H), 2.45 (s, 3H).

EXAMPLE 7(207)

1-(4-(2-(1,2,3,4-Tetrahydronaphthalen-5-yl)ethyloxy)benzoyl)-2-methylindole-4-acetic Acid

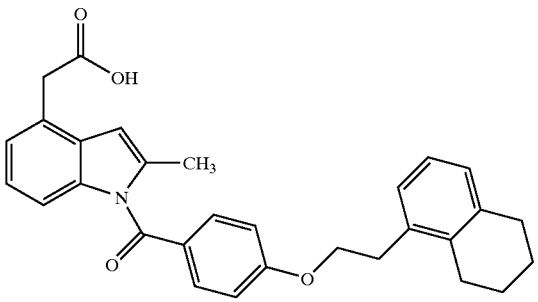

TLC: Rf 0.4 (chloroform:methanol=10:1);

MS: (APCI, Pos.): 468 (M+H)⁺;

NMR (CDCl$_3$): δ 7.69 (d, J=9.0 Hz, 2H), 7.10–6.92 (m, 8H), 6.49 (s, 1H), 4.22 (t, J=7.5 Hz, 2H), 3.86 (s, 2H), 3.12 (t, J=7.5 Hz, 2H), 2.79 (m, 4H), 2.44 (s, 3H), 1.89–1.77 (m, 4H).

EXAMPLE 7(208)

1-(4-(Quinoxalin-2-ylmethyloxy)benzoyl)-2-methylindole-4-acetic Acid

TLC: Rf 0.38 (chloroform:methanol=9:1);

MS: (APCI, Neg.): 450 (M–H)⁻;

NMR (CDCl$_3$): δ 9.12 (s, 1H), 8.20–8.08 (m, 2H), 7.88–7.78 (m, 2H), 7.75 (d, J=9.0 Hz, 2H), 7.13 (d, J=9.0 Hz, 2H), 7.10–6.90 (m, 3H), 6.50 (s, 1H), 5.51 (s, 2H), 3.88 (s, 2H), 2.45 (s, 3H).

EXAMPLE 7(209)
1-(4-(6-Chloro-4-methylbenzoxazin-2-ylmethyloxy)benzoyl)-2-methylindole-4-acetic Acid

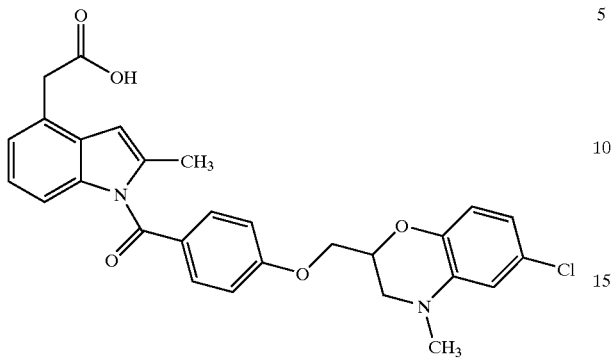

TLC: Rf 0.38 (chloroform:methanol=9:1);
MS: (APCI, Neg.): 503 (M−H)⁻;
NMR (CDCl$_3$): δ 7.72 (d J=9.0 Hz, 2H), 7.08–6.90 (m, 5H), 6.74 (dd, J=7.8, 0.9 Hz, 1H), 6.68–6.60 (m, 2H), 6.49 (t, J=0.9 Hz, 1H), 4.68–4.56 (m, 1H), 4.29 (dd, J=9.9, 4.8 Hz, 1H), 4.19 (dd, J=9.9, 6.0 Hz, 1H), 3.87 (s, 2H), 3.41 (dd, J=11.7, 2.7 Hz, 1H), 3.29 (dd, J=11.7, 6.6 Hz, 1H), 2.91 (s, 3H), 2.45 (s, 3H).

EXAMPLE 7(210)
1-(4-(2-(6,6-Dimethyl[3.1.1]bicyclohept-2-enyl)ethyloxy)benzoyl)-2-methylindole-4-acetic Acid TLC: Rf 0.52 (chloroform:methanol=10:1);
MS: (APCI, Neg.): 456 (M−H)⁻.

EXAMPLE 7(211)
1-(4-([2.2.1]Bicycloheptan-2-ylmethyloxy)benzoyl)-2-methylindole-4-acetic Acid TLC: Rf 0.52 (chloroform:methanol=10:1);
MS: (APCI, Neg.): 416 (M−H)⁻.

EXAMPLE 7(212)
1-(4-(Oxetan-2-ylmethyloxy)benzoyl)-2-methylindole-4-acetic Acid TLC: Rf 0.52 (chloroform:methanol=10:1);
MS: (APCI, Neg.): 378 (M−H)⁻.

EXAMPLE 7(213)
1-(4-(4-Methylpyrazino[2,3-b]oxazin-2-ylmethyloxy)benzoyl)-2-methylindole-4-acetic Acid TLC: Rf 0.34 (chloroform:methanol=10:1)
MS: (FAB, Pos.): 473 (M+H)⁺;
NMR (CDCl$_3$): δ 7.75–7.71 (m, 3H), 7.43 (d, J=3.3 Hz, 1H), 7.07–6.92 (m, 5H), 6.50 (s, 1H), 4.80 (m, 1H), 4.40 (dd, J=9.9, 4.5 Hz, 1H), 4.26 (dd, J=9.9, 6.6 Hz, 1H), 3.87 (s, 2H), 3.65 (dd, J=12.3, 3.3 Hz, 1H), 3.59 (dd, J=12.3, 6.9 Hz, 1H), 3.17 (s, 3H), 2.45 (d, J=0.9 Hz, 3H).

EXAMPLE 7(214)
1-(4-(Tetrahydropyran-2-ylmethyloxy)benzoyl)-2-methylindole-4-acetic Acid TLC: Rf 0.44 (chloroform:methanol=9:1);
MS: (FAB, Pos.): 407 (M+H)⁺.

EXAMPLE 7(215)

1-(4-(2-(N-(2-Cyanoethyl)-N-phenylamino)ethyloxy)benzoyl)-2-methylindole-4-acetic Acid

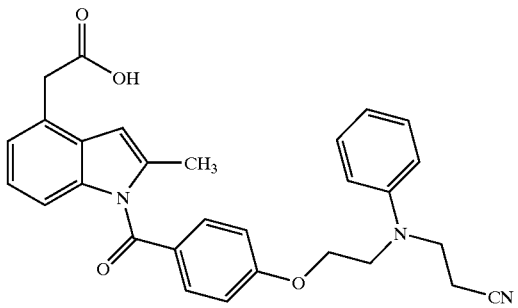

TLC: Rf 0.40 (chloroform:methanol=9:1);
MS: (FAB, Glycerin+m-NBA): 482 (M+H)$^+$.

EXAMPLE 7(216)

1-(4-(1,4-Dimethyl-1,2,3,4-tetrahydroquinoxalin-2-ylmethyloxy)benzoyl)-2-methylindole-4-acetic Acid

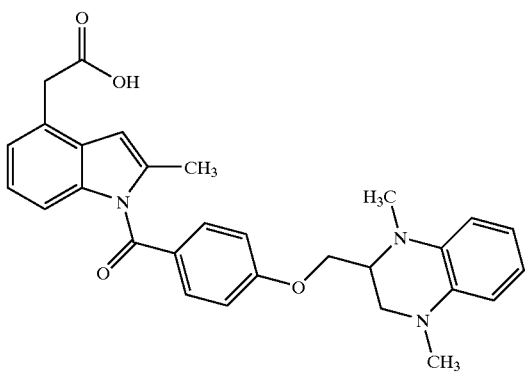

TLC: Rf 0.48 (chloroform:methanol=9:1);
MS: (APCI, Neg.): 482 (M−H)$^-$;
NMR (CDCl$_3$): δ 7.70 (d, J=9.0 Hz, 2H), 7.08–6.92 (m, 5H), 6.80–6.66 (m, 2H), 6.62–6.48 (m, 3H), 4.27–4.07 (m, 2H), 3.87 (s, 2H), 3.83–3.73 (m, 1H), 3.36–3.20 (m, 2H), 3.05 (s, 3H), 2.88 (s, 3H), 2.45 (s, 3H).

EXAMPLE 7(217)

1-(4-(5-Fluoro-4-methyl-3,4-dihydro-2H-benzoxazin-2-ylmethyloxy)benzoyl)-2-methylindole-4-acetic Acid

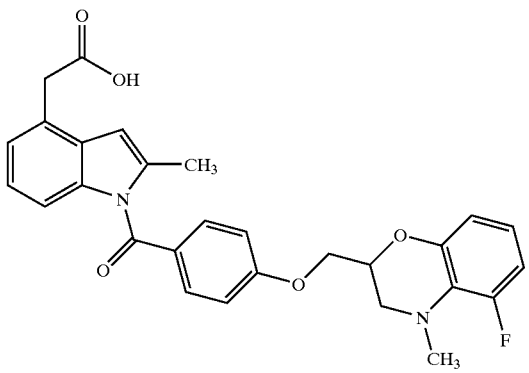

TLC: Rf 0.47 (chloroform:methanol=9:1);
MS: (Pos.): 488 (M)$^+$;
NMR (CDCl$_3$): δ 7.72 (d, J=9.0 Hz, 2H), 7.08–6.90 (m, 5H), 6.83–6.73 (m, 1H), 6.58–6.45 (m, 3H), 4.76–4.66 (m, 1H), 4.37 (dd, J=9.9, 5.1 HZ, 1H), 4.24 (dd, J=9.9, 6.6 Hz, 1H), 3.87 (s, 2H), 3.46 (dd, J=12.0, 2.7 Hz, 1H), 3.34 (dd, J=12.0, 6.6 Hz, 1H), 2.94 (s, 3H), 2.45 (s, 3H).

EXAMPLE 7(218)

1-(4-(4,8-Dimethyl-3,4-dihydro-2H-benzoxazin-2-ylmethyloxy)benzoyl)-2-methylindole-4-acetic Acid

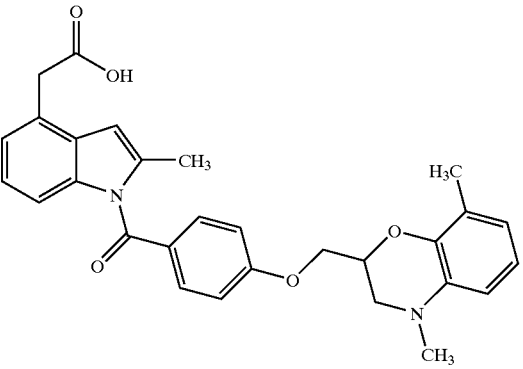

TLC: Rf 0.48 (chloroform:methanol=9:1);

MS: (Neg.): 483 (M−H)$^-$;

NMR (CDCl$_3$): δ 7.76–7.66 (m, 2H), 7.08–6.90 (m, 6H), 6.82–6.74 (m, 1H), 6.58 (d, J=7.5 Hz, 1H), 6.49 (s, 1H), 4.74–4.64 (m, 1H), 4.33 (dd, J=9.9, 5.4 Hz, 1H), 4.23 (dd, J=9.9, 6.3 Hz, 1H), 3.87 (s, 2H), 3.41 (dd, J=11.4, 2.7 Hz, 1H), 3.26 (dd, J=11.4, 6.3 Hz, 1H), 2.91 (s, 3H), 2.45 (s, 3H), 2.18 (s, 3H).

EXAMPLE 7(219)

1-(4-(4-Methyl-3,4-dihydro-2H-benzothiazin-2-ylmethyloxy)benzoyl)-2-methylindole-4-acetic Acid

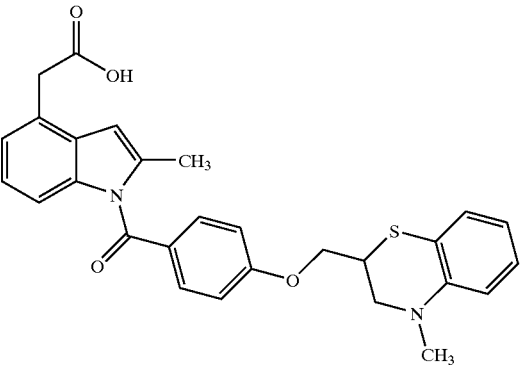

TLC: Rf 0.48 (chloroform:methanol=10:1);

MS: (APCI, Neg.): 485 (M−H)$^-$;

NMR (CDCl$_3$): δ 7.68 (d, J=8.7 Hz, 2H), 7.22–6.92 (m, 7H), 6.70–6.65 (m, 2H), 6.47 (s, 1H), 4.27 (dd, J=9.6, 9.3 Hz, 1H), 4.16 (dd, J=9.3, 5.1 Hz, 1H), 3.83 (s, 2H), 3.67 (m,1H), 3.57 (m, 2H), 2.91 (s, 3H), 2.42 (s, 3H).

EXAMPLE 7(220)

1-(4-(4-Methyl-3,4-dihydro-2H-pyrido[3,2-b]oxazin-2-ymethyloxy)benzoyl)-2-methylindole-4-acetic Acid

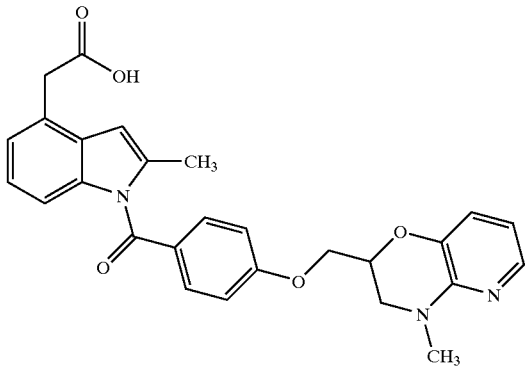

TLC: Rf 0.35 (chloroform:methanol=9:1);

MS: (FAB, Pos.): 472 (M+H)+;

NMR (CDCl$_3$): δ 7.81 (dd, J=5.1, 1.8 Hz, 1H), 7.73 (d, J=8.7 Hz, 2H), 7.10–6.90 (m, 6H), 6.56 (dd, J=7.8, 5.1 Hz, 1H), 6.50 (s, 1H), 4.67–4.58 (m, 1H), 4.31 (dd, J=9.9, 5.1 HZ, 1H), 4.20 (dd, J=9.9, 6.0 Hz, 1H), 3.87 (s, 2H), 3.58 (dd, J=12.0, 3.0 Hz, 1H), 3.49 (dd, J=12.0, 6.9 Hz, 1H), 3.15 (s, 3H), 2.45 (s, 3H).

EXAMPLE 7(221)

1-(4-(4-Methyl-3,4-dihydro-2H-pyrido[2,3-b]oxazin-2-ylmethyloxy)benzoyl)-2-methylindole-4-acetic Acid

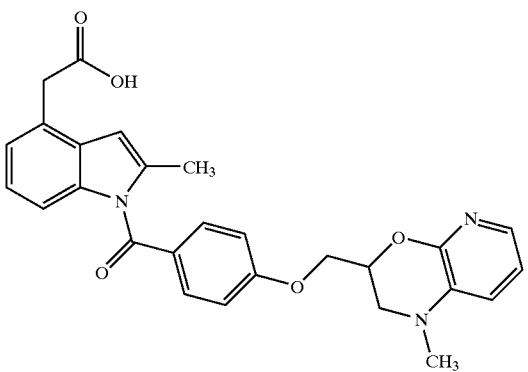

TLC: Rf 0.40 (chloroform:methanol=10:1);

MS: (FAB, Pos.): 472 (M+H)+;

NMR (CDCl$_3$): δ 7.74–7.69 (m, 2H), 7.67 (dd, J=5.1, 1.5 Hz, 1H), 7.05–6.85 (m, 7H), 6.51 (s, 1H), 4.82 (m, 1H), 4.37 (dd, J=9.6, 4.2 Hz, 1H), 4.23 (dd, J=9.6, 6.9 Hz, 1H), 3.87 (s, 2H), 3.45 (dd, J=12.0, 3.3 Hz, 1H), 3.31 (dd, J=12.0, 7.0 Hz, 1H), 2.92 (s, 3H), 2.44 (d, J=0.9 Hz, 3H).

EXAMPLE 7(222)

1-(4-(7-Fluoro-4-methyl-3,4-dihydro-2H-benzoxazin-2-ylmethyloxy)benzoyl)-2-methylindole-4-acetic Acid

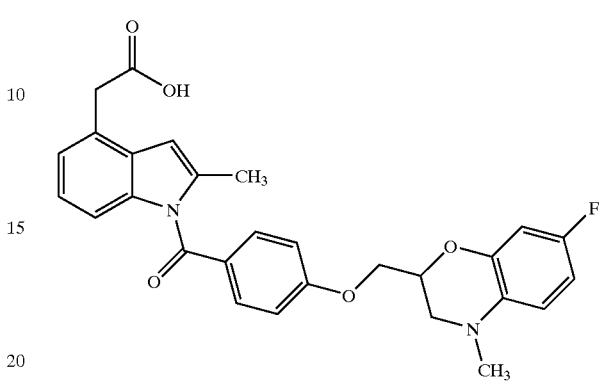

TLC: Rf 0.33 (chloroform:methanol=9:1);

MS: (MARDI, Pos.): 488 (M)+;

NMR (CDCl$_3$): δ 7.77–7.61 (m, 2H), 7.59–7.41 (m, 2H), 7.08–6.90 (m, 4H), 6.60 (d, J=8.1 Hz, 2H), 6.50 (s, 1H), 4.75–4.65 (m, 1H), 4.34–4.18 (m, 2H), 3.86 (s, 2H), 3.40–3.18 (m, 2H), 2.87 (s, 3H), 2.44 (s, 3H).

EXAMPLE 7(223)

1-(4-(7-Cyano-4-methyl-3,4-dihydro-2H-benzoxazin-2-ylmethyloxy)benzoyl)-2-methylindole-4-acetic Acid

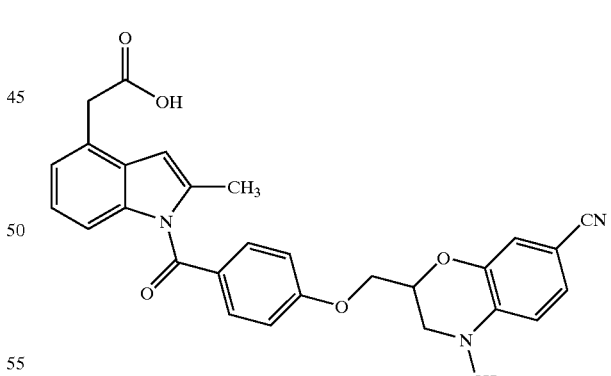

TLC: Rf 0.31 (chloroform:methanol=9:1);

MS: (APCI, Pos.): 495 (M)+, 518 (M+Na)+;

NMR (CDCl$_3$): δ 7.72 (d, J=8.7 Hz, 2H), 7.09–6.82 (m, 8H), 6.50 (s, 1H), 4.78–4.67 (m, 1H), 4.35–4.18 (m, 2H), 3.87 (s, 2H), 3.49–3.30 (m, 2H), 2.95 (s, 3H), 2.45 (s, 3H).

EXAMPLE 7(224)

1-(4-(4-Methyl-6-methoxy-3,4-dihydro-2H-benzoxazin-2-ylmethyloxy)benzoyl)-2-methylindole-4-acetic Acid

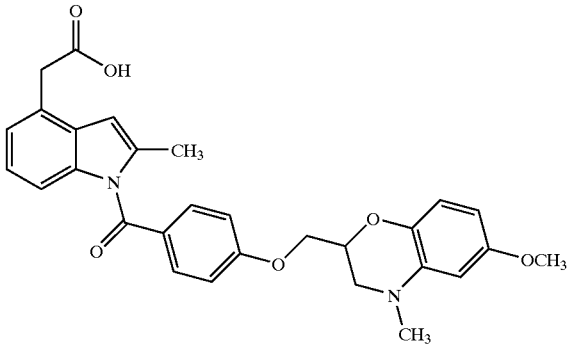

TLC: Rf 0.40 (chloroform:methanol=10:1);

MS: (APCI, Pos.): 501 (M+H)+;

NMR (CDCl₃): δ 7.72 (d, J=8.7 Hz, 2H), 7.08–6.90 (m, 5H), 6.75 (d, J=8.7 Hz, 1H), 6.49 (s, 1H), 6.29 (d, J=2.7 Hz, 1H), 6.23 (dd, J=8.7, 2.7 Hz, 1H), 4.61 (m, 1H), 4.30 (dd, J=9.9, 4.8 Hz, 1H), 4.18 (m, 1H), 3.87 (s, 2H), 3.76 (s, 3H), 3.40 (dd, J=11.4, 9.0 Hz, 1H), 3.28 (dd, J=11.4, 6.6 Hz, 1H), 2.91 (s, 3H), 2.44 (s, 3H).

EXAMPLE 7(225)

1-(4-(1-Methylindolin-3-ylmethyloxy)benzoyl)-2-methylindole-4-acetic Acid

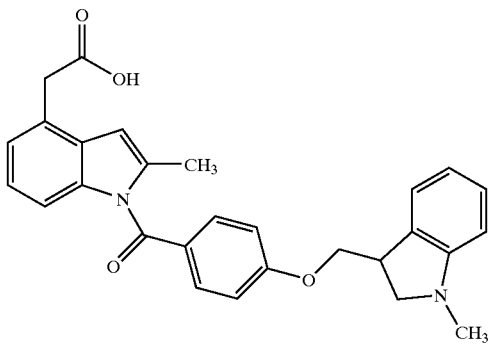

TLC: Rf 0.47 (chloroform:methanol=9:1);

MS: (APCI, Neg.): 453 (M−H)⁻;

NMR (CDCl₃): δ 7.74–7.68 (m, 3H), 7.22–7.10 (m, 2H), 7.08–6.90 (m, 4H), 6.72 (t, J=6.6 Hz, 1H), 6.53 (d, J=8.1 Hz, 1H), 6.49 (s, 1H), 4.24–4.06 (m, 2H), 3.87 (s, 2H), 3.78–3.70 (m, 1H), 3.49 (t, J=8.1 Hz, 1H), 3.38 (dd, J=9.0, 5.1 Hz, 1H), 2.79 (s, 3H), 2.45 (s, 3H).

EXAMPLE 7(226)

1-(4-(4-Methyl-3,4-dihydro-2H-benzoxazin-2-yl)carbonylamino)benzoyl)-2-methylindole-4-acetic Acid

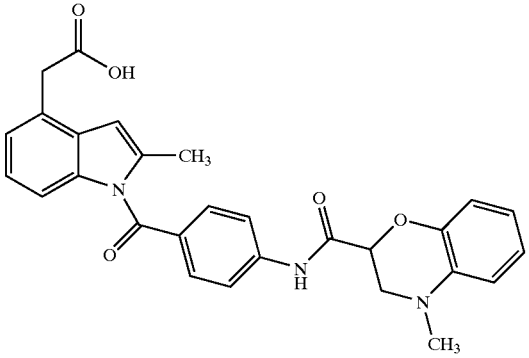

TLC: 0.48 (chloroform:methanol=10:1);

MS: (APCI, Neg.): 482 (M−H)⁻;

NMR (CDCl₃): δ 8.53 (s, 1H), 7.72 (s, 4H), 7.20–6.90 (m, 5H), 6.80–6.70 (m, 2H), 6.49 (s, 1H), 4.89 (dd, J=6.9, 3.3 Hz, 1H), 3.85 (s, 2H), 3.57 (dd, J=12.0, 3.3 Hz, 1H), 3.44 (dd, J=12.0, 6.9 Hz, 1H), 2.92 (s, 3H), 2.49 (s, 3H).

EXAMPLE 7(227)

1-(4-N-Methyl-N-(4-methyl-3,4-dihydro-2H-benzoxazin-2-ylcarbonyl)amino)benzoyl)-2-methylindole-4-acetic Acid

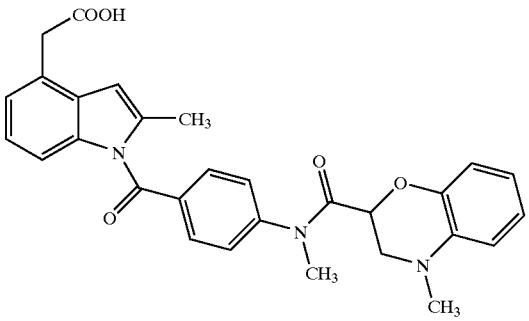

TLC: Rf 0.48 (chloroform:methanol=10:1);

NMR (CDCl₃): δ 7.77 (d, J=8.7 Hz, 2H), 7.43 (d, J=8.7 Hz, 2H), 7.05 (d, J=6.3 Hz, 1H), 6.90–6.75 (m, 3H), 6.70–6.55 (m, 3H), 6.49 (s, 1H), 4.77 (brd, J=6.3 Hz, 1H), 3.84 (s, 2H), 3.53 (dd, J=12.0, 7.8 Hz, 1H), 3.40 (s, 3H), 3.30 (dd, J=12.0, 2.4 Hz, 1H), 2.86 (s, 3H), 2.41 (s, 3H).

EXAMPLE 7(228)

1-(4-(5-Methyl-2,3,4,5-tetrahydrofuran-2-ylmethyloxy)benzoyl)-2-methylindole-4-acetic Acid

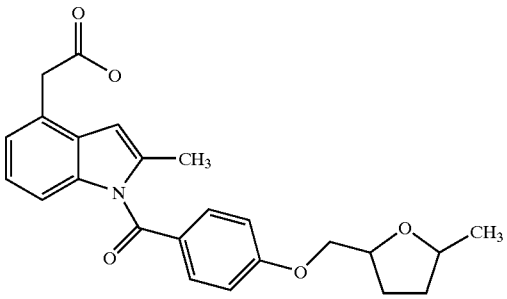

TLC: Rf 0.52 (chloroform methanol=10:1);

NMR (CDCl₃): δ 7.69 (d, J=9.3 Hz, 2H), 7.07–6.88 (m, 5H), 6.48 (s, 1H), 4.50–4.30 (m, 1H), 4.17–3.95 (m, 2H), 3.85 (s, 2H), 3.42 (dd, J=16.5, 8.1 Hz, 1H), 2.50–2.20 (m) and 2.44 (s) total 5H, 2.09–1.94 (m) and 1.79–1.67 (m) total 1H, 1.50–1.22 (m, 1H), 1.15–1.05 (m, 3H).

In addition, the compound prepared in Example 7(224) may be prepared by following procedures as a series of reactions of Reference Example 22→Reference Example 23→Reference Example 24→Reference Example 25→Reference Example 26→Reference Example 27→Reference Example 28→Example 8.

REFERENCE EXAMPLE 22

2-Ethoxycarbonyl-6-methoxy-3,4-dihydro-2H-benzoxazine

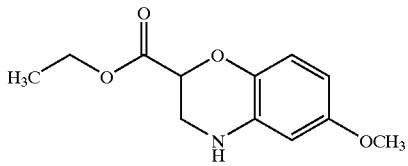

To a solution of 2-amino-4-methoxyphenol (5.5 g) in acetone (200 ml) was added potassium carbonate (5 g), and the mixture was stirred at 40° C. under an atmosphere of argon. To the mixture was added dropwise ethyl 1,2-dibromopropionate and potassium carbonate (15 g), and the mixture was refluxed for 15 hours. After cooling to room temperature, the mixture was filtered. The filtrate was poured into water and then extracted with ethyl acetate (3 times). The organic layer was washed with a saturated aqueous solution of sodium chloride, dried over anhydrous sodium sulfate and concentrated under reduced pressure. The residue was purified by column chromatoqraphy on silica gel (n-hexane:ethyl acetate=10:1) to give the title compound (1.65 g) having the following physical data.

TLC: Rf 0.44 (n-hexane:ethyl acetate=2:1).

REFERENCE EXAMPLE 23

2-Hydroxymethyl-6-methoxy-3,4-dihydro-2H-benzoxazine

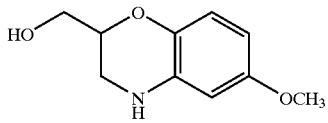

To a solution of lithium aluminum hydride (560 mg) in tetrahydrofuran (50 ml) was added dropwise a solution of the compound prepared in above-mentioned Reference Example (1.65 g) in tetrahydrofuran (30 ml) under an atmosphere of argon, and the mixture was stirred for 15 minutes. To the reaction mixture was added a saturated aqueous solution of sodium chloride, and the mixture was extracted with ethyl acetate (3 times). The organic layer was washed with a saturated aqueous solution of sodium chloride, dried over anhydrous sodium sulfate and concentrated under reduced pressure. The residue was purified by column chromatography on silica gel (n-hexane:ethyl acetate=4:1) to give the title compound (1.3 g) having the following physical data.

TLC: Rf 0.17(n-hexane:ethyl acetate=2:1).

REFERENCE EXAMPLE 24

2-Hydroxymethyl-6-methoxy-4-methyl-3,4-dihydro-2H-benzoxazine

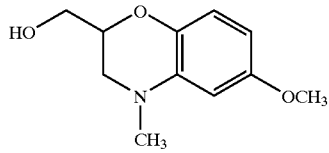

To a solution of the compound (1.3 g) prepared in above-mentioned Reference Example in acetone (50 ml)—N,N-dimethylformamide (10 ml) was added potassium carbonate (10 g) and methyl iodide (3 ml), and the mixture was stirred at 58° C. for 2 hours. To the mixture was added methyl iodide (3 ml) and the mixture was stirred for 12 hours. The reaction mixture was poured into water and then extracted with ethyl acetate (3 times). The organic layer was washed with a saturated aqueous solution of sodium chloride and concentrated under reduced pressure. The residue was purified by column chromatography on silica gel (n-hexane:ethyl acetate=2:1) to give the title compound (140 mg) having the following physical data.

TLC: Rf 0.25(n-hexane ethyl acetate=2:1).

REFERENCE EXAMPLE 25

2-Methylindole-4-acetic Acid Benzyl Ester

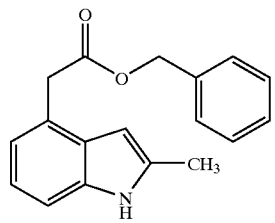

To a solution of the compound (55.0 g) prepared in Reference Example 5 in N,N-dimethylformamide (500 ml) was added potassium carbonate (109 g) with vigorously stirring under an atmosphere of argon. To the mixture was added benzyl bromide (34.6 ml) and the mixture was stirred at room temperature for 2 hours. The reaction solution was poured into water (2000 ml) and extracted with toluene. The organic layer was washed with a saturated aqueous solution of sodium bicarbonate and a saturated aqueous solution of sodium chloride, successively, dried over anhydrous magnesium sulfate and filtrated. The filtrate was concentrated under reduced pressure. The residue was purified by column chromatography on silica gel (n-hexane:ethyl acetate=5:1) to give the title compound (70.3 g) having the following physical data.

TLC: Rf 0.85(n-hexane:ethyl acetate=1:1).

REFERENCE EXAMPLE 26

1-(4-Acetoxybenzoyl)-2-methylindole-4-acetic Acid Benzyl Ester

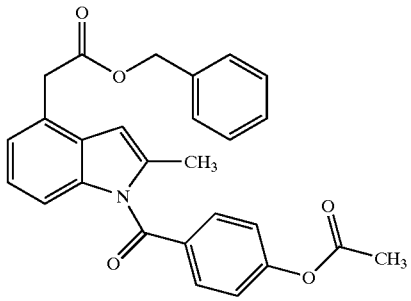

A mixture of 4-acetoxybenzoic acid (516 mg) and oxalyl chloride (0.5 ml) was stirred for 30 minutes. The mixture was concentrated under reduced pressure to give 4-acetoxybenzoyl chloride.

To a solution of the compound (400 mg) prepared in Reference Example 25 in methylene chloride (7 ml) was added sodium hydroxide (286 mg) and tetrabutylammonium chloride (20 mg) at room temperature. The mixture was added the above-mentioned solution of 4-acetoxybenzoyl chloride in methylene chloride (3 ml), and the mixture was stirred at room temperature overnight. The reaction mixture was filtrated, and the filtrate was concentrated. The residue was purified by column chromatography on silica gel (n-hexane:ethyl acetate=7:3) to give the title compound (500 mg) having the following physical data.

TLC: Rf 0.34(n-hexane:ethyl acetate=7:3);

NMR (CDCl$_3$): δ 7.76 (d, J=8.7 Hz, 2H), 7.40–7.20 (m, 7H), 7.08–6.92 (m, 3H), 6.47 (s, 1H), 5.15 (s, 2H), 3.88 (s, 2H), 2.40 (s, 3H), 2.35 (s, 3H).

REFERENCE EXAMPLE 27

1-(4-Hydroxybenzoyl)-2-methylindole-4-acetic Acid Benzyl Ester

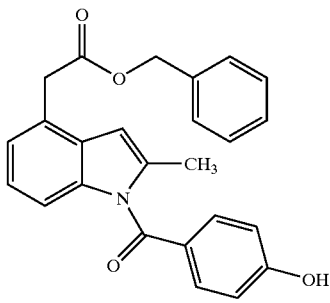

The compound (500 mg) prepared in Reference Example 26 was dissolved in 5% piperidine/methylene chloride (5 ml), and the mixture was stirred for 1 hours. The reaction mixture was concentrated and the residue was purified by column chromatography on silica gel (chloroform:methanol=19:1) to give the title compound (450 mg) having the following physical data.

TLC: Rf 0.61 (chloroform:methanol=9:1);

NMR (CDCl$_3$): δ 7.72 (m, 2H), 7.44–7.26 (m, 5H), 7.08–6.84 (m, 5H), 6.45 (s, 1H), 5.83 (brs, 1H), 5.15 (s, 2H), 3.88 (s, 2H), 2.42 (s, 3H).

REFERENCE EXAMPLE 28

1-(4-(6-Methoxy-4-methyl-3,4-dihydro-2H-1,4-benzoxazin-2-ylmethyloxy)benzoyl)-2-methylindole-4-acetic Acid Benzyl Ester

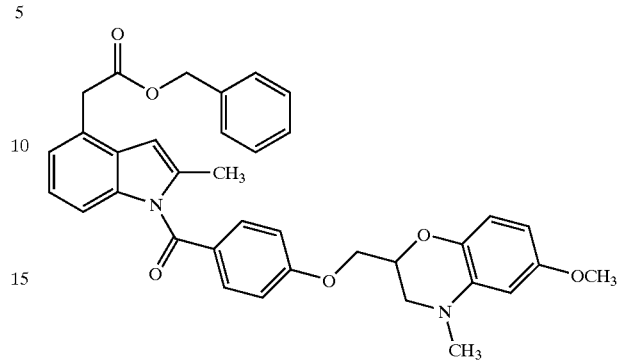

To a solution of the compound (60 mg) prepared in Reference Example 24 in methylene chloride (10 ml) was added triphenylphosphine (76 mg), the compound (95 mg) prepared in Reference Example 27 and diethyl azodicarboxylate (126 mg), successively, and the mixture was stirred for 3 hours. The mixture was poured into water and extracted with ethyl acetate. The organic layer was washed with a saturated aqueous solution of sodium chloride, dried over anhydrous sodium sulfate and concentrated under reduced pressure. The residue was purified by column chromatography on silica gel (n-hexane:ethyl acetate=4:1) to give the compound (85 mg) of the present invention having the following physical data.

TLC: Rf 0.57(n-hexane:ethyl acetate=1:1);

NMR (CDCl$_3$): 7.71 (d, J=9.0 Hz, 2H), 7.32 (m, 5H), 7.08–6.90(m, 5H), 6.75 (d, J=8.4 Hz, 1H), 6.46 (s, 1H), 6.28 (d, J=2.7 Hz, 1H), 6.23 (dd, J=8.7, 2.7 Hz, 1H), 5.15 (s, 2H), 4.60 (m, 1H), 4.27 (dd, J=9.9, 6.6 Hz, 1H), 4.18 (dd, J=9.9, 6.3 Hz, 1H), 3.88 (s, 2H), 3.76 (s, 3H), 3.39 (dd, J=11.7, 2.7 Hz, 1H), 3.27 (dd, J=11.7, 6.6 Hz, 1H), 2.90 (s, 3H), 2.42 (s, 3H).

EXAMPLE 8 (THE SAME COMPOUND AS EXAMPLE 7(224))

1-(4-(6-Methoxy-4-methyl-3,4-dihydro-2H-1,4-benzoxazin-2-ylmethyloxy)benzoyl)-2-methylindol-4-ylacetic Acid

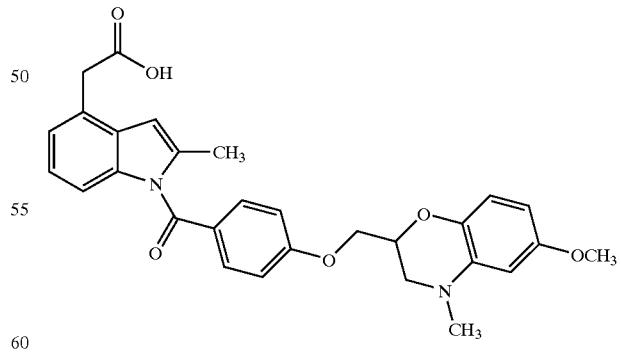

The compound (50 mg) prepared in above-mentioned example, ethyl acetate (5 ml) and palladium hydroxide (100 mg) were mixed. The mixture was stirred for 2 hours under an atmosphere of argon. The reaction mixture was filtrated and the filtrate was concentrated under reduced pressure. The residue was purified by column chromatography on silica gel (chloroform methanol=10:1) to give the compound of the present invention having the following physical data.

TLC: Rf 0.40 (chloroform:methanol=10:1);
MS: (APCI, Pos.): 501 (M+H)+;
NMR (CDCl$_3$): δ 7.72 (d, J=8.7 Hz, 2H), 7.08–6.90 (m, 5H), 6.75 (d, J=8.7 Hz, 1H), 6.49 (s, 1H), 6.29 (d, J=2.7 Hz, 1H), 6.23 (dd, J=8.7, 2.7 Hz, 1H), 4.61 (m, 1H), 4.30 (dd, J=9.9, 4.8 Hz, 1H), 4.18 (m, 1H), 3.87 (s, 2H), 3.76 (s, 3H), 3.40 (dd, J=11.4, 9.0 Hz, 1H), 3.28 (dd, J=11.4, 6.6 Hz, 1H), 2.91 (s, 3H), 2.44 (s, 3H).

In addition to the compound of Example 7(224), the compounds of Example 1 to Example 1(75), Example 7 to Example 7(223), (225) and (228) may be prepared by the same procedures as a series of reactions of Reference Example 28→Example 8, using corresponding compounds.

The compounds of Examples 1(8), 1(51), 1(67), 1(68), 1(69), Examples 7(37) and 7(151) may be prepared by protection of hydroxy or amino group by protective group followed by deprotection before the reaction corresponding example 9.

FORMULATION EXAMPLE 1

The following components were admixed in conventional method and punched out to obtain 100 tablets each containing 5 mg of active ingredient.

| | |
|---|---|
| 1-(4-(2-Propyloxyethoxy)benzoyl)-2-methylindole-4-acetic acid | 500 mg |
| Carboxymethyl Cellulose calcium | 200 mg |
| Magnesium stearate | 100 mg |
| Microcrystalline cellulose | 9.2 g |

What is claimed is:
1. An indole derivative represented by formula (I):

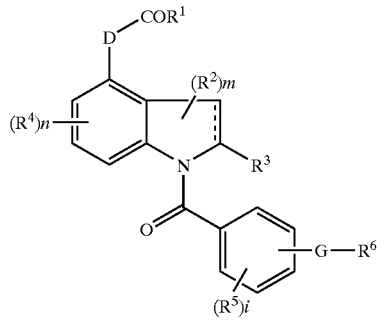

(I)

wherein R$^1$ represents hydroxy, C1–6 alkoxy, or NR$^8$R$^9$, in which R$^8$ and R$^9$ each independently represents a hydrogen atom, C1–6 alkyl, or SO$_2$R$^{13}$, in which R$^{13}$ represents C1–6 alkyl, a C3–15 saturated or unsaturated carbocyclic ring or a 4- to 15-membered heterocyclic ring containing 1 to 5 nitrogen atom(s), sulfur atom(s) and/or oxygen atom(s);

R$^2$ represents a hydrogen atom, C1–6 alkyl, C1–6 alkoxy, C2–6 alkoxyalkyl, a halogen atom, amino, trihalomethyl, cyano, hydroxy, benzyl, or 4-methoxybenzyl;

R$^3$ represents a hydrogen atom, C1–6 alkyl, C1–6 alkoxy, a halogen atom, trihalomethyl, cyano, or hydroxy;

R$^4$ and R$^5$ each independently represents a hydrogen atom, C1–6 alkyl, C1–6 alkoxy, C2–6 alkoxyalkyl, a halogen atom, nitro, amino, trihalomethyl, cyano, or hydroxy;

D represents C2–6 alkenylene;

G and R$^6$ are taken together to represent
(i) C1–15 alkyl which may be substituted with 1 to 5 oxygen atom(s) and/or sulfur atom(s);
(ii) C2–15 alkenyl which may be substituted with 1 to 5 oxygen atom(s) and/or sulfur atom(s); or
(iii) C2–15 alkynyl which may be substituted with 1 to 5 oxygen atom(s) and/or sulfur atom(s), in which the alkyl, the alkenyl and the alkynyl may be substituted with 1 to 12 substituent(s) selected from C1–6 alkoxy, a halogen atom, hydroxy, cyano, oxo and NR$^{11}$R$^{12}$, in which R$^{11}$ and R$^{12}$ each independently represents a hydrogen atom, C1–6 alkyl, C2–6 alkenyl, phenyl, benzoyl, naphthyl, phenyl substituted with C1–6 alkyl, or C1–6 alkyl substituted with phenyl or cyano;

n represents 1 to 3;
m represents 1 to 3;
i represents 1 to 4; and
----- represents a single bond or a double bond, or a non-toxic salt thereof.

2. An indole derivative represented by formula (I):

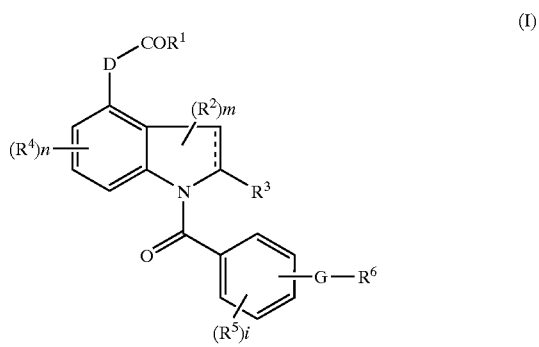

(I)

wherein R$^1$ represents hydroxy, C1–6 alkoxy, or NR$^8$R$^9$, in which R$^8$ and R$^9$ each independently represents a hydrogen atom, C1–6 alkyl, or SO$_2$R$^{13}$, in which R$^{13}$ represents C1–6 alkyl, a C3–15 saturated or unsaturated carbocyclic ring or a 4- to 15-membered heterocyclic ring containing 1 to 5 nitrogen atom(s), sulfur atom(s) and/or oxygen atom(s);

R$^2$ represents a hydrogen atom, C1–6 alkyl, C1–6 alkoxy, C2–6 alkoxyalkyl, a halogen atom, amino, trihalomethyl, cyano, hydroxy, benzyl, or 4-methoxybenzyl;

R$^3$ represents a hydrogen atom, C1–6 alkyl, C1–6 alkoxy, a halogen atom, trihalomethyl, cyano, or hydroxy;

R$^4$ and R$^5$ each independently represents a hydrogen atom, C1–6 alkyl, C1–6 alkoxy, C2–6 alkoxyalkyl, a halogen atom, nitro, amino, trihalomethyl, cyano, or hydroxy;

D represents C1–6 oxyalkylene;

in -G-R$^6$,

G and R$^6$ are taken together to represent
(i) C1–15 alkyl which may be substituted with 1 to 5 oxygen atom(s) and/or sulfur atom(s);
(ii) C2–15 alkenyl which may be substituted with 1 to 5 oxygen atom(s) and/or sulfur atom(s); or
(iii) C2–15 alkynyl which may be substituted with 1 to 5 oxygen atom(s) and/or sulfur atom(s), in which the alkyl, the alkenyl and the alkynyl may be substituted with 1 to 12 substituent(s) selected from C1–6 alkoxy, a halogen atom, hydroxy, cyano, oxo and $NR^{11}R^{12}$, in which $R^{11}$ and $R^{12}$ each independently represents a hydrogen atom, C1–6 alkyl, C2–6 alkenyl, phenyl, benzoyl, naphthyl, phenyl substituted with C1–6 alkyl, or C1–6 alkyl substituted with phenyl or cyano;

n represents 1 to 3;

m represents 1 to 3;

i represents 1 to 4; and

----- represents a single bond or a double bond, or a non-toxic salt thereof.

3. An indole derivative represented by formula (I):

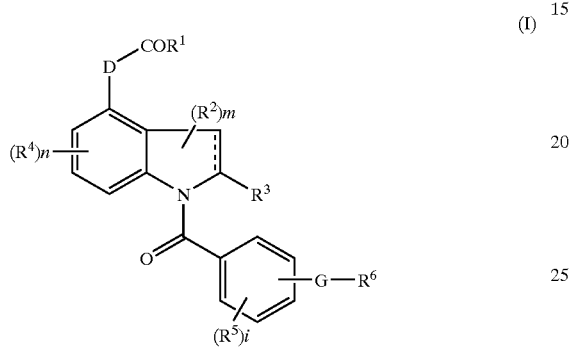

(I)

wherein $R^1$ represents hydroxy, C1–6 alkoxy, or $NR^8R^9$, in which $R^8$ and $R^9$ each independently represents a hydrogen atom, C1–6 alkyl, or $SO_2R^{13}$, in which $R^{13}$ represents C1–6 alkyl, a C3–15 saturated or unsaturated carbocyclic ring or a 4- to 15-membered heterocyclic ring containing 1 to 5 nitrogen atom(s), sulfur atom(s) and/or oxygen atom(s);

$R^2$ represents a hydrogen atom, C1–6 alkyl, C1–6 alkoxy, C2–6 alkoxyalkyl, a halogen atom, amino, trihalomethyl, cyano, hydroxy, benzyl, or 4-methoxybenzyl;

$R^3$ represents a hydrogen atom, C1–6 alkyl, C1–6 alkoxy, a halogen atom, trihalomethyl, cyano, or hydroxy;

$R^4$ and $R^5$ each independently represents a hydrogen atom, C1–6 alkyl, C1–6 alkoxy, C2–6 alkoxyalkyl, a halogen atom, nitro, amino, trihalomethyl, cyano, or hydroxy;

D represents a single bond, C1–6 alkylene, C2–6 alkenylene, or C1–6 oxyalkylene;

in -G-$R^6$,

G represents a single bond, C1–6 alkylene which may be substituted with 1 to 2 oxygen atom(s) and/or sulfur atom(s), C2–6 alkenylene which may be substituted with 1 to 2 oxygen atom(s) and/or sulfur atom(s), in which the alkylene and the alkenylene may be substituted with hydroxy or C1–4 alkoxy, —C(O)NH—, —NHC(O)—, —SO₂NH—, —NHSO₂—, or diazo;

$R^6$ represents a C3–15 saturated or unsaturated carbocyclic ring, in which the ring may be substituted with 1 to 5 group(s) selected from the group consisting of C1–6 alkyl, C1–10 alkoxy, C2–6 alkoxyalkyl, a halogen atom, trihalomethyl, hydroxy, nitro, amino, phenyl, phenoxy, oxo, C2–6 acyl, C1–6 alkanesulfonyl and cyano, n represents 1 to 3;

m represents 1 to 3;

i represents 1 to 4; and

----- represents a single bond or a double bond, or a non-toxic salt thereof.

4. An indole derivative represented by formula (I):

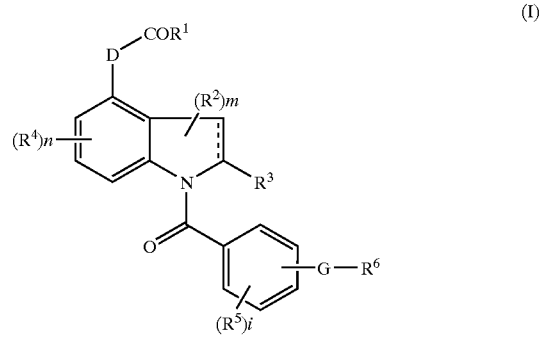

(I)

wherein $R^1$ represents hydroxy, C1–6 alkoxy, or $NR^8R^9$, in which $R^8$ and $R^9$ each independently represents a hydrogen atom, C1–6 alkyl, or $SO_2R^{13}$, in which $R^{13}$ represents C1–6 alkyl, a C3–15 saturated or unsaturated carbocyclic ring or a 4- to 15-membered heterocyclic ring containing 1 to 5 nitrogen atom(s), sulfur atom(s) and/or oxygen atom(s);

$R^2$ represents a hydrogen atom, C1–6 alkyl, C1–6 alkoxy, C2–6 alkoxyalkyl, a halogen atom, amino, trihalomethyl, cyano, hydroxy, benzyl, or 4-methoxybenzyl;

$R^3$ represents a hydrogen atom, C1–6 alkyl, C1–6 alkoxy, a halogen atom, trihalomethyl, cyano, or hydroxy;

$R^4$ and $R^5$ each independently represents a hydrogen atom, C1–6 alkyl, C1–6 alkoxy, C2–6 alkoxyalkyl, a halogen atom, nitro, amino, trihalomethyl, cyano, or hydroxy;

D represents a single bond, C1–6 alkylene, C2–6 alkenylene, or C1–6 oxyalkylene;

in -G-$R^6$,

G represents a single bond, C1–6 alkylene which may be substituted with 1 to 2 oxygen atom(s) and/or sulfur atom(s), C2–6 alkenylene which may be substituted with 1 to 2 oxygen atom(s) and/or sulfur atom(s), in which the alkylene and the alkenylene may be substituted with hydroxy or C1–4 alkoxy, —C(O)NH—, —NHC(O)—, —SO₂NH—, —NHSO₂—, or diazo;

$R^6$ represents a 4- to 15-membered heterocyclic ring containing 1 to 5 nitrogen atom(s), sulfur atom(s) and/or oxygen atom(s), in which the ring may be substituted with 1 to 5 group(s) selected from the group consisting of C1–6 alkyl, C1–10 alkoxy, C2–6 alkoxyalkyl, a halogen atom, trihalomethyl, hydroxy, nitro, amino, phenyl, phenoxy, oxo, C2–6 acyl, C1–6 alkanesulfonyl and cyano, n represents 1 to 3;

m represents 1 to 3;

i represents 1 to 4; and

----- represents a single bond or a double bond, or a non-toxic salt thereof.

* * * * *

UNITED STATES PATENT AND TRADEMARK OFFICE
CERTIFICATE OF CORRECTION

PATENT NO. : 6,743,793 B2
DATED : June 1, 2004
INVENTOR(S) : Kazuhiko Torisu, Kaoru Kobayashi and Fumio Nambu It is certified that error appears in the above-identified patent and that said Letters Patent is hereby corrected as shown below:

Column 6,
Line 57, delete "alkyl" and insert -- alkoxy --.
Line 58, delete "or C1-8 alkyl".

Signed and Sealed this

Fifteenth Day of November, 2005

JON W. DUDAS
*Director of the United States Patent and Trademark Office*